(12) United States Patent
Masuyama et al.

(10) Patent No.: US 11,815,813 B2
(45) Date of Patent: Nov. 14, 2023

(54) COMPOUND, RESIN, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Tatsuro Masuyama, Osaka (JP); Takuya Nakagawa, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 171 days.

(21) Appl. No.: 17/330,791

(22) Filed: May 26, 2021

(65) Prior Publication Data

US 2021/0389672 A1 Dec. 16, 2021

(30) Foreign Application Priority Data

Jun. 1, 2020 (JP) ................. 2020-095362

(51) Int. Cl.
*G03F 7/039* (2006.01)
*G03F 7/004* (2006.01)
*G03F 7/32* (2006.01)
*G03F 7/40* (2006.01)

(52) U.S. Cl.
CPC .......... *G03F 7/0392* (2013.01); *G03F 7/0045* (2013.01); *G03F 7/0046* (2013.01); *G03F 7/325* (2013.01); *G03F 7/40* (2013.01)

(58) Field of Classification Search
CPC ........ G03F 7/20; G03F 7/0392; G03F 7/0045; G03F 7/40; G03F 7/325; G03F 7/0046; G03F 7/0397; G03F 7/0384; C07C 62/24; C07C 43/315; C07C 43/23; C07C 69/54; C07C 69/84; C07C 69/76; C07C 43/205; C07C 43/225; C07C 69/07; C08F 220/22; C08F 220/301

See application file for complete search history.

(56) References Cited

U.S. PATENT DOCUMENTS

| 2005/0209260 | A1 | 9/2005 | Broka et al. | |
| 2011/0217654 | A1* | 9/2011 | Yamato | C07C 69/753 430/326 |
| 2018/0348632 | A1* | 12/2018 | Masuyama | G03F 7/38 |
| 2018/0362752 | A1* | 12/2018 | Aqad | C08L 73/00 |
| 2022/0348698 | A1* | 11/2022 | Omatsu | C07C 69/157 |

FOREIGN PATENT DOCUMENTS

| JP | 2000122291 A | 4/2000 |
| JP | 2015161823 A | 9/2015 |
| JP | 2018095851 A | 6/2018 |
| JP | 2018172640 A | 11/2018 |
| WO | 2015129355 A1 | 9/2015 |

OTHER PUBLICATIONS

Neuhaus William C. et al: "Vanadium-Catalyzed Selective Oxidative Homocoupling of Alkenyl Phenols To Synthesize Lignan Analogs", ACS Catalysis, vol. 9, No. 12, Dec. 6, 2019, pp 11067-11073, XP055853050.

Schmidt Bernd et al., "Synthesis of 8-Aryl-Substituted Coumarins Based on Ring-Closing Metathesis and Suzuki-Miyaura Coupling: Synthesis of a Furyl Coumarin Natural Product from Galipea panamensis", The Journal of Organic Chemistry, vol. 77, No. 5, Mar. 2, 2012, pp. 2360-2367, XP055853054.

Gagnier SV et al., "Palladium-Catalyzed Carbonylative Cyclization of Unsaturated Aryl Lodflides and Dienyl Triflates, Iodides, and Bromides to Indanones and 2-Cyclopentenones", Journal of the American Chemical Society, American Chemical Society, vol. 125, No. 16, Apr. 23, 2003, pp. 4804-4807, XP001144935.

Smolyar Ivan V. et al., "Heteroaryl Rings in Peptide Macrocycles", Chemical Reviews, vol. 119, No. 17, Sep. 11, 2019, pp. 10032-10240, XP055853059.

Waters Stephen P. et al., "Investigation of a Convergent Route to Purpuromycin: Benzofuran Formation vs Spiroketalization", Organic Letters, vol. 8, No. 15, Jul. 1, 2006 (Jul. 1, 2006), pp. 3243-3246, XP055853070.

(Continued)

*Primary Examiner* — Mark F. Huff
*Assistant Examiner* — Andrew Preston Traywick
(74) *Attorney, Agent, or Firm* — BUCHANAN INGERSOLL & ROONEY PC

(57) ABSTRACT

Disclosed are a compound represented by formula (I), a resin and a resist composition:

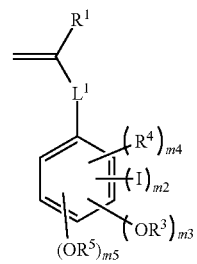

(I)

wherein $R^1$ represents an alkyl group which may have a halogen atom, a hydrogen atom or a halogen atom; $L^1$ represents a single bond or —CO—O*; $R^3$ represents an alkyl group, and —CH$_2$— included in the group may be replaced by —O— or —CO; $R^4$ represents a fluorine atom, an alkyl fluoride group or an alkyl group, and —CH$_2$— included in the alkyl fluoride group and the alkyl group may be replaced by —O— or —CO—; $R^5$ represents a hydrogen atom, an alkylcarbonyl group or an acid-labile group; m2 and m3 represent an integer of 1 to 3, m4 represents an integer of 0 to 2, and m5 represents 1 or 2, in which 3≤m2+m3+m4+m5≤5.

13 Claims, No Drawings

(56) References Cited

OTHER PUBLICATIONS

Norris Benjamin N. et al., "Iterative Synthesis of Heterotelechelic Oligo (phenylene-vinylene)s by Olefin Cross-Metathesis", Organic Letters, vol. 12, No. 23, Dec. 3, 2010 (Dec. 3, 2010), pp. 5514-5517, XP055853066.

Search Report and Written Opinion with an English translation dated Oct. 26, 2021, by the Belgian Patent Office for Belgian Application No. BN202105429. (21 pages).

* cited by examiner

COMPOUND, RESIN, RESIST COMPOSITION AND METHOD FOR PRODUCING RESIST PATTERN

TECHNICAL FIELD

The present disclosure relates to a compound, a resin including a structural unit derived from the compound, a resist composition comprising the resin, and a method for producing a resist pattern using the resist composition.

DESCRIPTION OF THE RELATED ART

JP 2000-122291 A mentions a resist composition comprising a resin including a structural unit derived from the following compound.

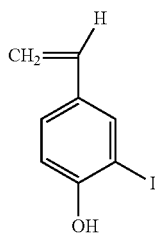

JP 2015-161823 A mentions resist compositions comprising a resin including each structural unit derived from the following compounds.

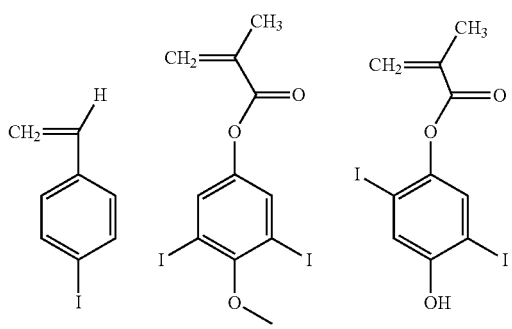

JP 2018-095851 A mentions a resist composition comprising a resin including a structural unit derived from the following compound.

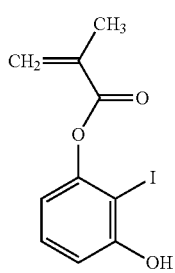

JP 2018-172640 A mentions a resist composition comprising a resin including a structural unit derived from the following compound.

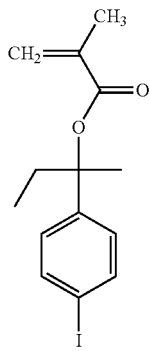

SUMMARY OF THE INVENTION

The present disclosure includes the following disclosures.

[1] A compound represented by formula (I):

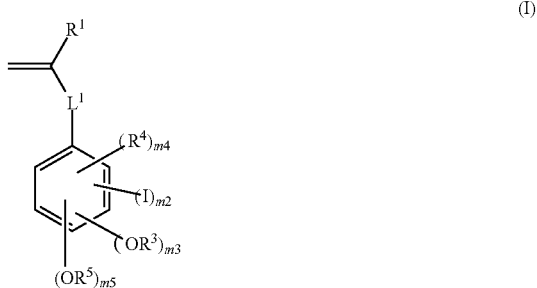

(I)

wherein, in formula (I),
- $R^1$ represents an alkyl group having 1 to 6 carbon atoms which may have a halogen atom, a hydrogen atom or a halogen atom,
- $L^1$ represents a single bond or —CO—O—* (* represents a bond to the benzene ring),
- $R^3$ represents an alkyl group having 1 to 6 carbon atoms, and —$CH_2$— included in the alkyl group may be replaced by —O— or —CO—,
- $R^4$ represents a fluorine atom, an alkyl fluoride group having 1 to 6 carbon atoms or an alkyl group having 1 to 12 carbon atoms, and —$CH_2$— included in the alkyl fluoride group and the alkyl group may be replaced by —O— or —CO—,
- $R^5$ represents a hydrogen atom, an alkylcarbonyl group having 2 to 6 carbon atoms or a first acid-labile group,
- m2 represents an integer of 1 to 3,
- m3 represents an integer of 1 to 3, and when m3 is 2 or more, a plurality of $R^3$ may be the same or different from each other,
- m4 represents an integer of 0 to 2, and when m4 is 2, two $R^4$ may be the same or different from each other, and
- m5 represents 1 or 2, and when m5 is 2, two $R^5$ may be the same or different from each other,
- in which $3 \leq m2+m3+m4+m5 \leq 5$.

[2] The compound according to [1], wherein m2 is 1 or 2, m3 is 1, and m5 is 1 or 2.

[3] The compound according to [1] or [2], wherein the first acid-labile group as for at least one of $R^5$ is a group represented by formula (R5-1) or a group represented by formula (R5-2):

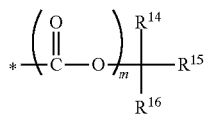
(R5-1)

wherein, in formula (R5-1), $R^{14}$, $R^{15}$ and $R^{16}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{14}$ and $R^{15}$ are bonded to each other to form an alicyclic hydrocarbon group having 3 to 20 carbon atoms together with carbon atoms to which $R^{14}$ and $R^{15}$ are bonded, m represents 0 or 1, and

* represents a bonding site:

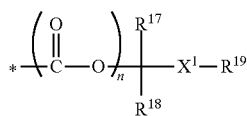
(R5-2)

wherein, in formula (R5-2), $R^{17}$ and $R^{18}$ each independently represent a hydrogen atom or a hydrocarbon group having 1 to 12 carbon atoms, $R^{19}$ represents a hydrocarbon group having 1 to 20 carbon atoms, or $R^{18}$ and $R^{19}$ are bonded to each other to form a heterocyclic group having 3 to 20 carbon atoms together with carbon atoms and X' to which $R^{18}$ and $R^{19}$ are bonded, and —$CH_2$— included in the hydrocarbon group and the heterocyclic group may be replaced by —O— or —S—, $X^1$ represents an oxygen atom or a sulfur atom, n represents 0 or 1, and

* represents a bonding site.

[4] The compound according to any one of [1] to [3], wherein at least one $R^5$ is a hydrogen atom or an alkyl-carbonyl group.

[5] The compound according to any one of [1] to [4], wherein a bonding site of at least one iodine atom is a m-position with respect to a bonding site of $L^1$ in the benzene ring.

[6] The compound according to any one of [1] to [5], wherein a bonding site of at least one $OR^5$ is an o-position or a p-position with respect to the bonding site of $L^1$ in the benzene ring.

[7] A resin including a first structural unit derived from the compound according to any one of [1] to [6].

[8] The resin according to [7], further including a second structural unit having a second acid-labile group other than the structural unit derived from the compound represented by formula (I).

[9] A resist composition comprising the resin according to [7] or [8] and an acid generator.

[10] The resist composition according to [9], wherein the acid generator comprises a salt represented by formula (B1):

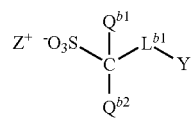
(B1)

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$— included in the alicyclic hydrocarbon group may be replaced by —O—, —$SO_2$— or —CO—, and $Z^+$ represents an organic cation.

[11] The resist composition according to [9] or [10], further comprising a salt generating an acid having an acidity lower than that of an acid generated from the acid generator.

[12] A method for producing a resist pattern, which comprises:

(1) a step of applying the resist composition according to any one of [9] to [11] on a substrate, (2) a step of drying the applied composition to form a composition layer, (3) a step of exposing the composition layer, (4) a step of heating the exposed composition layer, and (5) a step of developing the heated composition layer.

DETAILED DESCRIPTION OF THE PREFERRED EMBODIMENTS

In the present specification, unless otherwise specified, "(meth)acrylate" means "at least one selected from the group consisting of acrylate and methacrylate". Descriptions such as "(meth)acrylic acid" and "(meth)acryloyl" also have the same meanings. When a structural unit having "$CH_2$=C($CH_3$)—CO—" or "$CH_2$=CH—CO—" is exemplified, a structural unit having both groups shall be similarly exemplified. In groups mentioned in the present specification, regarding groups capable of having both a linear structure and a branched structure, they may have either the linear or branched structure. When —$CH_2$— contained in a hydrocarbon group or the like is replaced by —O—, —S—, —CO— or —$SO_2$—, the same example shall be applied to each group. "Combined group" means a group obtained by bonding two or more exemplified groups, and a valence of the group may appropriately vary depending on the bonding state. "Derived" means that a polymerizable C=C bond included in the molecule becomes a —C—C— group by polymerization. When stereoisomers exist, all stereoisomers are included.

In the present specification, "solid component of resist composition" means the total of components excluding the below-mentioned solvent (E) from the total amount of the resist composition.

[Compound Represented by Formula (I)]

The compound of the present disclosure relates to a compound represented by formula (I) (hereinafter sometimes referred to as "compound (I)"):

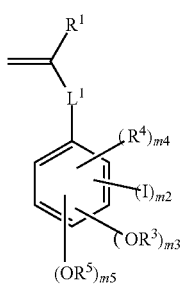

wherein, in formula (I), all symbols are the same as defined above.

In formula (I), examples of the alkyl group in $R^1$ and $R^3$ include a methyl group, an ethyl group, an n-propyl group, an isopropyl group, an n-butyl group, a sec-butyl group, a tert-butyl group, an n-pentyl group and an n-hexyl group. The number of carbon atoms of the alkyl group is preferably 1 to 4, more preferably 1 to 3, and still more preferably 1 or 2.

Examples of the halogen atom as for $R^1$ include a fluorine atom, a chlorine atom, a bromine atom and an iodine atom.

Examples of the alkyl group having a halogen atom as for $R^1$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a perchloromethyl group, a perbromomethyl group and a periodomethyl group.

When —$CH_2$— included in the alkyl group in $R^3$ is replaced by —O— or —CO—, the number of carbon atoms before replacement is taken as the total number of the alkyl group.

Examples of the group in which —$CH_2$— included in the alkyl group in $R^3$ is replaced by —O— or —CO— include a hydroxyalkyl group (a group in which —$CH_2$— of the methyl group included in the methylalkyl group is replaced by —O—), a carboxyalkyl group (a group in which —$CH_2$—$CH_2$— of the ethyl group included in the ethylalkyl group is replaced by —O—CO—), an alkoxy group (a group in which —$CH_2$— at any position included in the alkyl group is replaced by —O—), an alkoxycarbonyl group (a group in which —$CH_2$—$CH_2$— at any position included in the alkyl group is replaced by —O—CO—), an alkylcarbonyl group (a group in which —$CH_2$— at any position included in the alkyl group is replaced by —CO—), an alkylcarbonyloxy group (a group in which —$CH_2$—$CH_2$— at any position included in the alkyl group is replaced by —CO—O—), and a group obtained by combining two or more of these groups.

$R^1$ is preferably a hydrogen atom or a methyl group.

$R^3$ is preferably an alkyl group having 1 to 4 carbon atoms, more preferably an alkyl group having 1 to 3 carbon atoms, still more preferably a methyl group and an ethyl group, and yet more preferably a methyl group.

m2 is preferably 1 or 2.

m3 is preferably 1 or 2, and more preferably 1.

Examples of the alkyl fluoride group having 1 to 6 carbon atoms as for $R^4$ include alkyl fluoride groups such as a trifluoromethyl group, a difluoromethyl group, a perfluoroethyl group, a 2,2,2-trifluoroethyl group, a 1,1,2,2-tetrafluoroethyl group, a perfluoropropyl group, a 2,2,3,3,3-pentafluoropropyl group, a perfluorobutyl group, a 1,1,2,2,3,3,4,4-octafluorobutyl group, a perfluoropentyl group, a 2,2,3,3,4,4,5,5-nonafluoropentyl group and a perfluorohexyl group. The number of the alkyl fluoride group is preferably 1 to 4, and more preferably 1 to 3.

Examples of the alkyl group having 1 to 12 carbon atoms as for $R^4$ include alkyl groups such as a methyl group, an ethyl group, a propyl group, an isopropyl group, a butyl group, an isobutyl group, a tert-butyl group, a pentyl group, a hexyl group, an octyl group and a nonyl group. The number of carbon atoms of the alkyl group is preferably 1 to 9, more preferably 1 to 6, and still more preferably 1 to 4.

When —$CH_2$— included in the alkyl group in $R^4$ is replaced by —O— or —CO—, the number of carbon atoms before replacement is taken as the total number of the alkyl group.

Examples of the group in which —$CH_2$— included in the alkyl group in $R^4$ is replaced by —O— or —CO— include a hydroxy group (a group in which —$CH_2$— included in the methyl group is replaced by —O—), a carboxy group (a group in which —$CH_2$—$CH_2$— included in the ethyl group is replaced by —O—CO—), an alkoxy group (a group in which —$CH_2$— at any position included in the alkyl group is replaced by —O—), an alkoxycarbonyl group (a group in which —$CH_2$—$CH_2$— at any position included in the alkyl group is replaced by —O—CO—), an alkylcarbonyl group (a group in which —$CH_2$— at any position included in the alkyl group is replaced by —CO—), an alkylcarbonyloxy group (a group in which —$CH_2$—$CH_2$— at any position included in the alkyl group is replaced by —CO—O—), and a group obtained by combining two or more of these groups.

Examples of the group in which —$CH_2$— included in the alkyl fluoride group in $R^4$ is replaced by —O— or —CO— include an alkoxy fluoride group (a group in which —$CH_2$— at any position included in the alkyl fluoride group is replaced by —O—), an alkoxycarbonyl fluoride group (a group in which —$CH_2$—$CH_2$— at any position included in the alkyl fluoride group is replaced by —O—CO—), an alkylcarbonyl fluoride group (a group in which —$CH_2$— at any position included in the alkyl fluoride group is replaced by —CO—), an alkylcarbonyloxy fluoride group (a group in which —$CH_2$—$CH_2$— at any position included in the alkyl fluoride group is replaced by —CO—O—), and a group obtained by combining two or more of these groups.

Examples of the alkoxy group include alkoxy groups having 1 to 11 carbon atoms, for example, a methoxy group, an ethoxy group, a propoxy group, a butoxy group, a pentyloxy group, a hexyloxy group, a heptyloxy group, an octyloxy group, a nonyloxy group, a decyloxy group and an undecyloxy group.

Examples of the alkoxycarbonyl group include alkoxycarbonyl groups having 2 to 11 carbon atoms, for example, a methoxycarbonyl group, an ethoxycarbonyl group, a propoxycarbonyl group and a butoxycarbonyl group.

Examples of the alkylcarbonyl group include alkylcarbonyl groups having 2 to 12 carbon atoms, for example, an acetyl group, a propionyl group and a butyryl group.

Examples of the alkylcarbonyloxy group include alkylcarbonyloxy groups having 2 to 11 carbon atoms, for example, a methylcarbonyloxy group, an ethylcarbonyloxy group, a propylcarbonyloxy group and a butylcarbonyloxy group.

Examples of the alkoxy fluoride group, the alkoxycarbonyl fluoride group, the alkylcarbonyl fluoride group and the alkylcarbonyloxy fluoride group include alkoxy fluoride groups having 1 to 5 carbon atoms, alkoxycarbonyl fluoride groups having 2 to 5 carbon atoms, alkylcarbonyl fluoride groups having 2 to 6 carbon atoms and alkylcarbonyloxy fluoride groups having 2 to 5 carbon atoms, for example, one or more hydrogen atoms of the above-exemplified groups may be substituted with a fluorine atom.

$R^4$ is preferably a fluorine atom, an alkyl fluoride group having 1 to 4 carbon atoms or an alkyl group having 1 to 8 carbon atoms (—$CH_2$— included in the alkyl fluoride group and the alkyl group may be replaced by —O— or —CO—), more preferably an alkoxy group having 1 to 6 carbon atoms, and still more preferably an alkoxy group having 1 to 3 carbon atoms.

m4 is preferably 0 or 1, and more preferably 0.

Examples of the alkylcarbonyl group as for $R^5$ include an acetyl group, a propionyl group and a butyryl group. The number of the alkylcarbonyl group is preferably 2 to 4, and more preferably 2 or 3.

The first acid-labile group as for $R^5$ means a group which is eliminated by contact with an acid, thus forming a hydroxy group.

The first acid-labile group includes, for example, a group represented by formula (R5-1) (hereinafter sometimes referred to as "acid-labile group (R5-1)") and a group represented by formula (R5-2) (hereinafter sometimes referred to as "acid-labile group (R5-2)"):

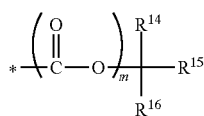
(R5-1)

wherein, in formula (R5-1), $R^{14}$, $R^{15}$ and $R^{16}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{14}$ and $R^{15}$ are bonded to each other to form an alicyclic hydrocarbon group having 3 to 20 carbon atoms together with carbon atoms to which $R^{14}$ and $R^{15}$ are bonded, m represents 0 or 1, and

* represents a bonding site:

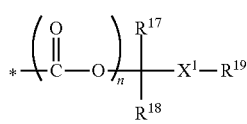
(R5-2)

wherein, in formula (R5-2), $R^{17}$ and $R^{18}$ each independently represent a hydrogen atom or a hydrocarbon group having 1 to 12 carbon atoms, $R^{19}$ represents a hydrocarbon group having 1 to 20 carbon atoms, or $R^{18}$ and $R^{19}$ are bonded to each other to form a heterocyclic group having 3 to 20 carbon atoms together with carbon atoms and $X^1$ to which $R^{18}$ and $R^{19}$ are bonded, and —$CH_2$— included in the hydrocarbon group and the heterocyclic group may be replaced by —O— or —S—, $X^1$ represents an oxygen atom or a sulfur atom, n represents 0 or 1, and

* represents a bonding site.

Examples of the alkyl group represented by $R^{14}$, $R^{15}$ and $R^{16}$ include a methyl group, an ethyl group, a propyl group, an n-butyl group, an n-pentyl group, an n-hexyl group, an n-heptyl group, an n-octyl group and the like. The number of carbon atoms of the alkyl group as for $R^{14}$, $R^{15}$ and $R^{16}$ is preferably 1 to 6, and more preferably 1 to 3.

Examples of the alkenyl group as for $R^{14}$, $R^{15}$ and $R^{16}$ include an ethenyl group, a propenyl group, an isopropenyl group, a butenyl group, an isobutenyl group, a tert-butenyl group, a pentenyl group, a hexenyl group, a heptenyl group, an octynyl group, an isooctynyl group and a nonenyl group.

The alicyclic hydrocarbon group represented by $R^{14}$, $R^{15}$ and $R^{16}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group, and the following groups (* represents a bond). The number of carbon atoms of the alicyclic hydrocarbon group as for $R^{14}$, $R^{15}$ and $R^{16}$ is preferably 3 to 16.

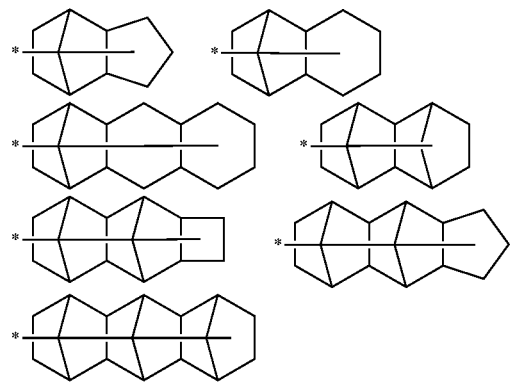

Examples of the aromatic hydrocarbon group as for $R^{14}$, $R^{15}$ and $R^{16}$ include aryl groups such as a phenyl group, a naphthyl group, an anthryl group, a biphenyl group and a phenanthryl group. The number of carbon atoms of the aromatic hydrocarbon group as for $R^{aa1}$, $R^{aa2}$ and $R^{aa3}$ is preferably 6 to 14, and more preferably 6 to 10.

Examples of the group obtained by combining an alkyl group with an alicyclic hydrocarbon group include a methylcyclohexyl group, a dimethylcyclohexyl group, a methylnorbornyl group, a cyclohexylmethyl group, an adamantylmethyl group, a norbornylethyl group and the like.

Examples of the group obtained by combining an alkyl group with an aromatic hydrocarbon group include a p-methylphenyl group, a p-tert-butylphenyl group, a tolyl group, a xylyl group, a cumenyl group, a mesityl group, a 2,6-diethylphenyl group, a 2-methyl-6-ethylphenyl group and the like.

Examples of the group obtained by combining an alicyclic hydrocarbon group with an aromatic hydrocarbon group include a p-cyclohexylphenyl group, a p-adamantylphenyl group and the like.

m is preferably 1.

When $R^{14}$ and $R^{15}$ are bonded to each other to form an alicyclic hydrocarbon group together with carbon atoms to which $R^{14}$ and $R^{15}$ are bonded, examples of —$C(R^{14})(R^{15})(R^{16})$— include the following groups. The alicyclic hydrocarbon group has preferably 3 to 16 carbon atoms, and more preferably 3 to 12 carbon atoms. * represents a bond to —O—.

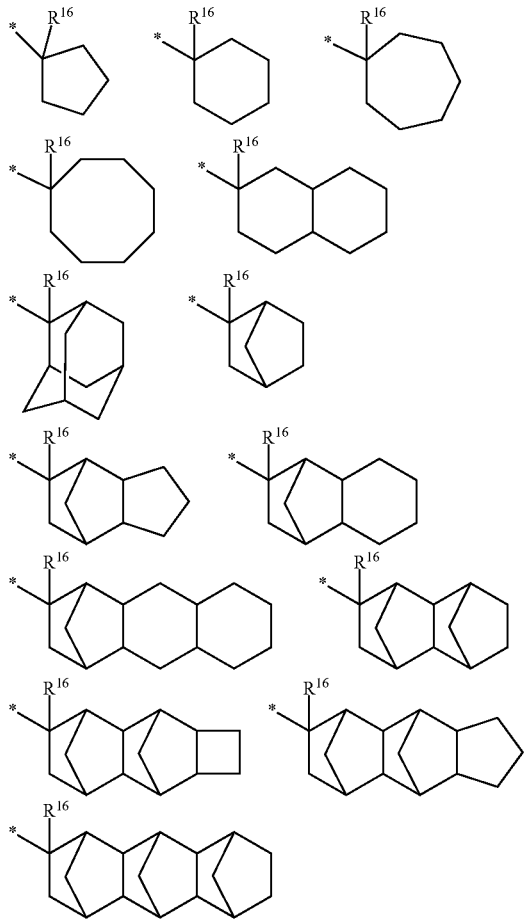

Examples of the hydrocarbon group as for $R^{17}$, $R^{18}$ and $R^{19}$ include an alkyl group, an alicyclic hydrocarbon group, an aromatic hydrocarbon group, and groups formed by combining these groups.

Examples of the alkyl group and the alicyclic hydrocarbon group include those which are the same as mentioned above.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (an alkylcycloalkyl group or a cycloalkylalkyl group, etc.), aralkyl groups (a benzyl group, etc.), aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups (a phenylcyclohexyl group, etc.), and the like.

When $R^{18}$ and $R^{19}$ are bonded to each other to form a heterocyclic group together with carbon atoms and $X^1$ to which $R^{18}$ and $R^{19}$ are bonded, examples of —C($R^{17}$)($R^{18}$)—$X^1$—$R^{19}$ include the following groups. * represents a bond.

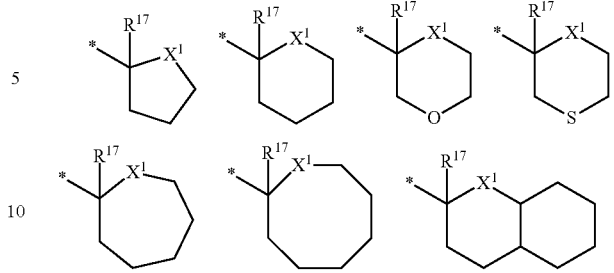

At least one of $R^{17}$ and $R^{18}$ is preferably a hydrogen atom.

n is preferably 0.

Specific examples of the acid-labile group (R5-1) include the following groups. * represents a bond.

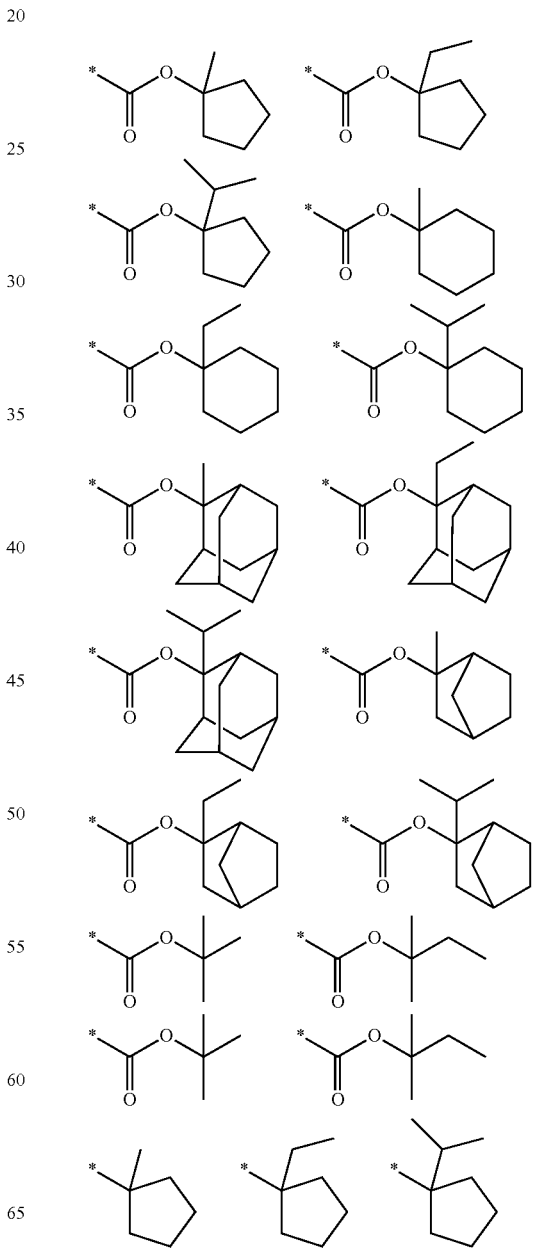

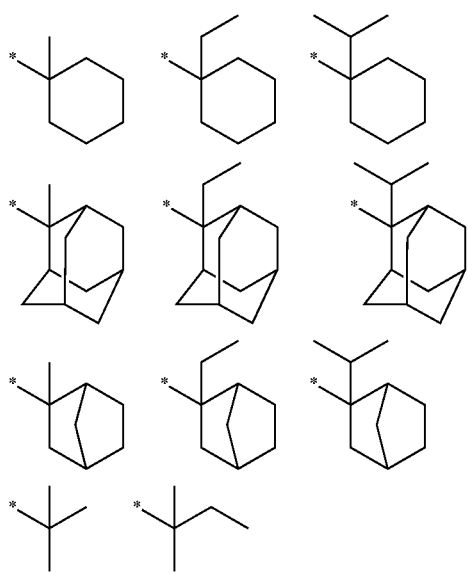

Specific examples of the acid-labile group (R5-2) include the following groups. * represents a bond.

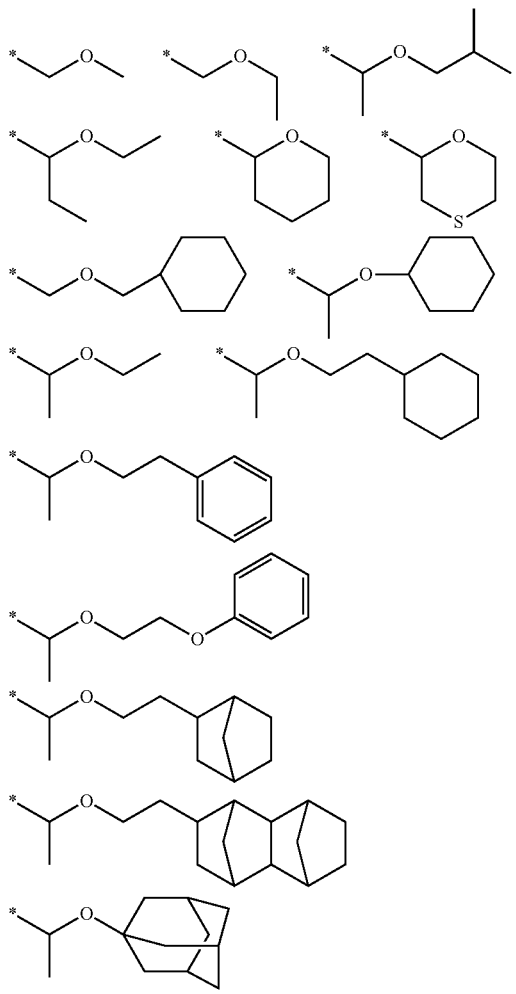

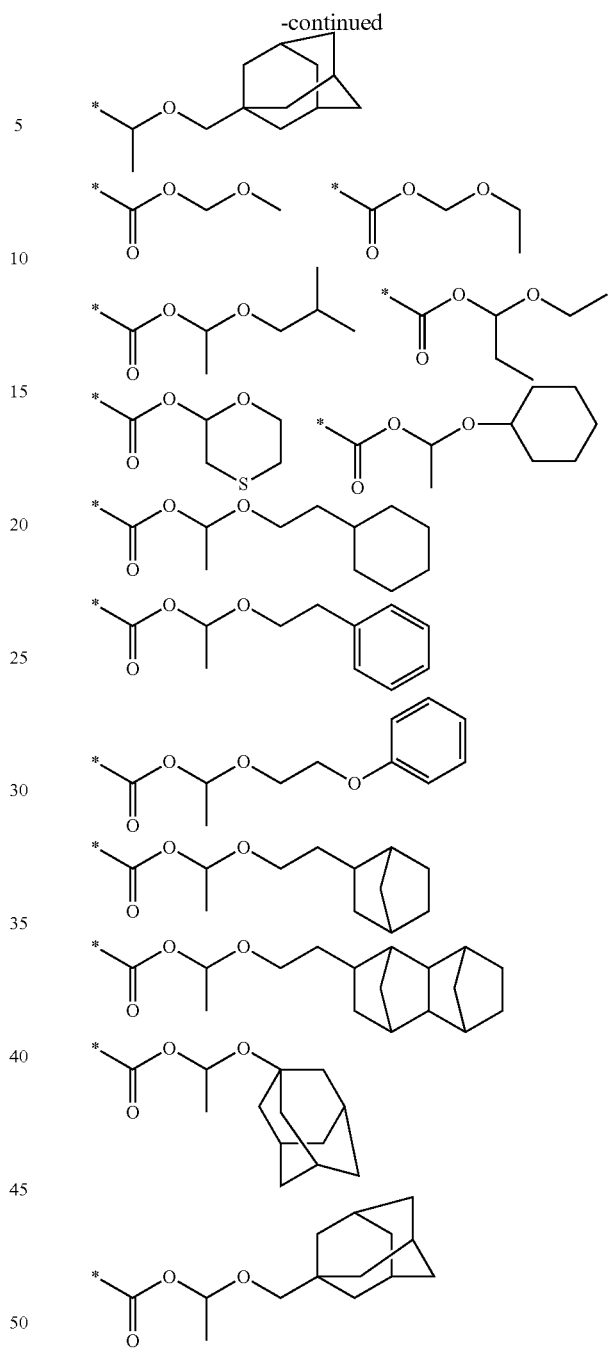

m5 is preferably 1 or 2.

The bonding site of —OR$^5$ may be the o-position, the m-position or the p-position with respect to the bonding site of L$^1$ in the benzene ring, preferably the o-position or the p-position, and more preferably the p-position. When m5 is 2, the bond sites of one of the two OR$^5$s is preferably the o-position and the bond sites of other of the two OR$^5$s is preferably the p-position with respect to the bond site of L$^1$ in the benzene ring.

The bonding site of the iodine atom may be the o-position, the m-position or the p-position with respect to the bonding site of L$^1$ in the benzene ring, and preferably the o-position or the m-position. When m2 is 2, the bond positions of the two iodine atoms are preferably both at the m-position.

The bonding site of —OR³ may be the o-position, the m-position or the p-position with respect to the bonding site of L¹ in the benzene ring, and preferably the o-position or the m-position.
Examples of the compound (I) include the following compounds.
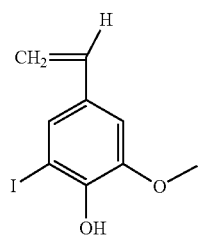
(I-1)
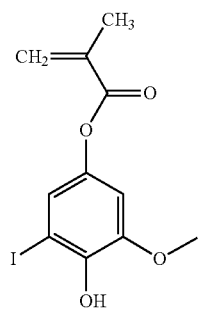
(I-2)
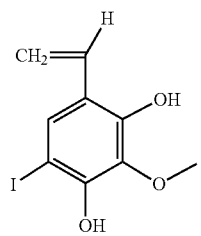
(I-3)
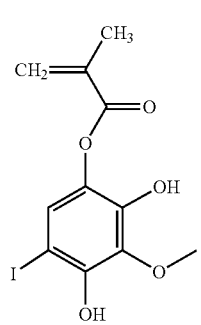
(I-4)
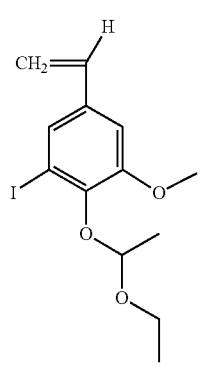
(I-5)
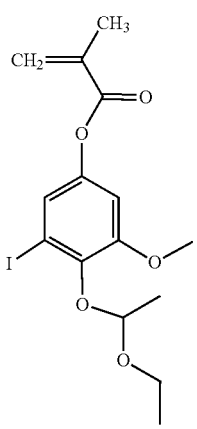
(I-6)
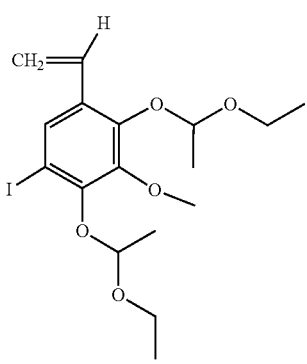
(I-7)
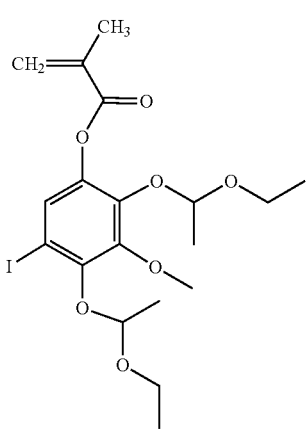
(I-8)
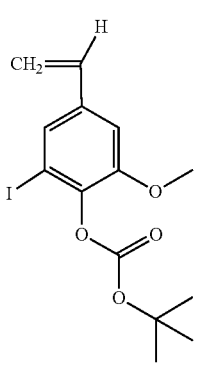
(I-9)

(I-10)
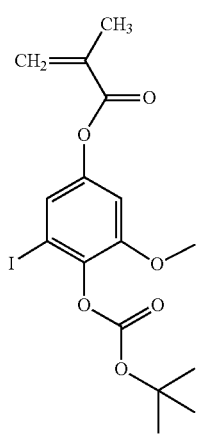
(I-11)
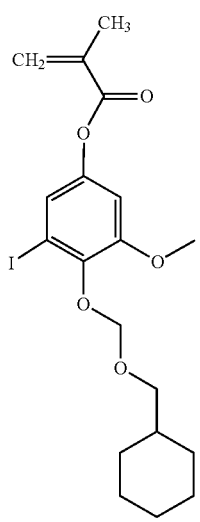
(I-12)
(I-13)
(I-14)
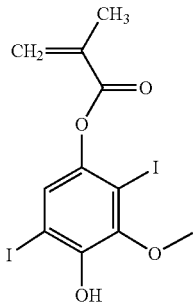
(I-15)
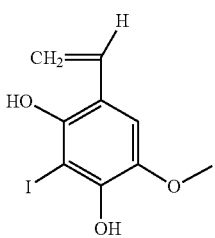
(I-16)
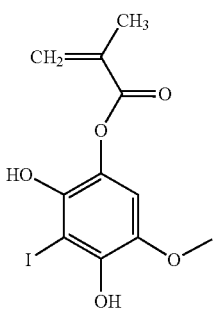
(I-17)
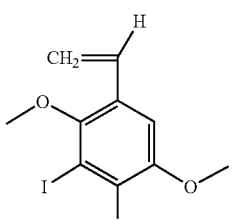
(I-18)
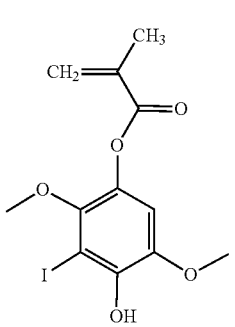
(I-19)
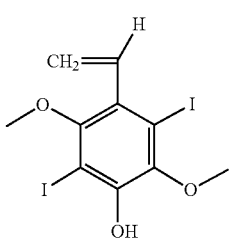

(I-20) 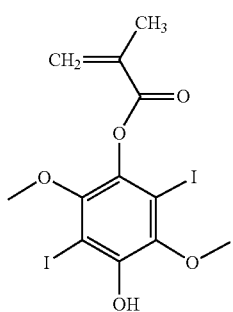
(I-21) 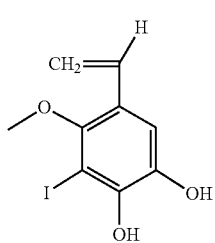
(I-22) 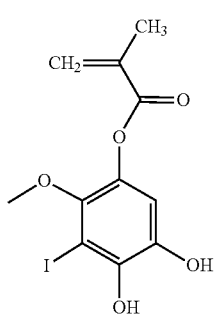
(I-23) 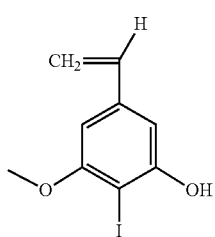
(I-24) 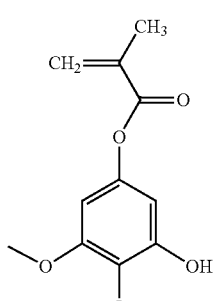
(I-25) 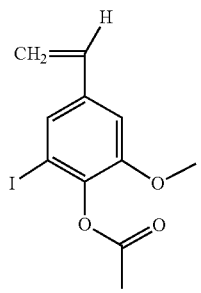
(I-26) 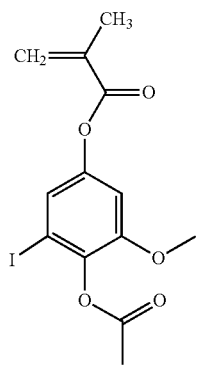
(I-27) 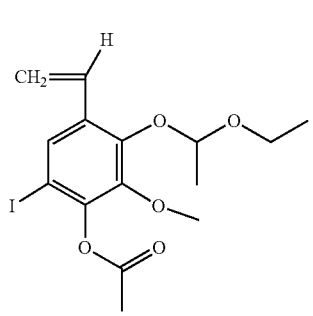
(I-28) 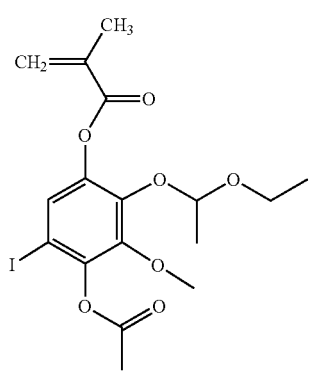
(I-29) 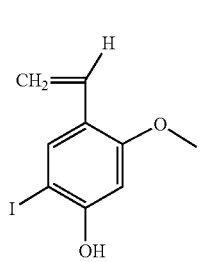

(I-30)
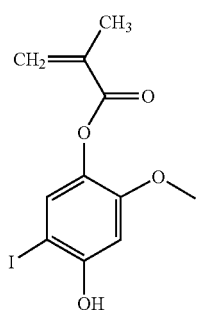
(I-31)
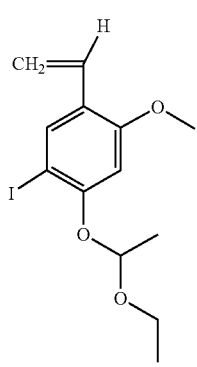
(I-32)
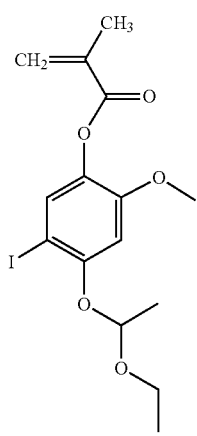
(I-33)
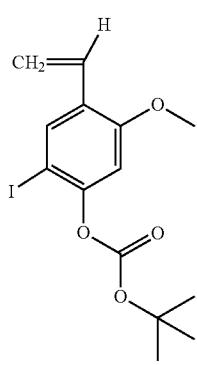
(I-34)
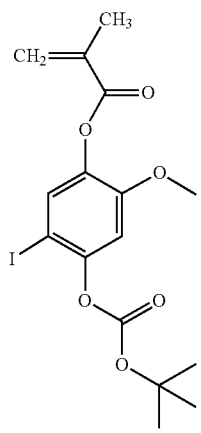
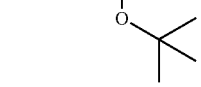
(I-35)
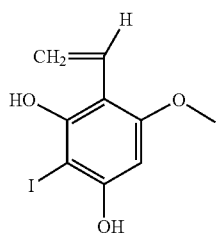
(I-36)
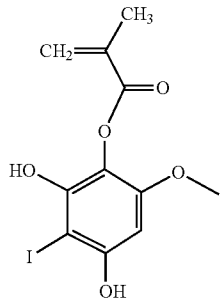
(I-37)
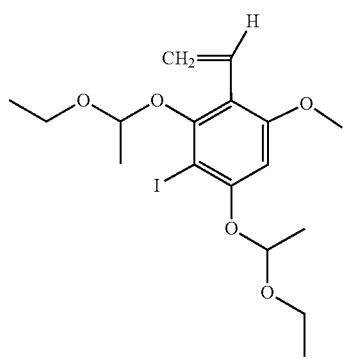

(I-38)
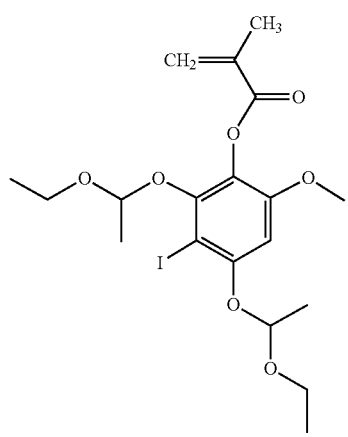
(I-39)
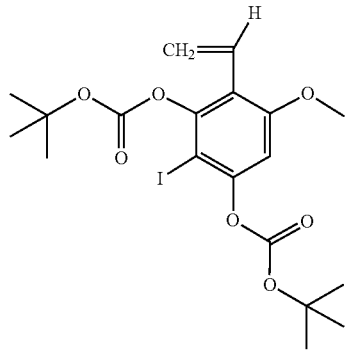
(I-40)
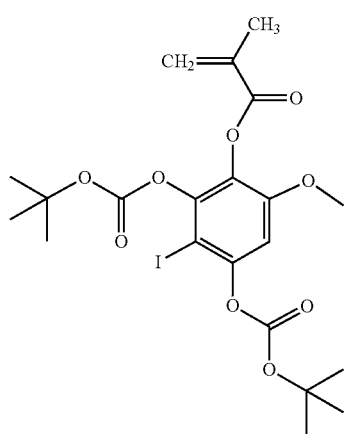
(I-41)
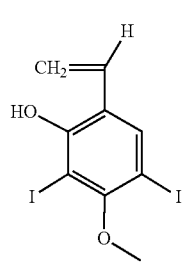
(I-42)
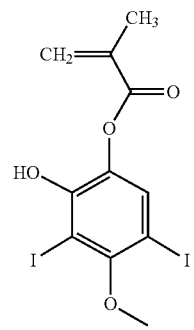
(I-43)
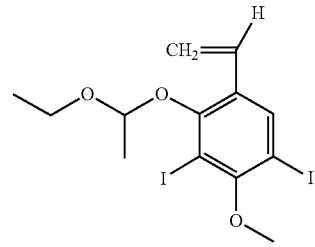
(I-44)
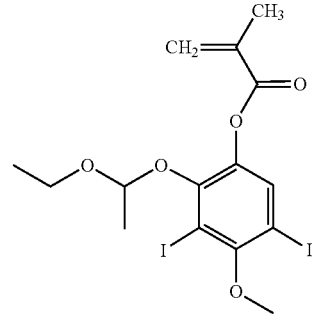
(I-45)
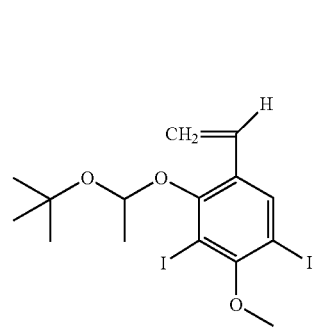
(I-46)
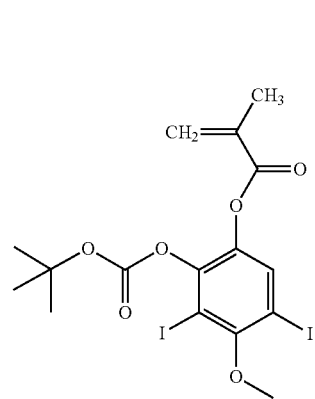

It is also possible to exemplify, as specific examples of the compound (I), compounds in which a hydrogen atom corresponding to $R^1$ of formula (I) is substituted with a methyl group in compounds represented by formula (I-1), formula (I-3), formula (I-5), formula (I-7), formula (I-9), formula (I-11), formula (I-13), formula (I-15), formula (I-17), formula (I-19), formula (I-21), formula (I-23), formula (I-25), formula (I-27), formula (I-29), formula (I-31), formula (I-33), formula (I-35), formula (I-37), formula (I-39), formula (I-41), formula (I-43), formula (I-45), formula (I-47), formula (I-49) and formula (I-51), and compounds in which a methyl group corresponding to $R^1$ of formula (I) is substituted with a hydrogen atom in compounds represented by formula (I-2), formula (I-4), formula (I-6), formula (I-8), formula (I-10), formula (I-12), formula (I-14), formula (I-16), formula (I-18), formula (I-20), formula (I-22), formula (I-24), formula (I-26), formula (I-28), formula (I-30), formula (I-32), formula (I-34), formula (I-36), formula (I-38), formula (I-40), formula (I-42), formula (I-44), formula (I-46), formula (I-48), formula (I-50) and formula (I-52). Of these, compounds represented by formula (I-1), formula (I-2), formula (I-5), formula (I-6), formula (I-25), formula (I-26), formula (I-29) to formula (I-32), formula (I-35) to formula (I-38) and formula (I-41) to formula (I-52) are preferable.

<Method for Producing Compound (I)>

It is possible to obtain a compound represented by formula (I1) in which $L^1$ is a single bond in the compound (I) by reacting a compound represented by formula (I1-a) with a compound represented by formula (I1-b) in the presence of a compound represented by formula (I1-c) in a solvent.

-continued

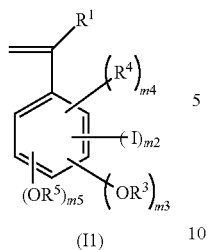

(I1)

wherein all symbols are the same as defined above.

Examples of the solvent include tetrahydrofuran, chloroform and acetonitrile.

The reaction temperature is usually 0° C. to 80° C., and the reaction time is usually 0.5 hour to 24 hours.

Examples of the compound represented by formula (I1-a) include compounds represented by the following formulas, which are easily available on the market and can also be synthesized easily by a known production process.

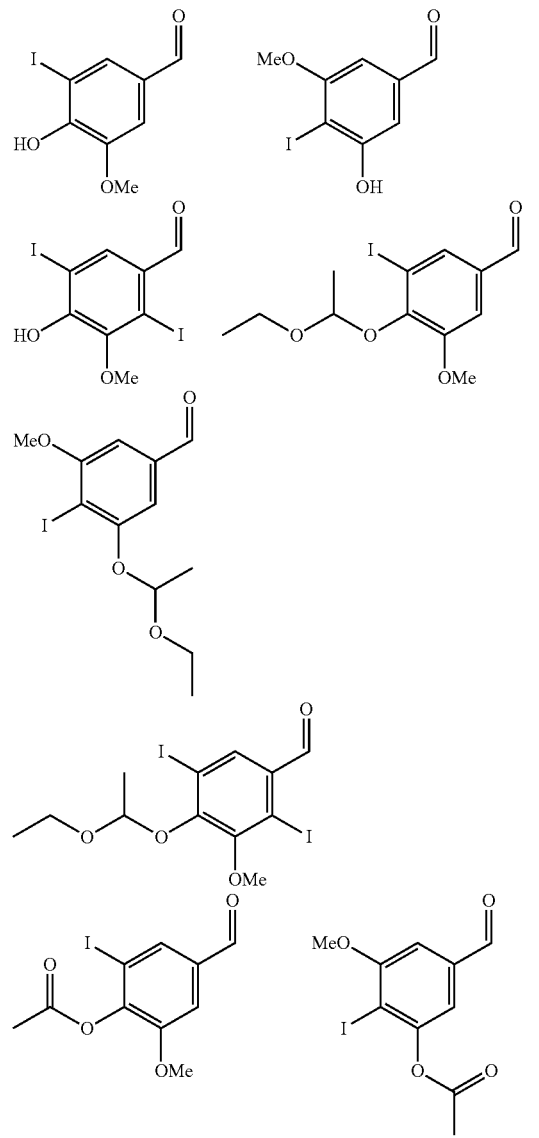

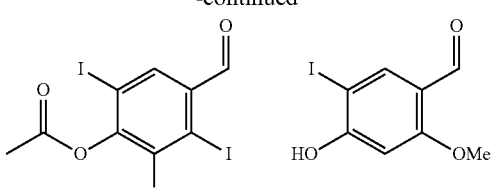

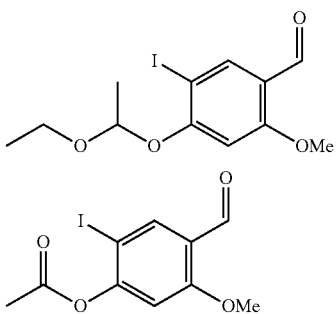

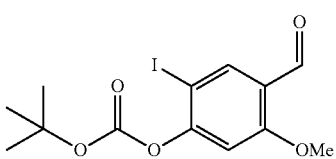

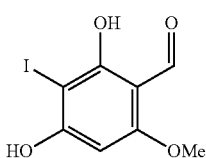

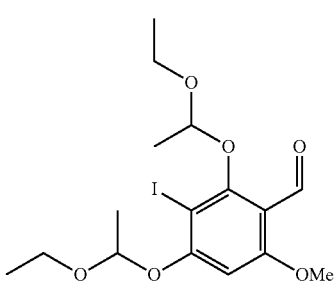

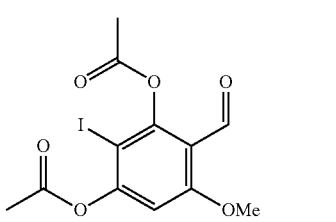

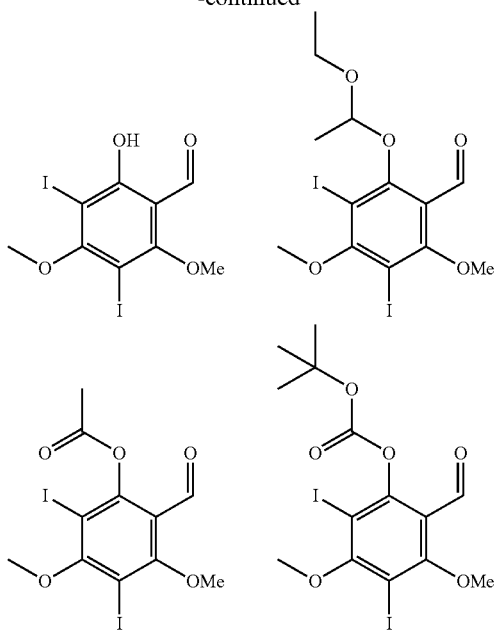

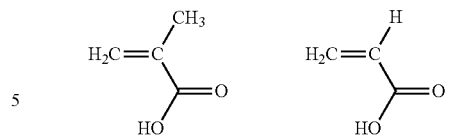

Examples of the compound represented by formula (I2-b) include compounds represented by the following formulas, which are easily available on the market and can also be synthesized easily by a known production process.

It is possible to obtain a compound represented by formula (I2) in which $L^1$ is —CO—O—* (* represents a bond to the benzene ring) in the compound (I) by reacting a compound represented by formula (I2-a) with carbonyldiimidazole in a solvent, followed by a reaction with a compound represented by formula (I2-b):

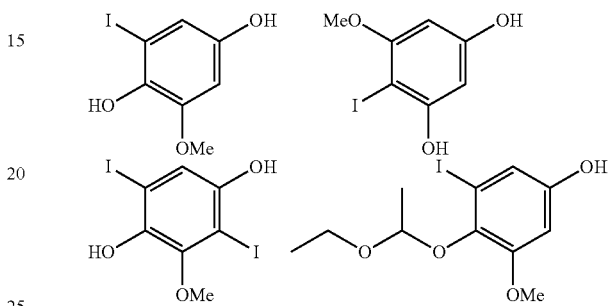

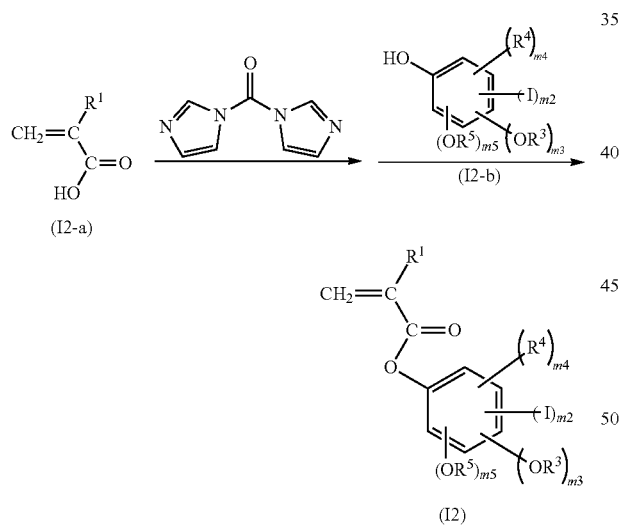

wherein all symbols are the same as defined above.

Examples of the solvent include tetrahydrofuran, chloroform and acetonitrile.

The reaction temperature is usually 0° C. to 80° C., and the reaction time is usually 0.5 hour to 24 hours.

Examples of the compound represented by formula (I2-a) include compounds represented by the following formulas, which are easily available on the market.

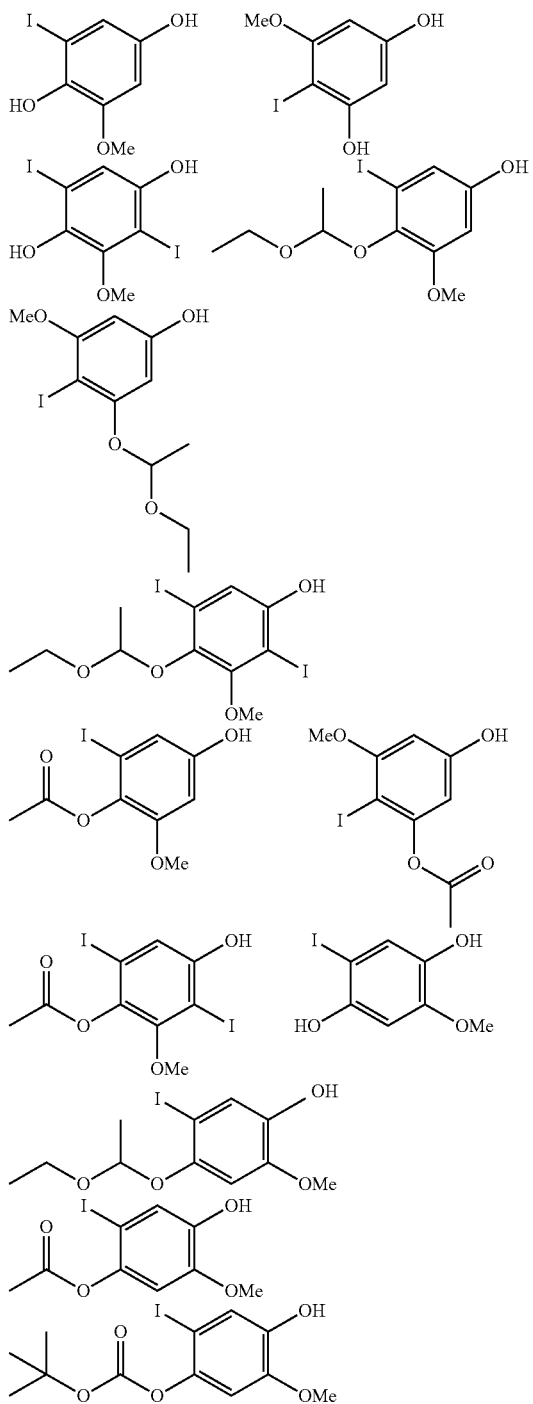

-continued

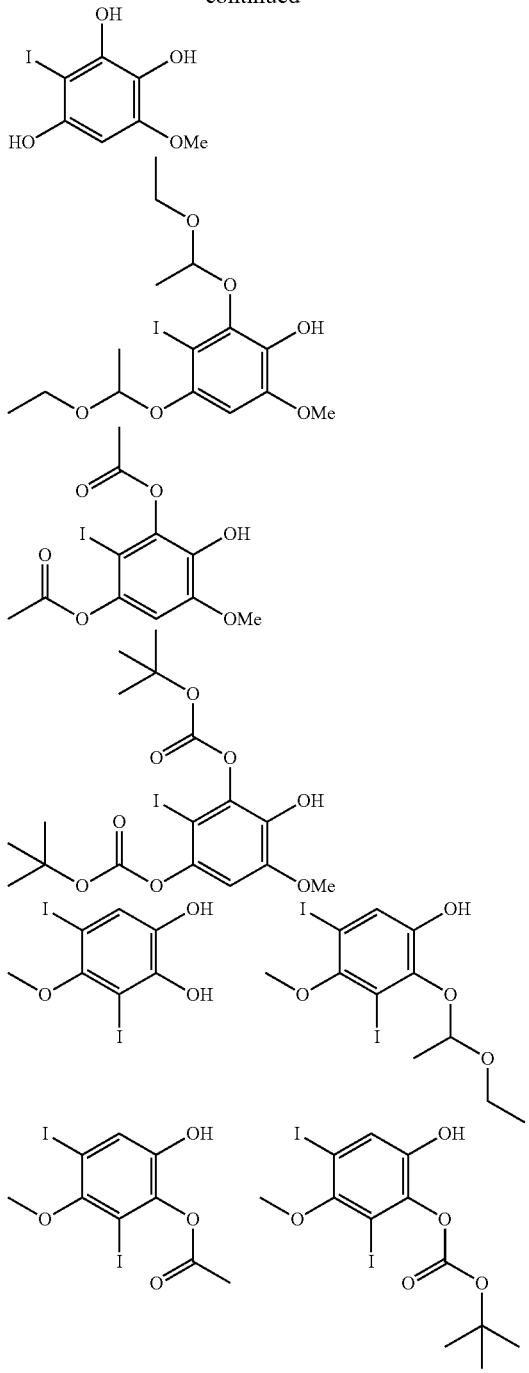

[Resin]

The resin of the present disclosure is a resin (hereinafter sometimes referred to as "resin (A)") including a structural unit derived from a compound (I) (hereinafter sometimes referred to as "structural unit (I)" or "first structural unit"). The resin (A) may be a homopolymer of a structural unit (I), a copolymer composed of only a structural unit (I), or a polymer including one or more structural units other than the structural unit (I). Examples of the structural unit other than the structural unit (I) include a structural unit having an acid-labile group (hereinafter sometimes referred to as "second acid-labile group") other than the structural unit (I) (hereinafter sometimes referred to as "structural unit (a1)" or "second structural unit")), a structural unit having a halogen atom other than the structural unit having an acid-labile group (hereinafter sometimes referred to as "structural unit (a4)"), a structural unit having no acid-labile group (hereinafter sometimes referred to as "structural unit (s)"), a structural unit having a non-leaving hydrocarbon group (hereinafter sometimes referred to as "structural unit (a5)") and the like. The "acid-labile group" means a group having a leaving group which is eliminated by contact with an acid, thus forming a hydrophilic group (e.g. a hydroxy group or a carboxy group).

The content of the structural unit (I) is usually 1 to 100 mol %, preferably 1 to 90 mol %, more preferably 1 to 80 mol %, and still more preferably 3 to 50 mol %, based on all monomers in the resin (A).

When the resin (A) includes a structural unit (a4) and/or (a5) mentioned later (hereinafter sometimes referred to as "resin (AX)"), the content of the structural unit (I) in the resin (AX) of the present disclosure is preferably 1 to 75 mol %, more preferably 1 to 70 mol %, still more preferably 3 to 65 mol %, and particularly preferably 3 to 60 mol %, based on the total of all structural units of the resin (AX) of the present disclosure.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

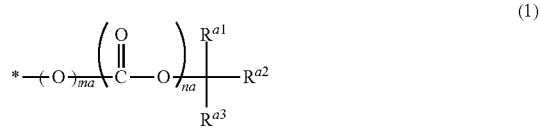

wherein, in formula (1), $R^{a1}$, $R^{a2}$ and $R^{a3}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or groups obtained by combining these groups, or $R^{a1}$ and $R^{a2}$ are bonded each other to form an alicyclic hydrocarbon group having 3 to 20 carbon atoms together with carbon atoms to which $R^{a1}$ and $R^{a2}$ are bonded, ma and na each independently represent 0 or 1, and at least one of ma and na represents 1, and

* represents a bond:

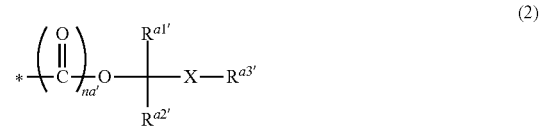

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded each other to form a heterocyclic group having 3 to 20 carbon atoms together with carbon atoms and X to which $R^{a2'}$ and $R^{a3'}$ are bonded, and —CH$_2$— included in the hydrocarbon group and the heterocyclic group may be replaced by —O— or —S—, X represents an oxygen atom or a sulfur atom, na' represents 0 or 1, and

* represents a bond.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

Examples of the alkenyl group in $R^{a1}$, $R^{a2}$ and $R^{a3}$ include an ethenyl group, a propenyl group, an isopropenyl group, a butenyl group, an isobutenyl group, a tert-butenyl group, a pentenyl group, a hexenyl group, a heptenyl group, an octynyl group, an isooctynyl group and a nonenyl group.

The alicyclic hydrocarbon group in $R^{a1}$, $R^{a2}$ and $R^{a3}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bond). The number of carbon atoms of the alicyclic hydrocarbon group as for $R^{a1}$, $R^{a2}$ and $R^{a3}$ is preferably 3 to 16.

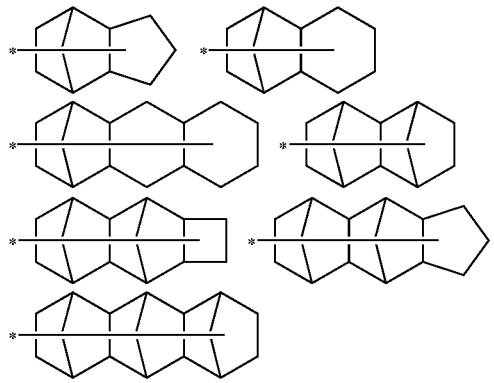

Examples of the aromatic hydrocarbon group in $R^{a1}$, $R^{a2}$ and $R^{a3}$ include aryl groups such as a phenyl group, a naphthyl group, an anthryl group, a biphenyl group and a phenanthryl group.

Examples of the combined group include groups obtained by the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group, a norbornylethyl group, etc.), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

Preferably, ma is 0 and na is 1.

When $R^{a1}$ and $R^{a2}$ are bonded each other to form an alicyclic hydrocarbon group, examples of —C($R^{a1}$)($R^{a2}$)($R^{a3}$) include the following groups. The alicyclic hydrocarbon group preferably has 3 to 12 carbon atoms. * represents a bond to —O—.

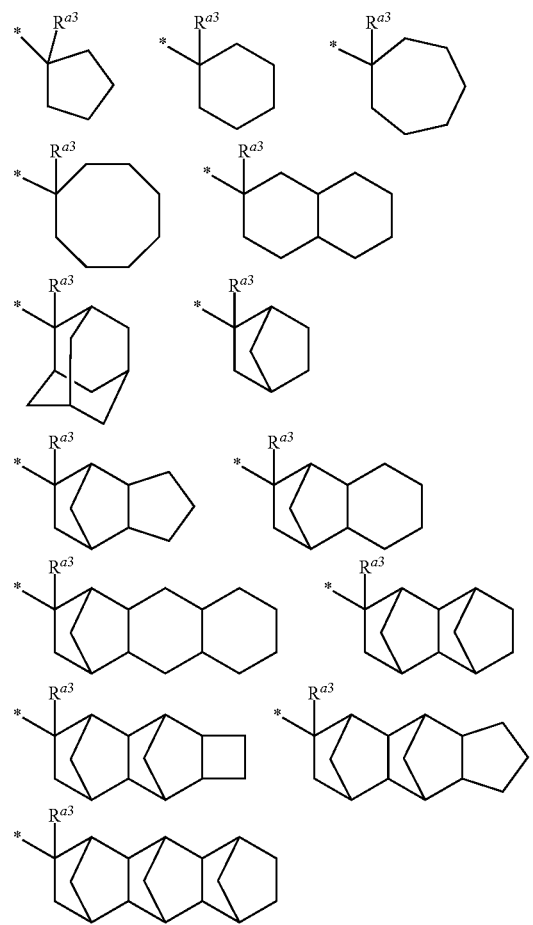

Examples of the hydrocarbon group in $R^{a1'}$, $R^{a2'}$ and $R^{a3'}$ include an alkyl group, an alicyclic hydrocarbon group, an aromatic hydrocarbon group, and groups obtained by combining these groups.

Examples of the alkyl group and the alicyclic hydrocarbon group include those which are the same as mentioned as for $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like.

When $R^{a2'}$ and $R^{a1'}$ are bonded each other to form a heterocyclic ring together with carbon atoms and X to which $R^{a2'}$ and $R^{a3'}$ are bonded, examples of —C($R^{a1'}$)($R^{a2'}$)—X—$R^{a3'}$ include the following groups. * represents a bond.

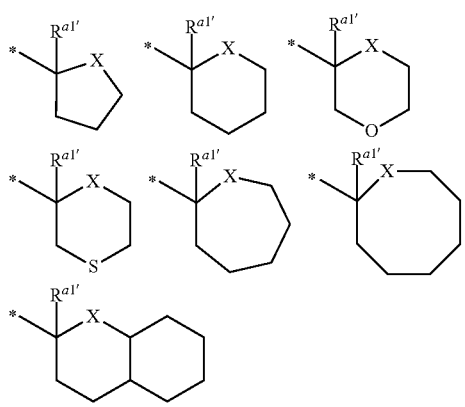

Of $R^{a1'}$ and $R^{a2'}$, at least one is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bond.

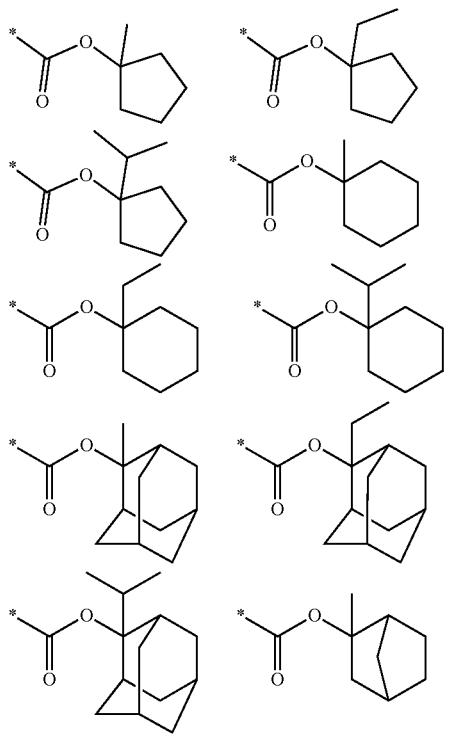
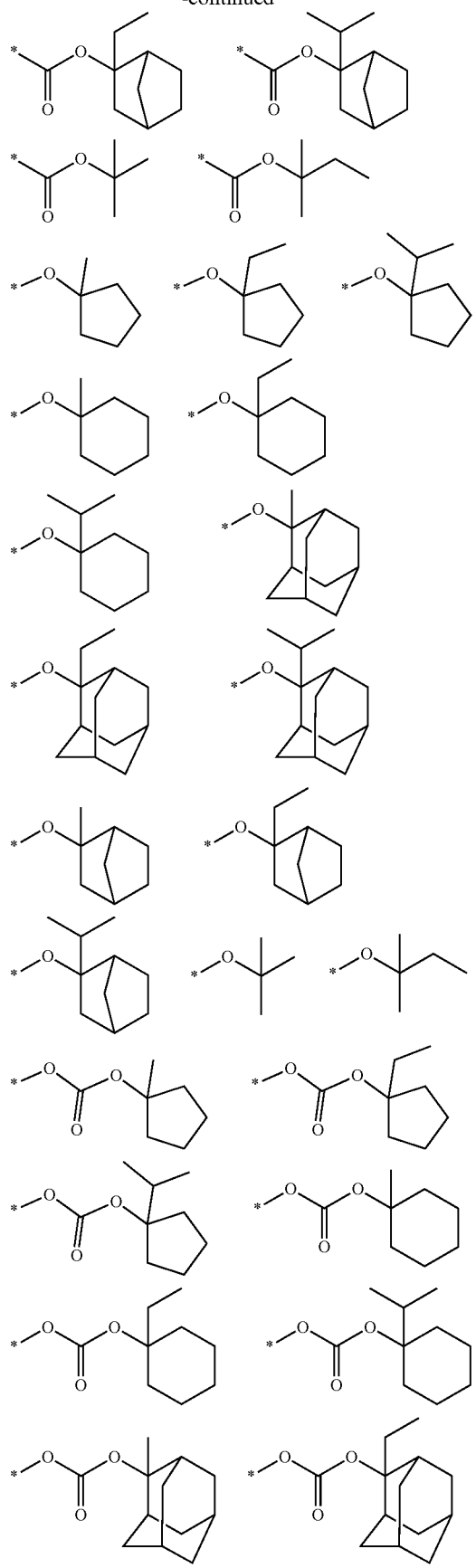

-continued
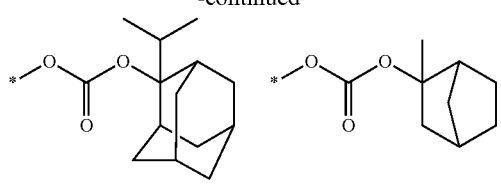
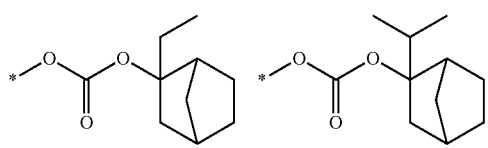
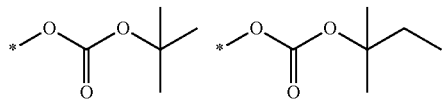
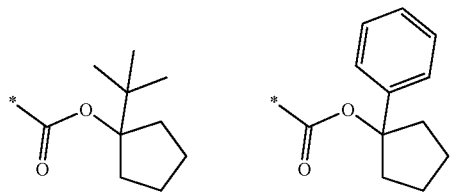
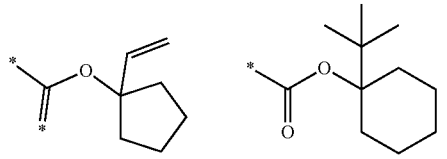
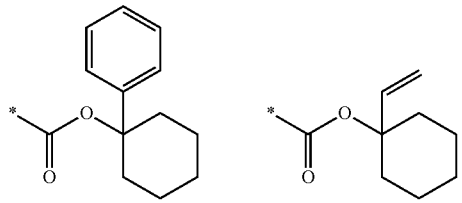
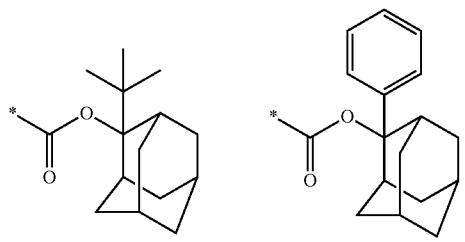
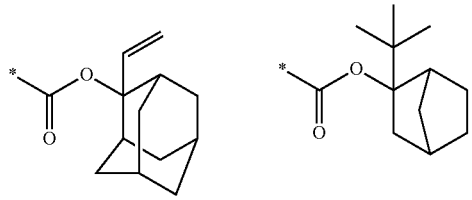
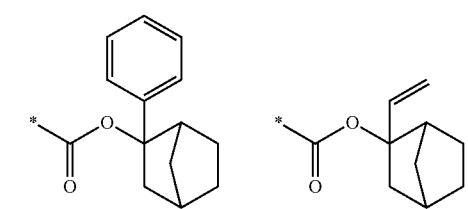
-continued
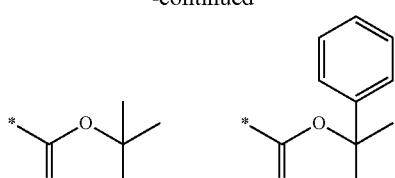
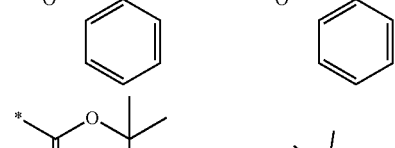
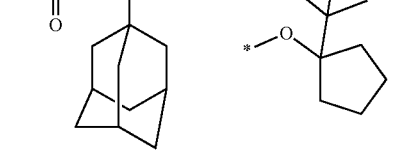
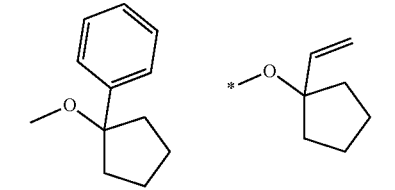
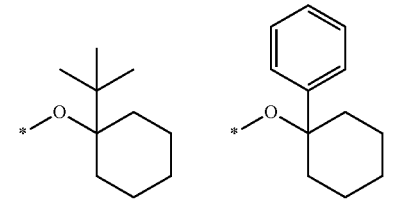
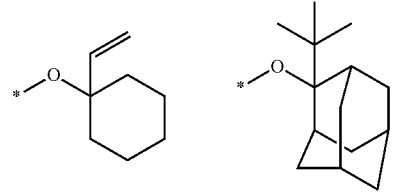
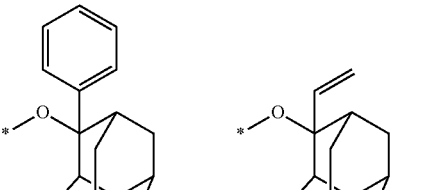
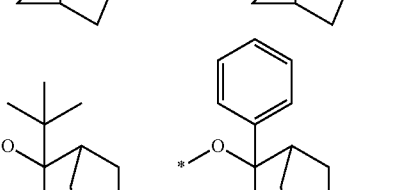
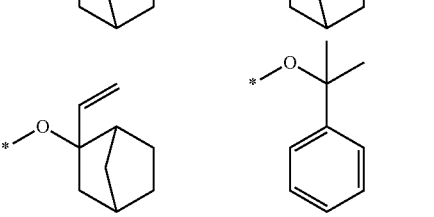

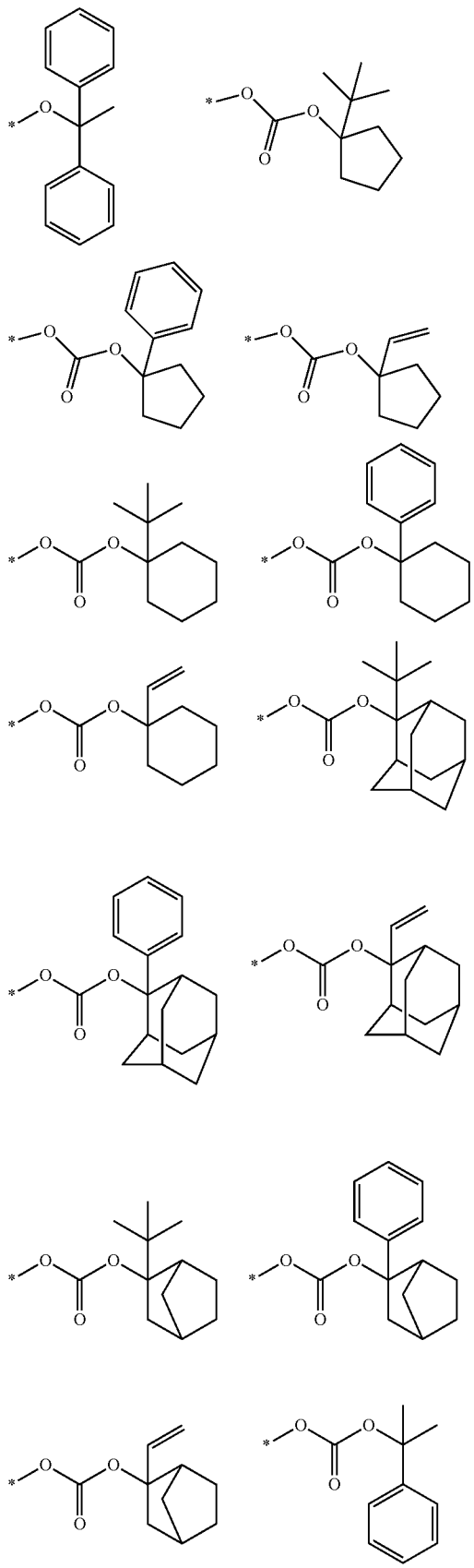
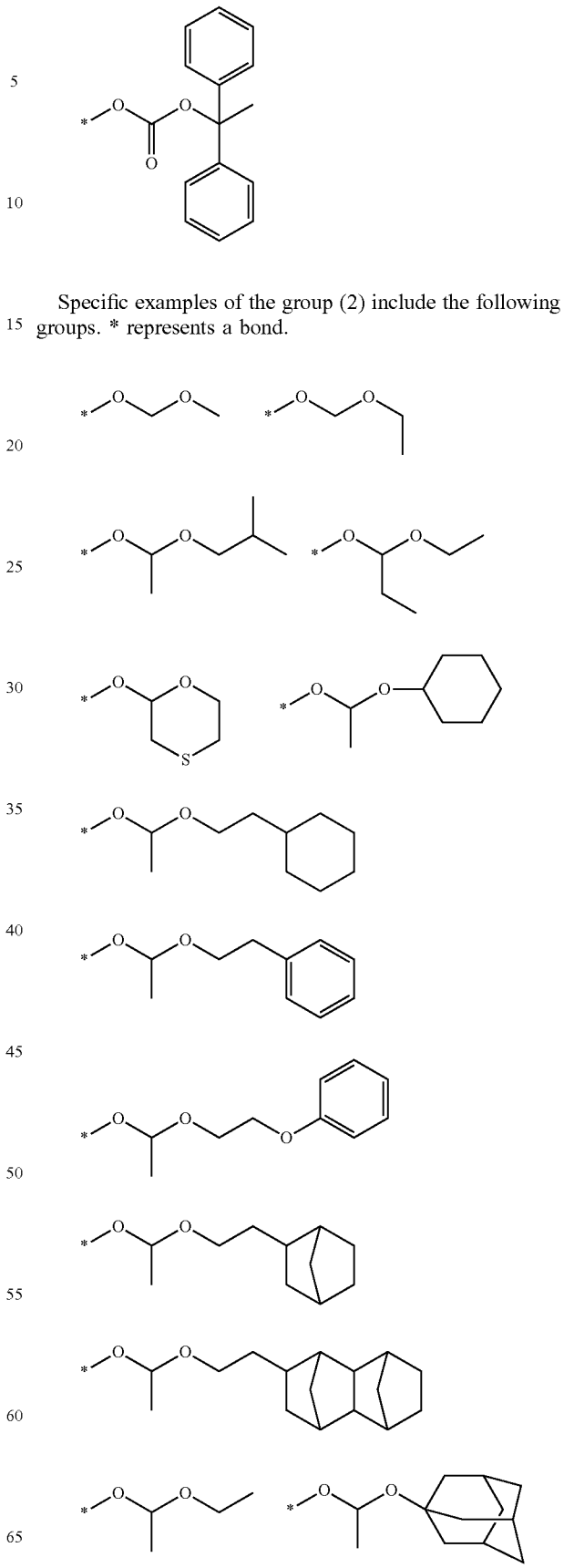
Specific examples of the group (2) include the following groups. * represents a bond.

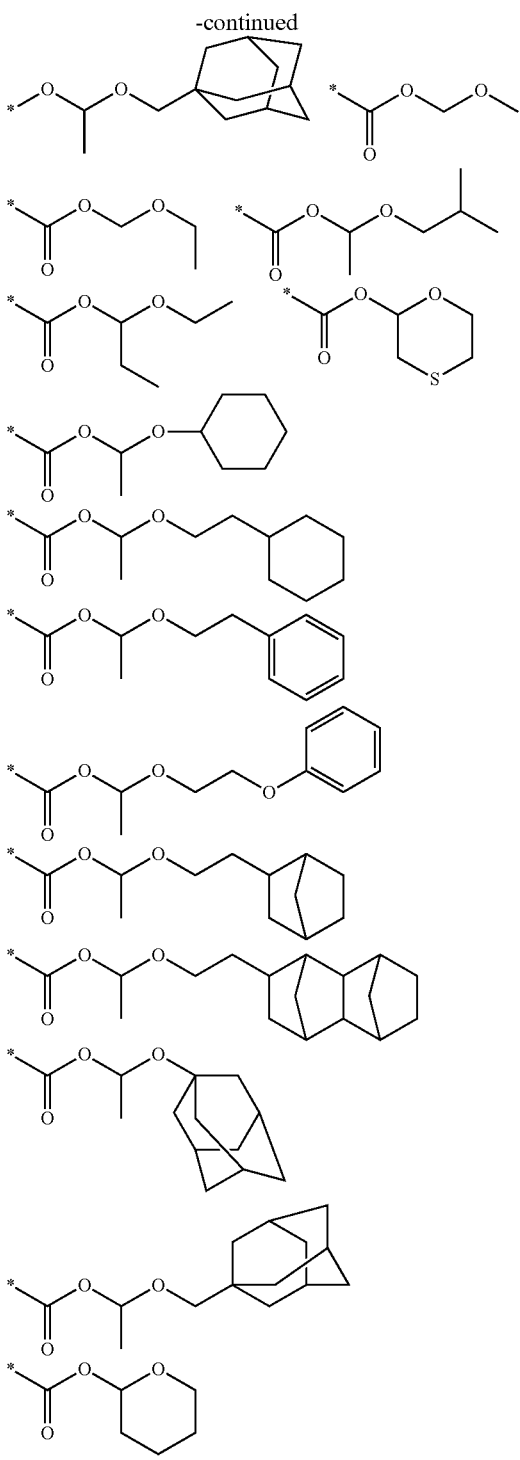

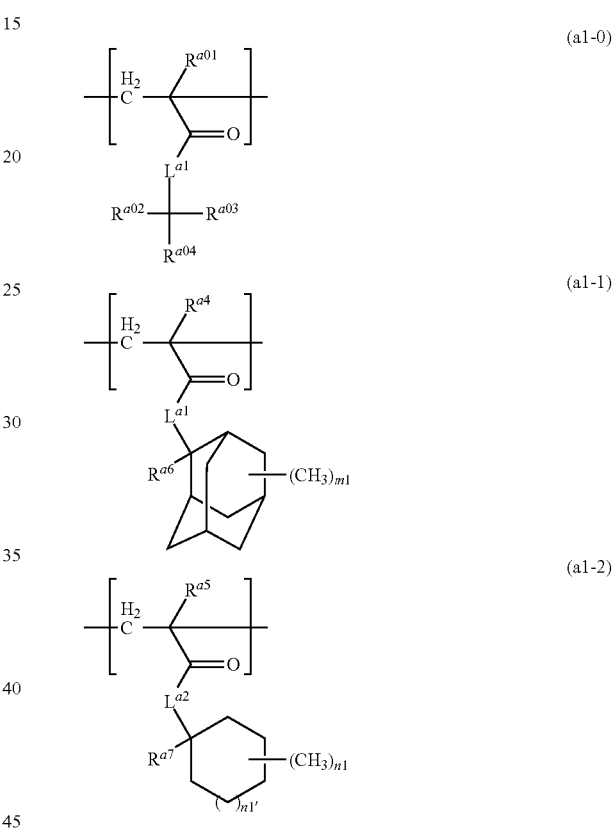

The monomer (a1) is preferably a monomer having an acid-labile group and an ethylenic unsaturated bond, and more preferably a (meth)acrylic monomer having an acid-labile group.

Of the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) is a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). Preferably, the structural unit is at least one structural unit selected from the group consisting of a structural unit (a1-1) and a structural unit (a1-2). These structural units may be used alone, or two or more structural units may be used in combination:

wherein, in formula (a1-0), formula (a1-1) and formula (a1-2), $L^{a01}$, $L^{a1}$ and $L^{a2}$ each independently represent —O— or *—O—$(CH_2)_{k1}$—CO—O—, k1 represents an integer of 1 to 7, and * represents a bond to —CO—, $R^{a01}$, $R^{a4}$ and $R^{a5}$ each independently represent a hydrogen atom, a halogen atom, or an alkyl group having 1 to 6 carbon atoms which may have a halogen atom, $R^{a02}$, $R^{a03}$ and $R^{a04}$ each independently represent an alkyl group having 1 to 8 carbon atoms, an alicyclic hydrocarbon group having 3 to 18 carbon atoms, an aromatic hydrocarbon group having 6 to 18 carbon atoms, or groups obtained by combining these groups, $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or groups formed by combining these groups, m1 represents an integer of 0 to 14,
n1 represents an integer of 0 to 10, and
n1' represents an integer of 0 to 3.

$R^{a01}$, $R^{a4}$ and $R^{a5}$ are preferably a hydrogen atom or a methyl group, and still more preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alicyclic hydrocarbon group, the aromatic hydrocarbon group, and groups obtained by combining these groups in $R^{a02}$, $R^{a03}$ and $R^{a04}$ include the same groups as mentioned as for $R^{a1}$, $R^{a2}$ and $R^{a3}$ of formula (1).

Examples of the alkyl group, the alkenyl group, the alicyclic hydrocarbon group, the aromatic hydrocarbon group, and groups obtained by combining these groups in $R^{a6}$ and $R^{a7}$ include the same groups as mentioned as for $R^{a1}$, $R^{a2}$ and $R^{a3}$ in formula (1).

The alkyl group in $R^{a02}$, $R^{a03}$ and $R^{a04}$ is preferably an alkyl group having 1 to 6 carbon atoms, more preferably a methyl group or an ethyl group, and still more preferably a methyl group.

The alkyl group in $R^{a6}$ and $R^{a7}$ is preferably an alkyl group having 1 to 6 carbon atoms, more preferably a methyl group, an ethyl group, an isopropyl group or a t-butyl group, and still more preferably an ethyl group, an isopropyl group or a t-butyl group.

The alkenyl group in $R^{a6}$ and $R^{a7}$ is preferably an alkenyl group having 2 to 6 carbon atoms, and more preferably an ethenyl group, a propenyl group, an isopropenyl group or a butenyl group.

The number of carbon atoms of the alicyclic hydrocarbon group as for $R^{a02}$, $R^{a03}$ and $R^{a04}$ is preferably 5 to 12, and more preferably 5 to 10.

The number of carbon atoms of the aromatic hydrocarbon group as for $R^{a02}$, $R^{a03}$, $R^{a04}$, $R^{a6}$ and $R^{a7}$ is preferably 6 to 12, and more preferably 6 to 10.

The total number of carbon atoms of the group obtained by combining the alkyl group with the alicyclic hydrocarbon group is preferably 18 or less.

The total number of carbon atoms of the group obtained by combining the alkyl group with the aromatic hydrocarbon group is preferably 18 or less.

$R^{a02}$ and $R^{a03}$ are preferably an alkyl group having 1 to 6 carbon atoms, and more preferably a methyl group or an ethyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

$R^{a6}$ and $R^{a7}$ are preferably an alkyl group having 1 to 6 carbon atoms, an alkenyl group having 2 to 6 carbon atoms or an aromatic hydrocarbon group having 6 to 12 carbon atoms, more preferably a methyl group, an ethyl group, an isopropyl group, a t-butyl group, an ethenyl group, a phenyl group or a naphthyl group, and still more preferably an ethyl group, an isopropyl group, a t-butyl group, an ethenyl group or a phenyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-18) and a structural unit in which a methyl group corresponding to $R^{a01}$ in the structural unit (a1-0) is substituted with a hydrogen atom, a halogen atom, a haloalkyl group (an alkyl group having a halogen atom) or other alkyl group, and is preferably a structural unit represented by any one of formula (a1-0-1) to formula (a1-0-10), formula (a1-0-13) and formula (a1-0-14).

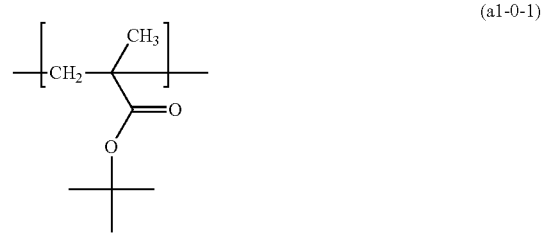

(a1-0-1)

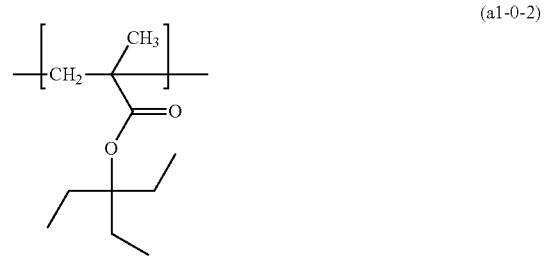

(a1-0-2)

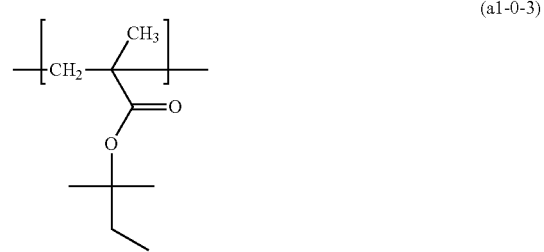

(a1-0-3)

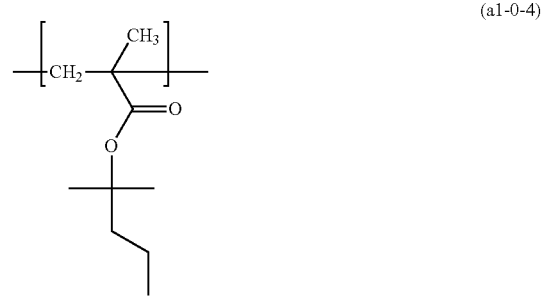

(a1-0-4)

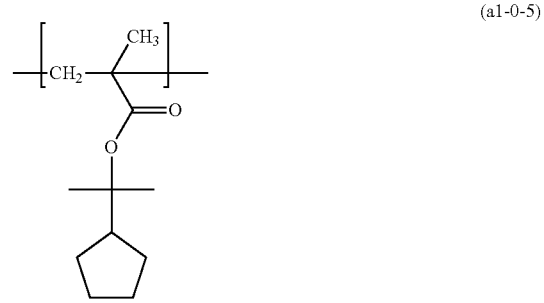

(a1-0-5)

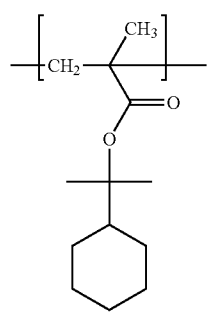 (a1-0-6)
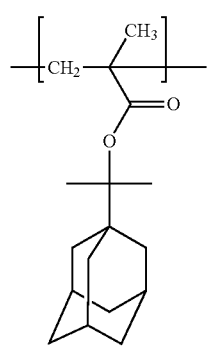 (a1-0-7)
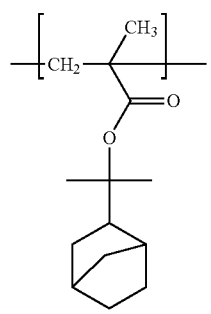 (a1-0-8)
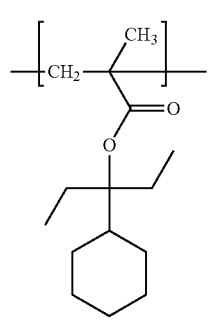 (a1-0-9)
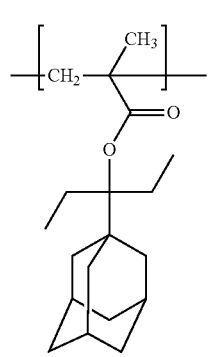 (a1-0-10)
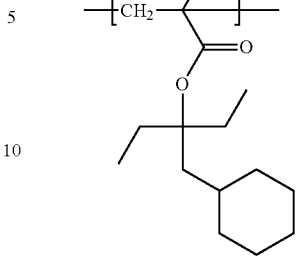 (a1-0-11)
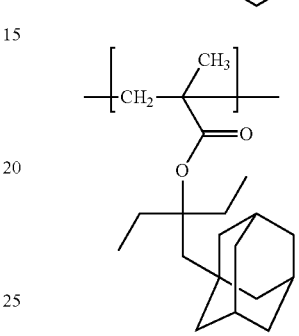 (a1-0-12)
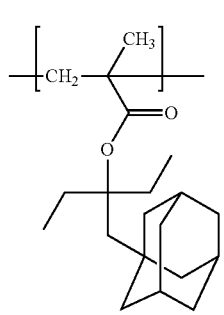 (a1-0-13)
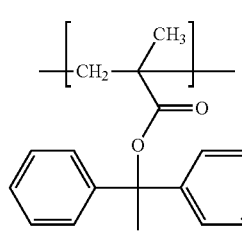 (a1-0-14)
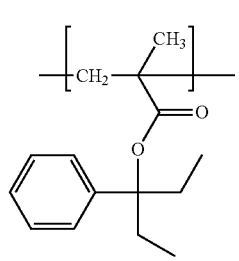 (a1-0-15)
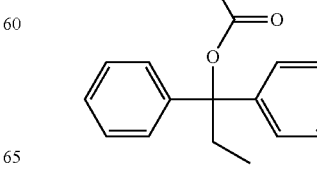 (a1-0-16)

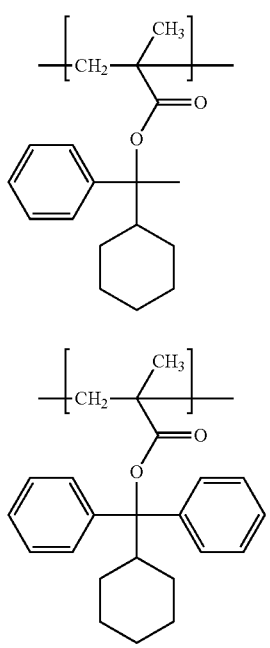

The structural unit (a1-1) includes, for example, structural units derived from the monomers mentioned in JP 2010-204646 A. Of these structural units, a structural unit represented by any one of formula (a1-1-1) to formula (a1-1-7) and a structural unit in which a methyl group corresponding to $R^{a4}$ in the structural unit (a1-1) is substituted with a hydrogen atom are preferable, and a structural unit represented by any one of formula (a1-1-1) to formula (a1-1-4) is more preferable.

(a1-1-1)
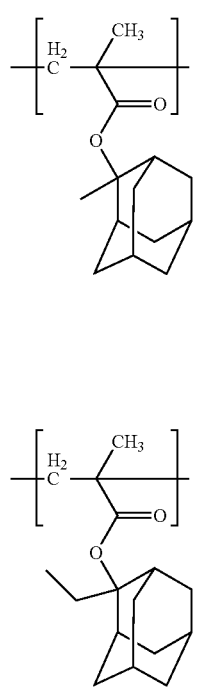

(a1-1-2)

(a1-1-3)
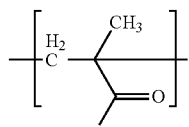

(a1-1-4)
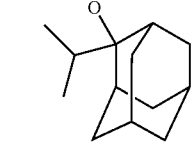

(a1-1-5)
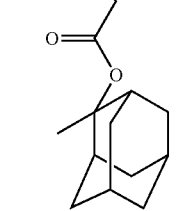

(a1-1-6)
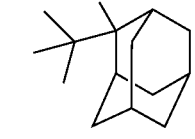

(a1-1-7)
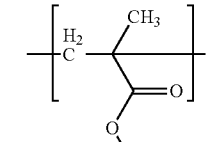

Examples of the structural unit (a1-2) include a structural unit represented by any one of formula (a1-2-1) to formula (a1-2-14) and a structural unit in which a methyl group corresponding to $R^{a5}$ in the structural unit (a1-2) is substituted with a hydrogen atom, a halogen atom, a haloalkyl group or other alkyl group and a structural unit represented by any one of formula (a1-2-2), formula (a1-2-5), formula (a1-2-6) and formula (a1-2-10) to formula (a1-2-14) is preferable.
(a1-2-1)
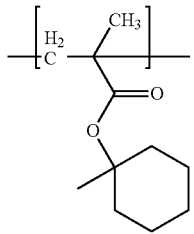
(a1-2-2)
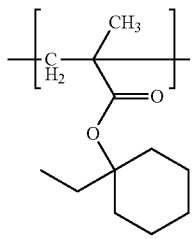
(a1-2-3)
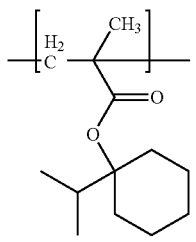
(a1-2-4)
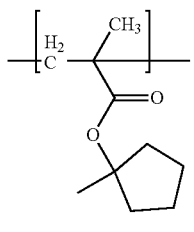
(a1-2-5)
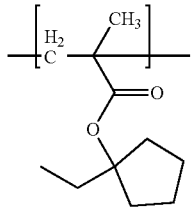
(a1-2-6)
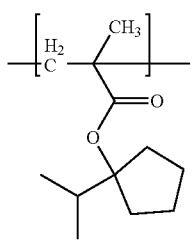
-continued
(a1-2-7)
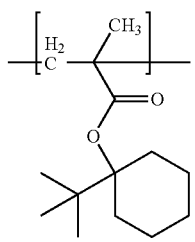
(a1-2-8)
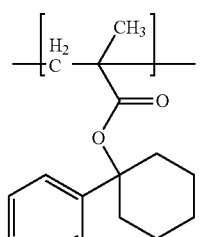
(a1-2-9)
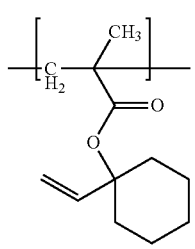
(a1-2-10)
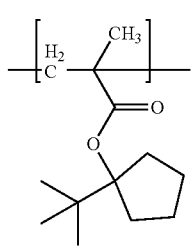
(a1-2-11)
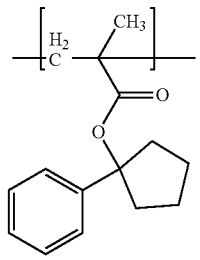
(a1-2-12)
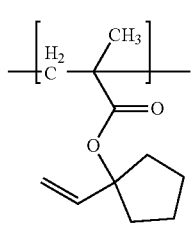

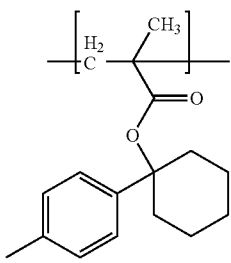

(a1-2-13)

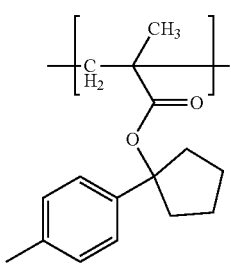

(a1-2-14)

When the resin (A) includes a structural unit (a1-0), the content is usually 5 to 60 mol %, preferably 5 to 50 mol %, and more preferably 10 to 40 mol %, based on all structural units of the resin (A).

When the resin (A) includes a structural unit (a1-1) and/or a structural unit (a1-2), the total content thereof is usually 10 to 95 mol %, preferably 15 to 90 mol %, more preferably 15 to 85 mol %, still more preferably 20 to 80 mol %, and yet more preferably 25 to 75 mol %, based on all structural units of the resin (A).

In the structural unit (a1), examples of the structural unit having a group (2) include a structural unit represented by formula (a1-4) (hereinafter sometimes referred to as "structural unit (a1-4)"):

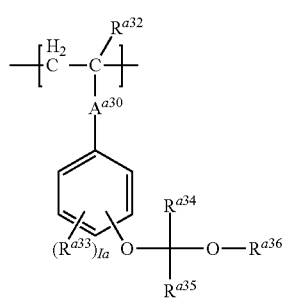

(a1-4)

wherein, in formula (a1-4), $R^{a32}$ represents a hydrogen atom, a halogen atom or an alkyl group having 1 to 6 carbon atoms which may have a halogen atom, $R^{a33}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a30}$ represents a single bond or *—$X^{a31}$-($A^{a32}$-$X^{a32}$)$_{nc}$—, and * represents a bonding site to carbon atoms to which —$R^{a32}$ is bonded, $A^{a32}$ represents an alkanediyl group having 1 to 6 carbon atoms, $X^{a31}$ and $X^{a32}$ each independently represent —O—, —CO—O— or —O—CO—, nc represents 0 or 1, la represents an integer of 0 to 4, and when la is an integer of 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded each other to form a divalent hydrocarbon group having 2 to 20 carbon atoms together with —C—O— to which $R^{a35}$ and $R^{a36}$ are bonded, and —$CH_2$— included in the hydrocarbon group and the divalent hydrocarbon group may be replaced by —O— or —S—.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom in $R^{a32}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a32}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a33}$ include a methyl group, an ethyl group, a propyl group, an isopropyl group, a butyl group, a sec-butyl group, a tert-butyl group, a pentyl group and a hexyl group.

Examples of the alkoxy group in $R^{a33}$ include a methoxy group, an ethoxy group, a propoxy group, an isopropoxy group, a butoxy group, a sec-butoxy group, a tert-butoxy group, a pentyloxy group and a hexyloxy group. The alkoxy group is preferably an alkoxy group having 1 to 4 carbon atoms, more preferably a methoxy group or an ethoxy group, and still more preferably a methoxy group.

Examples of the alkoxyalkyl group in $R^{a33}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in $R^{a33}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in $R^{a33}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in $R^{a33}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

$R^{a33}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of *—$X^{a31}$-($A^{a32}$-$X^{xa32}$)$_{nc}$— include *—O—, *—CO—O—, *—O—CO—, *—CO—O-$A^{a32}$-CO—O—, *—O—CO-$A^{a32}$-O—, *—O-$A^{a32}$-CO—O—, *—CO—O-$A^{a32}$-O—CO— and *—O—CO-$A^{a32}$-O—CO—. Of these, *—CO—O—, *—CO—O-$A^{a32}$-CO—O— or *—O-$A^{a32}$-CO—O— is preferable.

Examples of the alkanediyl group in $A^{a32}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a32}$ is preferably a methylene group or an ethylene group.

$A^{a30}$ is preferably a single bond, *—CO—O— or *—CO—O-$A^{a32}$-CO—O—, more preferably a single bond, *—CO—O— or *—CO—O—CH$_2$—CO—O—, and still more preferably a single bond or *—CO—O—.

1a is preferably 0, 1 or 2, more preferably 0 or 1, and still more preferably 0.

Examples of the hydrocarbon group in $R^{a34}$, $R^{a35}$ and $R^{a36}$ include an alkyl group, an alicyclic hydrocarbon group, an aromatic hydrocarbon group, and groups obtained by combining these groups.

Examples of the alkyl group include a methyl group, an ethyl group, a propyl group, a butyl group, a pentyl group, a hexyl group, a heptyl group, an octyl group and the like.

The alicyclic hydrocarbon group may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group, and the following groups (* represents a bonding site).

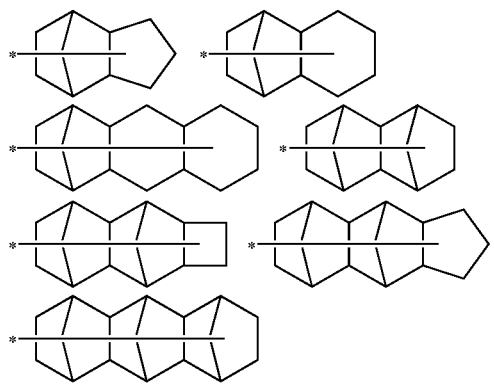

Examples of the aromatic hydrocarbon group include aryl groups such as a phenyl group, a naphthyl group, an anthryl group, a biphenyl group and a phenanthryl group.

Examples of the combined group include groups obtained by combining the above-mentioned alkyl group and alicyclic hydrocarbon group (e.g., alkylcycloalkyl groups or cycloalkylalkyl groups, such as a methylcyclohexyl group, a dimethylcyclohexyl group, a methylnorbornyl group, a cyclohexylmethyl group, an adamantylmethyl group, an adamantyldimethyl group and a norbornylethyl group), aralkyl groups such as a benzyl group, aromatic hydrocarbon groups having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), aromatic hydrocarbon groups having an alicyclic hydrocarbon group (a p-cyclohexylphenyl group, a p-adamantylphenyl group, etc.), aryl-cycloalkyl groups such as a phenylcyclohexyl group, and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms, or groups obtained by combining these groups.

$R^{a34}$ is preferably a hydrogen atom.

$R^{a35}$ is preferably a hydrogen atom, an alkyl group having 1 to 12 carbon atoms or an alicyclic hydrocarbon group having 3 to 12 carbon atoms, and more preferably a methyl group or an ethyl group.

The hydrocarbon group as for $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms or groups formed by combining these groups, and more preferably an alkyl group having 1 to 18 carbon atoms, an alicyclic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

—OC($R^{a34}$)($R^{a35}$)—O—$R^{a36}$ in the structural unit (a1-4) is eliminated by contacting with an acid (e.g., p-toluenesulfonic acid) to form a hydroxy group.

—OC($R^{a34}$)($R^{a35}$)—O—$R^{a36}$ is preferably bonded to the o-position or the p-position of the benzene ring, and more preferably the p-position.

The structural unit (a1-4) includes, for example, structural units derived from the monomers mentioned in JP 2010-204646 A. The structural unit preferably includes structural units represented by formula (a1-4-1) to formula (a1-4-18) and a structural unit in which a hydrogen atom corresponding to $R^{a32}$ in the structural unit (a1-4) is substituted with a halogen atom, a haloalkyl group or an alkyl group, and more preferably structural units represented by formula (a1-4-1) to formula (a1-4-5), formula (a1-4-10), formula (a1-4-13), formula (a1-4-14).

(a1-4-1)

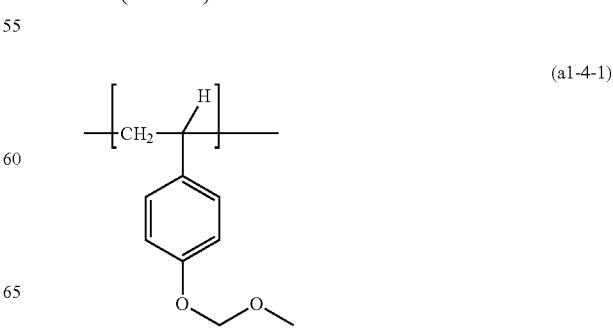

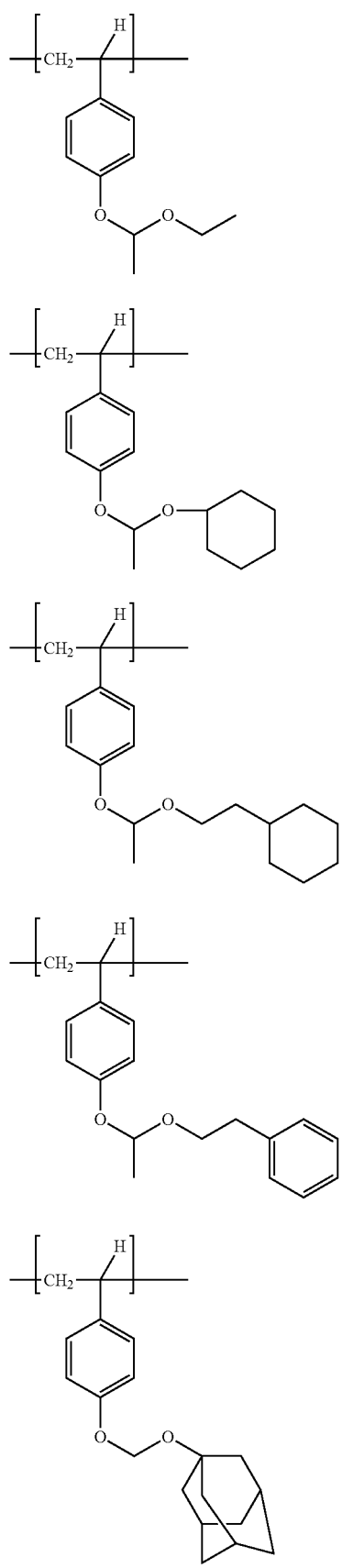
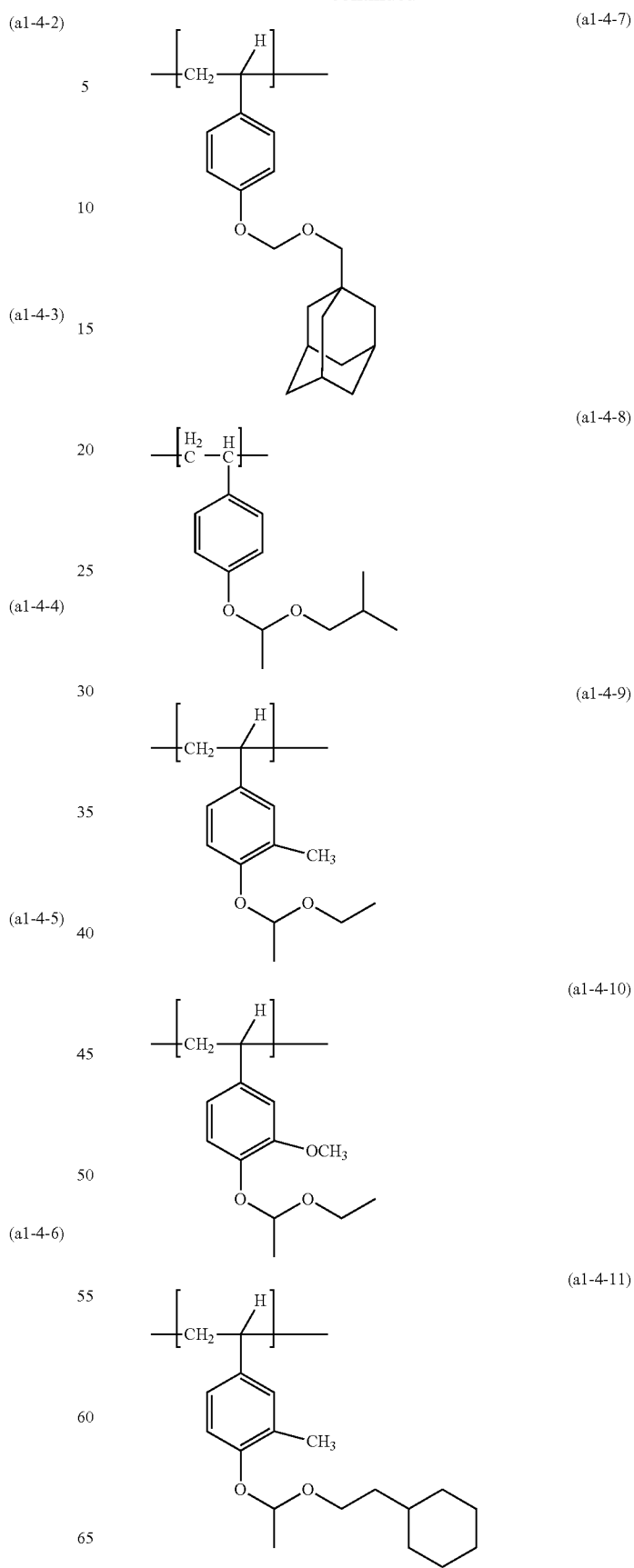

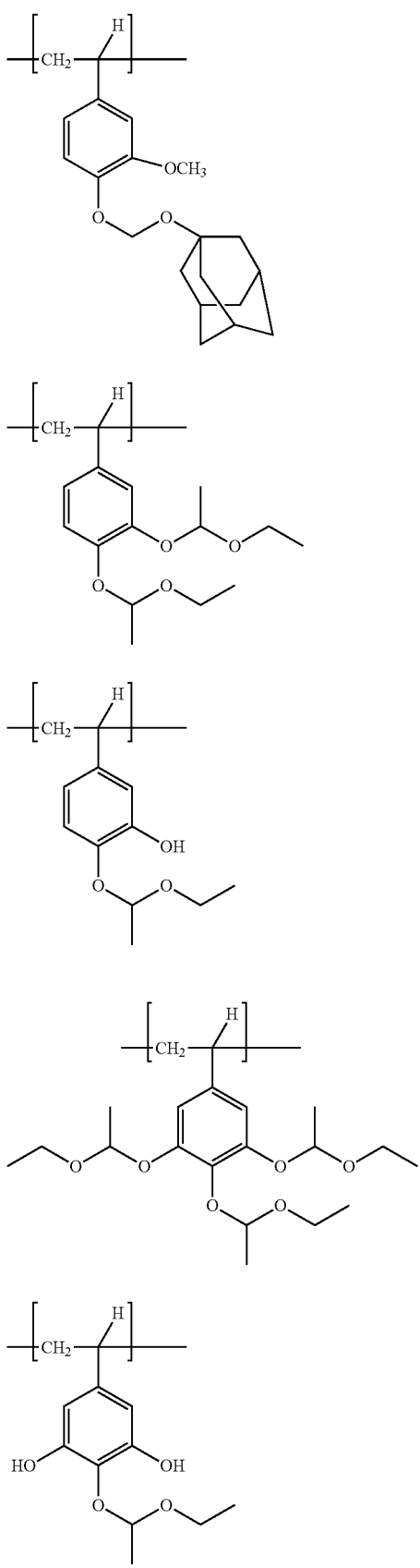

(a1-4-12)
(a1-4-13)
(a1-4-14)
(a1-4-15)
(a1-4-16)

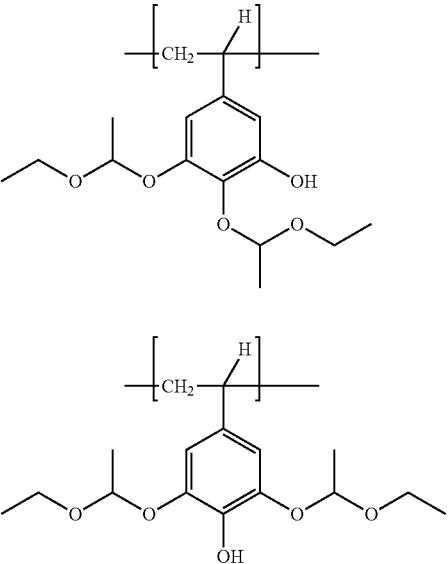

(a1-4-17)
(a1-4-18)

When the resin (A) includes the structural unit (a1-4), the content is preferably 5 to 60 mol %, more preferably 5 to 50 mol %, and still more preferably 10 to 40 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

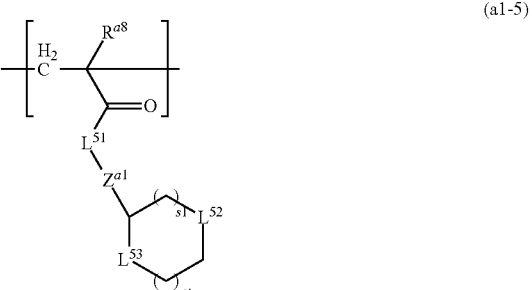

(a1-5)

In formula (a1-5), $R^{a8}$ represents an alkyl group having 1 to 6 carbon atoms which may have a halogen atom, a hydrogen atom or a halogen atom, $Z^{a1}$ represents a single bond or *—$(CH_2)_{h3}$—CO-$L^{54}$-, h3 represents an integer of 1 to 4, and * represents a bond to $L^{51}$, $L^{51}$, $L^{52}$, $L^{53}$ and $L^{54}$ each independently represent —O— or —S—, s1 represents an integer of 1 to 3, and s1' represents an integer of 0 to 3.

The halogen atom includes a fluorine atom and a chlorine atom and is preferably a fluorine atom. Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group, $L^{51}$ is preferably an oxygen atom, one of $L^{52}$ and $L^{53}$ is preferably —O— and the other one is preferably —S—, s1 is preferably 1, s1' is preferably an integer of 0 to 2, and $Z^{a1}$ is preferably a single bond or *—CH$_2$—CO—O—.

The structural unit (a1-5) includes, for example, structural units derived from the monomers mentioned in JP 2010-61117 A. Of these structural units, structural units represented by formula (a1-5-1) to formula (a1-5-4) are preferable, and structural units represented by formula (a1-5-1) or formula (a1-5-2) are more preferable.

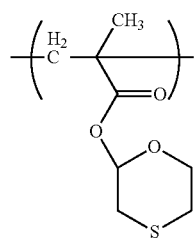
(a1-5-1)

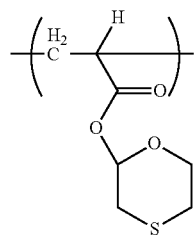
(a1-5-2)

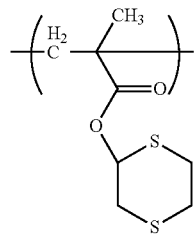
(a1-5-3)

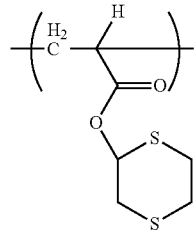
(a1-5-4)

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes the following structural units.

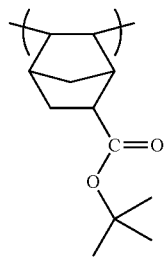
(a1-3-1)

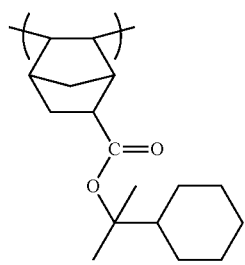
(a1-3-2)

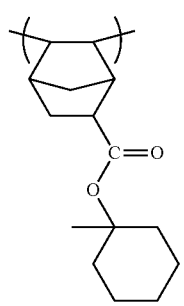
(a1-3-3)

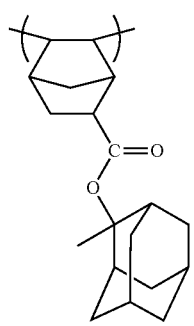
(a1-3-4)

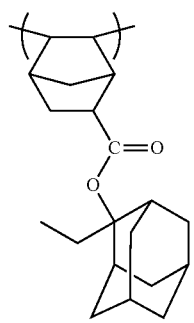
(a1-3-5)

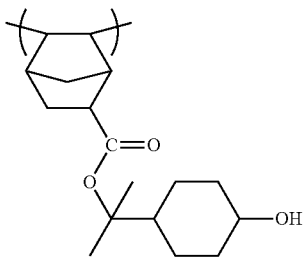
(a1-3-6)

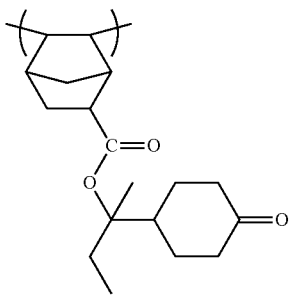
(a1-3-7)

When the resin (A) includes the above structural units, the content is preferably 5 to 60 mol %, more preferably 5 to 50 mol %, and still more preferably 10 to 40 mol %, based on all structural units of the resin (A).

<Structural Unit (s)>

The structural unit (s) is derived from a monomer having no acid-labile group (hereinafter sometimes referred to as "monomer (s)"). The monomer, from which the structural unit (s) is derived, has no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present disclosure, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present disclosure, in the case of using, as an exposure source, high energy rays such as KrF excimer laser (248 nm), electron beam or extreme ultraviolet light (EUV), it is more preferable to use, as the structural unit (a2), a structural unit (a2) having a phenolic hydroxy group and a structural unit (a2-A) mentioned below. When using ArF excimer laser (193 nm) or the like, a structural unit (a2) having an alcoholic hydroxy group is preferably used as the structural unit (a2), and it is more preferable to use a structural unit (a2-1) mentioned later. The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)"):

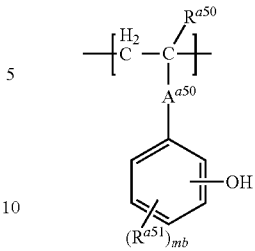
(a2-A)

wherein, in formula (a2-A), $R^{a50}$ represents a hydrogen atom, a halogen atom or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkoxyalkyl group having 2 to 12 carbon atoms, an alkoxyalkoxy group having 2 to 12 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or *—$X^{a51}$-($A^{a52}$-$X^{a52}$)$_{nb}$—, and * represents a bond to carbon atoms to which —$R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

Examples of the halogen atom in $R^{a50}$ and $R^{a51}$ include a fluorine atom, a chlorine atom and a bromine atom.

Examples of the alkyl group having 1 to 6 carbon atoms which may have a halogen atom in $R^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a51}$ include a methyl group, an ethyl group, a propyl group, an isopropyl group, a butyl group, a sec-butyl group, a tert-butyl group, a pentyl group and a hexyl group. The alkyl group is preferably an alkyl group having 1 to 4 carbon atoms, more preferably a methyl group or an ethyl group, and still more preferably a methyl group.

Examples of the alkoxy group in $R^{a51}$ include a methoxy group, an ethoxy group, a propoxy group, an isopropoxy group, a butoxy group, a sec-butoxy group and a tert-butoxy group. The alkoxy group is preferably an alkoxy group having 1 to 4 carbon atoms, more preferably a methoxy group or an ethoxy group, and still more preferably a methoxy group.

Examples of the alkoxyalkyl group in $R^{a51}$ include a methoxymethyl group, an ethoxyethyl group, a propoxymethyl group, an isopropoxymethyl group, a butoxymethyl group, a sec-butoxymethyl group and a tert-butoxymethyl group. The alkoxyalkyl group is preferably an alkoxyalkyl group having 2 to 8 carbon atoms, more preferably a methoxymethyl group or an ethoxyethyl group, and still more preferably a methoxymethyl group.

Examples of the alkoxyalkoxy group in $R^{a51}$ include a methoxymethoxy group, a methoxyethoxy group, an ethoxymethoxy group, an ethoxyethoxy group, a propoxymethoxy group, an isopropoxymethoxy group, a butoxymethoxy group, a sec-butoxymethoxy group and a tert-butoxymethoxy group. The alkoxyalkoxy group is preferably an alkoxyalkoxy group having 2 to 8 carbon atoms, and more preferably a methoxyethoxy group or an ethoxyethoxy group.

Examples of the alkylcarbonyl group in $R^{a51}$ include an acetyl group, a propionyl group and a butyryl group. The alkylcarbonyl group is preferably an alkylcarbonyl group having 2 to 3 carbon atoms, and more preferably an acetyl group.

Examples of the alkylcarbonyloxy group in $R^{a51}$ include an acetyloxy group, a propionyloxy group and a butyryloxy group. The alkylcarbonyloxy group is preferably an alkylcarbonyloxy group having 2 to 3 carbon atoms, and more preferably an acetyloxy group.

$R^{a51}$ is preferably a halogen atom, a hydroxy group, an alkyl group having 1 to 4 carbon atoms, an alkoxy group having 1 to 4 carbon atoms or an alkoxyalkoxy group having 2 to 8 carbon atoms, more preferably a fluorine atom, an iodine atom, a hydroxy group, a methyl group, a methoxy group, an ethoxy group, an ethoxyethoxy group or an ethoxymethoxy group, and still more preferably a fluorine atom, an iodine atom, a hydroxy group, a methyl group, a methoxy group or an ethoxyethoxy group.

Examples of *—$X^{a51}$-($A^{a52}$-$X^{a52}$)$_{nb}$— include *—O—, *—CO—O—, *—O—CO—, *—CO—O-$A^{a52}$-OC—O—, *—O—CO-$A^{a52}$-O—, *—O-$A^{a52}$-CO—O—, *—CO—O-$A^{a52}$-O—CO— and *—O—CO-$A^{a52}$-O—CO—. Of these, *—CO—O—, *—CO—O-$A^{a52}$-CO—O— or *—O-$A^{a52}$-CO—O— is preferable.

Examples of the alkanediyl group in $A^{a52}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a52}$ is preferably a methylene group or an ethylene group.

$A^{a50}$ is preferably a single bond, *—CO—O— or *—CO—O-$A^{a52}$-CO—O—, more preferably a single bond, *—CO—O— or *—CO—O—CH$_2$—CO—O—, and still more preferably a single bond or *—CO—O—.

mb is preferably 0, 1 or 2, more preferably 0 or 1, and still more preferably 0.

The hydroxy group is preferably bonded to the ortho-position or the para-position of a benzene ring, and more preferably the para-position.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-16), and a structural unit in which a methyl group corresponding to $R^{a50}$ is substituted with a hydrogen atom, a halogen atom, a haloalkyl group or other alkyl group in structural units represented by formula (a2-2-1) to formula (a2-2-16). The structural unit (a2-A) is preferably a structural unit represented by formula (a2-2-1), a structural unit represented by formula (a2-2-3), a structural unit represented by formula (a2-2-6), a structural unit represented by formula (a2-2-8) and structural units represented by formula (a2-2-12) to formula (a2-2-14), and a structural unit in which a methyl group corresponding to $R^{a50}$ in the structural unit (a2-A) is substituted with a hydrogen atom in these structural units and the structural unit represented by formula (a2-2-1), the structural unit represented by formula (a2-2-3), the structural unit represented by formula (a2-2-6), the structural unit represented by formula (a2-2-8) and the structural units represented by formula (a2-2-12) to formula (a2-2-14), more preferably a structural unit represented by formula (a2-2-3), a structural unit represented by formula (a2-2-8), structural units represented by formula (a2-2-12) to formula (a2-2-14), and a structural unit in which a methyl group corresponding to $R^{a50}$ in the structural unit (a2-A) is substituted with a hydrogen atom in the structural unit represented by formula (a2-2-3) or the structural unit represented by formula (a2-2-8) and the structural units represented by formula (a2-2-12) to formula (a2-2-14), and still more preferably a structural unit represented by formula (a2-2-8), and a structural unit in which a methyl group corresponding to $R^{a50}$ in the structural unit (a2-A) is substituted with a hydrogen atom in the structural unit represented by formula (a2-2-8).

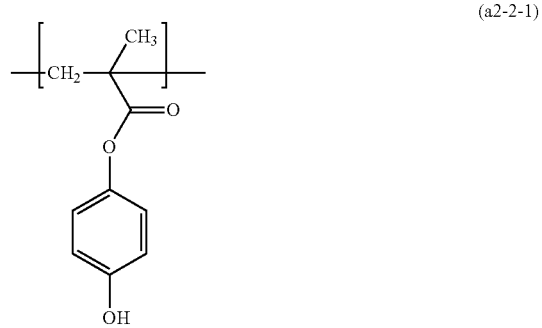

(a2-2-1)

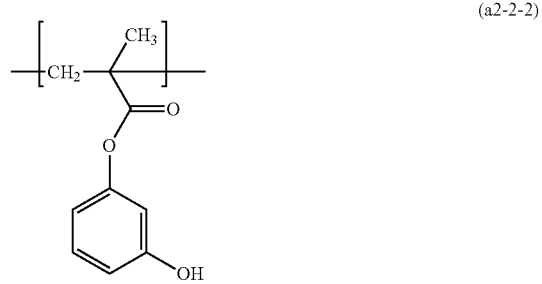

(a2-2-2)

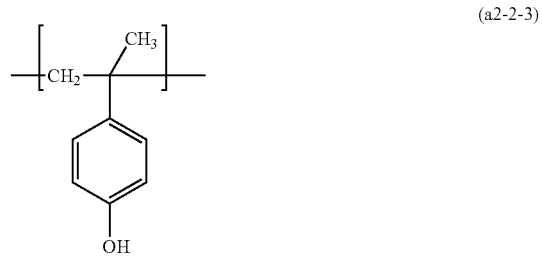

(a2-2-3)

(a2-2-4)
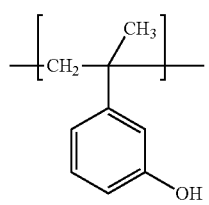
(a2-2-5)
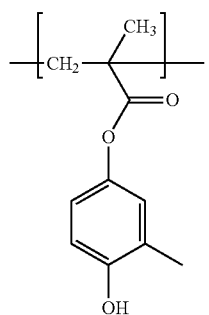
(a2-2-6)
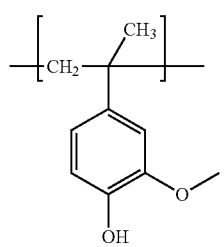
(a2-2-7)
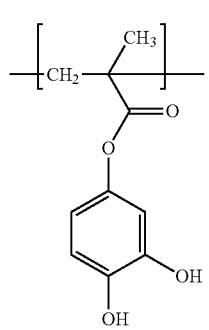
(a2-2-8)
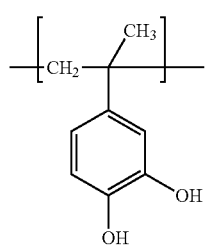
(a2-2-9)
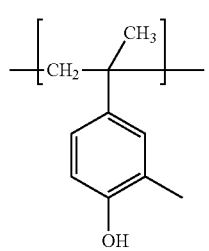
(a2-2-10)
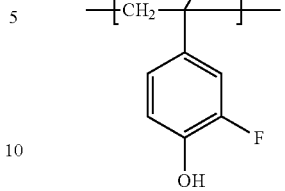
(a2-2-11)
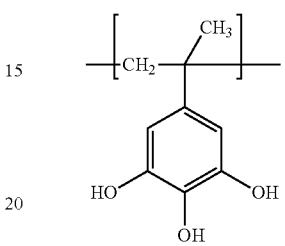
(a2-2-12)
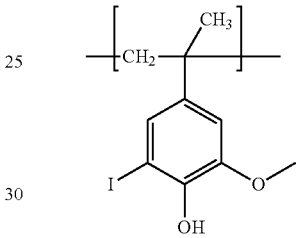
(a2-2-13)
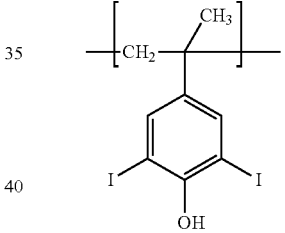
(a2-2-14)
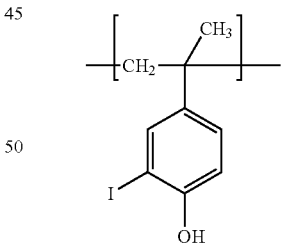
(a2-2-15)
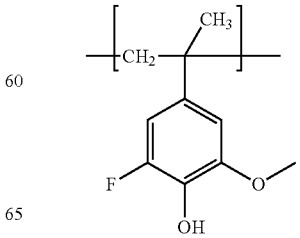

-continued

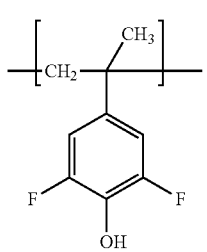
(a2-2-16)

When the structural unit (a2-A) is included in the resin (A), the content of the structural unit (a2-A) is preferably 5 to 80 mol %, more preferably 10 to 70 mol %, still more preferably 15 to 65 mol %, and yet more preferably 15 to 50 mol %, based on all structural units.

The structural unit (a2-A) can be included in a resin (A) by polymerizing, for example, with a structural unit (a1-4) and treating with an acid such as p-toluenesulfonic acid. The structural unit (a2-A) can also be included in the resin (A) by polymerizing with acetoxystyrene and treating with an alkali such as tetramethylammonium hydroxide.

Examples of the structural unit having an alcoholic hydroxy group in the structural unit (a2) include a structural unit represented by formula (a2-1) (hereinafter sometimes referred to as "structural unit (a2-1)").

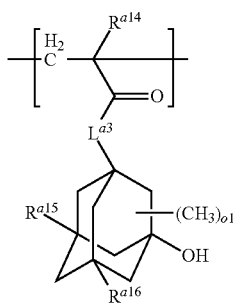
(a2-1)

In formula (a2-1), $L^{a3}$ represents —O— or *—O—(CH$_2$)$_{k2}$—CO—O—, k2 represents an integer of 1 to 7, and * represents a bond to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In formula (a2-1), $L^{a3}$ is preferably —O— or —O—(CH$_2$)$_{f1}$—CO—O— (f1 represents an integer of 1 to 4), and more preferably —O—, $R^{a14}$ is preferably a methyl group, $R^{a15}$ is preferably a hydrogen atom, $R^{a16}$ is preferably a hydrogen atom or a hydroxy group, and o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferable, a structural unit represented by any one of formula (a2-1-1) to formula (a2-1-4) is more preferable, and a structural unit represented by formula (a2-1-1) or formula (a2-1-3) is still more preferable.

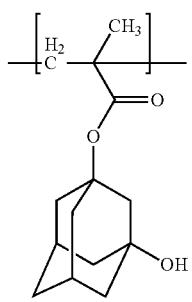
(a2-1-1)

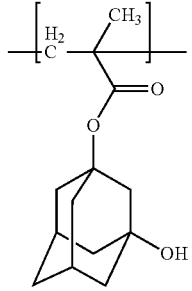
(a2-1-2)

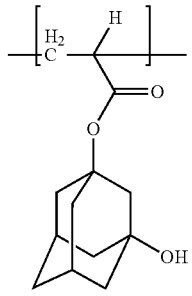
(a2-1-3)

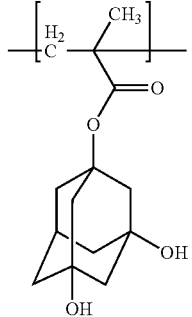
(a2-1-4)

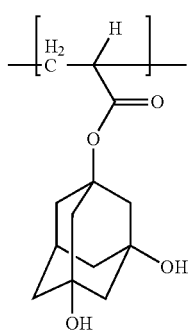

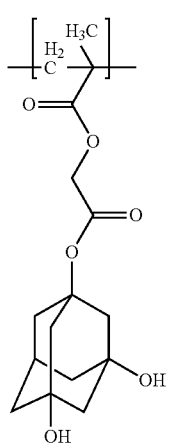
(a2-1-5)

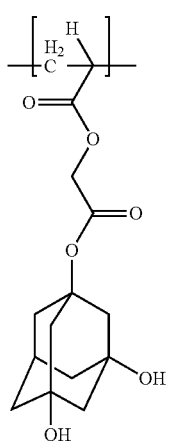
(a2-1-6)

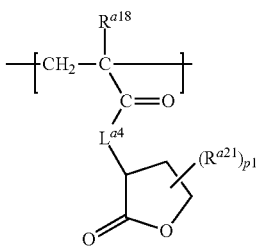
(a3-1)

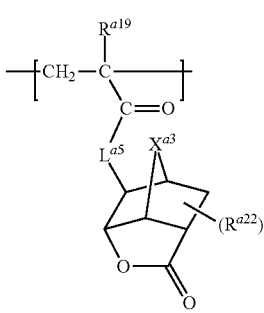
(a3-2)

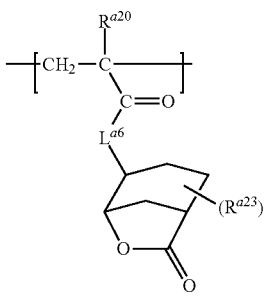
(a3-3)

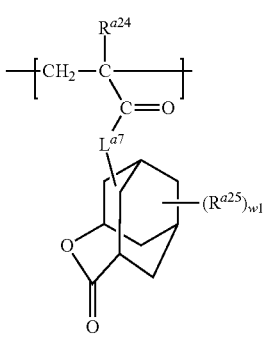
(a3-4)

When the resin (A) includes the structural unit (a2-1), the content is usually 1 to 45 mol %, preferably 1 to 40 mol %, more preferably 1 to 35 mol %, still more preferably 2 to 20 mol %, and yet more preferably 2 to 10 mol %, based on all structural units of the resin (A).

<Structural Unit (a3)>

The lactone ring possessed by the structural unit (a3) may be a monocyclic ring such as a β-propiolactone ring, a γ-butyrolactone ring or a δ-valerolactone ring, or a condensed ring of a monocyclic lactone ring and the other ring. Preferably, a γ-butyrolactone ring, an adamantanelactone ring or a bridged ring including a γ-butyrolactone ring structure (e.g., a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

wherein, in formula (a3-1), formula (a3-2), formula (a3-3) and formula (a3-4), $L^{a4}$, $L^{a5}$ and $L^{a6}$ each independently represent —O— or a group represented by *—O—$(CH_2)_{k3}$—CO—O— (k3 represents an integer of 1 to 7), $L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^{a9}$-O—, $L^{a8}$ and $L^{a9}$ each independently represent an alkanediyl group having 1 to 6 carbon atoms,

* represents a bonding site to a carbonyl group, $R^{a18}$, $R^{a19}$ and $R^{a20}$ each independently represent a hydrogen atom or a methyl group, $R^{a24}$ represents an alkyl group having 1 to 6 carbon atoms which may have a halogen atom, a hydrogen atom or a halogen atom, $X^{a3}$ represents —$CH_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{a23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), preferably, $L^{a4}$ to $L^{a6}$ are each independently —O— or a group in which k3 is an integer of 1 to 4 in *—O—(CH$_2$)$_{k3}$—CO—O—, more preferably —O— and *—O—CH$_2$—CO—O—, and still more preferably an oxygen atom, $R^{a18}$ to $R^{a21}$ are preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—CH$_2$—CO—O— or —O—C$_2$H$_4$—CO—)—, and w1 is preferably an integer of 0 to 2, and more preferably 0 or 1.

Particularly, formula (a3-4) is preferably formula (a3-4)':

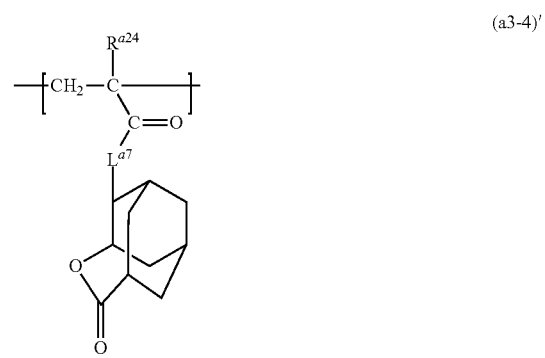

(a3-4)' wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are substituted with hydrogen atoms in the above structural units.

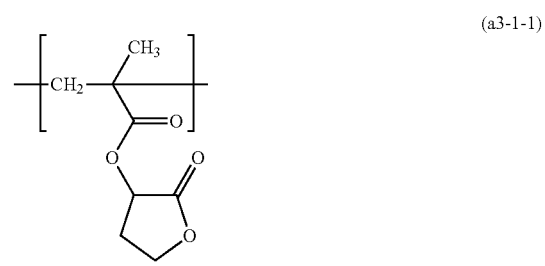

(a3-1-1)

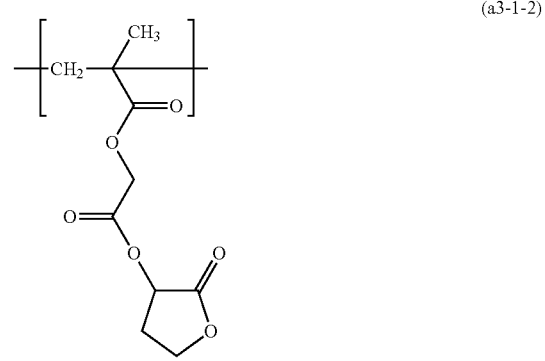

(a3-1-2)

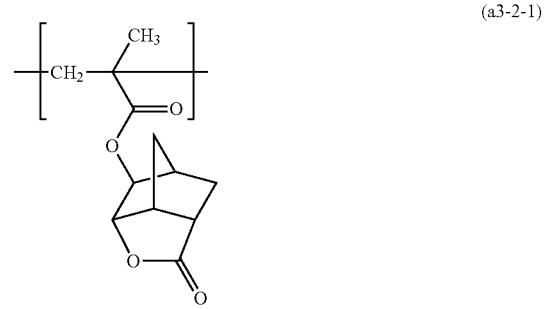

(a3-2-1)

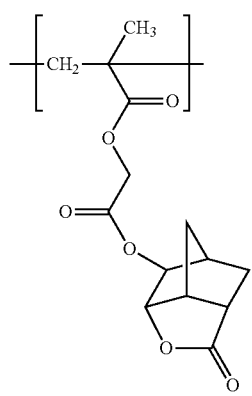
(a3-2-2)
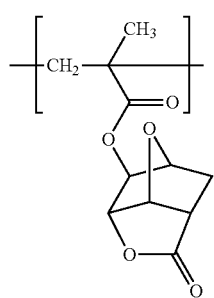
(a3-2x-1)
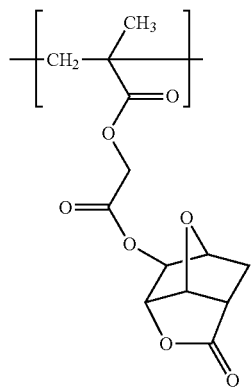
(a3-2x-2)
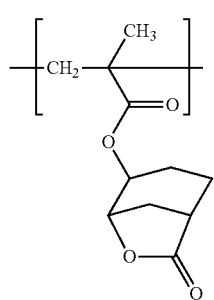
(a3-3-1)
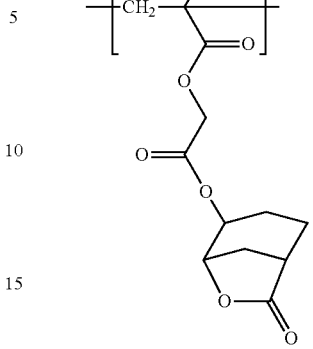
(a3-3-2)
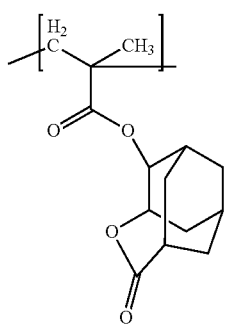
(a3-4-1)
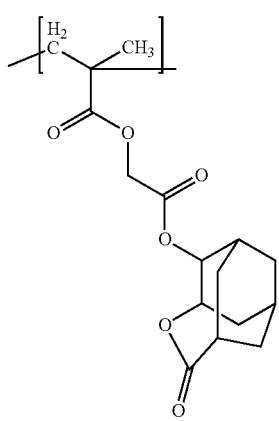
(a3-4-2)
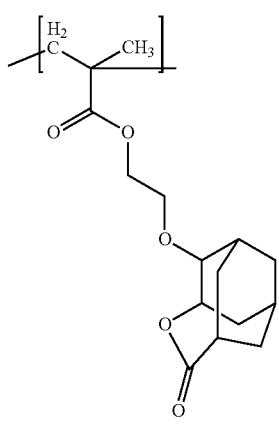
(a3-4-3)

-continued
(a3-4-4)
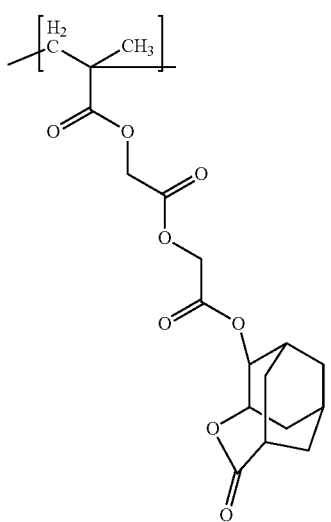
(a3-4-5)
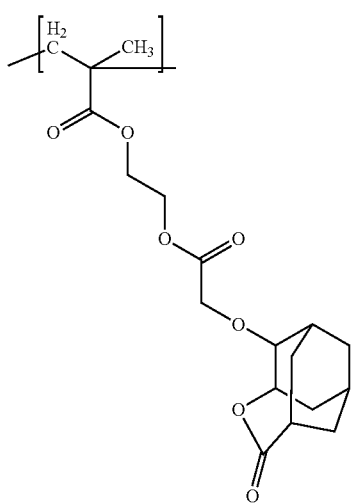
(a3-4-6)
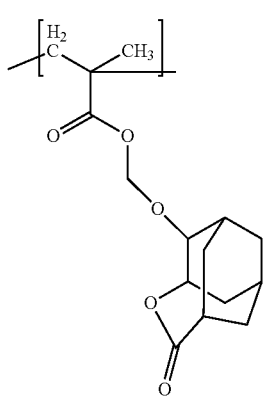
-continued
(a3-4-7)
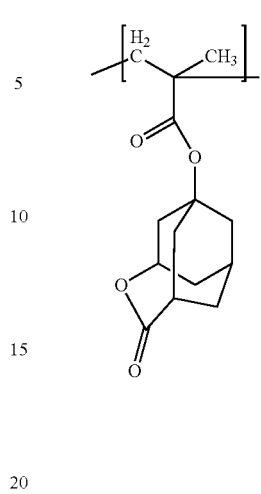
(a3-4-8)
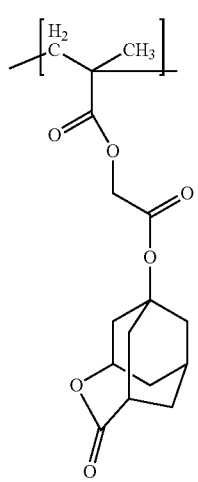
(a3-4-9)
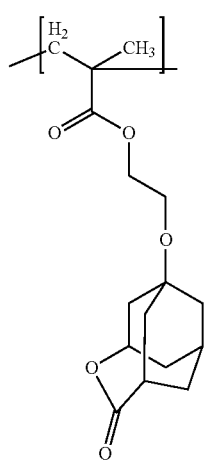

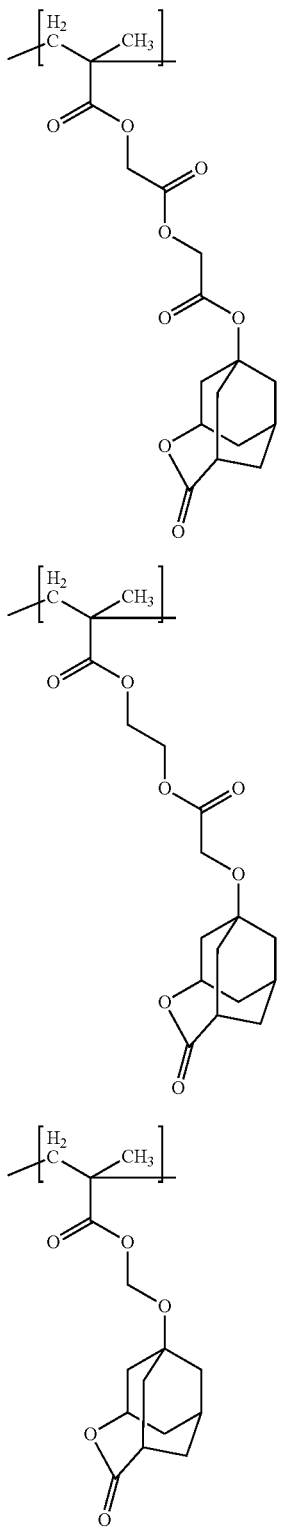

(a3-4-10)

(a3-4-11)

(a3-4-12)

When the resin (A) includes the structural unit (a3), the total content is usually 1 to 70 mol %, preferably 1 to 65 mol %, and more preferably 1 to 60 mol %, based on all structural units of the resin (A).

Each content of the structural unit (a3-1), the structural unit (a3-2), the structural unit (a3-3) or the structural unit (a3-4) is preferably 1 to 60 mol %, more preferably 1 to 50 mol %, and still more preferably 1 to 50 mol %, based on all structural units of the resin (A).

<Structural Unit (a4)>

Examples of the structural unit (a4) include the following structural unit:

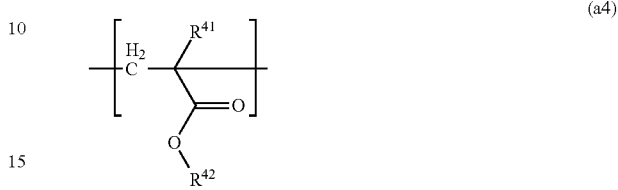

(a4)

wherein, in formula (a4), $R^{41}$ represents a hydrogen atom or a methyl group, and
$R^{42}$ represents a saturated hydrocarbon group having 1 to 24 carbon atoms having a fluorine atom, and —$CH_2$— included in the saturated hydrocarbon group may be replaced by —O— or —CO—.

Examples of the saturated hydrocarbon group represented by $R^{42}$ include a chain hydrocarbon group and a monocyclic or polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bond).

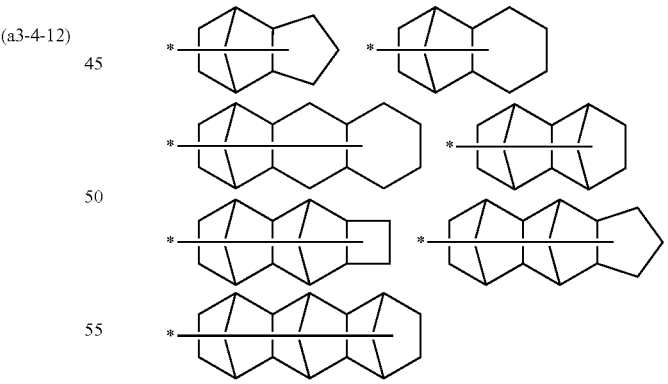

Examples of the group formed by combination include groups formed by combining one or more alkyl groups or one or more alkanediyl groups with one or more alicyclic hydrocarbon groups, and include an -alkanediyl group-alicyclic hydrocarbon group, an -alicyclic hydrocarbon group-alkyl group, an -alkanediyl group-alicyclic hydrocarbon group-alkyl group and the like.

Examples of the structural unit (a4) include a structural unit represented by at least one selected from the group consisting of formula (a4-0), formula (a4-1), formula (a4-2), formula (a4-3) and formula (a4-4):

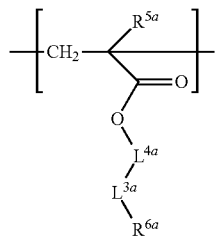 (a4-0)

wherein, in formula (a4-0), $R^{5a}$ represents a hydrogen atom or a methyl group, $L^{4a}$ represents a single bond or an alkanediyl group having 1 to 4 carbon atoms, $L^{3a}$ represents a perfluoroalkanediyl group having 1 to 8 carbon atoms or a perfluorocycloalkanediyl group having 3 to 12 carbon atoms, and $R^{6a}$ represents a hydrogen atom or a fluorine atom.

Examples of the alkanediyl group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^{3a}$ include a difluoromethylene group, a perfluoroethylene group, a perfluoropropane-1,1-diyl group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^{3a}$ include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^{5a}$ in the structural unit (a4-0) in the following structural units is substituted with a hydrogen atom:

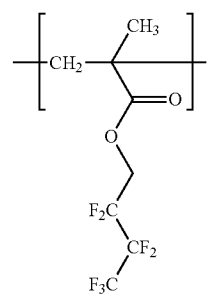 (a4-0-1)

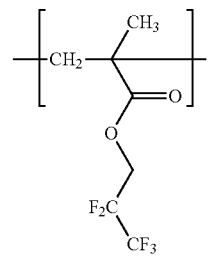 (a4-0-2)

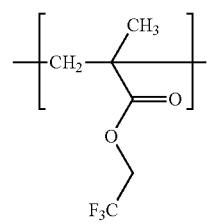 (a4-0-3)

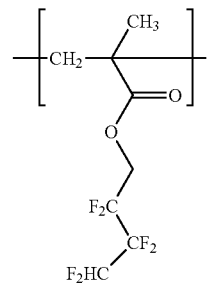 (a4-0-4)

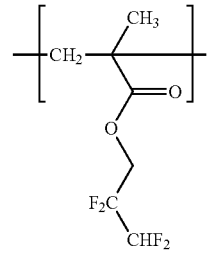 (a4-0-5)

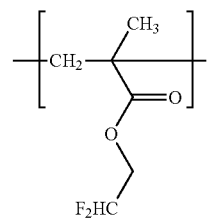 (a4-0-6)

(a4-0-7) 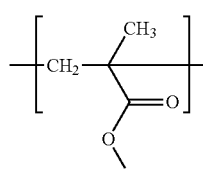

(a4-0-8) 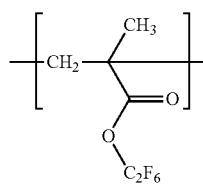

(a4-0-9) 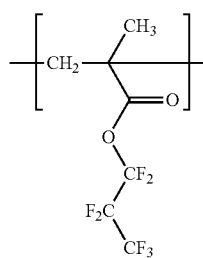

(a4-0-10) 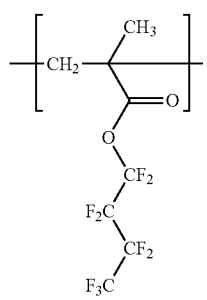

(a4-0-11) 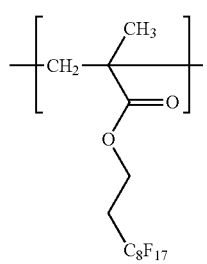

(a4-0-12) 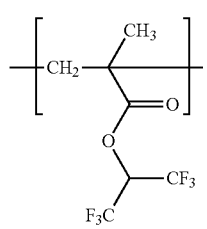

(a4-0-13) 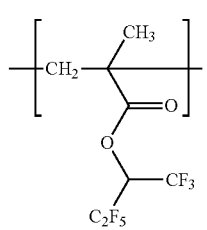

(a4-0-14) 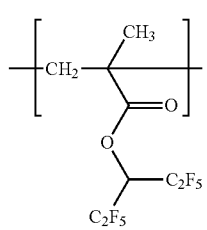

(a4-0-15) 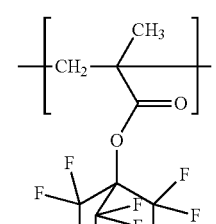

(a4-0-16) 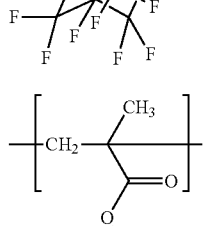

(a4-1) 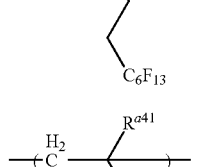

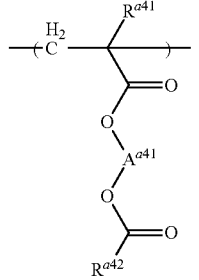

wherein, in formula (a4-1), $R^{a41}$ represents a hydrogen atom or a methyl group, $R^{a42}$ represents a saturated hydrocarbon group having 1 to 20 carbon atoms which may have a substituent, and —$CH_2$— included in the saturated hydrocarbon group may be replaced by —O— or —CO—, $A^{a41}$ represents an alkanediyl group having 1 to 6 carbon atoms which may have a substituent or a group represented by formula (a-g1), in which at least one of $A^{a41}$ and $R^{a42}$ has, as a substituent, a halogen atom (preferably a fluorine atom):

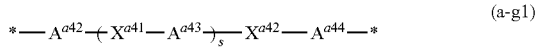

(a-g1)

[wherein, in formula (a-g1), s represents 0 or 1, $A^{a42}$ and $A^{a44}$ each independently represent a divalent saturated hydrocarbon group having 1 to 5 carbon atoms which may have a substituent, $A^{a43}$ represents a single bond or a divalent aliphatic hydrocarbon group having 1 to 5 carbon atoms which may have a substituent, $X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and

* is a bond and * at the right side is a bond to —O—CO—$R^{a42}$.

Examples of the saturated hydrocarbon group in $R^{a42}$ include a chain saturated hydrocarbon group and a monocyclic or polycyclic alicyclic saturated hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bond).

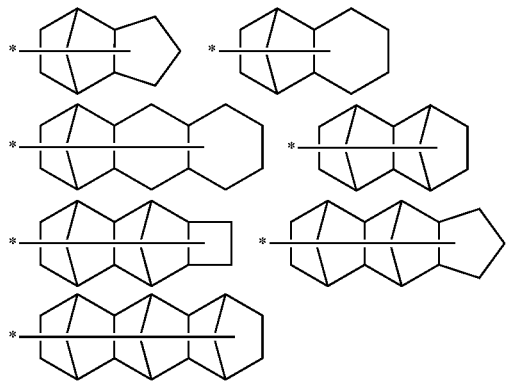

Examples of the group formed by combination include groups formed by combining one or more alkyl groups or one or more alkanediyl groups with one or more alicyclic saturated hydrocarbon groups, and include an -alkanediyl group-alicyclic saturated hydrocarbon group, an -alicyclic saturated hydrocarbon group-alkyl group, an -alkanediyl group-alicyclic saturated hydrocarbon group-alkyl group and the like.

Examples of the substituent which may be possessed by $R^{a42}$ include at least one selected from the group consisting of a halogen atom and a group represented by formula (a-g3). Examples of the halogen atom include a fluorine atom, a chlorine atom, a bromine atom and an iodine atom, and the halogen atom is preferably a fluorine atom:

(a-g3)

wherein, in formula (a-g3), $X^{a43}$ represents an oxygen atom, a carbonyl group, *—O—CO— or *—CO—O—, $A^{a45}$ represents an aliphatic hydrocarbon group having 1 to 17 carbon atoms which may have a halogen atom, and

* represents a bond to $R^{a42}$.

In $R^{a42}$—$X^{a43}$-$A^{a45}$ when $R^{a42}$ has no halogen atom, $A^{a45}$ represents an aliphatic hydrocarbon group having 1 to 17 carbon atoms which has at least one halogen atom.

Examples of the aliphatic hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group;

monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bond).

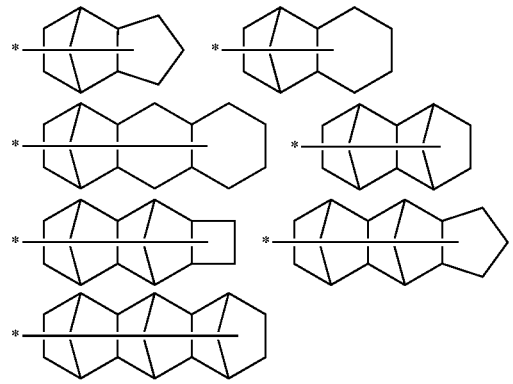

Examples of the group formed by combination include groups formed by combining one or more alkyl groups or one or more alkanediyl groups with one or more alicyclic hydrocarbon groups, and include an -alkanediyl group-alicyclic hydrocarbon group, an -alicyclic hydrocarbon group-alkyl group, an -alkanediyl group-alicyclic hydrocarbon group-alkyl group and the like.

$R^{a42}$ is preferably a saturated hydrocarbon group which may have a halogen atom, and more preferably an alkyl group having a halogen atom and/or a saturated hydrocarbon group having a group represented by formula (a-g3).

When $R^{a42}$ is a saturated hydrocarbon group which has a halogen atom, a saturated hydrocarbon group having a fluorine atom is preferable, a perfluoroalkyl group or a perfluorocycloalkyl group is more preferable, a perfluoroalkyl group having 1 to 6 carbon atoms is still more preferable, and a perfluoroalkyl group having 1 to 3 carbon atoms is particularly preferable. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is a saturated hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is a saturated hydrocarbon group having the group represented by formula (a-g3), $R^{a42}$ is still more preferably a group represented by formula (a-g2):

  (a-g2)

wherein, in formula (a-g2),
$A^{a46}$ represents a saturated hydrocarbon group having 1 to 17 carbon atoms which may have a halogen atom,
$X^{a44}$ represents —O—CO— or —CO—O— (** represents a bond to $A^{a46}$),
$A^{a47}$ represents an aliphatic hydrocarbon group having 1 to 17 carbon atoms which may have a halogen atom, the total number of carbon atoms of $A^{a46}$, $A^{a47}$ and $X^{a44}$ is 18 or less, and at least one of $A^{a46}$ and $A^{a47}$ has at least one halogen atom, and
* represents a bond to a carbonyl group.

The number of carbon atoms of the saturated hydrocarbon group as for $A^{a46}$ is preferably 1 to 6, and more preferably 1 to 3.

The number of carbon atoms of the aliphatic hydrocarbon group as for $A^{a47}$ is preferably 4 to 15, and more preferably 5 to 12, and $A^{a47}$ is still more preferably a cyclohexyl group or an adamantyl group.

Preferred structure of the group represented by formula (a-g2) is the following structure (* is a bond to a carbonyl group).

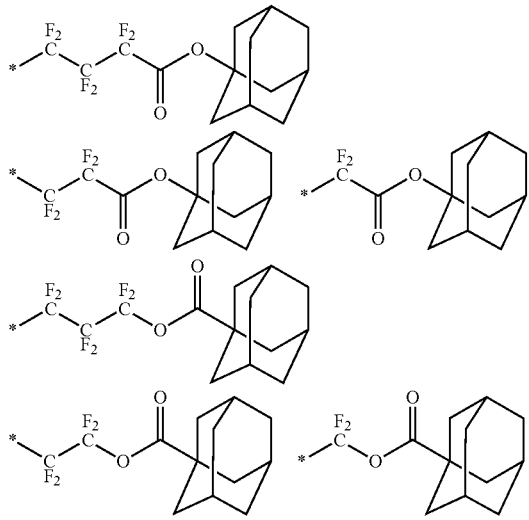

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group represented by $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the divalent saturated hydrocarbon group represented by $A^{a42}$, $A^{a43}$ and $A^{a44}$ in the group represented by formula (a-g1) include a linear or branched alkanediyl group and a monocyclic or polycyclic divalent alicyclic hydrocarbon group, and groups formed by combining an alkanediyl group and a divalent alicyclic hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the divalent saturated hydrocarbon group represented by $A^{a42}$, $A^{a43}$ and $A^{a44}$ include a hydroxy group and an alkoxy group having 1 to 6 carbon atoms.

s is preferably 0.

In a group represented by formula (a-g1), examples of the group in which $X^{a42}$ is —O—, —CO—, —CO—O— or —O—CO— include the following groups. In the following exemplification, * and  each represent a bond, and  is a bond to —O—CO—$R^{a42}$.

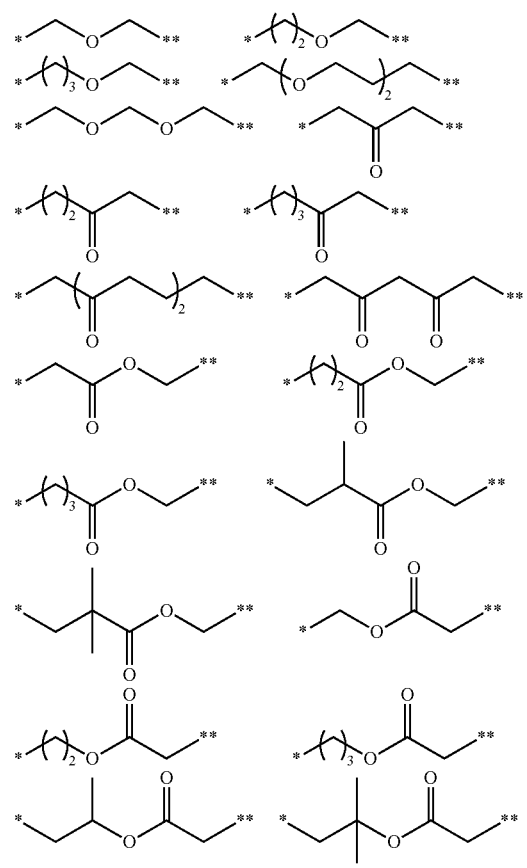

Examples of the structural unit represented by formula (a4-1) include the following structural units, and structural units in which a methyl group corresponding to $R^{a41}$ in the structural unit represented by formula (a4-1) in the following structural units is substituted with a hydrogen atom.
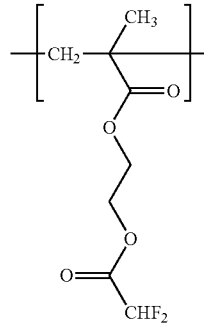
(a4-1-1)
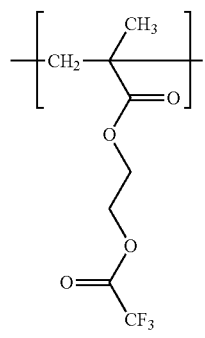
(a4-1-2)
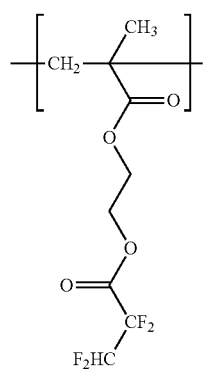
(a4-1-3)
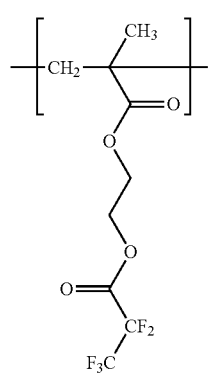
(a4-1-4)
-continued
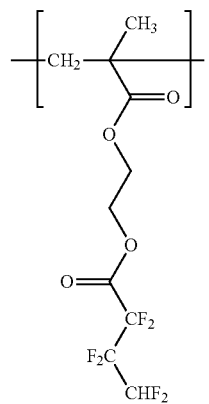
(a4-1-5)
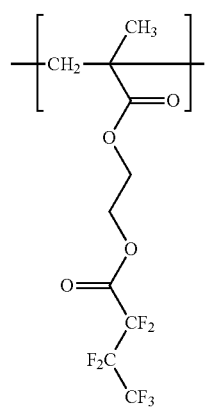
(a4-1-6)
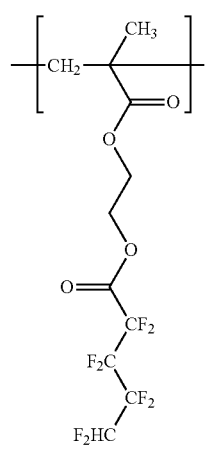
(a4-1-7)

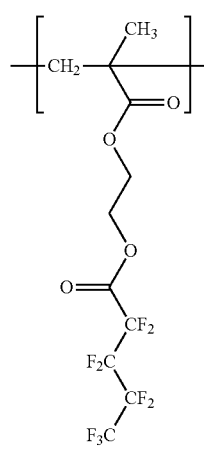 (a4-1-8)
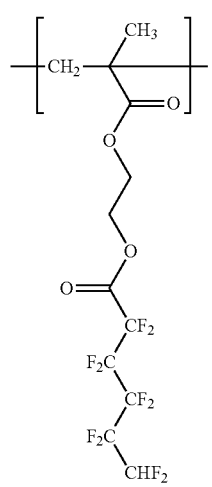 (a4-1-9)
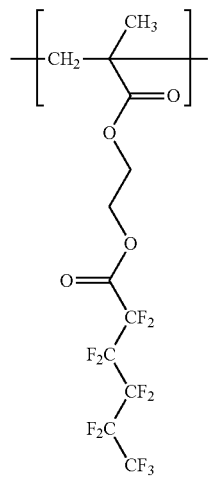 (a4-1-10)
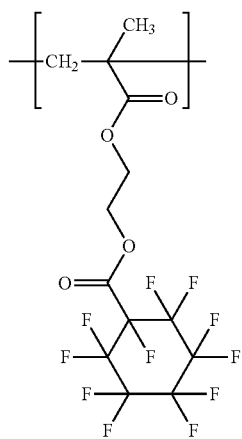 (a4-1-11)
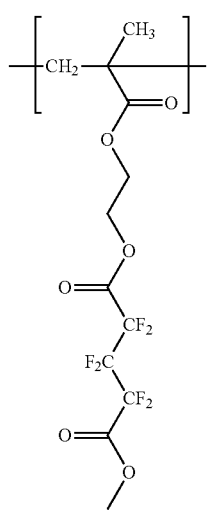 (a4-1'-1)
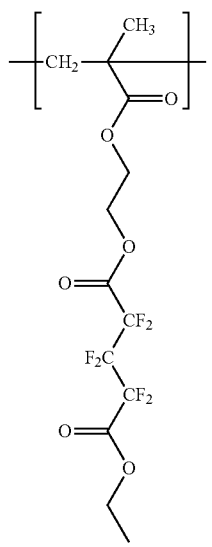 (a4-1'-2)

(a4-1'-3)
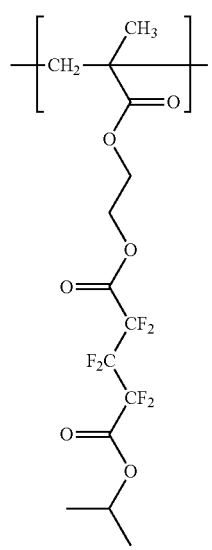
(a4-1'-4)
(a4-1'-5)
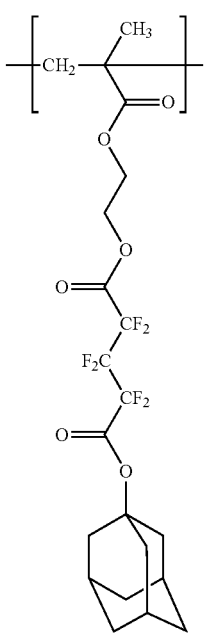
(a4-1'-6)
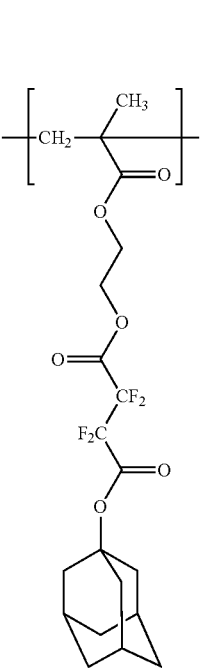

(a4-1'-7)
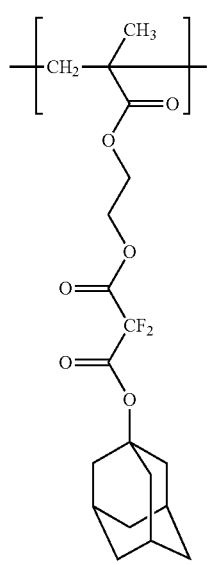
(a4-1'-8)
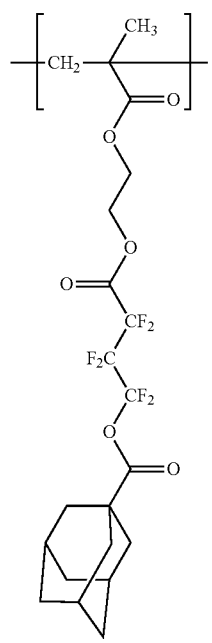
(a4-1'-9)
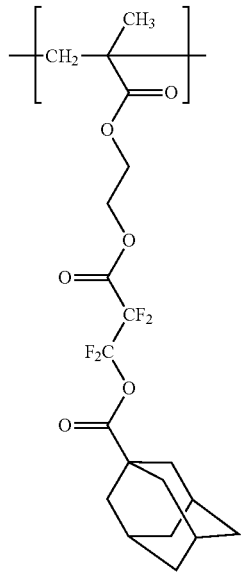
(a4-1'-10)
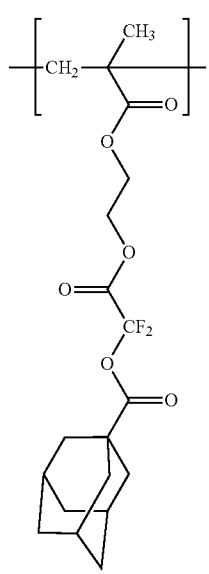
(a4-1'-11)
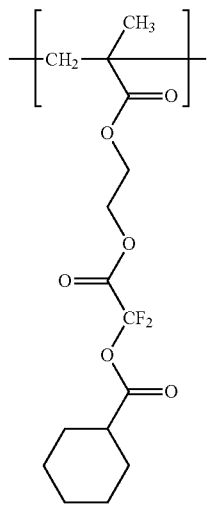

The structural unit represented by formula (a4-1) is preferably a structural unit represented by formula (a4-2):

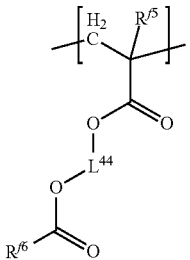

(a4-2)

wherein, in formula (a4-2),
$R^{f5}$ represents a hydrogen atom or a methyl group,
$L^{44}$ represents an alkanediyl group having 1 to 6 carbon atoms, and the —$CH_2$— included in the alkanediyl group may be replaced by —O— or —CO—,
$R^{f6}$ represents a saturated hydrocarbon group having 1 to 20 carbon atoms having a fluorine atom, and
the upper limit of the total number of carbon atoms of $L^{44}$ and $R^{f6}$ is 21.

Examples of the alkanediyl group as for $L^{44}$ include the same groups as mentioned as for $A^{a41}$.

Examples of the saturated hydrocarbon group as for $R^{f6}$ include the same groups as mentioned as for $R^{a42}$.

The alkanediyl group in $L^{44}$ is preferably an alkanediyl group having 2 to 4 carbon atoms, and more preferably an ethylene group.

Examples of the structural unit represented by formula (a4-2) include structural units each represented by formula (a4-1-1) to formula (a4-1-11). Examples of the structural unit represented by formula (a4-2) also include a structural unit in which a methyl group corresponding to $R^{f3}$ in a structural unit (a4-2) is substituted with a hydrogen atom:

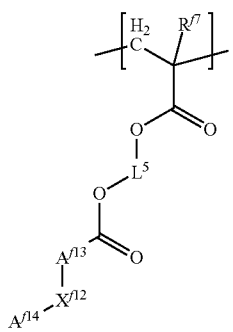

(a4-3)

wherein, in formula (a4-3),
$R^{f7}$ represents a hydrogen atom or a methyl group,
$L^5$ represents an alkanediyl group having 1 to 6 carbon atoms,
$A^{f13}$ represents a divalent saturated hydrocarbon group having 1 to 18 carbon atoms which may have a fluorine atom,
$X^{f12}$ represents *—O—CO— or *—CO—O— (* represents a bond to $A^{f13}$),
$A^{f14}$ represents a saturated hydrocarbon group having 1 to 17 carbon atoms which may have a fluorine atom, and at least one of $A^{f13}$ and $A^{f14}$ has a fluorine atom, and the upper limit of the total number of carbon atoms of $L^5$, $A^{f13}$ and $A^{f14}$ is 20.

Examples of the alkanediyl group in $L^5$ include those which are the same as mentioned in the alkanediyl group as for $A^{a41}$.

The divalent saturated hydrocarbon group which may have a fluorine atom in $A^{f13}$ is preferably a divalent chain saturated hydrocarbon group which may have a fluorine atom and a divalent alicyclic saturated hydrocarbon group which may have a fluorine atom, and more preferably a perfluoroalkanediyl group.

Examples of the divalent chain hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The divalent alicyclic hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom as for $A^{f14}$ include the same groups as mentioned as for $R^{a42}$. Of these groups, preferable are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; a cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), $L^5$ is preferably an ethylene group.

The divalent saturated hydrocarbon group as for $A^{f13}$ is preferably a group including a divalent chain hydrocarbon group having 1 to 6 carbon atoms and a divalent alicyclic hydrocarbon group having 3 to 12 carbon atoms, and more preferably a divalent chain hydrocarbon group having 2 to 3 carbon atoms.

The saturated hydrocarbon group as for $A^{f14}$ is preferably a group including a chain hydrocarbon group having 3 to 12 carbon atoms and an alicyclic hydrocarbon group having 3 to 12 carbon atoms, and more preferably a group including a chain hydrocarbon group having 3 to 10 carbon atoms and an alicyclic hydrocarbon group having 3 to 10 carbon atoms. Of these groups, $A^{f14}$ is preferably a group including an alicyclic hydrocarbon group having 3 to 12 carbon atoms, and more preferably a cyclopropylmethyl group, a cyclopentyl group, a cyclohexyl group, a norbornyl group and an adamantyl group.

Examples of the structural unit represented by formula (a4-3) include structural units each represented by formula (a4-1'-1) to formula (a4-1'-11). Examples of the structural unit represented by formula (a4-3) also include a structural unit in which a methyl group corresponding to R^$f7$ in a structural unit (a4-3) is substituted with a hydrogen atom.

The structural unit (a4) also includes a structural unit represented by formula (a4-4):

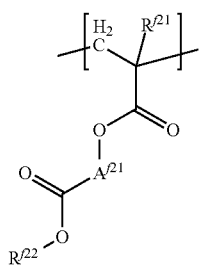
(a4-4)

wherein, in formula (a4-4), $R^{f21}$ represents a hydrogen atom or a methyl group, $A^{f21}$ represents —$(CH_2)_{j1}$—, —$(CH_2)_{j2}$—O—$(CH_2)_{j3}$— or —$(CH_2)_{j4}$—CO—O—$(CH_2)_{j5}$—, j1 to j5 each independently represent an integer of 1 to 6, and $R^{f22}$ represents a saturated hydrocarbon group having 1 to 10 carbon atoms having a fluorine atom.

Examples of the saturated hydrocarbon group as for $R^{f22}$ include those which are the same as the saturated hydrocarbon group represented by $R^{a42}$. $R^{f22}$ is preferably an alkyl group having 1 to 10 carbon atoms having a fluorine atom or an alicyclic hydrocarbon group having 1 to 10 carbon atoms having a fluorine atom, more preferably an alkyl group having 1 to 10 carbon atoms having a fluorine atom, and still more preferably an alkyl group having 1 to 6 carbon atoms having a fluorine atom.

In formula (a4-4), $A^{f21}$ is preferably —$(CH_2)_{j1}$—, more preferably an ethylene group or a methylene group, and still more preferably a methylene group.

The structural unit represented by formula (a4-4) includes, for example, the following structural units and structural units in which a methyl group corresponding to $R^{f21}$ in the structural unit (a4-4) is substituted with a hydrogen atom in structural units represented by the following formulas.

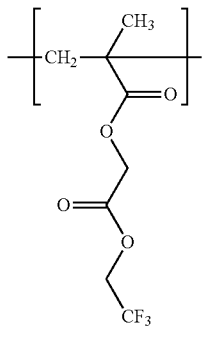 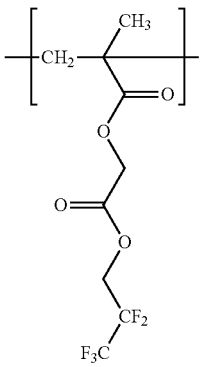

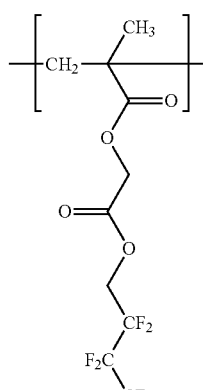 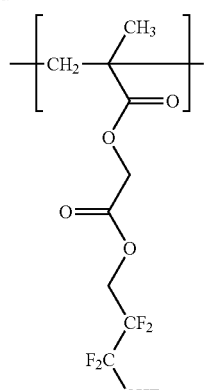

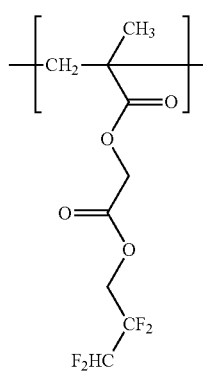 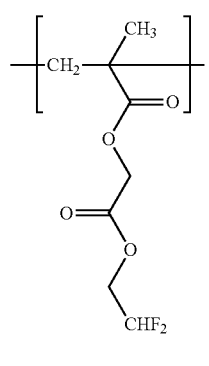

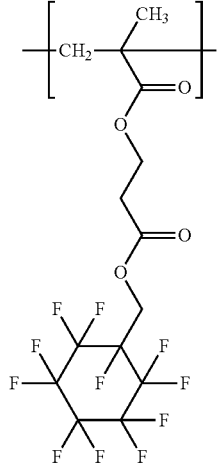 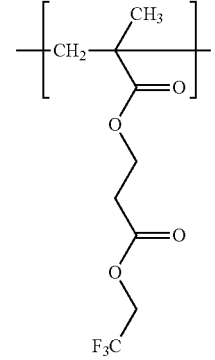

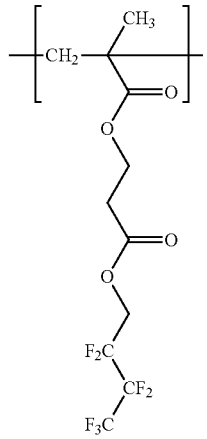 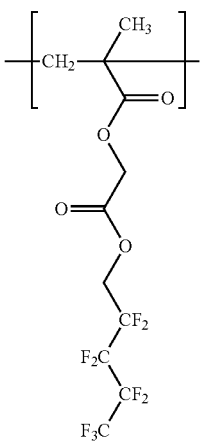

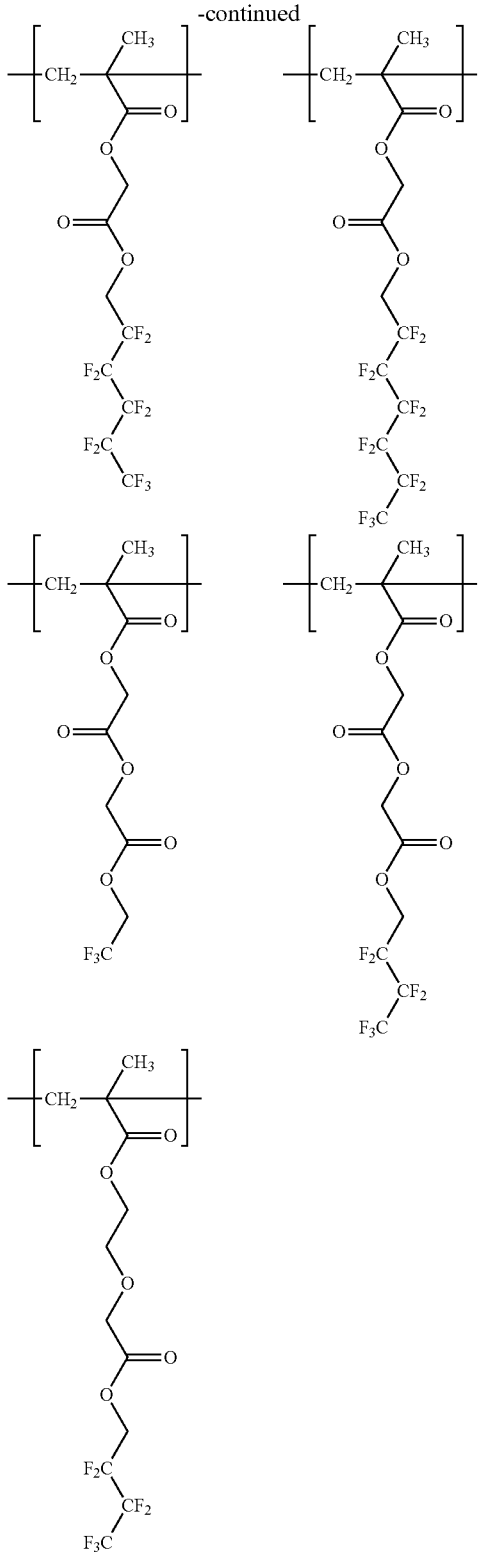

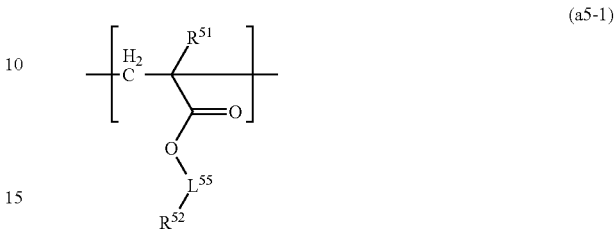

wherein, in formula (a5-1),
$R^{51}$ represents a hydrogen atom or a methyl group,
$R^{52}$ represents an alicyclic hydrocarbon group having 3 to 18 carbon atoms, and a hydrogen atom included in the alicyclic hydrocarbon group may be substituted with an aliphatic hydrocarbon group having 1 to 8 carbon atoms, and
$L^{55}$ represents a single bond or a divalent saturated hydrocarbon group having 1 to 18 carbon atoms, and —CH$_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the divalent saturated hydrocarbon group in $L^{55}$ include a divalent chain saturated hydrocarbon group and a divalent alicyclic saturated hydrocarbon group, and a divalent chain saturated hydrocarbon group is preferable.

The divalent chain saturated hydrocarbon group includes, for example, alkanediyl groups such as a methylene group, an ethylene group, a propanediyl group, a butanediyl group and a pentanediyl group.

The divalent alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

Examples of the group in which —CH$_2$— included in the divalent saturated hydrocarbon group represented by $L^{55}$ is replaced by —O— or —CO— include groups represented by formula (L1-1) to formula (L1-4). In the following When the resin (A) includes the structural unit (a4), the content is preferably 1 to 20 mol %, more preferably 2 to 15 mol %, and still more preferably 3 to 10 mol %, based on all structural units of the resin (A).

<Structural Unit (a5)>

Examples of a non-leaving hydrocarbon group possessed by the structural unit (a5) include groups having a linear, branched or cyclic hydrocarbon group. Of these, the structural unit (a5) is preferably a group having an alicyclic hydrocarbon group.

The structural unit (a5) includes, for example, a structural unit represented by formula (a5-1):

formulas, * and ** each represent a bonding site, and * represents a bond to an oxygen atom.

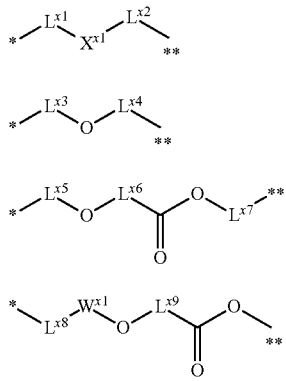

In formula (L1-1),
$X^{x1}$ represents *—O—CO— or *—CO—O— (* represents a bond to $L^{x1}$),
$L^{x1}$ represents a divalent aliphatic saturated hydrocarbon group having 1 to 16 carbon atoms,
$L^{x2}$ represents a single bond or a divalent aliphatic saturated hydrocarbon group having 1 to 15 carbon atoms, and the total number of carbon atoms of $L^{x1}$ and $L^{x2}$ is 16 or less.
In formula (L1-2),
$L^{x3}$ represents a divalent aliphatic saturated hydrocarbon group having 1 to 17 carbon atoms,
$L^{x4}$ represents a single bond or a divalent aliphatic saturated hydrocarbon group having 1 to 16 carbon atoms, and
the total number of carbon atoms of $L^{x3}$ and $L^{x4}$ is 17 or less.
In formula (L1-3),
$L^{x5}$ represents a divalent aliphatic saturated hydrocarbon group having 1 to 15 carbon atoms,
$L^{x6}$ and $L^{x7}$ each independently represent a single bond or a divalent aliphatic saturated hydrocarbon group having 1 to 14 carbon atoms, and
the total number of carbon atoms of $L^{x5}$, $L^{x6}$ and $L^{x7}$ is 15 or less.
In formula (L1-4),
$L^{x8}$ and $L^{x9}$ represent a single bond or a divalent aliphatic saturated hydrocarbon group having 1 to 12 carbon atoms,
$W^{x1}$ represents a divalent alicyclic saturated hydrocarbon group having 3 to 15 carbon atoms, and
the total number of carbon atoms of $L^{x8}$, $L^{x9}$ and $W^{x1}$ is 15 or less.
$L^{x1}$ is preferably a divalent aliphatic saturated hydrocarbon group having 1 to 8 carbon atoms, and more preferably a methylene group or an ethylene group.
$L^{x2}$ is preferably a single bond or a divalent aliphatic saturated hydrocarbon group having 1 to 8 carbon atoms, and more preferably a single bond.
$L^{x3}$ is preferably a divalent aliphatic saturated hydrocarbon group having 1 to 8 carbon atoms.
$L^{x4}$ is preferably a single bond or a divalent aliphatic saturated hydrocarbon group having 1 to 8 carbon atoms.
$L^{x5}$ is preferably a divalent aliphatic saturated hydrocarbon group having 1 to 8 carbon atoms, and more preferably a methylene group or an ethylene group.

$L^{x6}$ is preferably a single bond or a divalent aliphatic saturated hydrocarbon group having 1 to 8 carbon atoms, and more preferably a methylene group or an ethylene group.
$L^{x7}$ is preferably a single bond or a divalent aliphatic saturated hydrocarbon group having 1 to 8 carbon atoms.
$L^{x8}$ is preferably a single bond or a divalent aliphatic saturated hydrocarbon group having 1 to 8 carbon atoms, and more preferably a single bond or a methylene group.
$L^{x9}$ is preferably a single bond or a divalent aliphatic saturated hydrocarbon group having 1 to 8 carbon atoms, and more preferably a single bond or a methylene group.
$W^{x1}$ is preferably a divalent alicyclic saturated hydrocarbon group having 3 to 10 carbon atoms, and more preferably a cyclohexanediyl group or an adamantanediyl group.

The group represented by formula (L1-1) includes, for example, the following divalent groups.

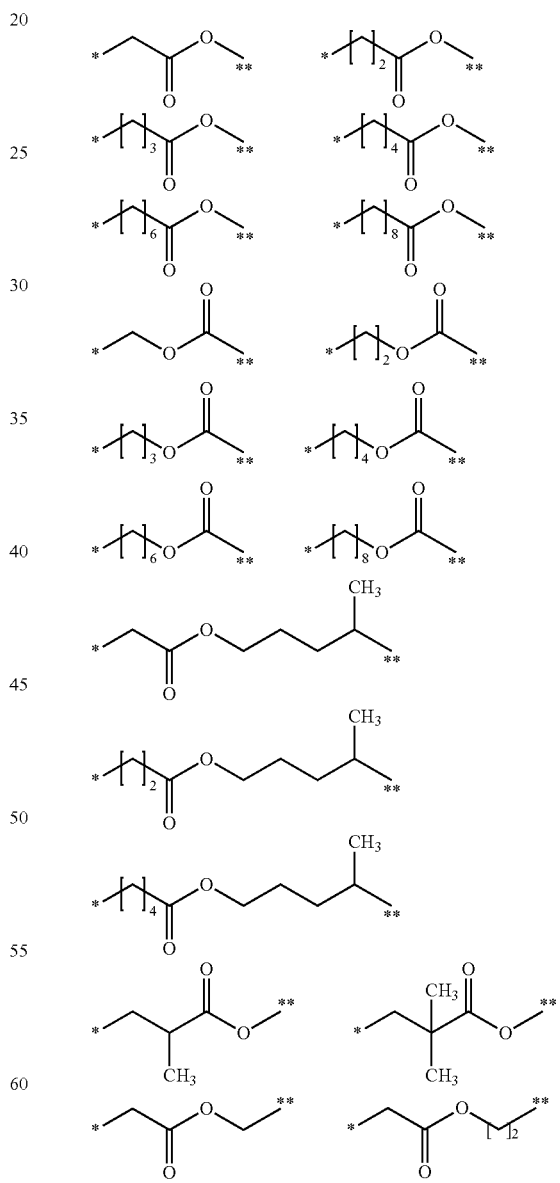

The group represented by formula (L1-2) includes, for example, the following divalent groups.

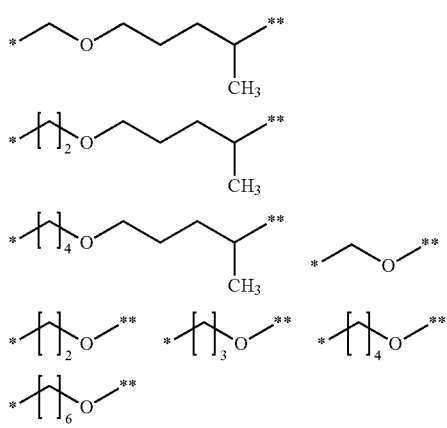

The group represented by formula (L1-3) includes, for example, the following divalent groups.

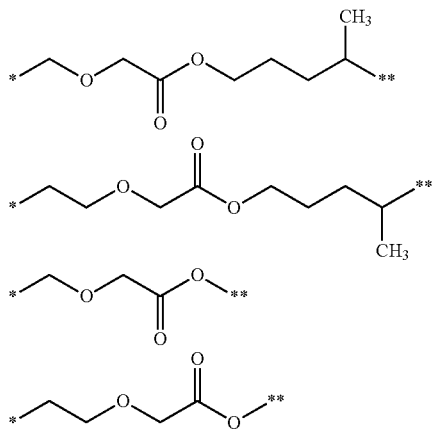

The group represented by formula (L1-4) includes, for example, the following divalent groups.

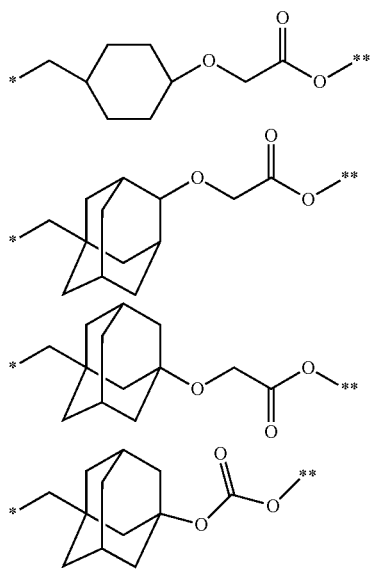

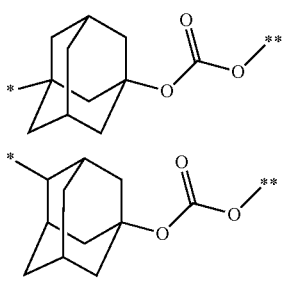

$L^{55}$ is preferably a single bond or a group represented by formula (L1-1).

Examples of the structural unit (a5-1) include the following structural units and structural units in which a methyl group corresponding to $R^{51}$ in the structural unit (a5-1) in the following structural units is substituted with a hydrogen atom.

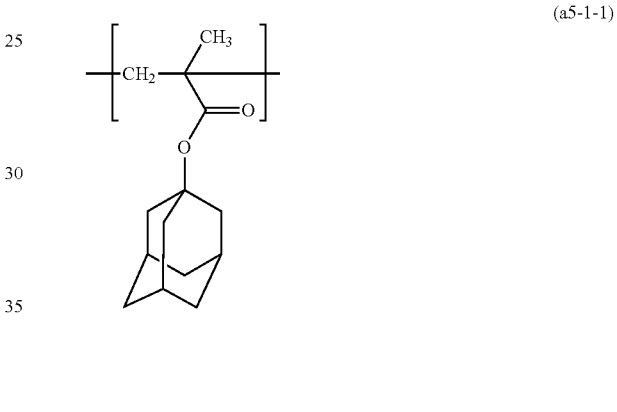

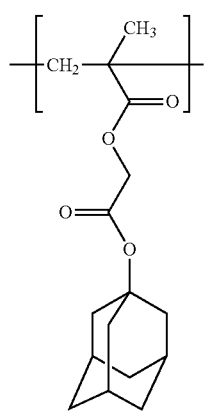 (a5-1-4)
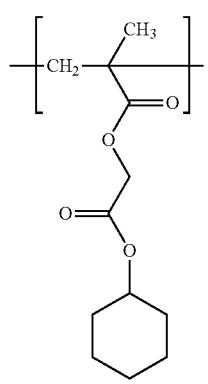 (a5-1-5)
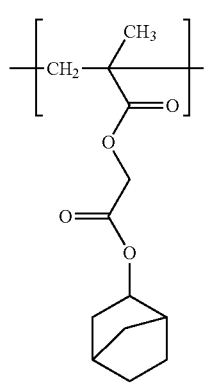 (a5-1-6)
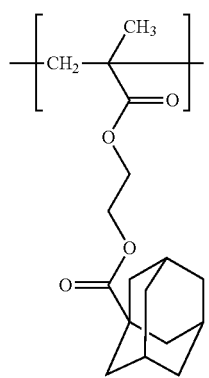 (a5-1-7)
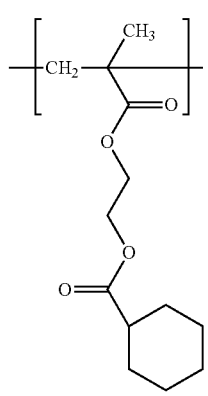 (a5-1-8)
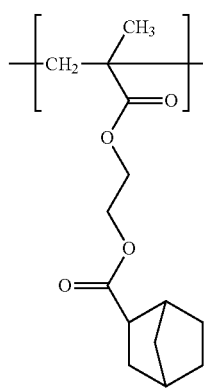 (a5-1-9)
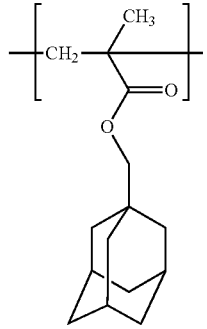 (a5-1-10)
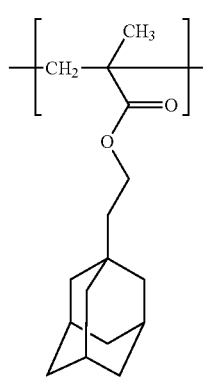 (a5-1-11)

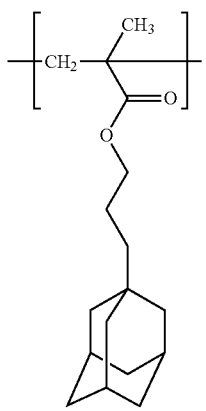

(a5-1-12)

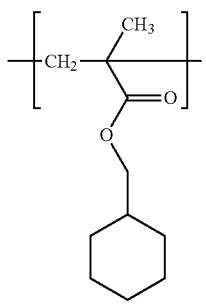

(a5-1-13)

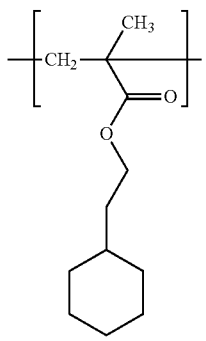

(a5-1-14)

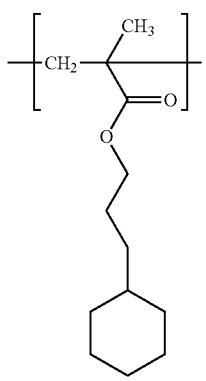

(a5-1-15)

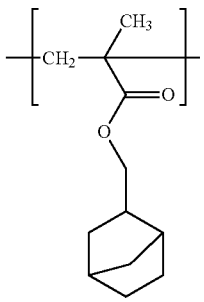

(a5-1-16)

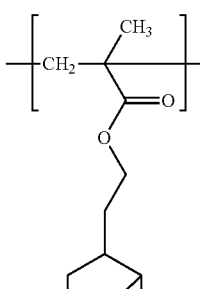

(a5-1-17)

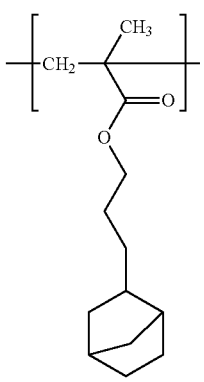

(a5-1-18)

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (a6)>

The structural unit (a6) is a structural unit having a —SO$_2$— group, and preferably has a —SO$_2$— group in the side chain.

The structural unit having a —SO$_2$— group may have a linear structure having a —SO$_2$— group, a branched structure having a —SO$_2$— group, or —SO$_2$—. It may have a cyclic structure having a group (monocyclic and polycyclic structure). A structural unit having a cyclic structure having a —SO$_2$— group is preferable, and a structural unit having a cyclic structure (sultone ring) containing —SO2-O— is more preferable.

Examples of the sultone ring include rings represented by the following formulas (T1-1), formulas (T1-2), formulas (T1-3) and formulas (T1-4). The binding site can be at any position. The sultone ring may be a monocyclic type, but is preferably a polycyclic type. The polycyclic sultone ring means a bridging ring containing —SO2-O— as an atomic group constituting the ring, and examples thereof include rings represented by the formulas (T1-1) and (T1-2). Be done. Like the ring represented by the formula (T1-2), the sultone ring may further contain a heteroatom in addition to —SO2-O— as an atomic group constituting the ring. Examples of the hetero atom include an oxygen atom, a sulfur atom or a nitrogen atom, and an oxygen atom is preferable.

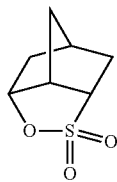

(T¹-1)

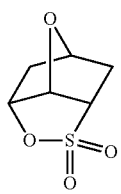

(T¹-2)

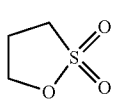

(T¹-3)

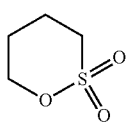

(T¹-4)

The sulton ring may have a substituent, and as the substituent, an alkyl group having 1 to 12 carbon atoms, a halogen atom, a hydroxy group, a cyano group, or a hydroxy group may have a halogen atom or a hydroxy group. Examples thereof include an alkoxy group having 12 to 12, an aryl group having 6 to 12 carbon atoms, an aralkyl group having 7 to 12 carbon atoms, a glycidyloxy group, an alkoxycarbonyl group having 2 to 12 carbon atoms and an alkylcarbonyl group having 2 to 4 carbon atoms.

Examples of the halogen atom include a fluorine atom, a chlorine atom, a bromine atom and an iodine atom.

Examples of the alkyl group include a methyl group, an ethyl group, a propyl group, a butyl group, a pentyl group, a hexyl group, an octyl group and a decyl group, preferably an alkyl group having 1 to 6 carbon atoms, and more preferably a methyl group.

Examples of the alkyl group having a halogen atom include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, and a perfluorohexyl group. Examples thereof include a trichloromethyl group, a tribromomethyl group and a triiodomethyl group, and preferably a trifluoromethyl group.

Examples of the alkyl group having a hydroxy group include a hydroxyalkyl group of a hydroxymethyl group and a 2-hydroxyethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

The aryl group includes a phenyl group, a naphthyl group, an anthryl group, a p-methylphenyl group, a p-tert-butylphenyl group, a p-adamantylphenyl group, a tolyl group, a xsilyl group, a cumyl group, a mesityl group, a biphenyl group and a phenanthryl group. Groups include 2,6-diethylphenyl groups and 2-methyl-6-ethylphenyl groups. Examples of the aralkyl group include a benzyl group, a phenethyl group, a phenylpropyl group, a naphthylmethyl group and a naphthylethyl group.

Examples of the alkoxycarbonyl group include a group in which an alkoxy group such as a methoxycarbonyl group and an ethoxycarbonyl group is bonded to a carbonyl group, preferably an alkoxycarbonyl group having 6 or less carbon atoms, and more preferably a methoxycarbonyl group.

Examples of the alkylcarbonyl group include an acetyl group, a propionyl group and a butyryl group.

A sultone ring having no substituent is preferable from the viewpoint that the monomer for which the structural unit (a6) is derived can be easily produced.

As the sultone ring, a ring represented by the following formula (T1') is preferable.

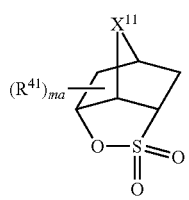

(T1')

[In the formula (T1'), $X^{11}$ represents an oxygen atom, a sulfur atom or a methylene group.

$R^{41}$ has an alkyl group having 1 to 12 carbon atoms, a halogen atom, a hydroxy group, a cyano group, an alkoxy group having 1 to 12 carbon atoms, and an aryl group having 6 to 12 carbon atoms, which may have a halogen atom or a hydroxy group. An aralkyl group having 7 to 12 carbon atoms, a glycidyloxy group, an alkoxycarbonyl group having 2 to 12 carbon atoms, or an alkylcarbonyl group having 2 to 4 carbon atoms.

ma represents an integer from 0 to 9. When ma is 2 or more, a plurality of $R^{41}$s may be the same or different. The binding site of $R^{41}$ is at any position of the sultone ring.]

$X^{11}$ is preferably an oxygen atom or a methylene group, and more preferably a methylene group.

Examples of $R^{41}$ include those similar to the substituent of the sultone ring, and an alkyl group having 1 to 12 carbon atoms which may have a halogen atom or a hydroxy group is preferable.

As the sultone ring, the ring represented by the formula (T1) is more preferable.

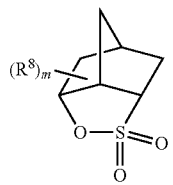

(T1)

[In the formula (T1),

R⁸ is an alkyl group having 1 to 12 carbon atoms, a halogen atom, a hydroxy group, a cyano group, an alkoxy group having 1 to 12 carbon atoms, or an aryl group having 6 to 12 carbon atoms, which may have a halogen atom or a hydroxy group. An aralkyl group having 7 to 12 carbon atoms, a glycidyloxy group, an alkoxycarbonyl group having 2 to 12 carbon atoms, or an alkylcarbonyl group having 2 to 4 carbon atoms.

m represents an integer from 0 to 9. When m is 2 or more, the plurality of R8s may be the same or different. The binding site of $(R^8)_m$ is at any position of a sultone ring.]

R⁸ is the same as $R^{41}$.

The ma in the formula (T1') and m in the formula (T1) are preferably 0 or 1, and more preferably 0.

Examples of the ring represented by the formula (T1') and the ring represented by the formula (T1) include the following rings. The binding site is at any position.

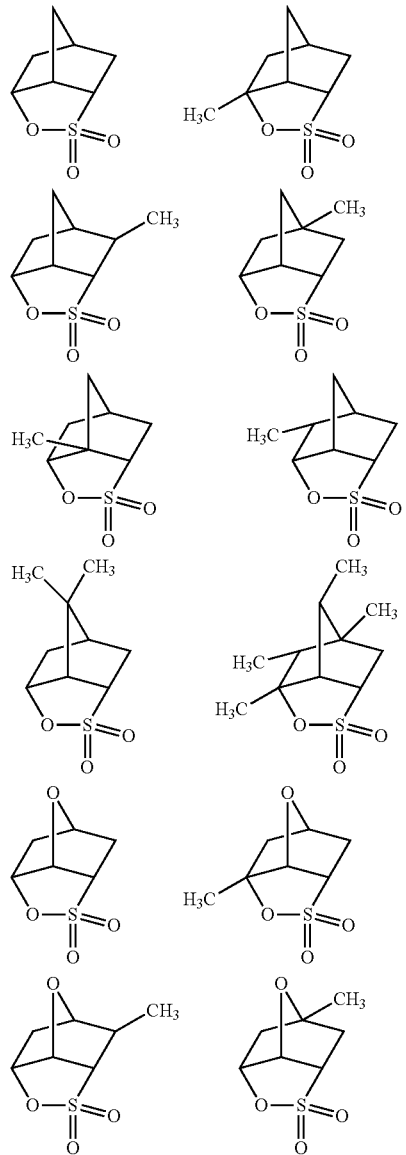

The structural unit having a sultone ring preferably has the following groups. * In the following groups represents the binding site.

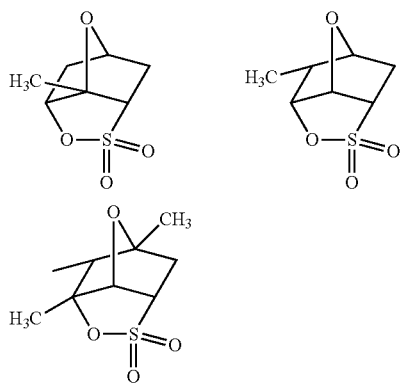

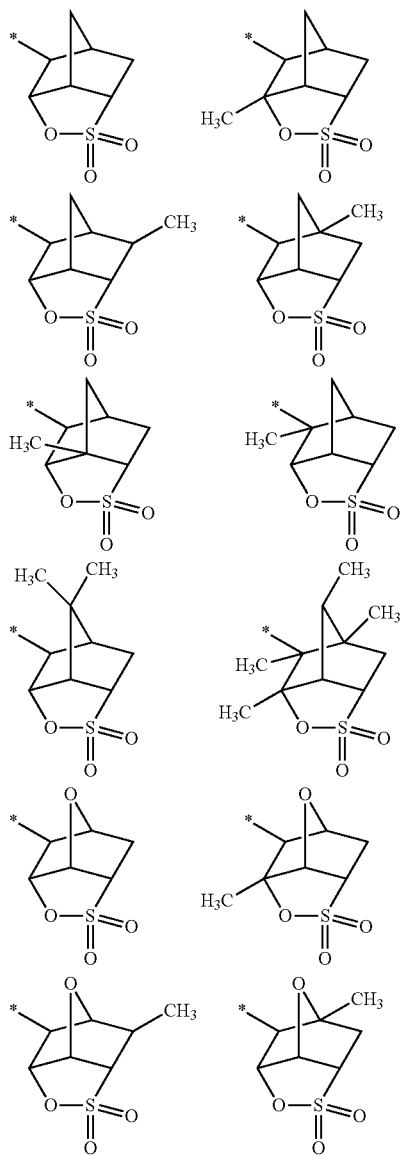

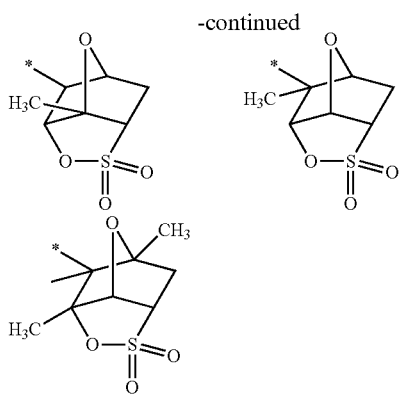

The structural unit having a —SO$_2$— group further preferably has a group derived from a polymerizable group. Examples of the polymerizable group include a vinyl group, an acryloyl group, a methacryloyl group, an acryloyloxy group, a methacryloyloxy group, an acryloylamino group, a methacryloylamino group, an acryloylthio group, a methacryloylthio group and the like.

Among them, the monomer that leads to the structural unit (a6) is preferably a monomer having an ethylenically unsaturated bond, and more preferably a (meth) acrylic monomer.

The structural unit (a6) is preferably a structural unit represented by the formula (Ix).

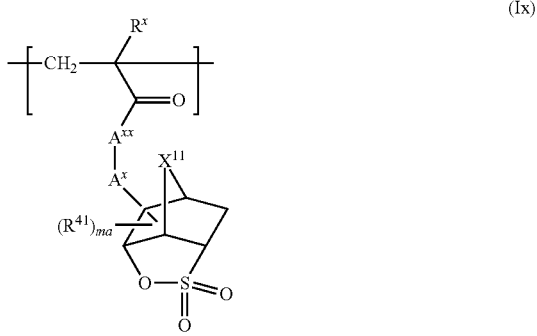

(Ix)

[In the formula (Ix), Rx represents an alkyl group having 1 to 6 carbon atoms, a hydrogen atom or a halogen atom which may have a halogen atom.

A$^{xx}$ represents an oxygen atom, —N(R$^c$)— or a sulfur atom.

A$^x$ represents a divalent saturated hydrocarbon group having 1 to 18 carbon atoms, and —CH$_2$— contained in the saturated hydrocarbon group may be replaced with —O—, —CO— or —N(R$^d$)—.

X$^{11}$ represents an oxygen atom, a sulfur atom or a methylene group.

R$^{41}$ has an alkyl group having 1 to 12 carbon atoms, a halogen atom, a hydroxy group, a cyano group, an alkoxy group having 1 to 12 carbon atoms, and an aryl group having 6 to 12 carbon atoms, which may have a halogen atom or a hydroxy group. An aralkyl group having 7 to 12 carbon atoms, a glycidyloxy group, an alkoxycarbonyl group having 2 to 12 carbon atoms, or an alkylcarbonyl group having 2 to 4 carbon atoms.

ma represents an integer from 0 to 9. When ma is 2 or more, a plurality of R41s may be the same or different. R$^c$ and R$^d$ independently represent a hydrogen atom or an alkyl group having 1 to 6 carbon atoms.]

Examples of the halogen atom of Rx include a fluorine atom, a chlorine atom, a bromine atom and an iodine atom.

Examples of the alkyl group of Rx include a methyl group, an ethyl group, an n-propyl group, an isopropyl group, an n-butyl group, a sec-butyl group, a tert-butyl group, an n-pentyl group and an n-hexyl group. It is preferably an alkyl group having 1 to 4 carbon atoms, and more preferably a methyl group or an ethyl group.

Examples of the alkyl group having a halogen atom of Rx include a trifluoromethyl group, a perfluoroethyl group, a perfluoropropyl group, a perfluoroisopropyl group, a perfluorobutyl group, a perfluorosec-butyl group, a perfluorotert-butyl group, and a perfluoropentyl group. Perfluorohexyl group, trichloromethyl group, tribromomethyl group, triiodomethyl group and the like can be mentioned.

R$^x$ is preferably a hydrogen atom or an alkyl group having 1 to 4 carbon atoms, more preferably a hydrogen atom, a methyl group or an ethyl group, and further preferably a hydrogen atom or a methyl group.

Examples of the divalent saturated hydrocarbon group of A$^x$ include a linear alkanediyl group, a branched alkanediyl group, a monocyclic or polycyclic divalent alicyclic saturated hydrocarbon group, and these groups. A combination of two or more of these may be used.

Specifically, methylene group, ethylene group, propane-1,3-diyl group, propane-1,2-diyl group, butane-1,4-diyl group, pentane-1,5-diyl group, hexane-1,6-Diyl group, heptan-1,7-diyl group, octane-1,8-diyl group, nonan-1,9-diyl group, decan-1,10-diyl group, undecane-1,11-diyl group, Dodecane-1,12-diyl group, tridecane-1,13-diyl group, tetradecane-1,14-diyl group, pentadecane-1,15-diyl group, hexadecane-1,16-diyl group, heptadecane-1, Linear alkanediyl groups such as 17-diyl group, ethane-1,1-diyl group, propane-1,1-diyl group and propane-2,2-diyl group; Butane-1, 3-diyl group, 2-methylpropane-1,3-diyl group, 2-methylpropane-1,2-diyl group, pentane-1,4-diyl group, 2-methylbutane-1,4-Branched alkanediyl groups such as diyl groups;

Monocyclic 2 which is a cycloalkanediyl group such as cyclobutane-1,3-diyl group, cyclopentane-1,3-diyl group, cyclohexane-1,4-diyl group, cyclooctane-1,5-diyl group, etc. Valuable alicyclic saturated hydrocarbon group; Polycyclic divalent alicyclic saturated hydrocarbons such as norbornane-1,4-diyl group, norbornane-2,5-diyl group, adamantane-1,5-diyl group, and adamantane-2,6-diyl group. The group etc. can be mentioned.

Examples of R$^{41}$, X$^{11}$ and ma are the same as those in the formula (T1').

Examples of the sultone ring include the above-mentioned ones, and among them, the above-mentioned ones in which the bonding position is specified are preferable.

Examples of the structural unit (a6) include the following structural units.

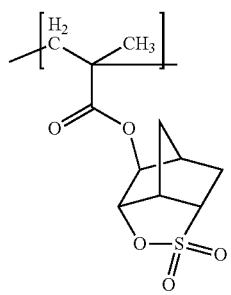

(a6-1)

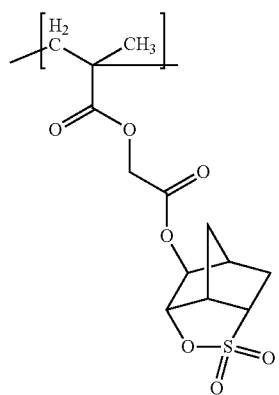
(a6-2)
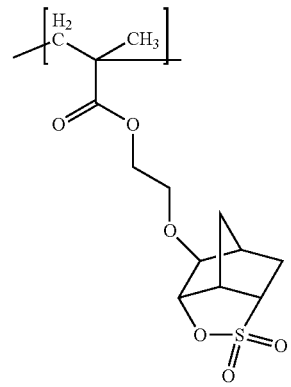
(a6-6)
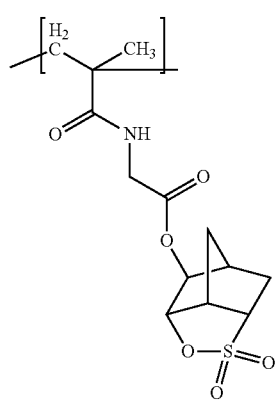
(a6-3)
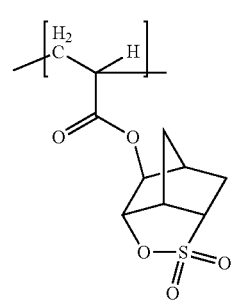
(a6-7)
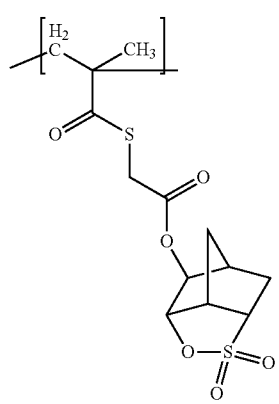
(a6-4)
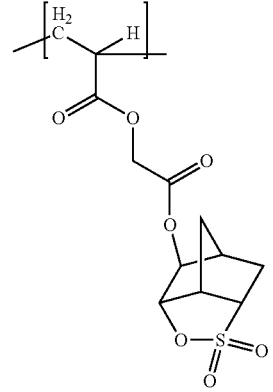
(a6-8)
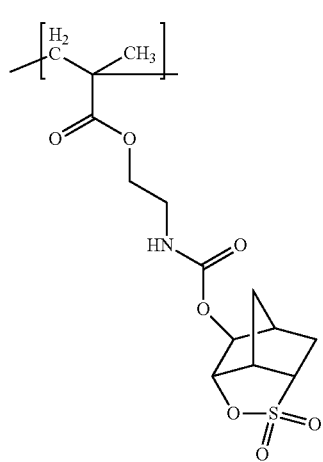
(a6-5)
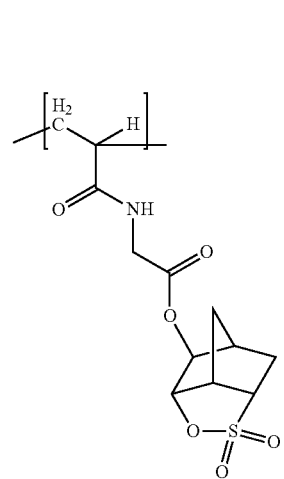
(a6-9)

-continued (a6-10)
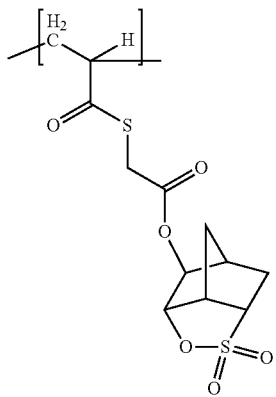

(a6-11)
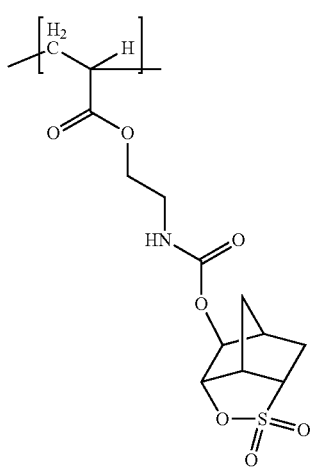

(a6-12)
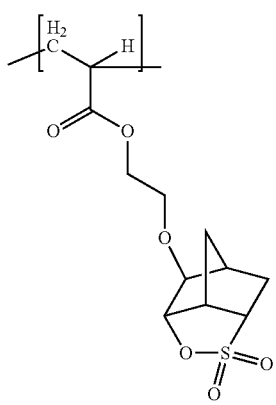

Among them, the structural units represented by the formula (a6-1), the formula (a6-2), the formula (a6-6), the formula (a6-7), the formula (a6-8) and the formula (a6-12) are preferable, and the structural units represented by the formulas (a6-1), the formula (a6-2), the formulas (a6-7) and (a6-8) are more preferable.

When the resin (A) has a structural unit (a6), the content of a structural unit (a6) is preferably 1 to 50 mol %, more preferably 2 to 40 mol %, and more preferably 3 to 30 mol % with respect to all the structural units of the resin (A).

<Structural Unit (II)>

The resin (A) may further include a structural unit which is decomposed upon exposure to radiation to generate an acid (hereinafter sometimes referred to as "structural unit (II)"). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferable.

The structural unit having a sulfonate group or a carboxylate group in a side chain is preferably a structural unit represented by formula (II-2-A'):

(II-2-A')
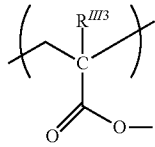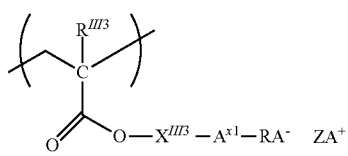

wherein, in formula (II-2-A'), $X^{III3}$ represents a divalent saturated hydrocarbon group having 1 to 18 carbon atoms, —$CH_2$— included in the saturated hydrocarbon group may be replaced by —O—, —S— or —CO—, and a hydrogen atom included in the saturated hydrocarbon group may be substituted with a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms which may be substituted with $A^{x1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or polycyclic divalent alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group are replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site, and * represents a bond to $A^{x1}$.

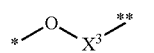 (X1)

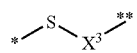 (X2)

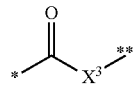 (X3)

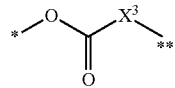 (X4)

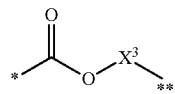 (X5)

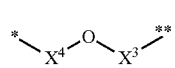 (X6)

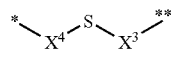 (X7)

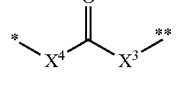 (X8)

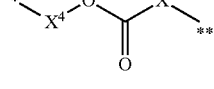 (X9)

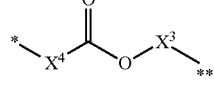 (X10)

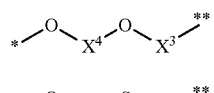 (X11)

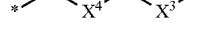 (X12)

-continued

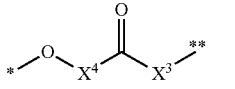 (X13)

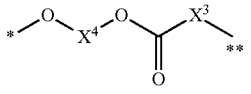 (X14)

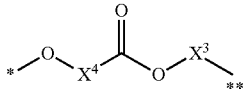 (X15)

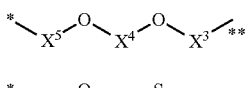 (X16)

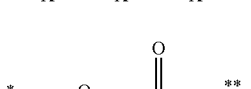 (X17)

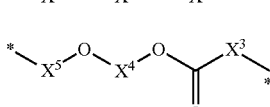 (X18)

 (X19)

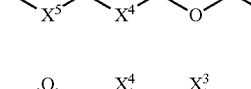 (X20)

 (X21)

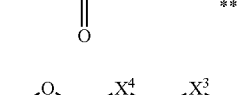 (X22)

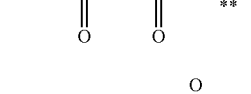 (X23)

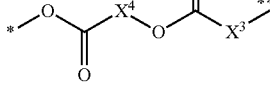 (X24)

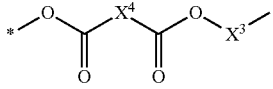 (X25)

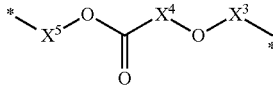 (X26)

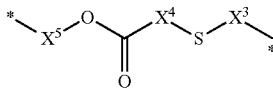 (X27)

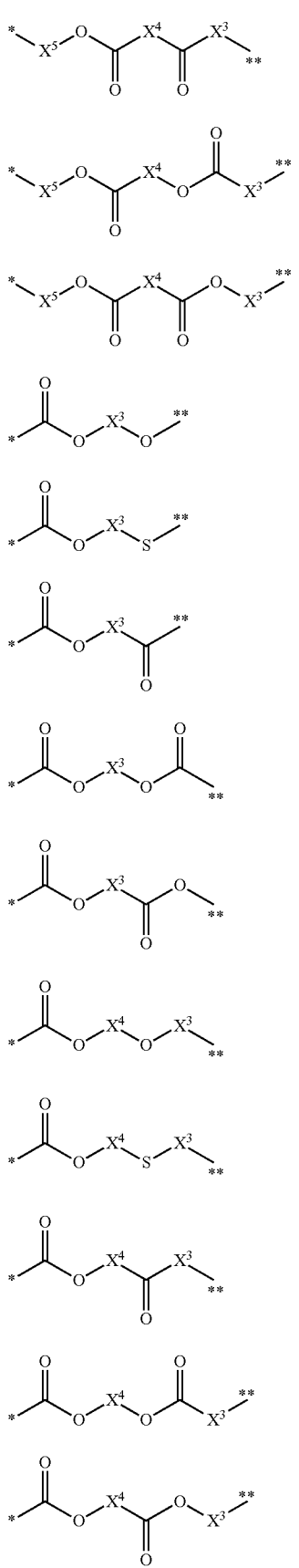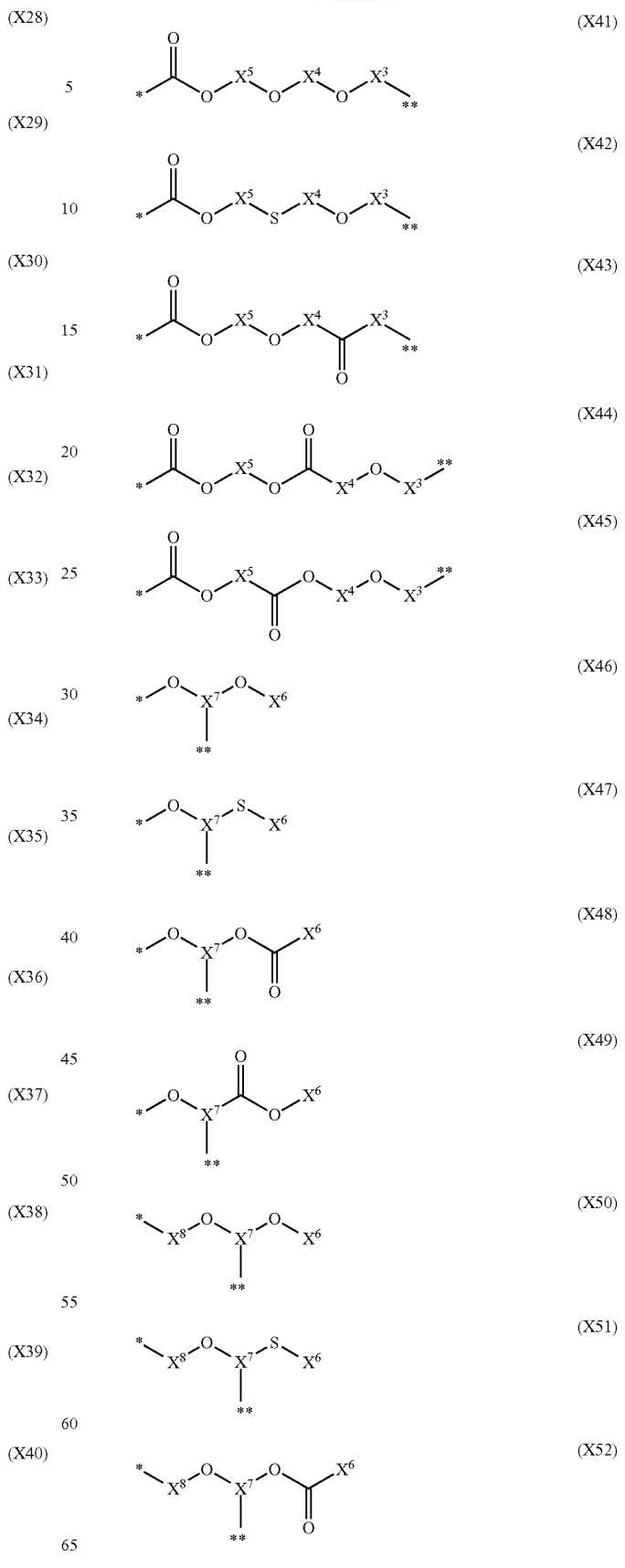

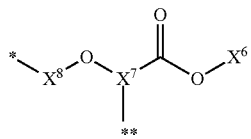

(X53)

$X^3$ represents a divalent saturated hydrocarbon group having 1 to 16 carbon atoms.

$X^4$ represents a divalent saturated hydrocarbon group having 1 to 15 carbon atoms.

$X^5$ represents a divalent saturated hydrocarbon group having 1 to 13 carbon atoms.

$X^6$ represents a divalent saturated hydrocarbon group having 1 to 14 carbon atoms.

$X^7$ represents a divalent saturated hydrocarbon group having 1 to 14 carbon atoms.

$X^8$ represents a divalent saturated hydrocarbon group having 1 to 13 carbon atoms.

Examples of $ZA^+$ in formula (II-2-A') include those which are the same as the cation $Z^+$ in the salt represented by formula (B1) mentioned later.

The structural unit represented by formula (II-2-A') is preferably a structural unit represented by formula (II-2-A):

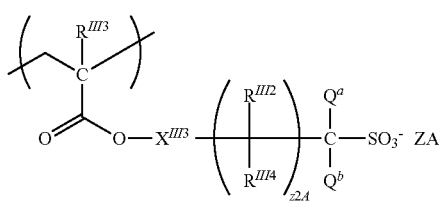

(II-2-A)

wherein, in formula (II-2-A), $R^{III3}$, $X^{III3}$ and $ZA^+$ are the same as defined above, z2A represents an integer of 0 to 6, $R^{III2}$ and $R^{III4}$ each independently represent a hydrogen atom, a fluorine atom or a perfluoroalkyl group having 1 to 6 carbon atoms, and when z2A is 2 or more, a plurality of $R^{III2}$ and $R^{III4}$ may be the same or different from each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms represented by the below-mentioned $Q^{b1}$.

The structural unit represented by formula (II-2-A) is preferably a structural unit represented by formula (II-2-A-1):

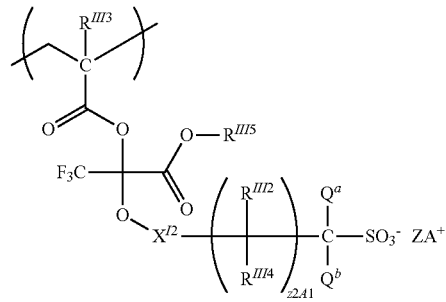

(II-2-A-1)

wherein, in formula (II-2-A-1), $R^{III2}$, $R^{III3}$, $R^{III4}$, $Q^a$, $Q^b$ and $ZA^+$ are the same as defined above, $R^{III5}$ represents a saturated hydrocarbon group having 1 to 12 carbon atoms, z2A1 represents an integer of 0 to 6, and $X^{I2}$ represents a divalent saturated hydrocarbon group having 1 to 11 carbon atoms, —$CH_2$— included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{I2}$ include the same as those of the divalent saturated hydrocarbon group represented by $X^{III3}$.

The structural unit represented by formula (II-2-A-1) is more preferably a structural unit represented by formula (II-2-A-2):

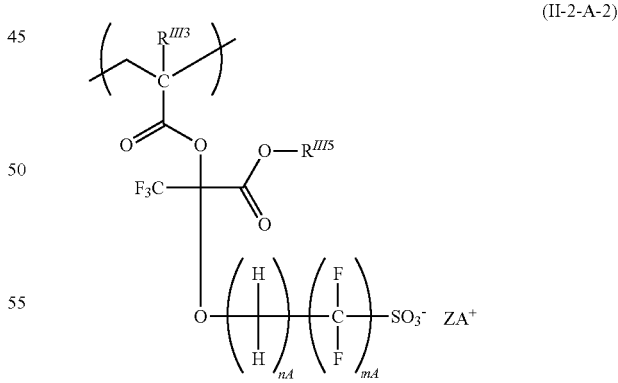

(II-2-A-2)

wherein, in formula (II-2-A-2), $R^{III3}$, $R^{III5}$ and $ZA^+$ are the same as defined above, and mA and nA each independently represent 1 or 2.

Examples of structural unit represented by the formula (II-2-A') include the following structural units, structural units in which a group corresponding to a methyl group of $R^{III3}$ is substituted with a hydrogen atom, a halogen atom (e.g., a fluorine atom) or an alkyl group having 1 to 6 carbon atoms which may have a halogen atom (e.g., a trifluoromethyl group, etc.), and the structural units mentioned in WO 2012/050015 A. $ZA^+$ represents an organic cation.

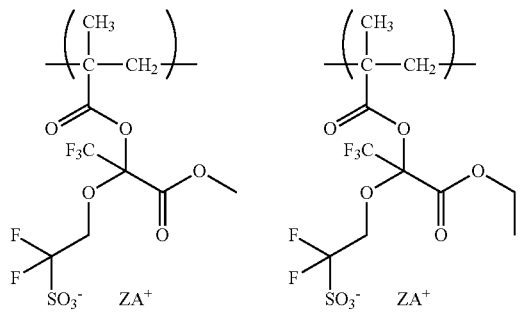

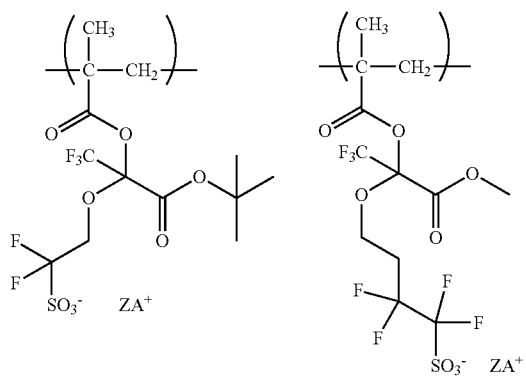

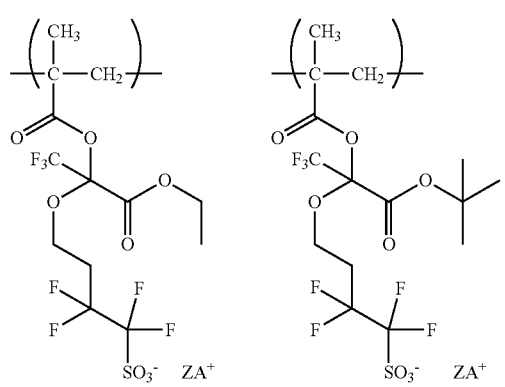

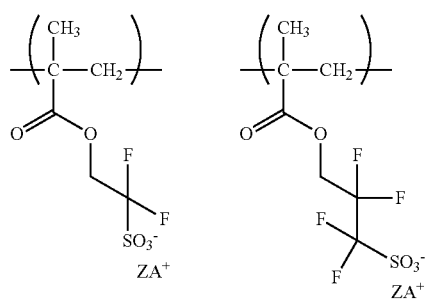

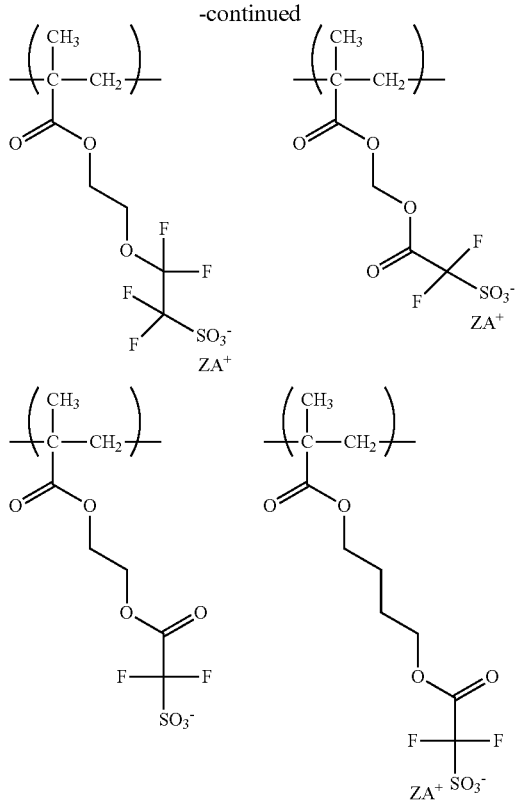

The structural unit having a sulfonio group and an organic anion in a side chain is preferably a structural unit represented by formula (II-1-1):

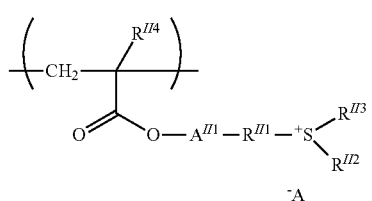

(II-1-1)

wherein, in formula (II-1-1),
$A^{II1}$ represents a single bond or a divalent linking group,
$R^{II1}$ represents a divalent aromatic hydrocarbon group having 6 to 18 carbon atoms,
$R^{II2}$ and $R^{II3}$ each independently represent a hydrocarbon group having 1 to 18 carbon atoms, and $R^{II2}$ and $R^{II3}$ may be bonded each other to form a ring together with a sulfur atom to which $R^{II2}$ and $R^{II3}$ are bonded,
$R^{II4}$ represents a hydrogen atom, a halogen atom or an alkyl group having 1 to 6 carbon atoms which may have a halogen atom, and
$A^-$ represents an organic anion.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include an alkyl group, an alicyclic hydrocarbon group, an aromatic hydrocarbon group, and groups formed by combining these groups.

Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the divalent linking group represented by include a divalent saturated hydrocarbon group having 1 to 18 carbon atoms, and —$CH_2$— included in the divalent saturated hydrocarbon group may be replaced by —O—, —S— or —CO—. Specific examples thereof include those which are the same as the divalent saturated hydrocarbon group having 1 to 18 carbon atoms represented by $X^{III3}$.

Examples of the structural unit including a cation in formula (II-1-1) include the following structural units and structural units in which a group corresponding to a methyl group of $R^{II4}$ is substituted with a hydrogen atom, a fluorine atom, a trifluoromethyl group or the like.

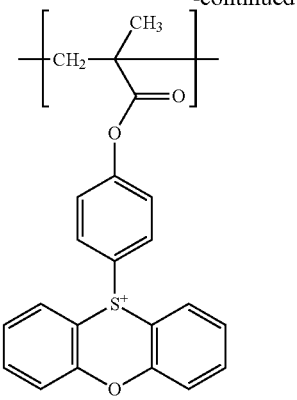

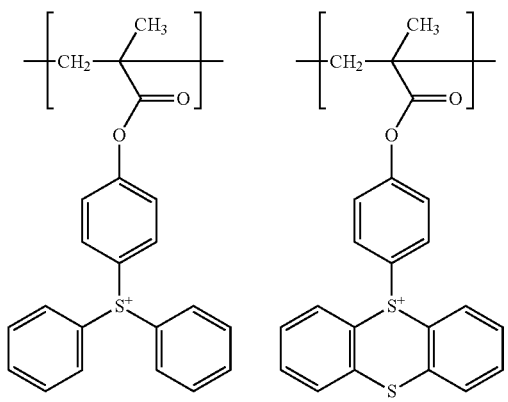

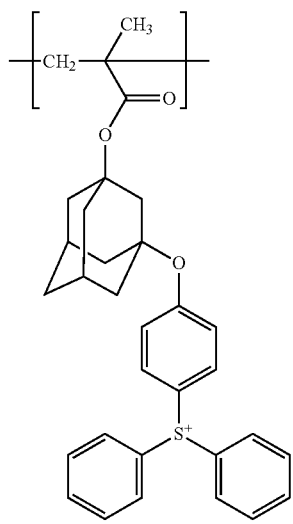

-continued

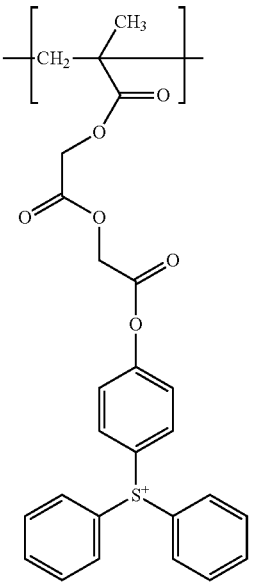

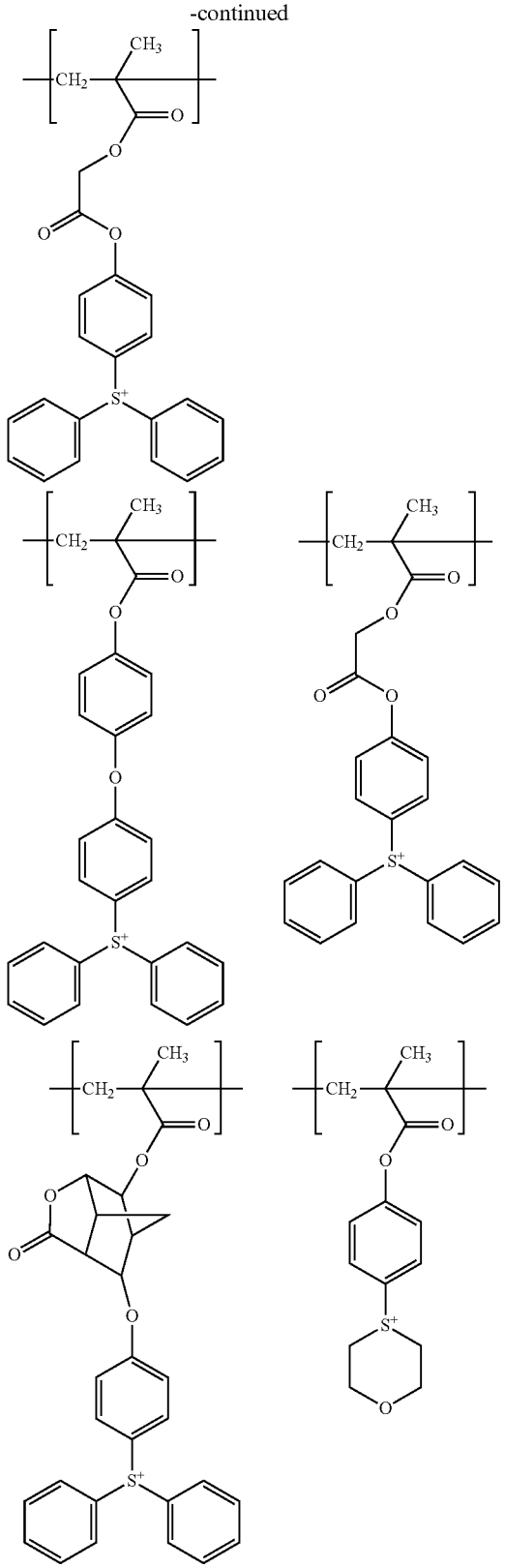

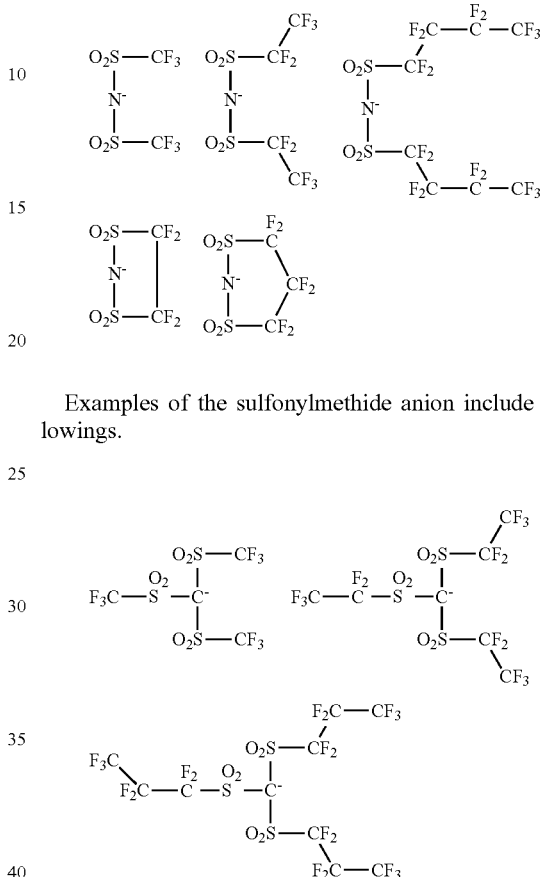

sulfonic acid anion is more preferably an anion included in the below-mentioned salt represented by formula (B1).

Examples of the sulfonylimide anion represented by $A^-$ include the followings.

Examples of the sulfonylmethide anion include the followings.

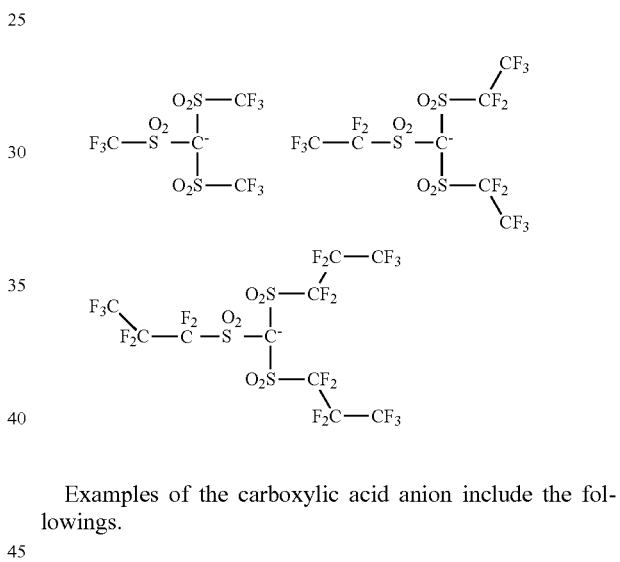

Examples of the carboxylic acid anion include the followings.

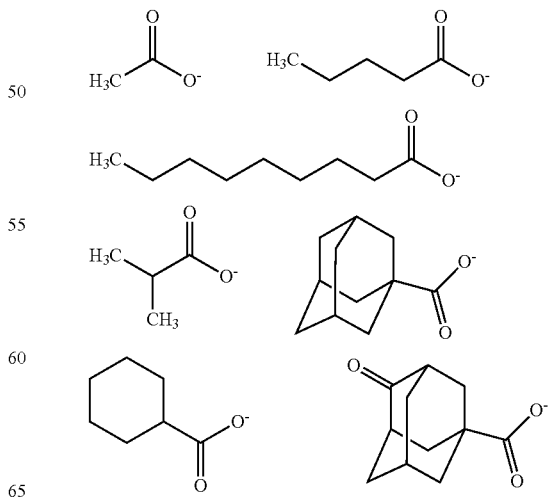

Examples of the organic anion represented by $A^-$ include a sulfonic acid anion, a sulfonylimide anion, a sulfonylmethide anion and a carboxylic acid anion. The organic anion represented by $A^-$ is preferably a sulfonic acid anion, and the

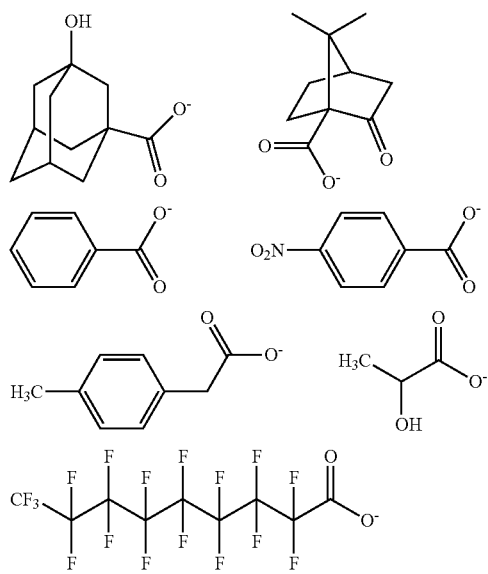
Examples of the structural unit represented by formula (II-1-1) include the following structural units.
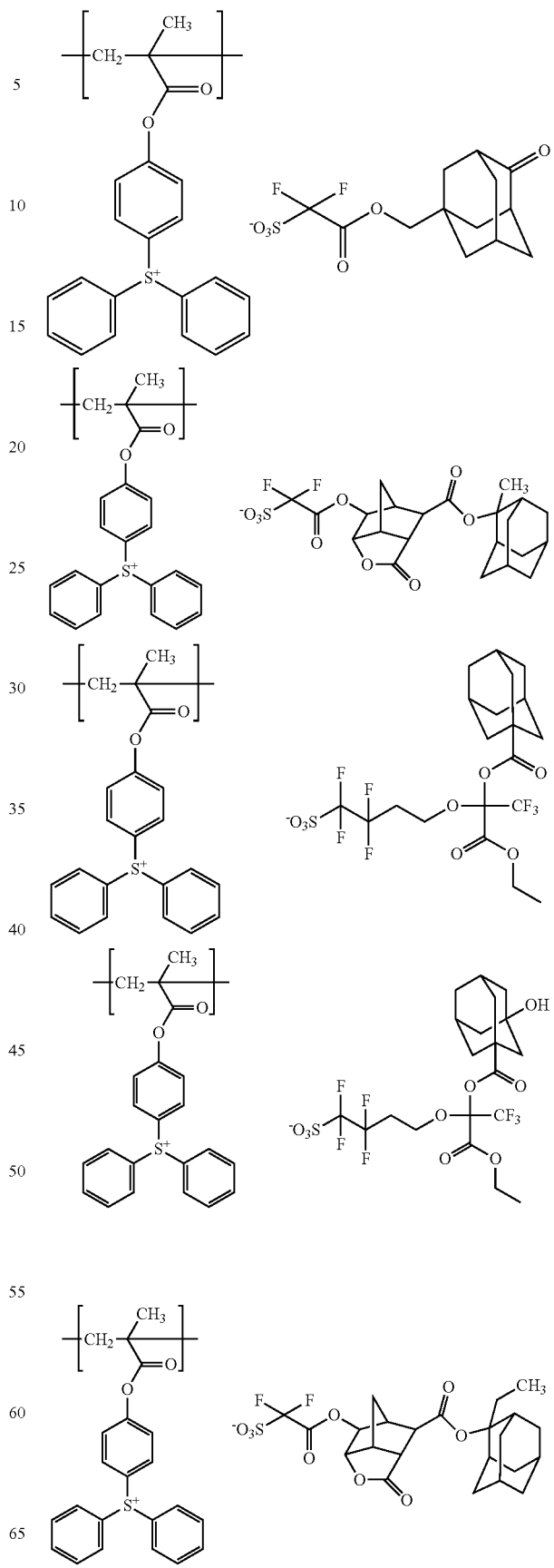

-continued

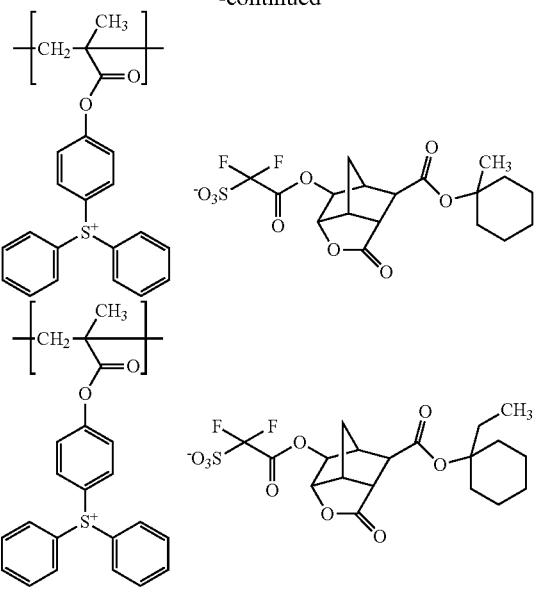

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include a structural unit other than the above-mentioned structural units, and examples of the structural unit include structural units well-known in this technical field.

The resin (A) is preferably a resin composed of a structural unit (I), a resin composed of a structural unit (I) and a structural unit (a1), a resin composed of a structural unit (I) and a structural unit (s), a resin composed of a structural unit (I), a structural unit (a1) and a structural unit (s), a resin composed of a structural unit (I), a structural unit (a1), a structural unit (s), a structural unit (a4) and/or a structural unit (a5), a resin composed only of a structural unit (I), or a resin composed only of a structural unit (I) and a structural unit (a4), and more preferably a resin composed of a structural unit (I), a resin composed of a structural unit (I) and a structural unit (a1), a resin composed of a structural unit (I), a structural unit (a1) and a structural unit (s), a resin composed of a structural unit (I) and a structural unit (s), or a resin composed only of a structural unit (I), a structural unit (a4) and a structural unit (a5), a resin composed only of a structural unit (I) and a structural unit (a4), a resin composed only of a structural unit (I), a structural unit (a4) and a structural unit (a1).

The structural unit (a1) is preferably at least one selected from the group consisting of a structural unit (a1-0), a structural unit (a1-0X), a structural unit (a1-1) and a structural unit (a1-2) (preferably the structural unit having a cyclohexyl group and a cyclopentyl group), and more preferably at least two selected from the group consisting of a structural unit (a1-0), a structural unit (a1-0X), a structural unit (a1-1) and a structural unit (a1-2) (preferably the structural unit having a cyclohexyl group or a cyclopentyl group).

The structural unit (s) is preferably at least one selected from the group consisting of a structural unit (a2) and a structural unit (a3). The structural unit (a2) is preferably a structural unit (a2-A) or a structural unit (a2-1). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g., radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less).

In the present specification, the weight-average molecular weight is a value determined by gel permeation chromatography. The gel permeation chromatography can be measured under the analysis conditions mentioned in Examples.

[Resist Composition]

The resist composition of the present disclosure preferably includes a resin (A) and an acid generator known in a resist field (hereinafter sometimes referred to as "acid generator (B)").

The resist composition of the present disclosure may further include a resin other than resin (A).

The resist composition of the present disclosure preferably includes a quencher such as a salt generating an acid having an acidity lower than that of an acid generated from an acid generator (hereinafter sometimes referred to as "quencher (C)"), and preferably includes a solvent (hereinafter sometimes referred to as "solvent (E)").

<Resin Other than Resin (A)>

In the resist composition of the present disclosure, a resin other than resin (A) may be used in combination. The resin other than resin (A) is a resin including no structural unit (I), and examples of the resin include a resin including a structural unit having an acid-labile group and including no structural unit (I) (hereinafter sometimes referred to as "resin (A2)"), a resin composed only of a structural unit (a4) and a resin composed of a structural unit (a4) and a structural unit (a5) (hereinafter, a resin composed only of a structural unit (a4) and a resin composed of a structural unit (a4) and a structural unit (a5) may be sometimes referred collectively as resin (X)).

In the resin (X), the content of the structural unit (a4) is preferably 30 mol % or more, more preferably 40 mol % or more, and still more preferably 45 mol % or more, based on the total of all structural units of the resin (X).

The respective structural unit constituting the resin (X) may be used alone, or two or more structural units may be used in combination. Using a monomer from which these structural units are derived, it is possible to produce by a known polymerization method (e.g., radical polymerization method). The content of the respective structural units included in the resin (X) can be adjusted according to the amount of the monomer used in the polymerization.

The weight-average molecular weight of the resin (A2) and the resin (X) is each independently preferably 6,000 or more (more preferably 7,000 or more), and 80,000 or less (more preferably 60,000 or less). The measurement means of the weight-average molecular weight of the resin (A2) and the resin (X) is the same as in the case of the resin (A).

When the resist composition of the present disclosure includes the resin (A2), the content is usually 1 to 2,500 parts by mass (more preferably 10 to 1,000 parts by mass) based on 100 parts by mass of the resin (A).

When the resist composition includes the resin (X), the content is preferably 1 to 60 parts by mass, more preferably 1 to 50 parts by mass, still more preferably 1 to 40 parts by mass, yet more preferably 1 to 30 parts by mass, and further preferably 1 to 8 parts by mass, based on 100 parts by mass of the resin (A).

The content of the resin (A) in the resist composition is preferably 80% by mass or more and 99% by mass or less, and more preferably 90% by mass or more and 99% by mass or less, based on the solid component of the resist composition. When including the resin other than the resin (A), the total content of the resin (A) and the resin other than the resin (A) is preferably 80% by mass or more and 99% by mass or less, and more preferably 90% by mass or more and 99% by mass or less, based on the solid component of the resist composition. The solid component of the resist composition and the content of the resin thereto can be measured by a known analysis means such as liquid chromatography or gas chromatography.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a fluorine-containing acid generator, and more preferably a salt represented by formula (B1) (hereinafter sometimes referred to as "acid generator (B1)"):

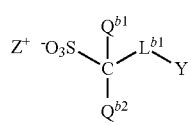

(B1)

wherein, in formula (B1),
$Q^{b1}$ and $Q^{b2}$ each independently represent a fluorine atom or a perfluoroalkyl group having 1 to 6 carbon atoms,
$L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the saturated hydrocarbon group may be substituted with a fluorine atom or a hydroxy group,
Y represents a methyl group which may have a substituent or an alicyclic hydrocarbon group having 3 to 24 carbon atoms which may have a substituent, and —$CH_2$— included in the alicyclic hydrocarbon group may be replaced by —O—, —$SO_2$— or —CO—, and
$Z^+$ represents an organic cation.

Examples of the perfluoroalkyl group represented by $Q^{b1}$ and $Q^{b2}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Preferably, $Q^{b1}$ and $Q^{b2}$ are each independently a fluorine atom or a trifluoromethyl group, and more preferably, both are fluorine atoms.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by using two or more of these groups in combination.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which —$CH_2$— included in the divalent saturated hydrocarbon group represented by $L^{b1}$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site, and * represents a bond to —Y.

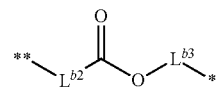

(b1-1)

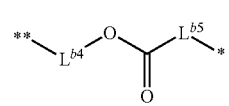

(b1-2)

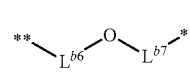

(b1-3)

In formula (b1-1), $L^{b2}$ represents a single bond or a divalent saturated hydrocarbon group having 1 to 22 carbon atoms, and a hydrogen atom included in the saturated hydrocarbon group may be substituted with a fluorine atom, $L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b2}$ and $L^{b3}$ is 22 or less.

In formula (b1-2), $L^{b4}$ represents a single bond or a divalent saturated hydrocarbon group having 1 to 22 carbon atoms, and a hydrogen atom included in the saturated hydrocarbon group may be substituted with a fluorine atom, $L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b4}$ and $L^{b5}$ is 22 or less.

In formula (b1-3), $L^{b6}$ represents a single bond or a divalent saturated hydrocarbon group having 1 to 23 carbon atoms, and a hydrogen atom included in the saturated hydrocarbon group may be substituted with a fluorine atom or a hydroxy group, $L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and —CH$_2$— included in the saturated hydrocarbon group may be replaced by —O— or —CO—, and the total number of carbon atoms of $L^{b6}$ and $L^{b7}$ is 23 or less.

In groups represented by formula (b1-1) to formula (b1-3), when —CH$_2$— included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the saturated hydrocarbon group of $L^{b1}$.

$L^{b2}$ is preferably a single bond.

$L^{b3}$ is preferably a divalent saturated hydrocarbon group having 1 to 4 carbon atoms.

$L^{b4}$ is preferably a divalent saturated hydrocarbon group having 1 to 8 carbon atoms, and a hydrogen atom included in the divalent saturated hydrocarbon group may be substituted with a fluorine atom.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and —CH$_2$— included in the divalent saturated hydrocarbon group may be replaced by —O— or —CO—.

The group in which —CH$_2$— included in the divalent saturated hydrocarbon group represented by $L^{b1}$ is replaced by —O— or —CO— is preferably a group represented by formula (b1-1) or formula (b1-3).

Examples of the group represented by formula (b1-1) include groups represented by formula (b1-4) to formula (b1-8).

(b1-4)

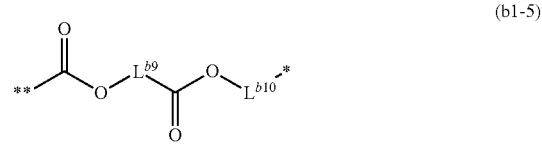

(b1-5)

(b1-6)

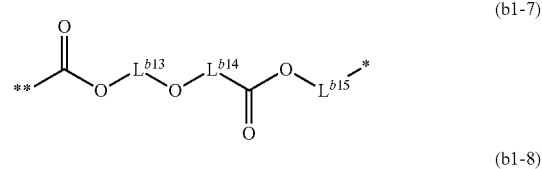

(b1-7)

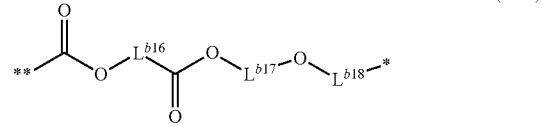

(b1-8)

In formula (b1-4), $L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5), $L^{b9}$ represents a divalent saturated hydrocarbon group having 1 to 20 carbon atoms, and —CH$_2$— included in the divalent saturated hydrocarbon group may be replaced by —O— or —CO—, $L^{b10}$ represents a single bond or a saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b20}$ is 20 or less.

In formula (b1-6), $L^{b11}$ represents a divalent saturated hydrocarbon group having 1 to 21 carbon atoms, $L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b11}$ and $L^{b12}$ is 21 or less.

In formula (b1-7),
$L^{b13}$ represents a divalent saturated hydrocarbon group having 1 to 19 carbon atoms,
$L^{b14}$ represents a single bond or a divalent saturated hydrocarbon group having 1 to 18 carbon atoms, and —CH$_2$— included in the divalent saturated hydrocarbon group may be replaced by —O— or —CO—,
$L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and the total number of carbon atoms of $L^{b13}$ to $L^{b15}$ is 19 or less.

In formula (b1-8),
$L^{b16}$ represents a divalent saturated hydrocarbon group having 1 to 18 carbon atoms, and —CH$_2$— included in the divalent saturated hydrocarbon group may be replaced by —O— or —CO—,
$L^{b17}$ represents a divalent saturated hydrocarbon group having 1 to 18 carbon atoms,
$L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and
the total number of carbon atoms of $L^{b16}$ to $L^{b18}$ is 19 or less.

$L^{b8}$ is preferably a divalent saturated hydrocarbon group having 1 to 4 carbon atoms.
$L^{b9}$ is preferably a divalent saturated hydrocarbon group having 1 to 8 carbon atoms.
$L^{b10}$ is preferably a single bond or a divalent saturated hydrocarbon group having 1 to 19 carbon atoms, and more preferably a single bond or a divalent saturated hydrocarbon group having 1 to 8 carbon atoms.
$L^{b11}$ is preferably a divalent saturated hydrocarbon group having 1 to 8 carbon atoms.
$L^{b12}$ is preferably a single bond or a divalent saturated hydrocarbon group having 1 to 8 carbon atoms.
$L^{b13}$ is preferably a divalent saturated hydrocarbon group having 1 to 12 carbon atoms.
$L^{b14}$ is preferably a single bond or a divalent saturated hydrocarbon group having 1 to 6 carbon atoms.
$L^{b15}$ is preferably a divalent saturated hydrocarbon group having 1 to 18 carbon atoms, and more preferably a single bond or a divalent saturated hydrocarbon group having 1 to 8 carbon atoms.
$L^{b16}$ is preferably a divalent saturated hydrocarbon group having 1 to 12 carbon atoms.
$L^{b17}$ is preferably a divalent saturated hydrocarbon group having 1 to 6 carbon atoms.
$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

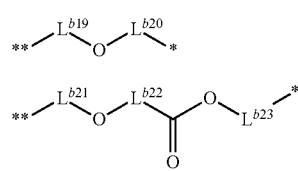

(b1-9)

(b1-10)

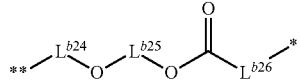

(b1-11)

In formula (b1-9),
$L^{b19}$ represents a single bond or a divalent saturated hydrocarbon group having 1 to 23 carbon atoms, and a hydrogen atom included in the saturated hydrocarbon group may be substituted with a fluorine atom,
$L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b19}$ and $L^{b20}$ is 23 or less.

In formula (b1-10),
$L^{b21}$ represents a single bond or a divalent saturated hydrocarbon group having 1 to 21 carbon atoms, and a hydrogen atom included in the saturated hydrocarbon group may be substituted with a fluorine atom,
$L^{b22}$ represents a single bond or a divalent saturated hydrocarbon group having 1 to 21 carbon atoms,
$L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b21}$, $L^{b22}$ and $L^{b23}$ is 21 or less.

In formula (b1-11),
$L^{b24}$ represents a single bond or a divalent saturated hydrocarbon group having 1 to 20 carbon atoms, and a hydrogen atom included in the saturated hydrocarbon group may be substituted with a fluorine atom,
$L^{b25}$ represents a divalent saturated hydrocarbon group having 1 to 21 carbon atoms,
$L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, —CH$_2$— included in the alkylcarbonyloxy group may be replaced by —O— or —CO—, and a hydrogen atom included in the alkylcarbonyloxy group may be substituted with a hydroxy group, and
the total number of carbon atoms of $L^{b24}$, $L^{b25}$ and $L^{b26}$ is 21 or less.

In the group represented by formula (b1-9) to the group represented by formula (b1-11), when a hydrogen atom included in the saturated hydrocarbon group is substituted with an alkylcarbonyloxy group, the number of carbon atoms before substitution is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings:

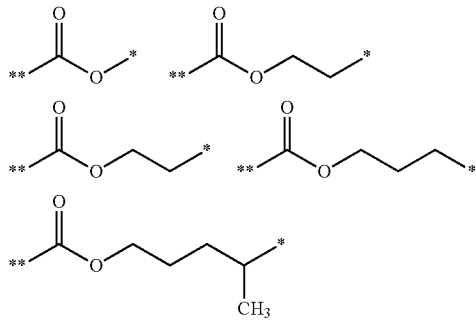

Examples of the group represented by formula (b1-5) include the followings:

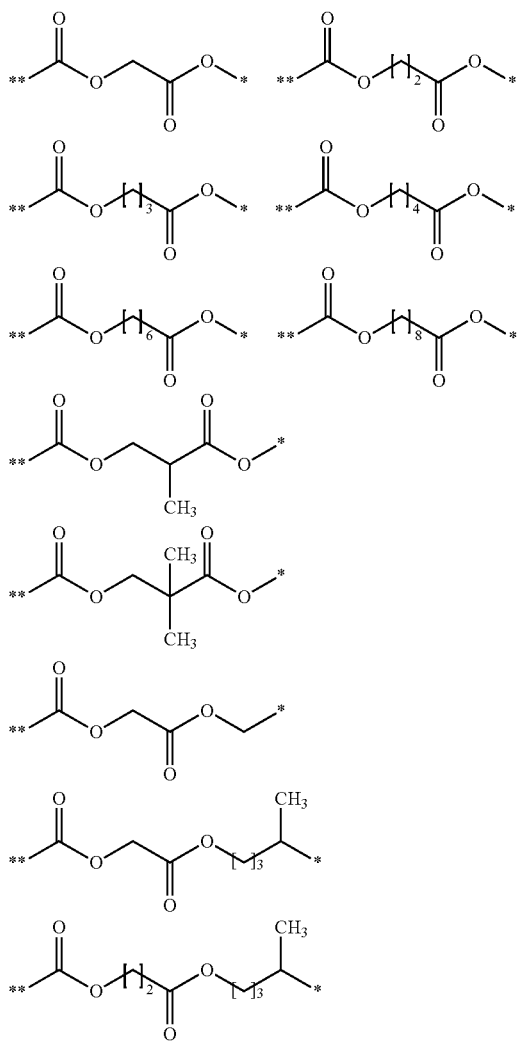

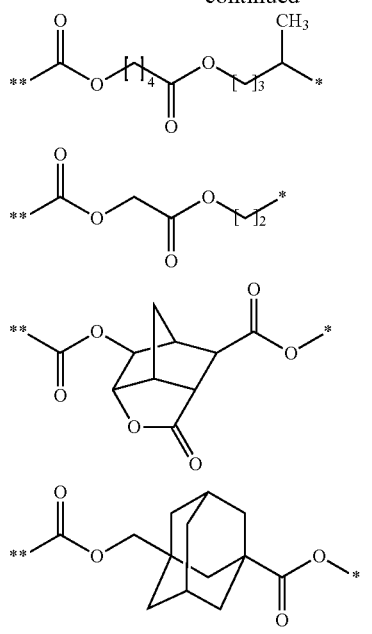

Examples of the group represented by formula (b1-6) include the followings:

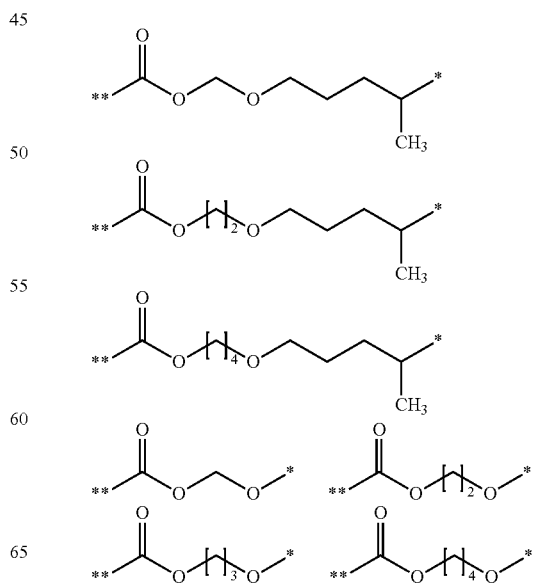

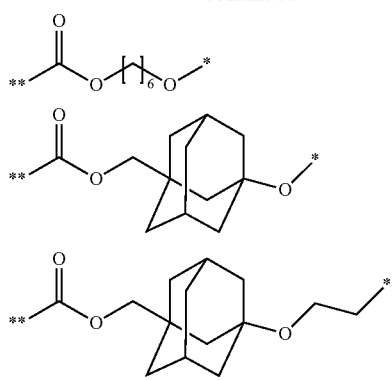
Examples of the group represented by formula (b1-7) include the followings:
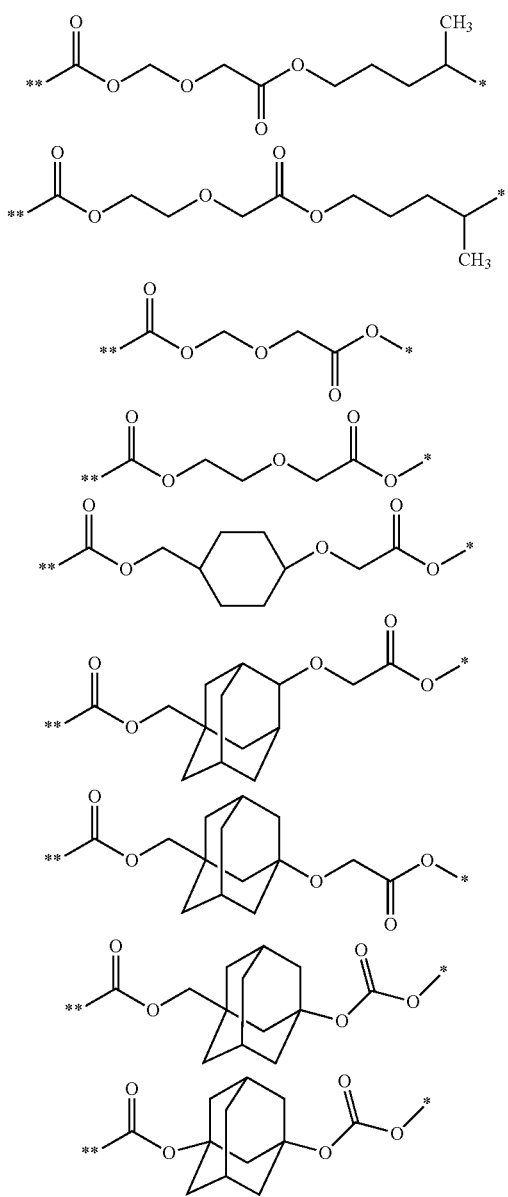
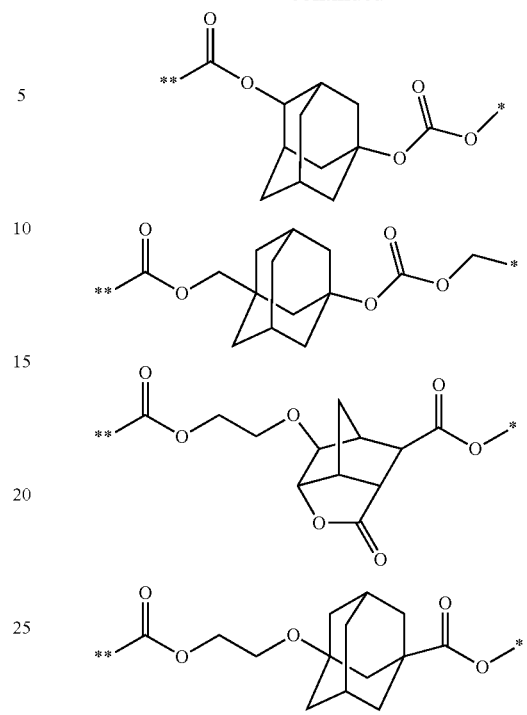
Examples of the group represented by formula (b1-8) include the followings:
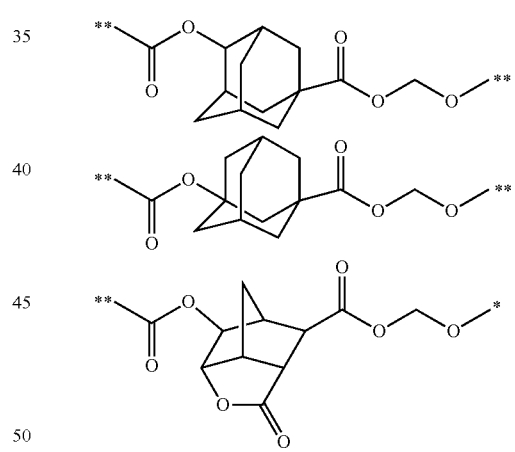
Examples of the group represented by formula (b1-2) include the followings:
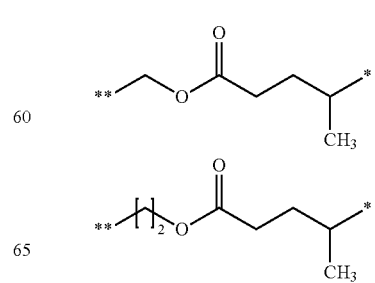

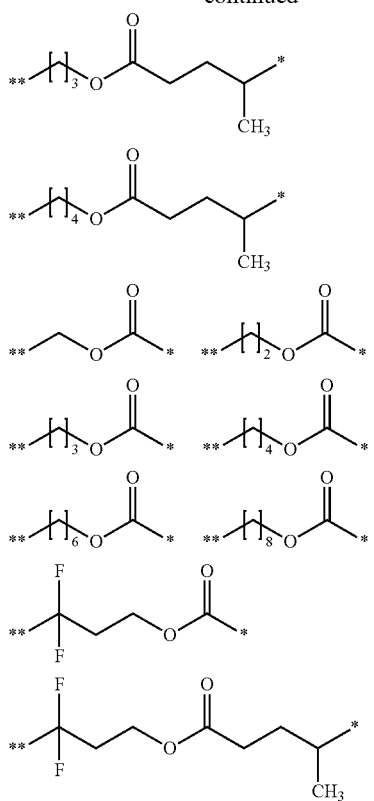
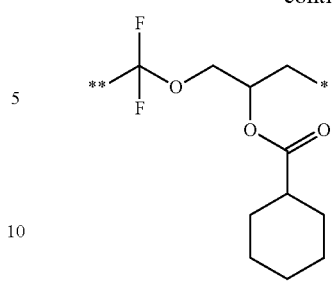
Examples of the group represented by formula (b1-9) include the followings:
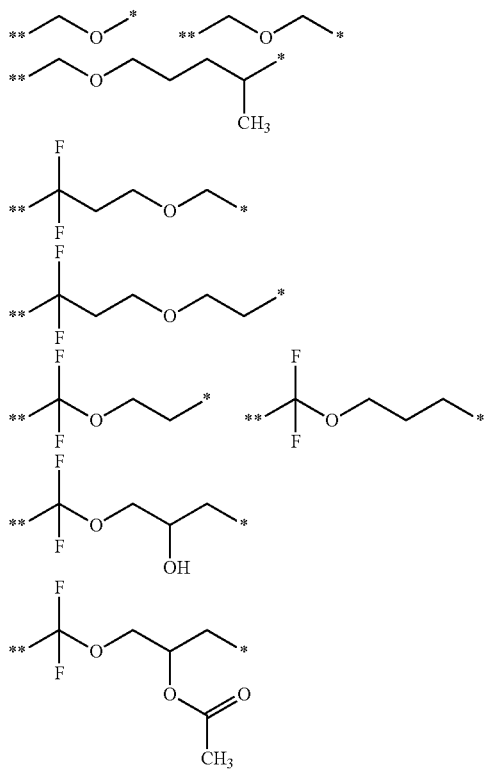
Examples of the group represented by formula (b1-10) include the followings:
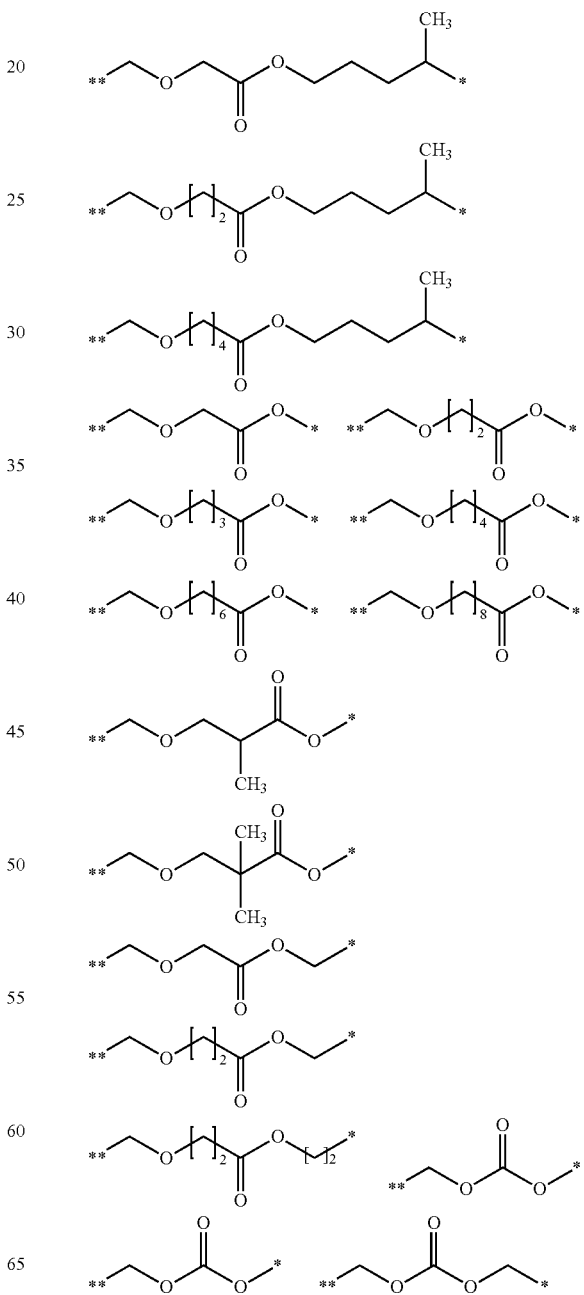

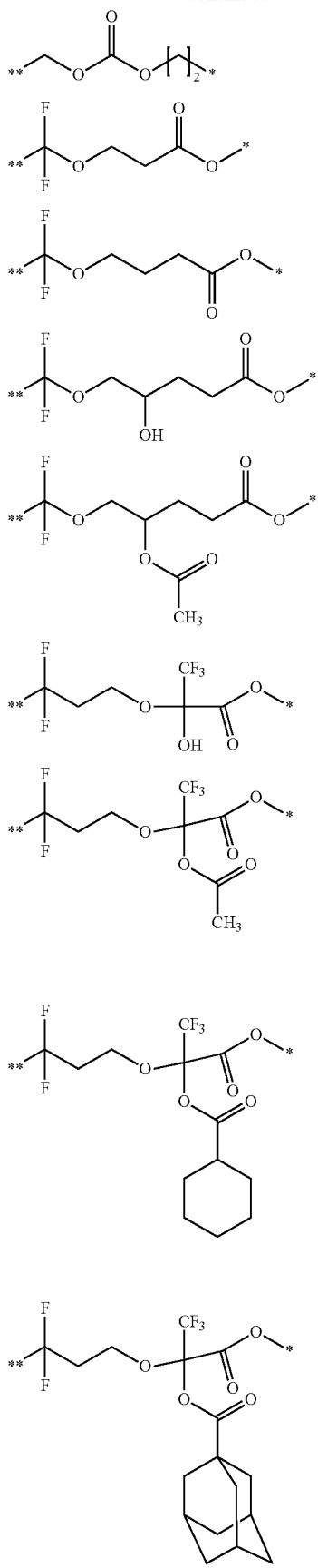
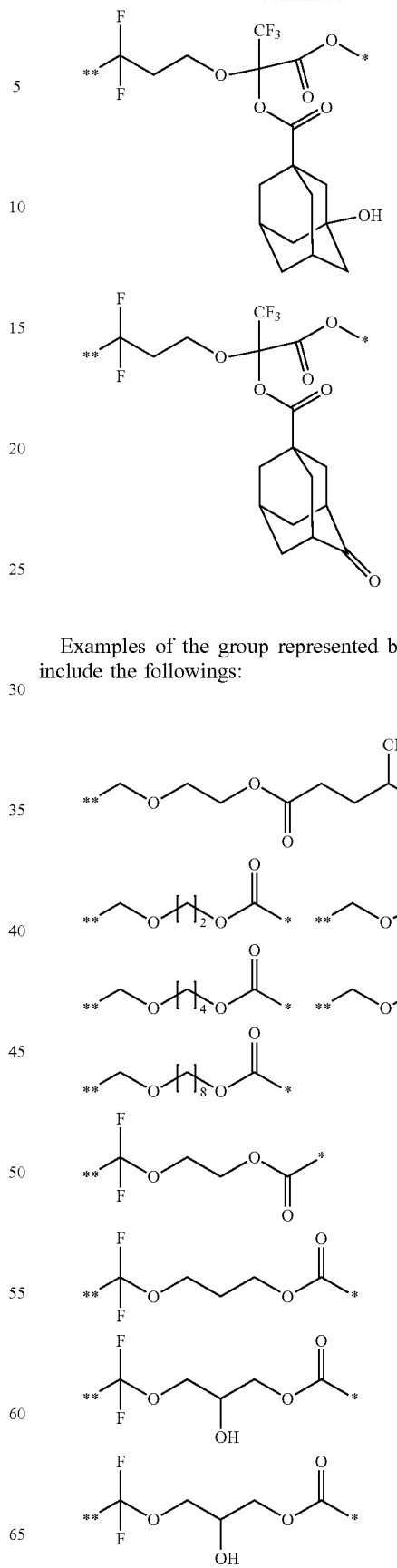
Examples of the group represented by formula (b1-11) include the followings:

-continued

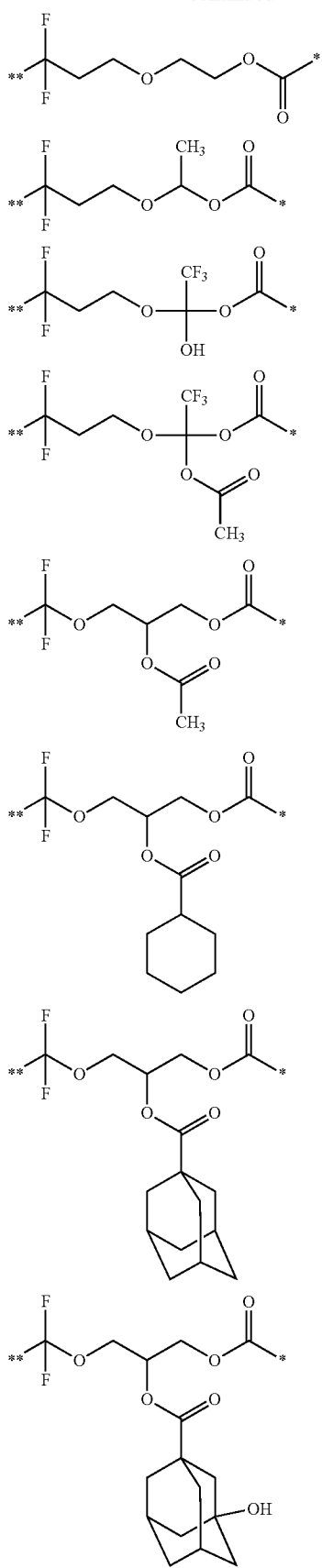

-continued

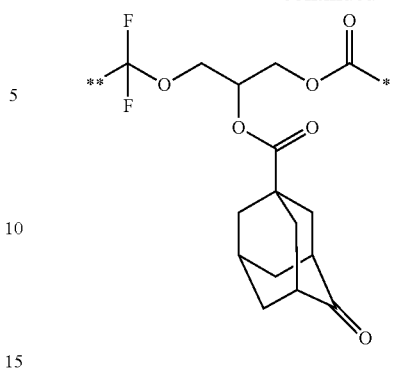

Examples of the alicyclic hydrocarbon group represented by Y include groups represented by formula (Y1) to formula (Y11) and formula (Y36) to formula (Y38).

When —$CH_2$— included in the alicyclic hydrocarbon group represented by Y is replaced by —O—, —$SO_2$— or —CO—, the number may be 1, or 2 or more. Examples of such group include groups represented by formula (Y12) to formula (Y35) and formula (Y39) and formula (Y43). * represents a bond to $L^{b1}$.

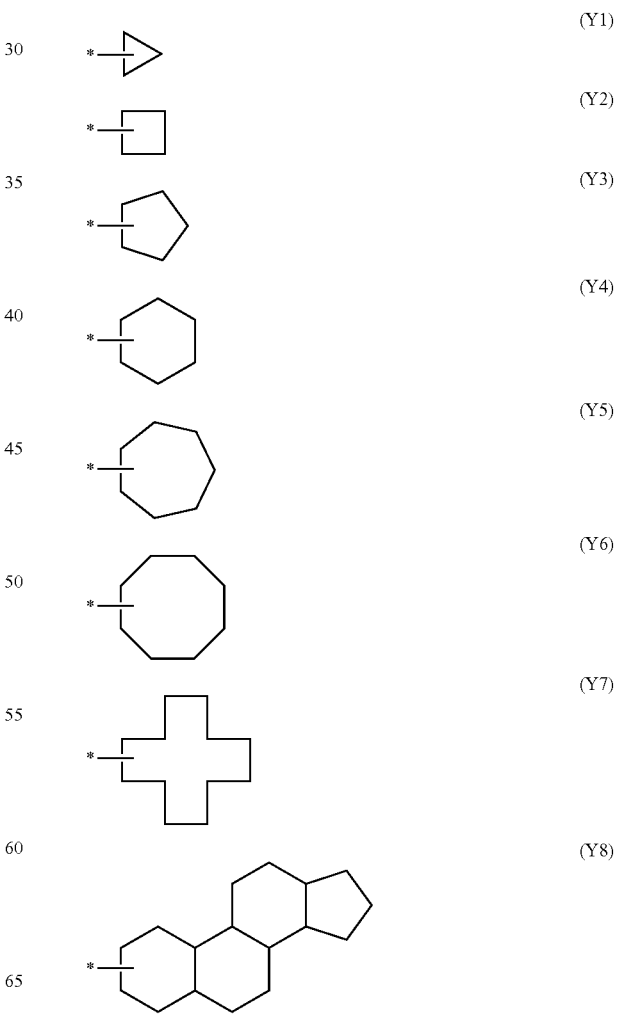

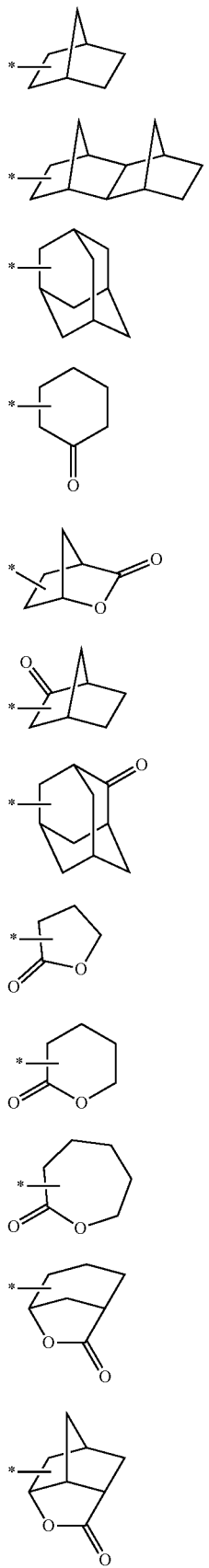
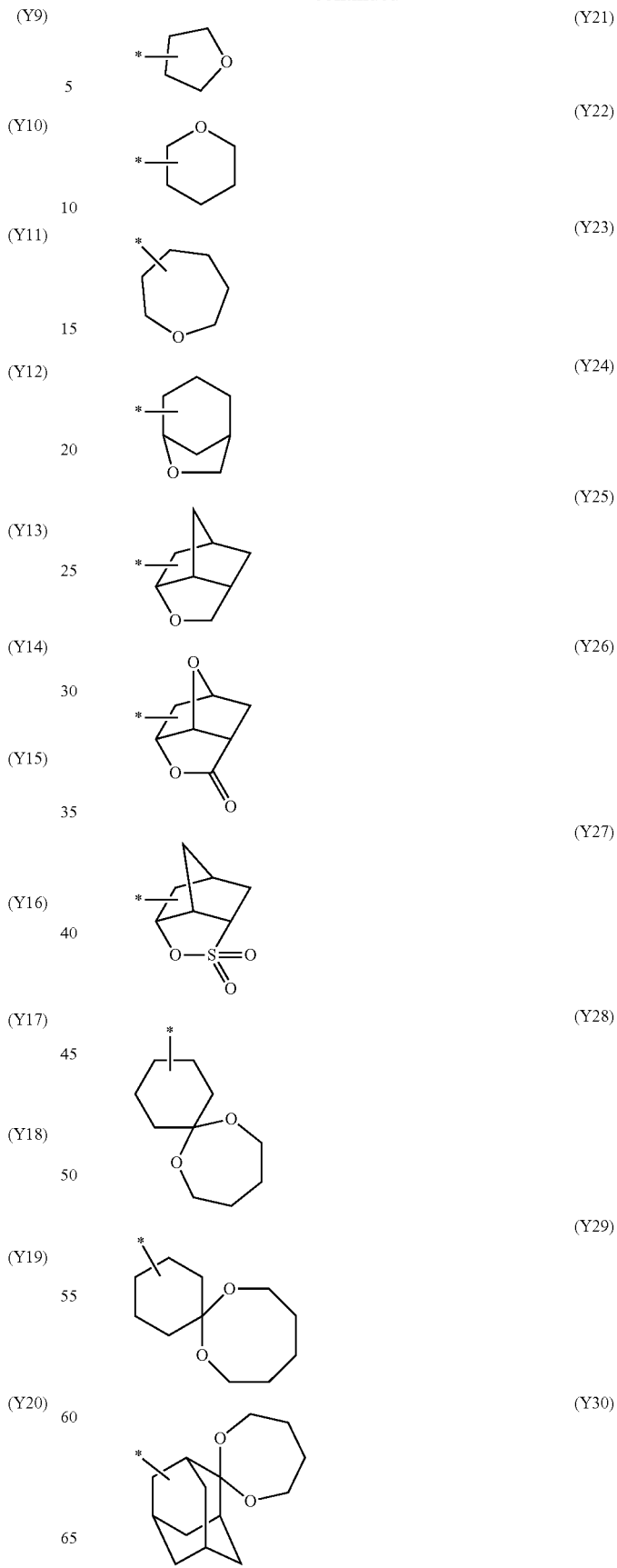

-continued (Y31) 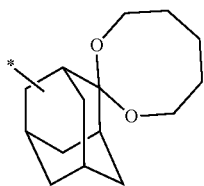

(Y32) 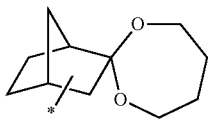

(Y33) 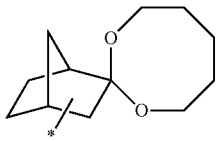

(Y34) 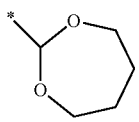

(Y35) 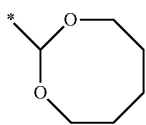

(Y36) 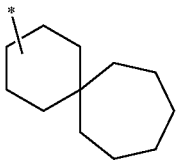

(Y37) 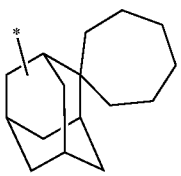

(Y38) 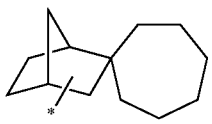

(Y39) 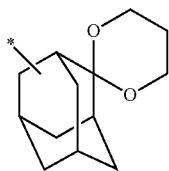

(Y40) 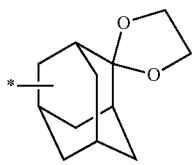

-continued (Y41) 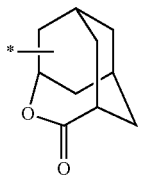

(Y42) 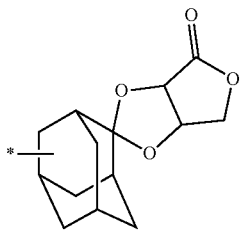

(Y43) 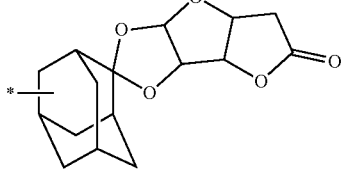

The alicyclic hydrocarbon group represented by Y is preferably a group represented by any one of formula (Y1) to formula (Y20), formula (Y26), formula (Y27), formula (Y30), formula (Y31) and formula (Y39) to formula (Y43), more preferably a group represented by formula (Y11), formula (Y15), formula (Y16), formula (Y20), formula (Y26), formula (Y27), formula (Y30), formula (Y31), formula (Y39), formula (Y40), formula (Y42) or formula (Y43), and still more preferably a group represented by formula (Y11), formula (Y15), formula (Y20), formula (Y26), formula (Y27), formula (Y30), formula (Y31), formula (Y39), formula (Y40), formula (Y42) or formula (Y43).

When the alicyclic hydrocarbon group represented by Y is a spiro ring having an oxygen atom, such as formula (Y28) to formula (Y35) and formula (Y39) or formula (Y40), formula (Y42) or formula (Y43), the alkanediyl group between two oxygen atoms preferably includes one or more fluorine atoms. Of alkanediyl groups included in a ketal structure, it is preferable that a methylene group adjacent to the oxygen atom is not substituted with a fluorine atom.

Examples of the substituent of the methyl group represented by Y include a halogen atom, a hydroxy group, an alicyclic hydrocarbon group having 3 to 16 carbon atoms, an aromatic hydrocarbon group having 6 to 18 carbon atoms, a glycidyloxy group, a —(CH$_2$)$_{ja}$—CO—O—R$^{b1}$ group or a —(CH$_2$)$_{ja}$—O—CO—R$^{b1}$ group (wherein R$^{b1}$ represents an alkyl group having 1 to 16 carbon atoms, an alicyclic hydrocarbon group having 3 to 16 carbon atoms, an aromatic hydrocarbon group having 6 to 18 carbon atoms, or groups obtained by combining these groups, —CH$_2$— included in the alkyl group and the alicyclic hydrocarbon group may be replaced by —O—, —SO$_2$— or —CO—, a hydrogen atom included in the alkyl group, the alicyclic hydrocarbon group and the aromatic hydrocarbon group may be substituted with a hydroxy group or a fluorine atom, and ja represents an integer of 0 to 4).

Examples of the substituent of the alicyclic hydrocarbon group represented by Y include a halogen atom, a hydroxy group, an alkyl group having 1 to 16 carbon atoms which may be substituted with a hydroxy group (—$CH_2$— included in the alkyl group may be replaced by —O— or —CO—), an alicyclic hydrocarbon group having 3 to 16 carbon atoms, an aromatic hydrocarbon group having 6 to 18 carbon atoms, an aralkyl group having 7 to 21 carbon atoms, a glycidyloxy group, a —$(CH_2)_{ja}$—CO—O—$R^{b1}$ group or a —$(CH_2)_{ja}$—O—CO—$R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or groups obtained by combining these groups, —$CH_2$— included in the alkyl group and the alicyclic hydrocarbon group may be replaced by —O—, —$SO_2$— or —CO—, a hydrogen atom included in the alkyl group, the alicyclic hydrocarbon group and the aromatic hydrocarbon group may be substituted with a hydroxy group or a fluorine atom, and ja represents an integer of 0 to 4).

Examples of the halogen atom include a fluorine atom, a chlorine atom, a bromine atom and an iodine atom.

Examples of the alicyclic hydrocarbon group include a cyclopentyl group, a cyclohexyl group, a methylcyclohexyl group, a dimethylcyclohexyl group, a cycloheptyl group, a cyclooctyl group, a norbornyl group, an adamantyl group and the like. The alicyclic hydrocarbon group may have a chain hydrocarbon group, and examples thereof include a methylcyclohexyl group, a dimethylcyclohexyl group and the like. The number of carbon atoms of the alicyclic hydrocarbon group is preferably 3 to 12, and more preferably 3 to 10.

Examples of the aromatic hydrocarbon group include aryl groups such as a phenyl group, a naphthyl group, an anthryl group, a biphenyl group and a phenanthryl group. The aromatic hydrocarbon group may have a chain hydrocarbon group or an alicyclic hydrocarbon group, and examples of the aromatic hydrocarbon group having a chain hydrocarbon group include a tolyl group, a xylyl group, a cumenyl group, a mesityl group, a p-ethylphenyl group, a p-tert-butylphenyl group, a 2,6-diethylphenyl group, a 2-methyl-6-ethylphenyl group and the like, and examples of the aromatic hydrocarbon group having an alicyclic hydrocarbon group include a p-cyclohexylphenyl group, a p-adamantylphenyl group and the like. The number of carbon atoms of the aromatic hydrocarbon group is preferably 6 to 14, and more preferably 6 to 10.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like. The number of carbon atoms of the alkyl group is preferably 1 to 12, more preferably 1 to 6, and still more preferably 1 to 4.

Examples of the alkyl group substituted with a hydroxy group include hydroxyalkyl groups such as a hydroxymethyl group and a hydroxyethyl group.

Examples of the aralkyl group include a benzyl group, a phenethyl group, a phenylpropyl group, a naphthylmethyl group and a naphthylethyl group.

Examples of the group in which —$CH_2$— included in the alkyl group is replaced by —O—, —$SO_2$— or —CO— include an alkoxy group, an alkylsulfonyl group, an alkoxycarbonyl group, an alkylcarbonyl group, an alkylcarbonyloxy group, or groups obtained by combining these groups.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. The number of carbon atoms of the alkoxy group is preferably 1 to 12, more preferably 1 to 6, and still more preferably 1 to 4.

Examples of the alkoxycarbonyl group include a methoxycarbonyl group, an ethoxycarbonyl group, a butoxycarbonyl group and the like. The number of carbon atoms of the alkoxycarbonyl group is preferably 2 to 12, more preferably 2 to 6, and still more preferably 2 to 4.

Examples of the alkylsulfonyl group include a methylsulfonyl group, an ethylsulfonyl group, a propylsulfonyl group and the like. The number of carbon atoms of the alkylsulfonyl group is preferably 1 to 11, more preferably 1 to 6, and still more preferably 1 to 4.

Examples of the alkylcarbonyl group include an acetyl group, a propionyl group and a butyryl group. The number of the alkylcarbonyl group is preferably 2 to 12, more preferably 2 to 6, and still more preferably 2 to 4.

Examples of the alkylcarbonyloxy group include an acetyloxy group, a propionyloxy group and a butyryloxy group. The number of the alkylcarbonyloxy group is preferably 2 to 12, more preferably 2 to 6, and still more preferably 2 to 4.

Examples of the combined group include a group obtained by combining an alkoxy group with an alkyl group, a group obtained by combining an alkoxy group with an alkoxy group, a group obtained by combining an alkoxy group with an alkylcarbonyl group, a group obtained by combining an alkoxy group with an alkylcarbonyloxy group and the like.

Examples of the group obtained by combining an alkoxy group with an alkyl group include alkoxyalkyl groups such as a methoxymethyl group, a methoxyethyl group, an ethoxyethyl group, an ethoxymethyl group and the like. The number of carbon atoms of the alkoxyalkyl group is preferably 2 to 12, more preferably 2 to 6, and still more preferably 2 to 4.

Examples of the group obtained by combining an alkoxy group with an alkoxy group include alkoxyalkoxy groups such as a methoxymethoxy group, a methoxyethoxy group, an ethoxymethoxy group, an ethoxyethoxy group and the like. The number of carbon atoms of the alkoxyalkoxy group is preferably 2 to 12, more preferably 2 to 6, and still more preferably 2 to 4.

Examples of the group obtained by combining an alkoxy group with an alkylcarbonyl group include alkoxyalkylcarbonyl groups such as a methoxyacetyl group, a methoxypropionyl group, an ethoxyacetyl group, an ethoxypropionyl group and the like. The number of carbon atoms of the alkoxyalkylcarbonyl group is preferably 3 to 13, more preferably 3 to 7, and still more preferably 3 to 5.

Examples of the group obtained by combining an alkoxy group with an alkylcarbonyloxy group include alkoxyalkylcarbonyloxy groups such as a methoxyacetyloxy group, a methoxypropionyloxy group, an ethoxyacetyloxy group, an ethoxypropionyloxy group and the like. The number of carbon atoms of the alkoxyalkylcarbonyloxy group is preferably 3 to 13, more preferably 3 to 7, and still more preferably 3 to 5.

Examples of the group in which —$CH_2$— included in the alicyclic hydrocarbon group is replaced by —O—, —$SO_2$— or —CO— include groups represented by formula (Y12) to formula (Y35), formula (Y39) to formula (Y43) and the like.

Examples of Y include the followings.
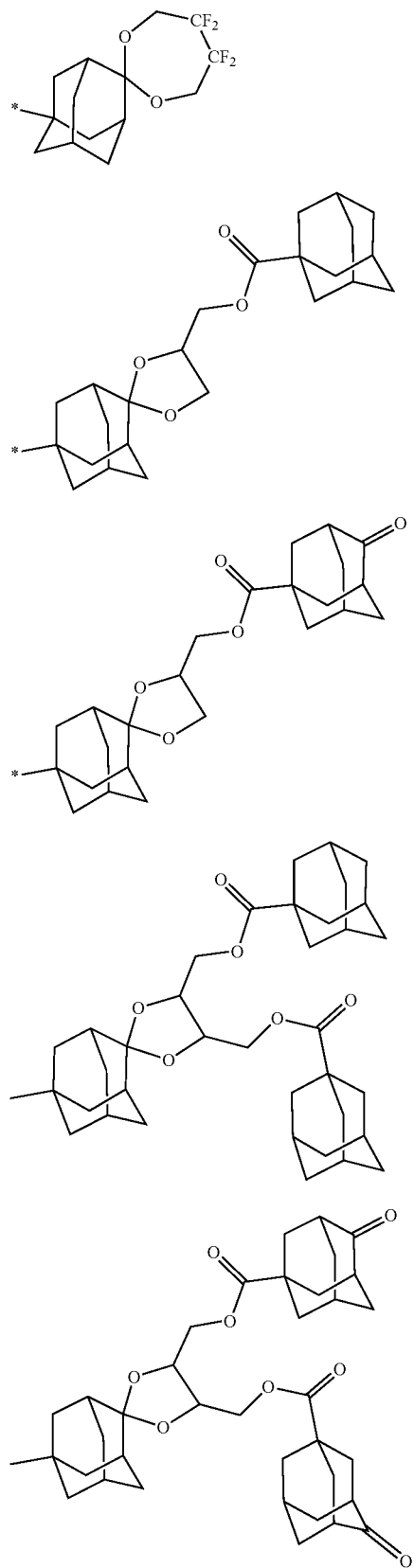
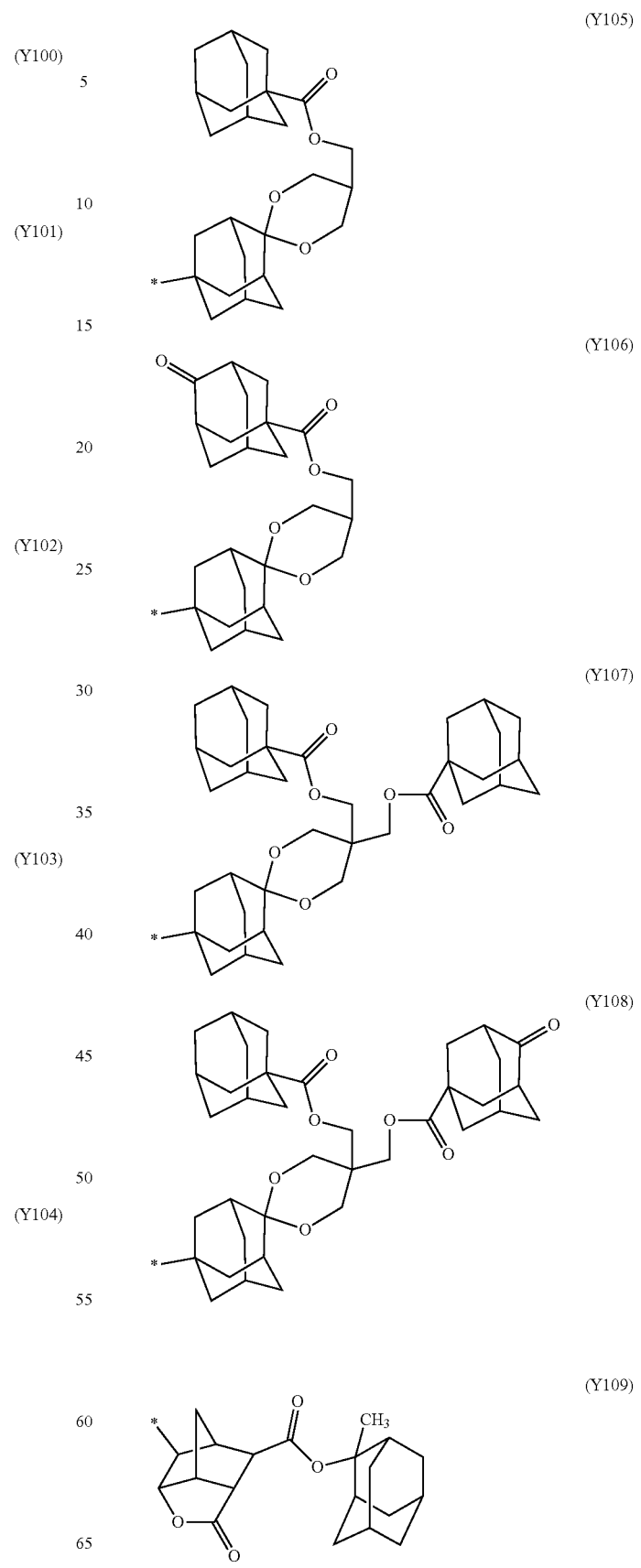

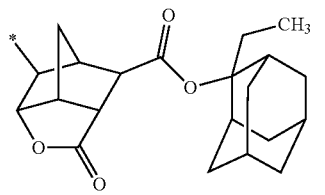 (Y110)
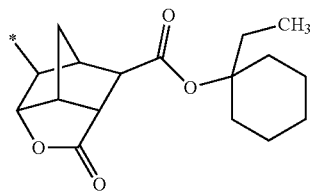 (Y111)
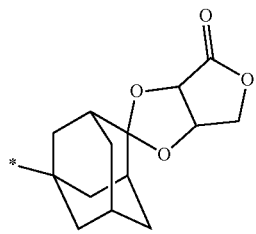 (Y42)
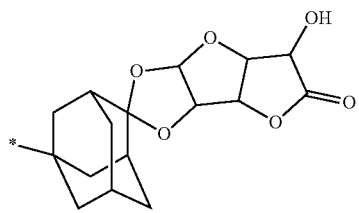 (Y112)
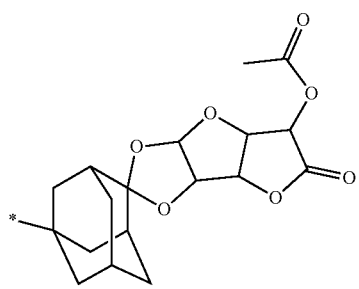 (Y113)
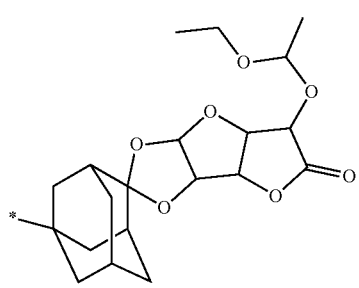 (Y114)
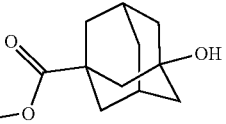 (Y115)
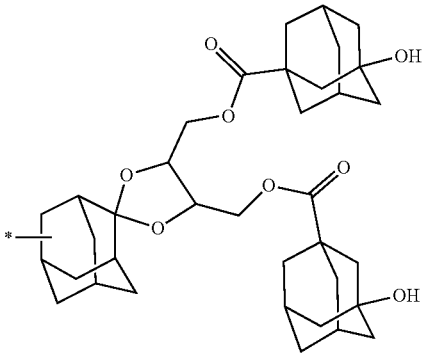 (Y116)
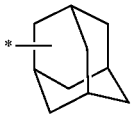 (Y11)
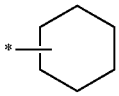 (Y4)
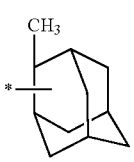 (Y117)
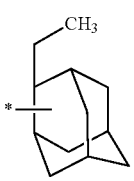 (Y118)
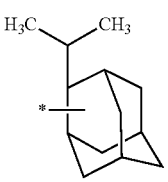 (Y119)
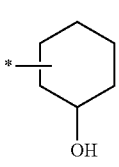 (Y120)

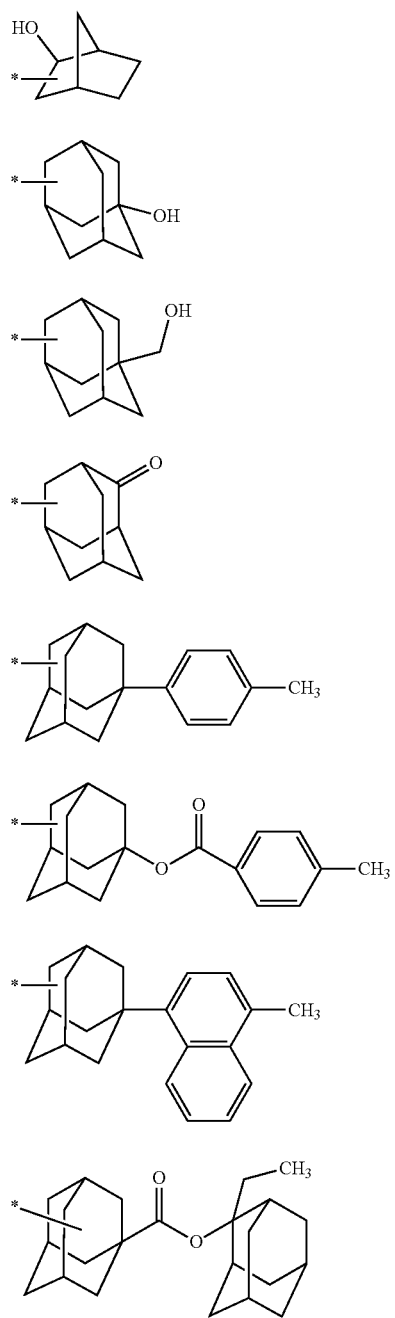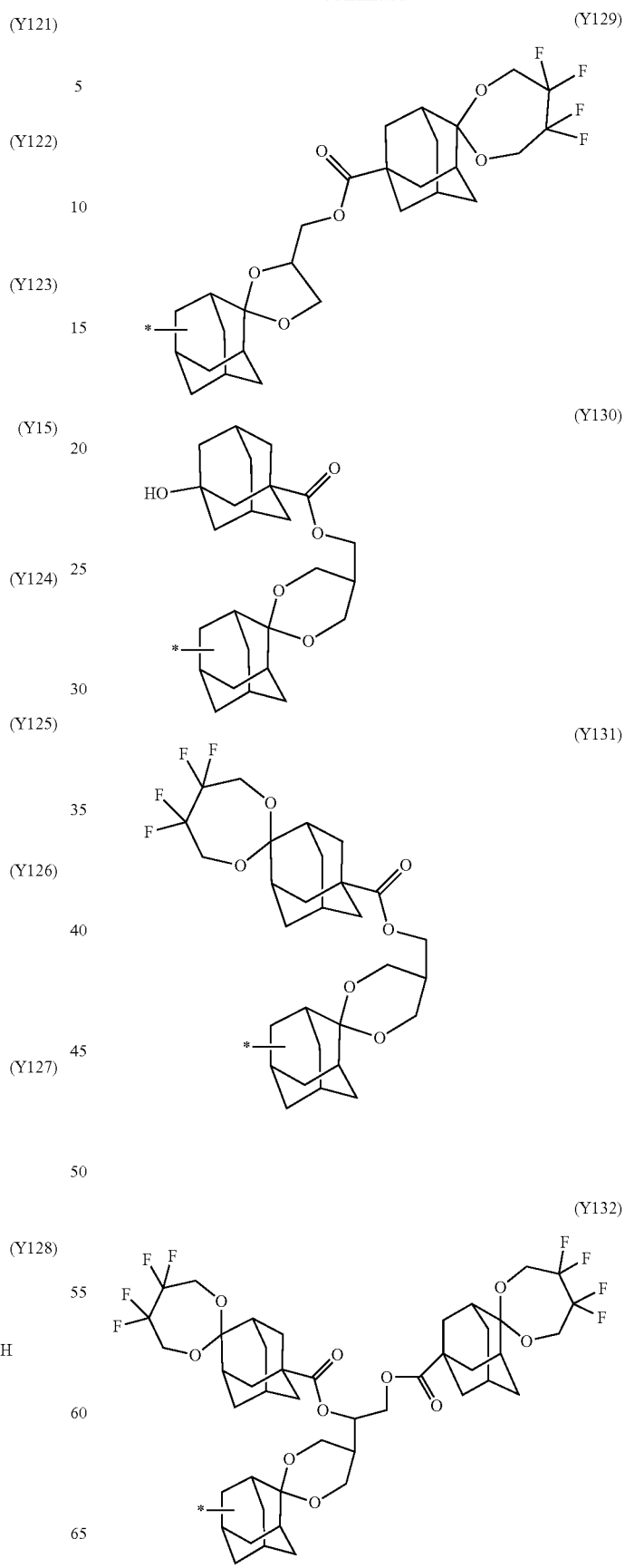

(Y133)

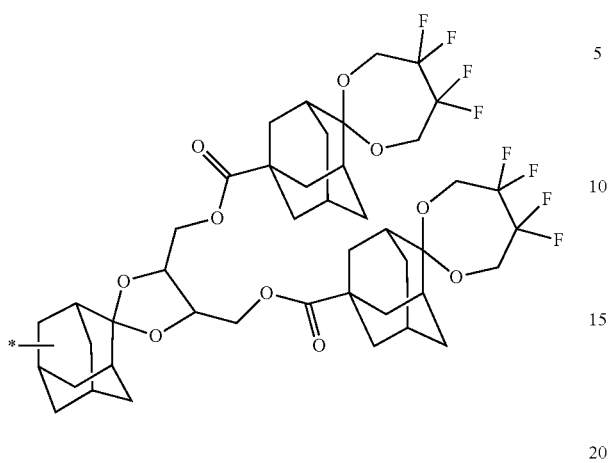

Y is preferably an alicyclic hydrocarbon group having 3 to 24 carbon atoms which may have a substituent, more preferably an alicyclic hydrocarbon group having 3 to 20 carbon atoms which may have a substituent, still more preferably an alicyclic hydrocarbon group having 3 to 18 carbon atoms which may have a substituent, yet more preferably an adamantyl group which may have a substituent, and —CH$_2$— constituting the alicyclic hydrocarbon group or the adamantyl group may be replaced by —CO—, —SO$_2$— or —CO—. Specifically, Y is preferably an adamantyl group, a hydroxyadamantyl group, an oxoadamantyl group, or groups represented by formula (Y42) and formula (Y100) to formula (Y114).

The anion in the salt represented by formula (B1) is preferably anions represented by formula (B1-A-1) to formula (B1-A-59) [hereinafter sometimes referred to as "anion (B1-A-1)" according to the number of formula], and more preferably an anion represented by any one of formula (B1-A-1) to formula (B1-A-4), formula (B1-A-9), formula (B1-A-10), formula (B1-A-24) to formula (B1-A-33), formula (B1-A-36) to formula (B1-A-40) and formula (B1-A-47) to formula (B1-A-59).

(B1-A-1)

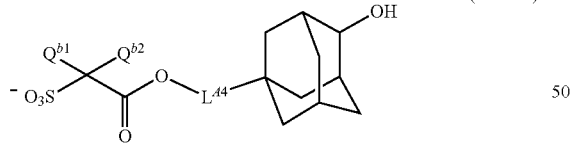

(B1-A-2)

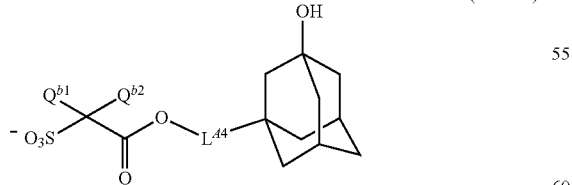

(B1-A-3)

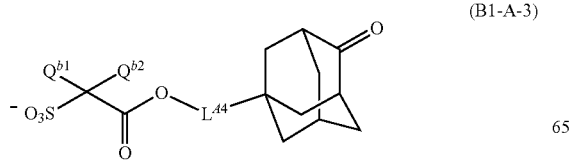

(B1-A-4)

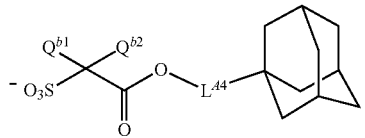

(B1-A-5)

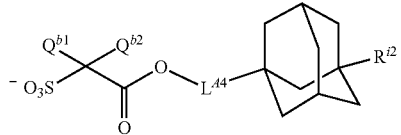

(B1-A-6)

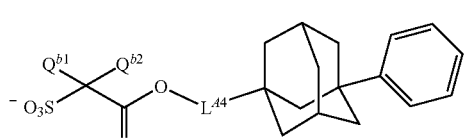

(B1-A-7)

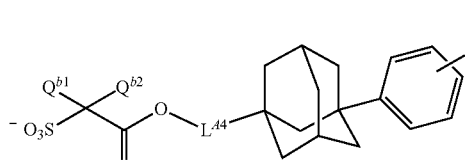

(B1-A-8)

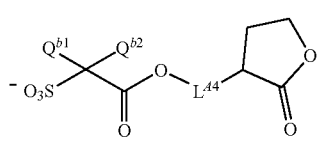

(B1-A-9)

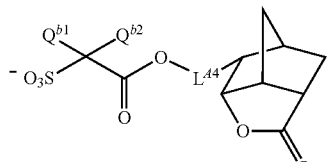

(B1-A-10)

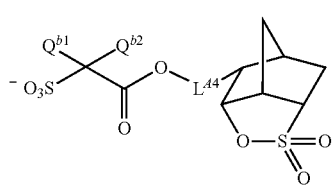

(B1-A-11)

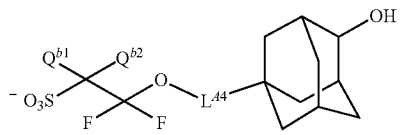

(B1-A-12)

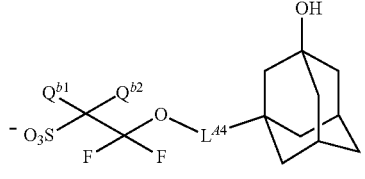

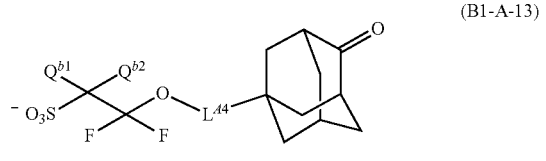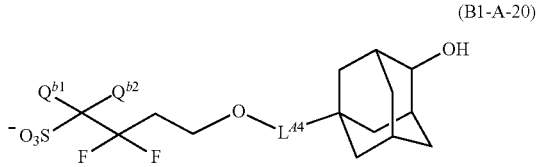

(B1-A-28) 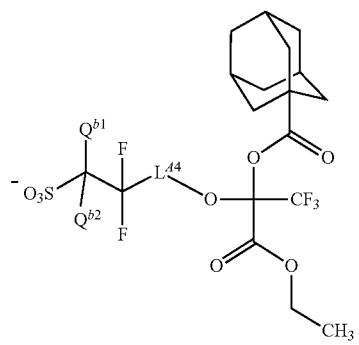
(B1-A-29) 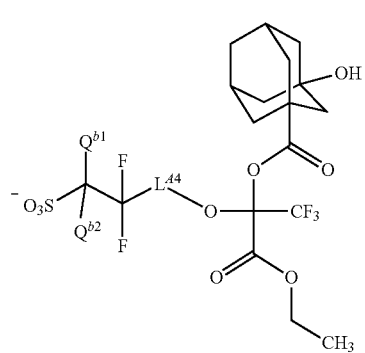
(B1-A-30) 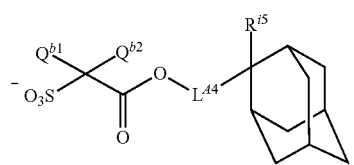
(B1-A-31) 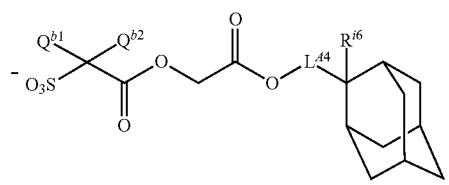
(B1-A-32) 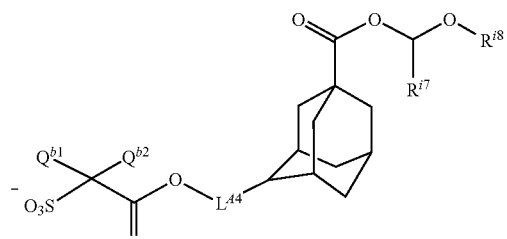
(B1-A-33) 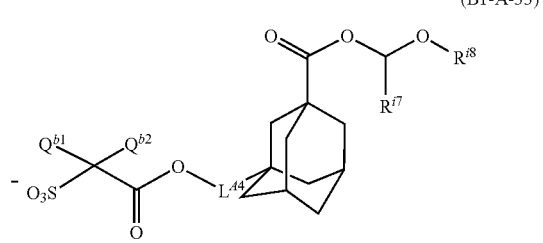
(B1-A-34) 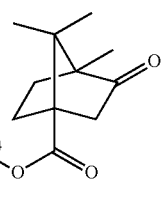
(B1-A-35) 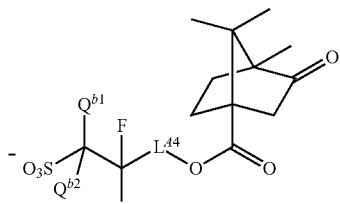
(B1-A-36) 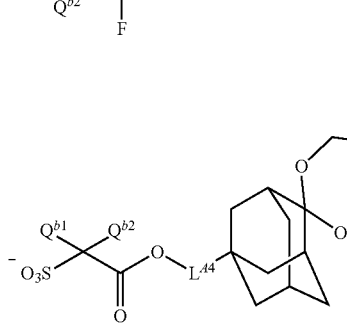
(B1-A-37) 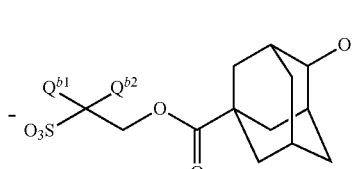
(B1-A-38) 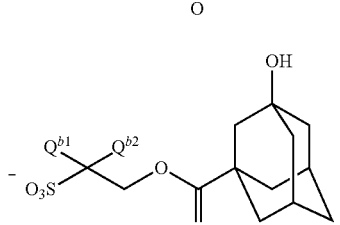
(B1-A-39) 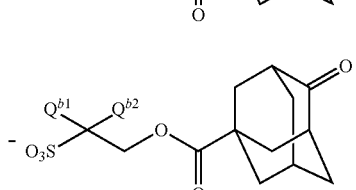
(B1-A-40) 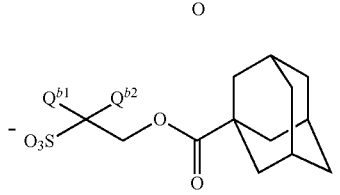
(B1-A-41) 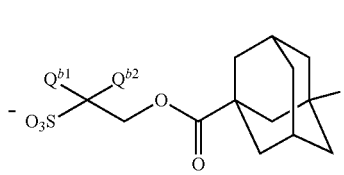

(B1-A-42) 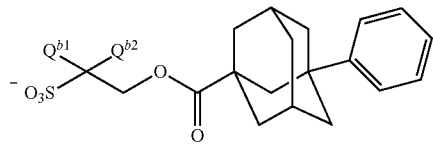
(B1-A-43) 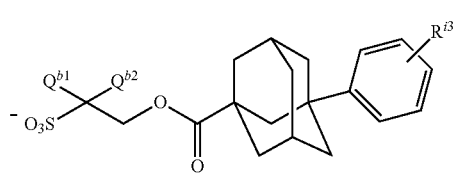
(B1-A-44) 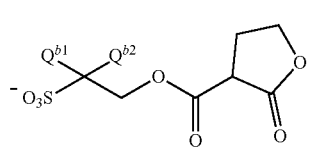
(B1-A-45) 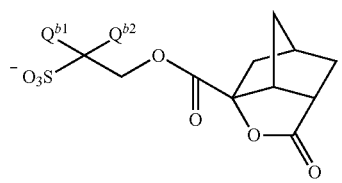
(B1-A-46) 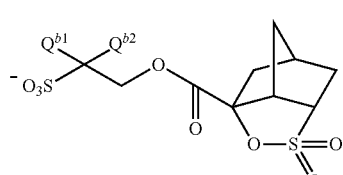
(B1-A-47) 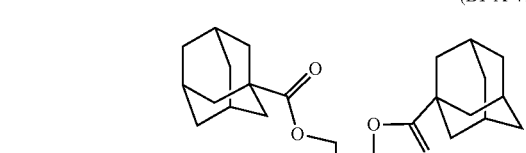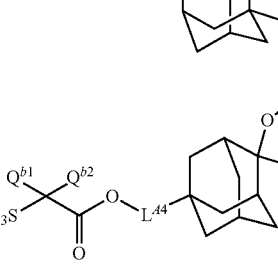
(B1-A-48) 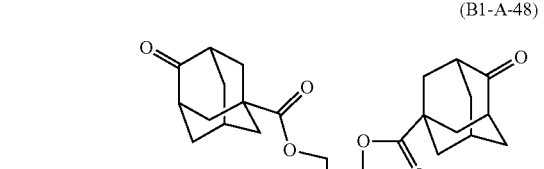
(B1-A-49) 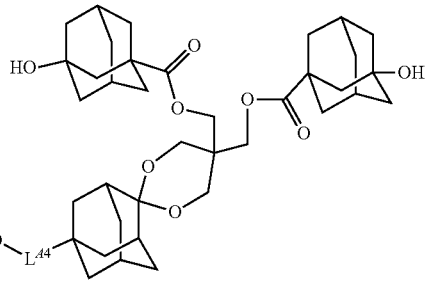
(B1-A-50) 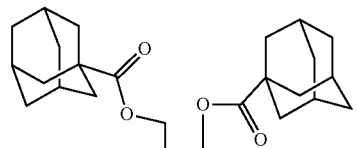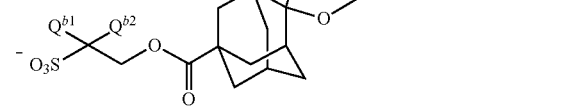
(B1-A-51) 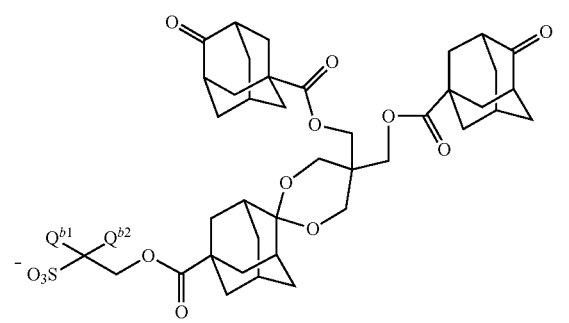
(B1-A-52) 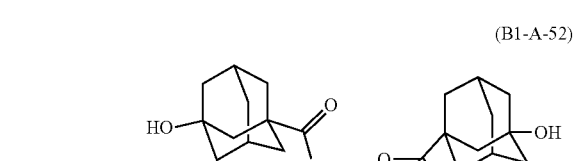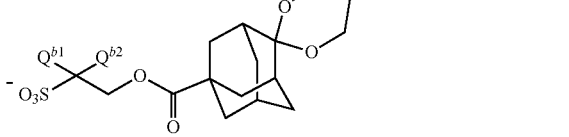
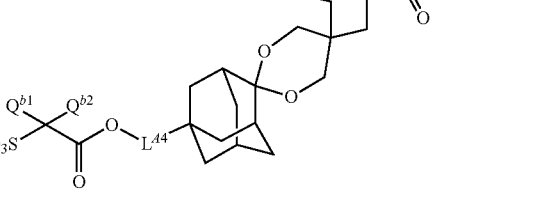

(B1-A-53)
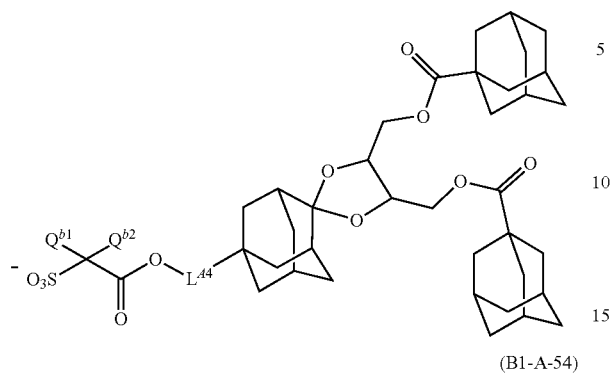

(B1-A-54)
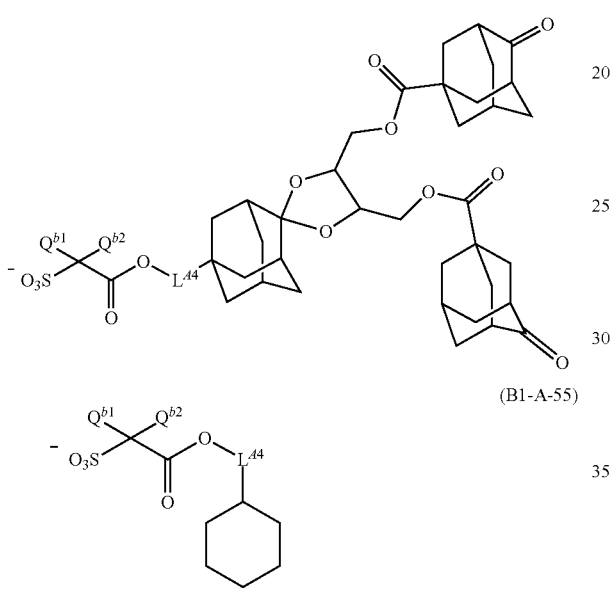

(B1-A-55)
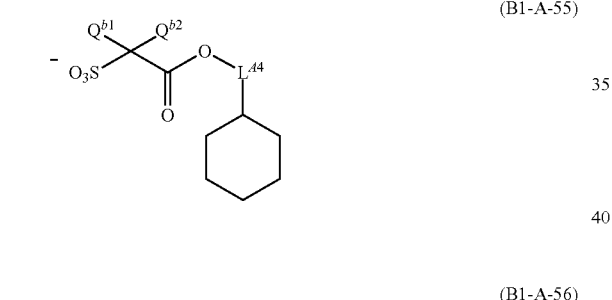

(B1-A-56)
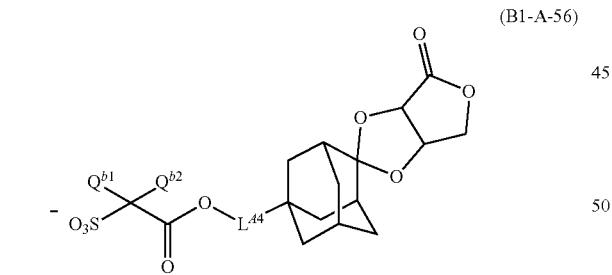

(B1-A-57)
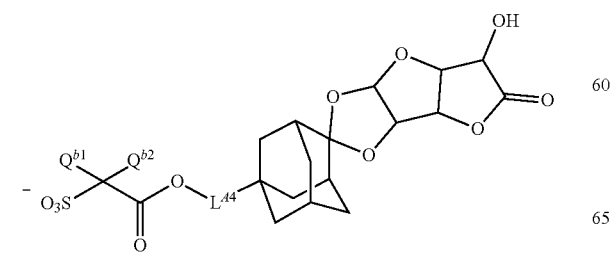

(B1-A-58)
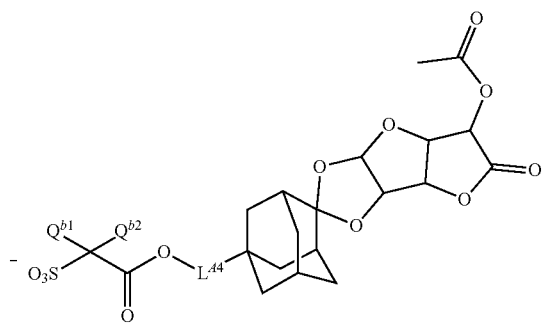

(B1-A-59)
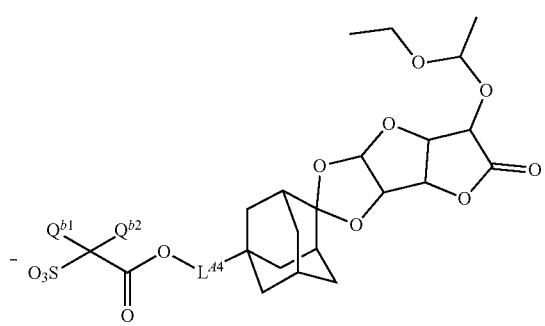

$R^{i2}$ to $R^{i7}$ each independently represent, for example, an alkyl group having 1 to 4 carbon atoms, and preferably a methyl group or an ethyl group. $R^{i8}$ is, for example, an aliphatic hydrocarbon group having 1 to 12 carbon atoms, preferably an alkyl group having 1 to 4 carbon atoms, an alicyclic hydrocarbon group having 5 to 12 carbon atoms or groups formed by combining these groups, and more preferably a methyl group, an ethyl group, a cyclohexyl group or an adamantyl group. $L^{A4}$ is a single bond or an alkanediyl group having 1 to 4 carbon atoms.

$Q^{b1}$ and $Q^{b2}$ are the same as defined above.

Specific examples of the anion in the salt represented by formula (B1) include anions mentioned in JP 2010-204646 A.

Examples of the anion in the salt represented by formula (B1) preferably include anions represented by formula (B1a-1) to formula (B1a-38).

(B1a-1)
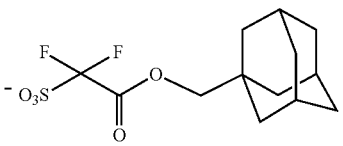

(B1a-2)
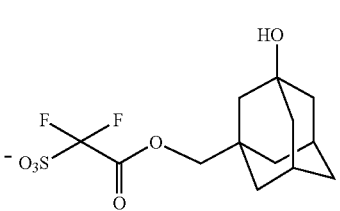

(B1a-3)
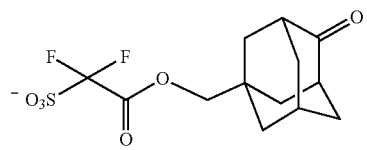
(B1a-4)
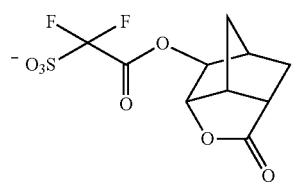
(B1a-5)
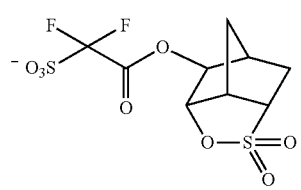
(B1a-6)
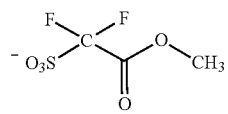
(B1a-7)
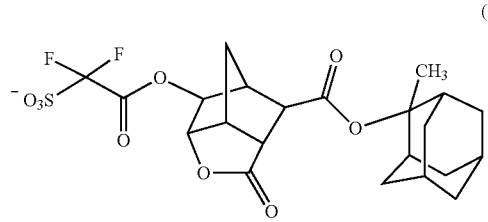
(B1a-8)
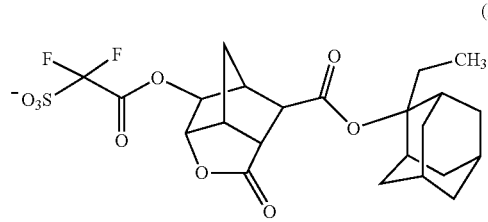
(B1a-9)
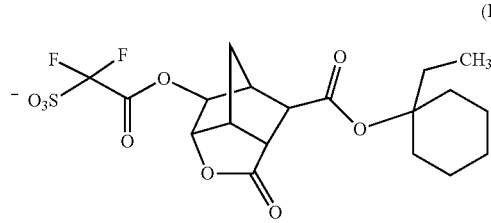
(B1a-10)
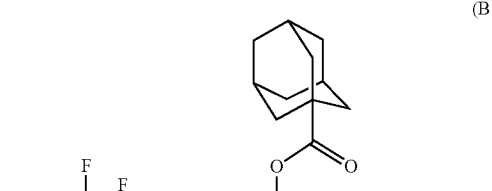
(B1a-11)
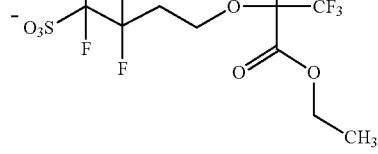
(B1a-12)
(B1a-13)
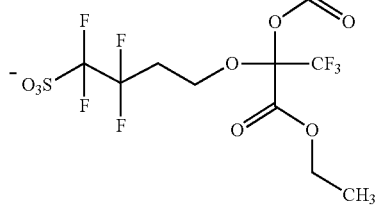
(B1a-14)
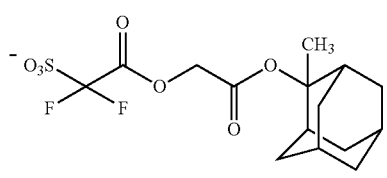
(B1a-15)
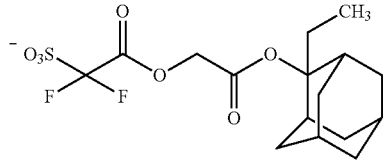
(B1a-16)
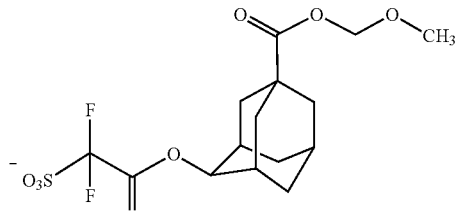

173
-continued
(B1a-17)
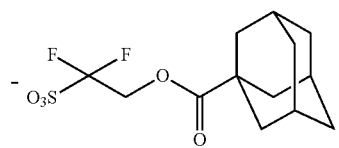
(B1a-18)
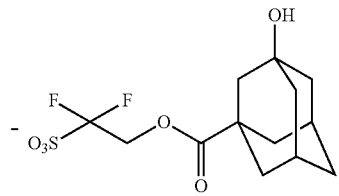
(B1a-19)
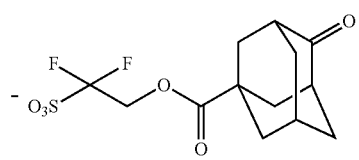
(B1a-20)
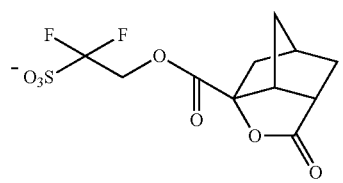
(B1a-21)
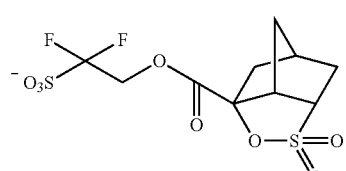
(B1a-22)
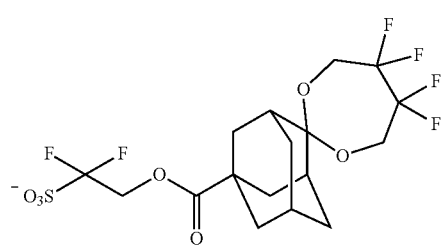
(B1a-23)
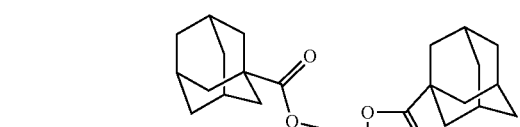
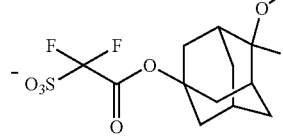
174
-continued
(B1a-24)
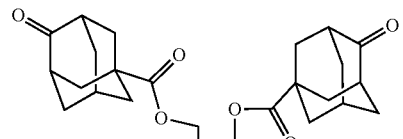
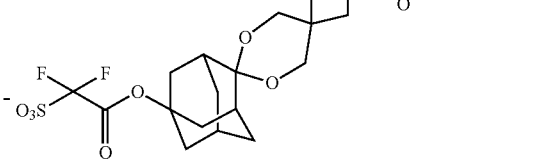
(B1a-25)
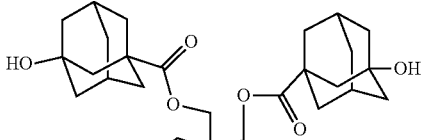
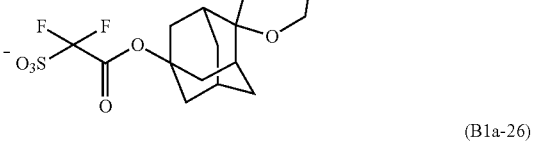
(B1a-26)
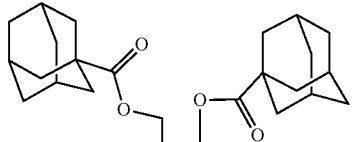
(B1a-27)
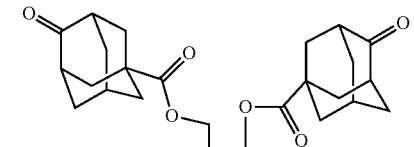
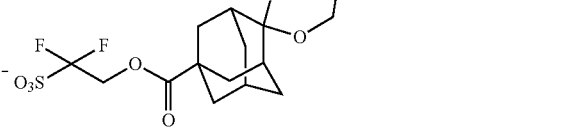
(B1a-28)
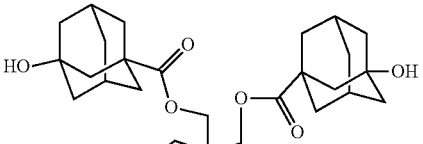

(B1a-29)
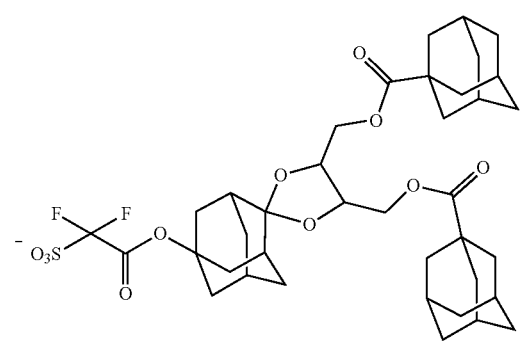

(B1a-30)

(B1a-31)
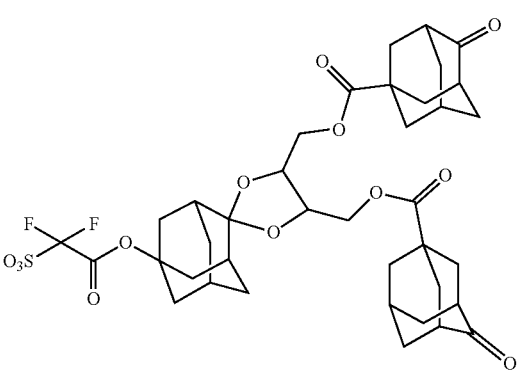

(B1a-32)
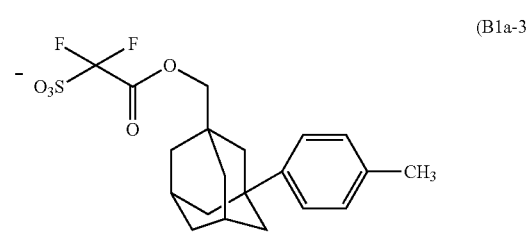

(B1a-33)
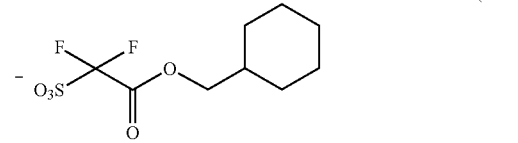

(B1a-34)
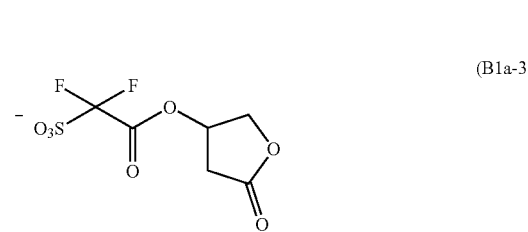

(B1a-35)
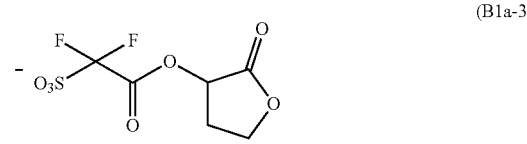

(B1a-36)
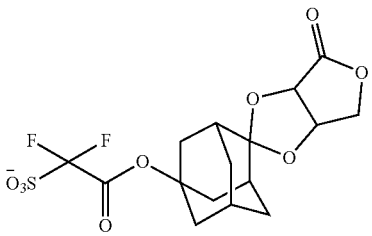

(B1a-37)
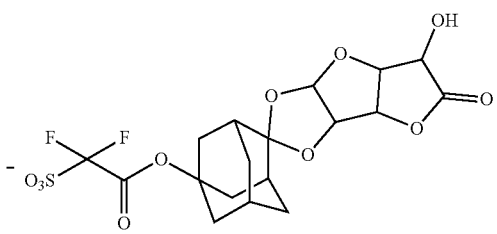

(B1a-38)
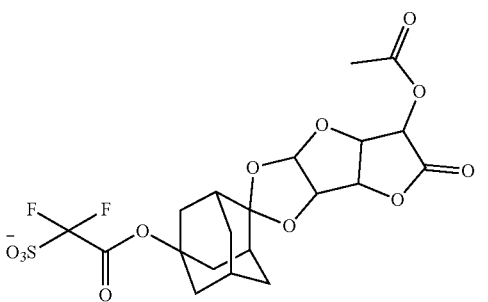

Of these anions, the anion is preferably an anion represented by any one of formula (B1a-1) to formula (B1a-3), formula (B1a-7) to formula (B1a-16), formula (B1a-18), formula (B1a-19) and formula (B1a-22) to formula (B1a-38).

Examples of the organic cation of $Z^+$ include an organic onium cation, an organic sulfonium cation, an organic iodonium cation, an organic ammonium cation, a benzothiazolium cation and an organic phosphonium cation. Of these, an organic sulfonium cation and an organic iodonium cation are preferable, and an arylsulfonium cation is more preferable. Specific examples thereof include a cation represented by any one of formula (b2-1) to formula (b2-4) (hereinafter sometimes referred to as "cation (b2-1)" according to the number of formula).

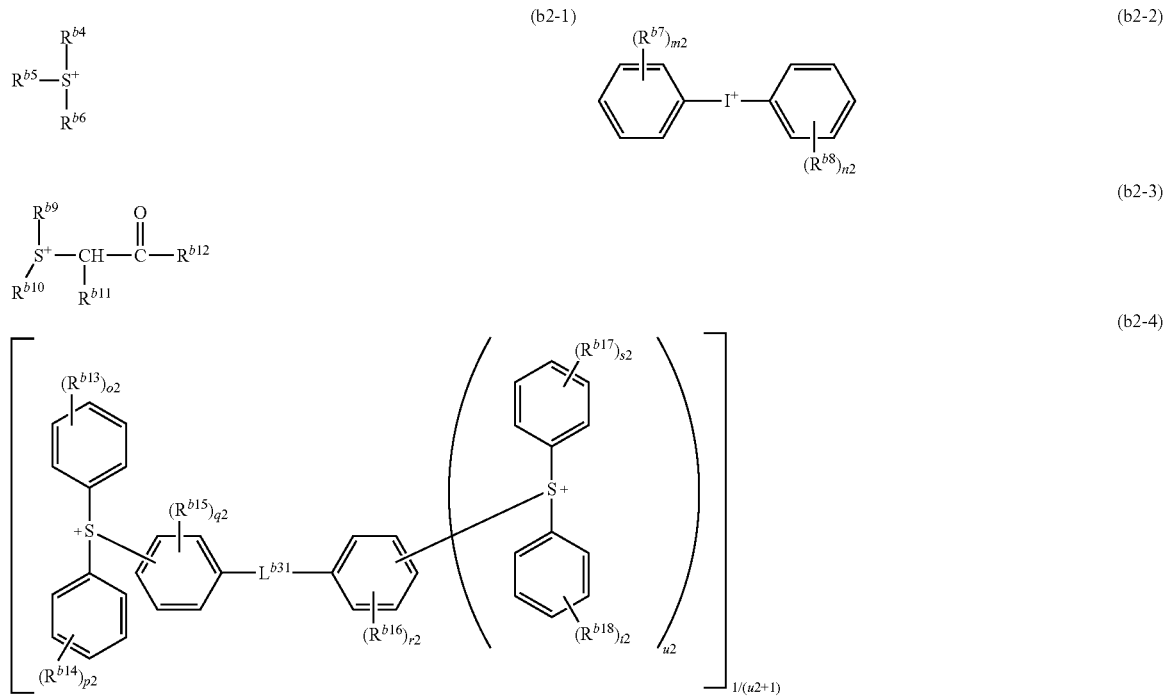

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom, a hydroxy group, an aliphatic hydrocarbon group having 1 to 18 carbon atoms, an alkyl fluoride group having 1 to 12 carbon atoms or an alkoxy group having 1 to 12 carbon atoms, $R^{b4}$ and $R^{b5}$ may be bonded to form a ring together with sulfur atoms to which $R^{b4}$ and $R^{b5}$ are bonded, and —CH$_2$— included in the ring may be replaced by —O—, —S— or —CO—, $R^{b7}$ and $R^{b8}$ each independently represent a halogen atom, a hydroxy group, an aliphatic hydrocarbon group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may be bonded to form a ring together with sulfur atoms to which $R^{b9}$ and $R^{b10}$ are bonded, and —CH$_2$— included in the ring may be replaced by —O—, —S— or —CO—, $R^{b11}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon group may be substituted with an aromatic hydrocarbon group having 6 to 18 carbon atoms, and a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may be bonded to form a ring together with —CH—CO— to which $R^{b11}$ and $R^{b12}$ are bonded, and —CH$_2$— included in the ring may be replaced by —O—, —S— or —CO—, $R^{b13}$ to $R^{b18}$ each independently represent a halogen atom, a hydroxy group, an aliphatic hydrocarbon group having 1 to 12 carbon atoms or an alkoxy group having 1 to 12 carbon atoms, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, when o2 is 2 or more, a plurality of $R^{b13}$ may be the same or different, when p2 is 2 or more, a plurality of $R^{b14}$ may be the same or different, when q2 is 2 or more, a plurality of $R^{b15}$ may be the same or different, when r2 is 2 or more, a plurality of $R^{b16}$ may be the same or different, when s2 is 2 or more, a plurality of $R^{b17}$ may be the same or different, and when t2 is 2 or more, a plurality of $R^{b18}$ may be the same or different, and the aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Particularly, the chain hydrocarbon group as for $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group, and the following groups.

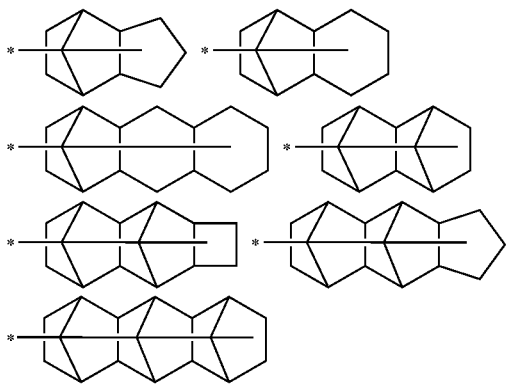

Particularly, the alicyclic hydrocarbon group as for $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

The alkyl fluoride group means an alkyl group having 1 to 12 carbon atoms which has a fluorine atom, and examples thereof include a fluoromethyl group, a difluoromethyl group, a trifluoromethyl group, a perfluorobutyl and the like. The number of the alkyl fluoride group is preferably 1 to 9, more preferably 1 to 6, and still more preferably 1 to 4.

Examples of the aromatic hydrocarbon group include aryl groups such as a phenyl group, a biphenyl group, a naphthyl group and a phenanthryl group. The aromatic hydrocarbon group may have a chain hydrocarbon group or an alicyclic hydrocarbon group, and examples thereof include an aromatic hydrocarbon group which has a chain hydrocarbon group having 1 to 18 carbon atoms (a tolyl group, a xylyl group, a cumenyl group, a mesityl group, a p-ethylphenyl group, a p-tert-butylphenyl group, a 2,6-diethylphenyl group, a 2-methyl-6-ethylphenyl group, etc.) and an aromatic hydrocarbon group which has an alicyclic hydrocarbon group having 3 to 18 carbon atoms (a p-cyclohexylphenyl group, a p-adamantylphenyl group, etc.). When the aromatic hydrocarbon group has the chain hydrocarbon group or the alicyclic hydrocarbon group, a chain hydrocarbon group having 1 to 18 carbon atoms and an alicyclic hydrocarbon group having 3 to 18 carbon atoms are preferable.

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed together with sulfur atoms to which $R^{b4}$ and $R^{b5}$ are bonded may be a monocyclic, polycyclic, aromatic, nonaromatic, saturated or unsaturated ring. This ring includes a ring having 3 to 18 carbon atoms and is preferably a ring having 4 to 18 carbon atoms. The ring containing a sulfur atom includes a 3-membered to 12-membered ring and is preferably a 3-membered to 7-membered ring and specifically includes the following rings. * represents a bonding site.

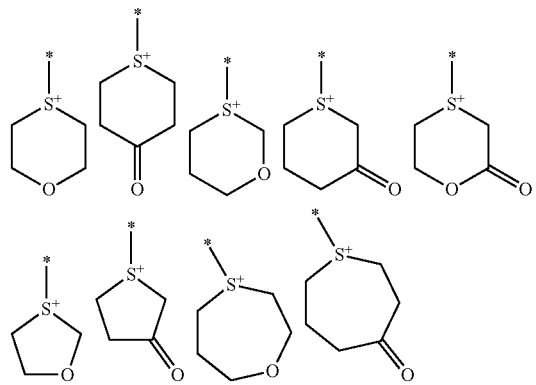

The ring formed by bonding $R^{b9}$ and $R^{b10}$ each other may be a monocyclic, polycyclic, aromatic, nonaromatic, saturated or unsaturated ring. This ring includes a 3-membered to 12-membered ring and is preferably a 3-membered to 7-membered ring. Examples of the ring include a thiolan-1-ium ring (a tetrahydrothiophenium ring), a thian-1-ium ring, a 1,4-oxathian-4-ium ring and the like.

The ring formed by bonding $R^{b11}$ and $R^{b12}$ each other may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.

Of cation (b2-1) to cation (b2-4), a cation (b2-1) is preferable.

Examples of the cation (b2-1) include the following cations.

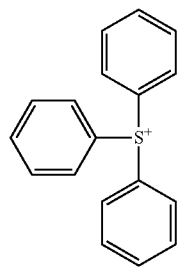
(b2-c-1)

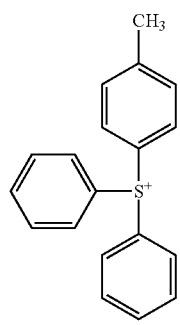
(b2-c-2)

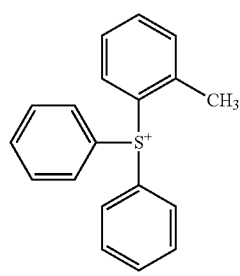
(b2-c-3)

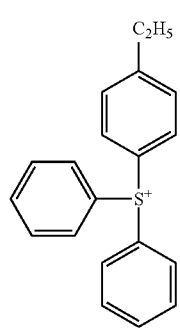
(b2-c-4)

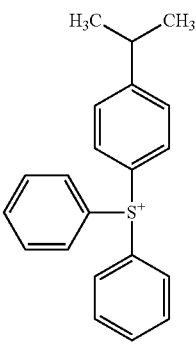
(b2-c-5)

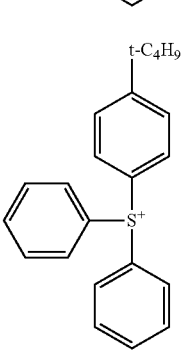
(b2-c-6)

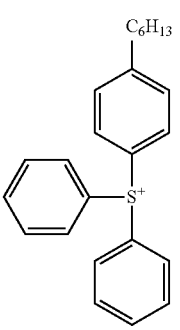
(b2-c-7)

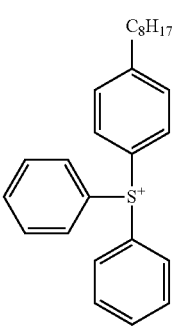
(b2-c-8)

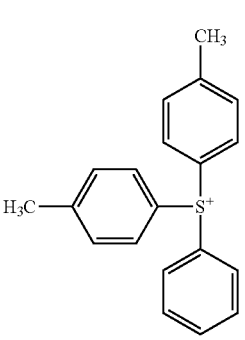
(b2-c-9)

(b2-c-10)
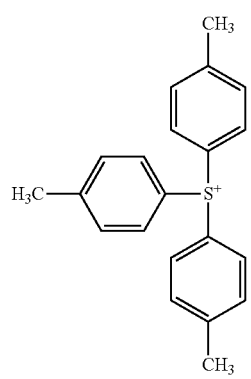
(b2-c-11)
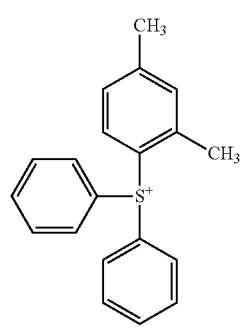
(b2-c-12)
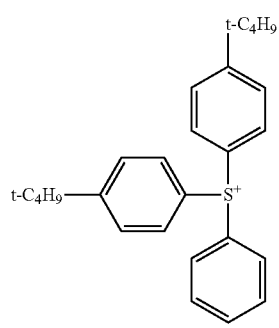
(b2-c-13)
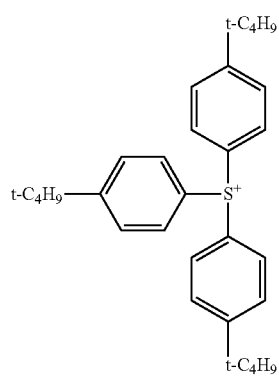
(b2-c-14)
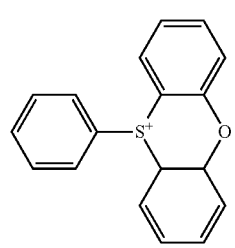
(b2-c-15)
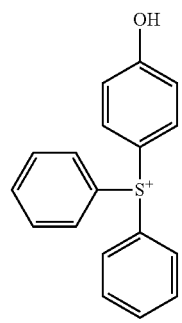
(b2-c-16)
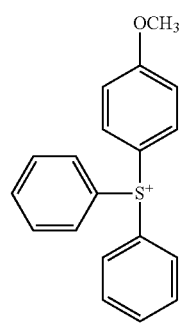
(b2-c-17)
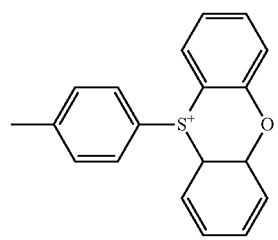
(b2-c-18)
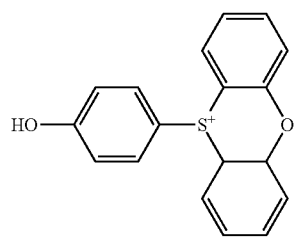
(b2-c-19)
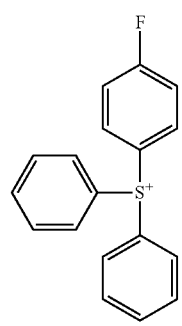

(b2-c-20)
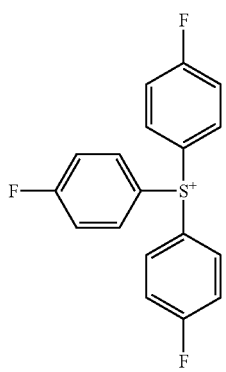
(b2-c-21)
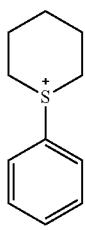
(b2-c-22)
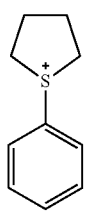
(b2-c-23)
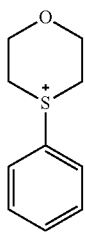
(b2-c-24)
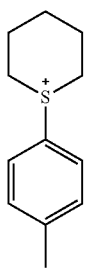
(b2-c-25)
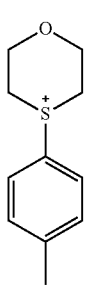
(b2-c-26)
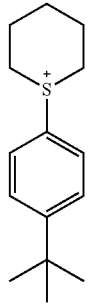
(b2-c-27)
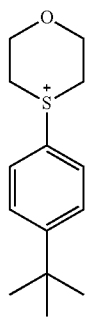
(b2-c-47)
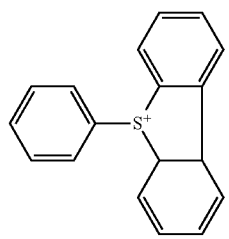
(b2-c-48)
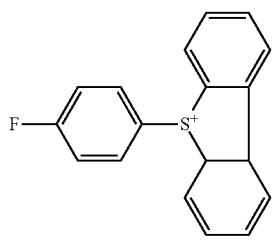
(b2-c-49)
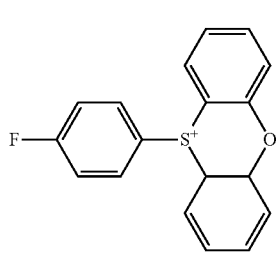

(b2-c-50)
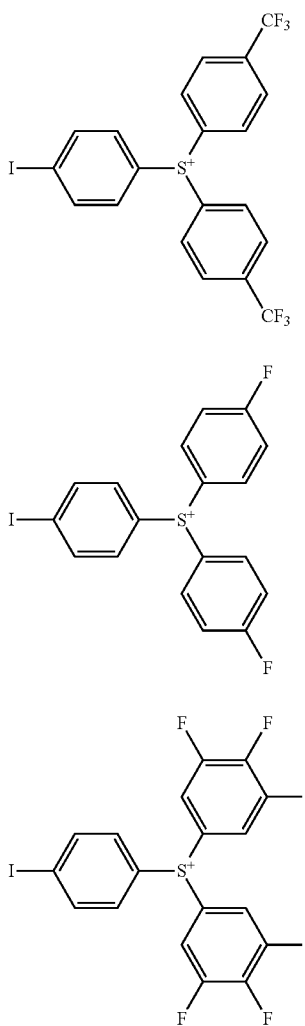
(b2-c-51)
(b2-c-53)
Examples of the cation (b2-2) include the following cations.
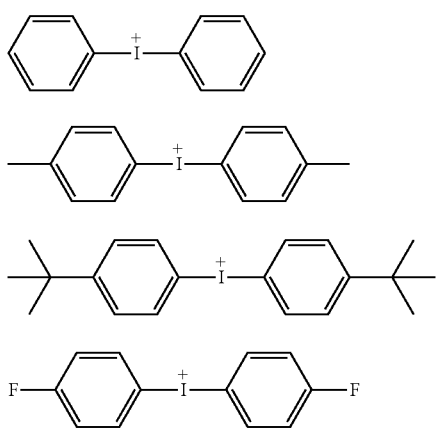
(b2-c-28)
(b2-c-29)
(b2-c-30)
(b2-c-50)
Examples of the cation (b2-3) include the following cations.
(b2-c-31)
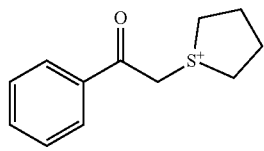
(b2-c-32)
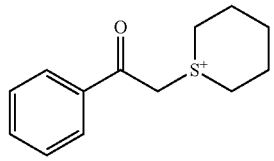
(b2-c-33)
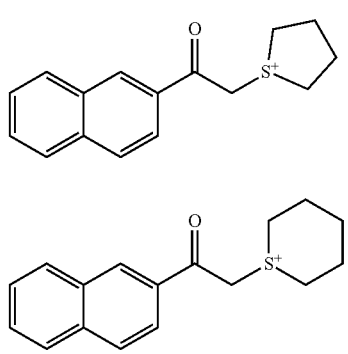
(b2-c-34)
Examples of the cation (b2-4) include the following cations.
(b2-c-35)
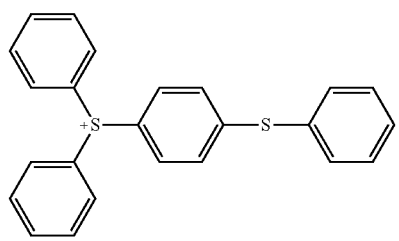
(b2-c-36)
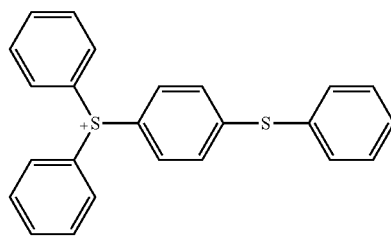
(b2-c-37)
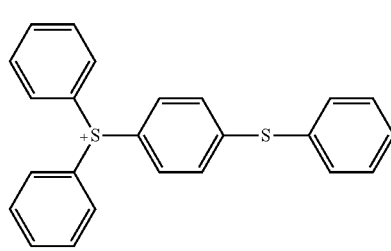

(b2-c-38)
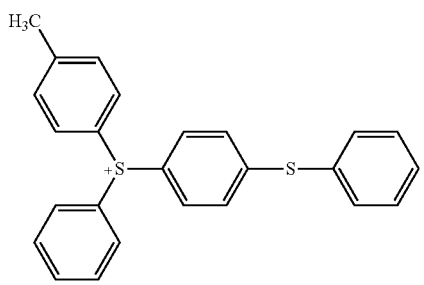
(b2-c-39)
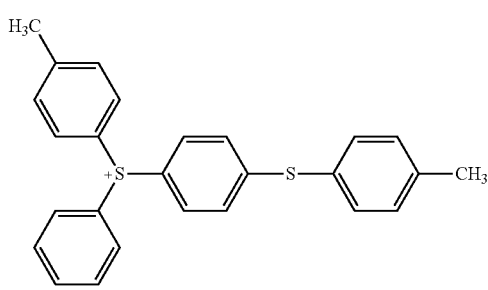
(b2-c-40)
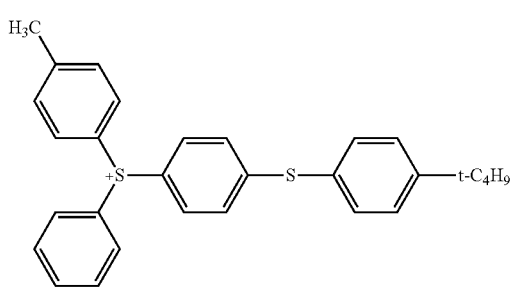
(b2-c-41)
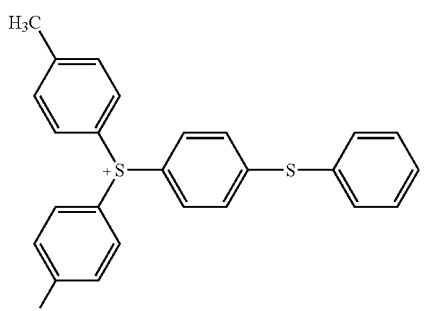
(b2-c-42)
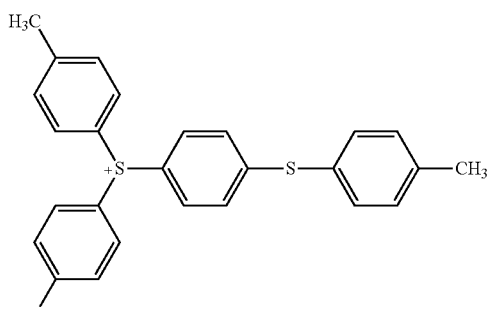
(b2-c-43)
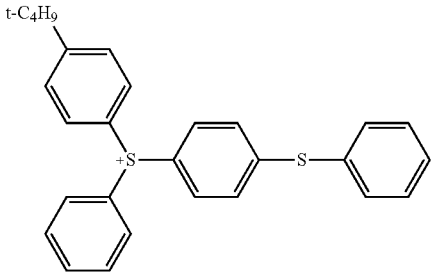
(b2-c-44)
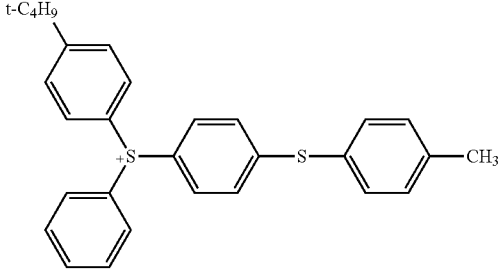
(b2-c-45)
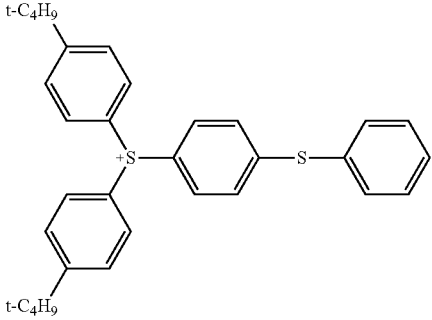
(b2-c-46)
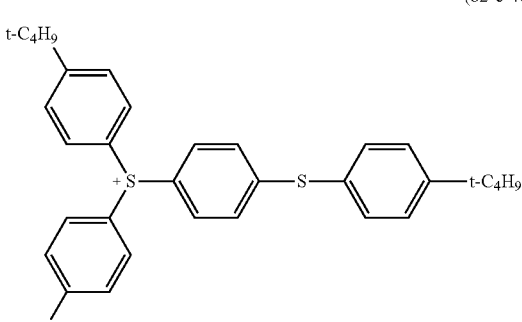
(b2-c-54)
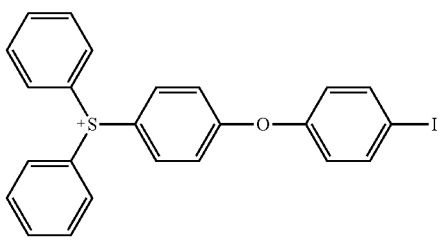
The acid generator (B) is a combination of the above-mentioned anions and the above-mentioned organic cations, and these can be optionally combined. Examples of the acid generator (B) are preferably combinations of anions represented by any one of (B1a-1) to formula (B1a-3), formula (B1a-7) to formula (B1a-16), formula (B1a-18), formula (B1a-19) and formula (B1a-22) to formula (B1a-38) with a cation (b2-1), a cation (b2-3) or a cation (b2-4).

Examples of the acid generator (B) are preferably those represented by formula (B1-1) to formula (B1-56). Of these, those containing an arylsulfonium cation are preferable, and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-56) are particularly preferable.

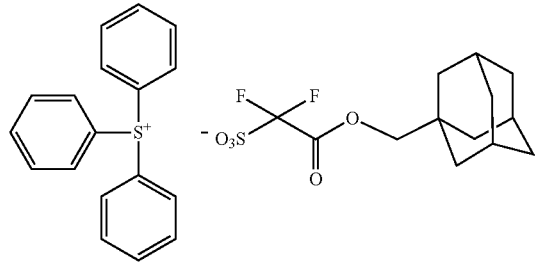

(B1-1)

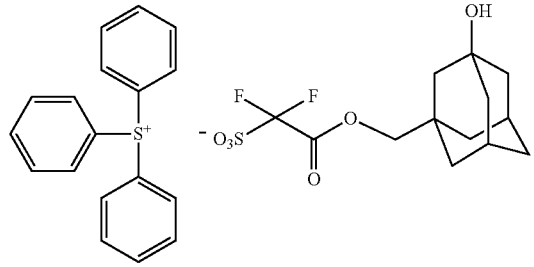

(B1-2)

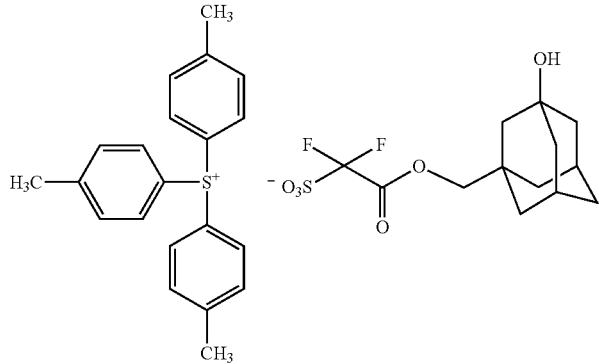

(B1-3)

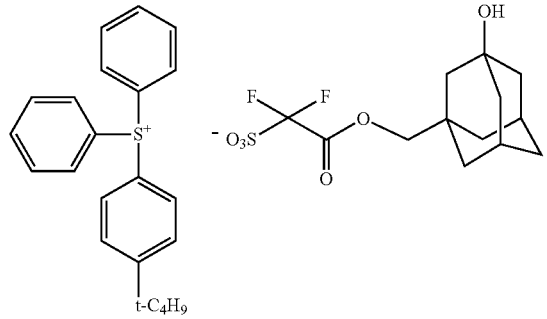

(B1-4)

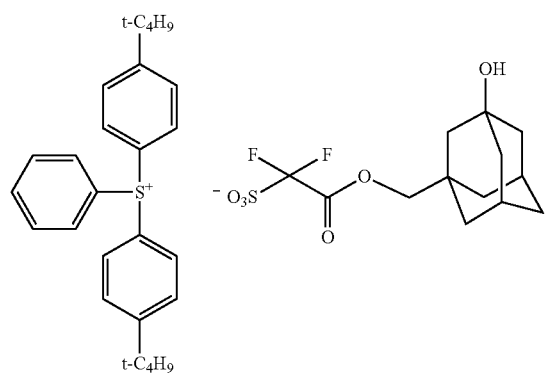
(B1-5)
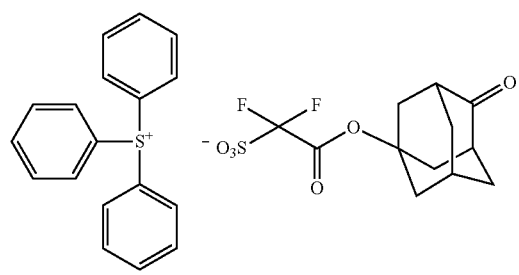
(B1-6)
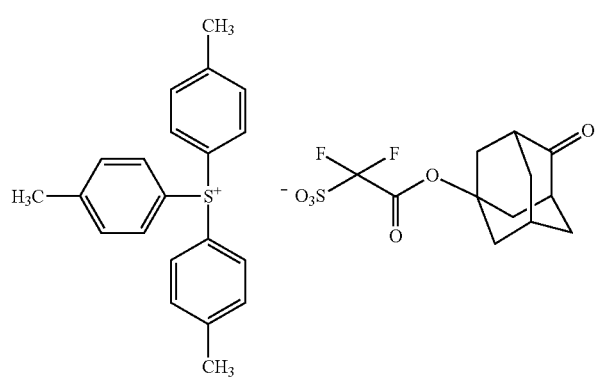
(B1-7)
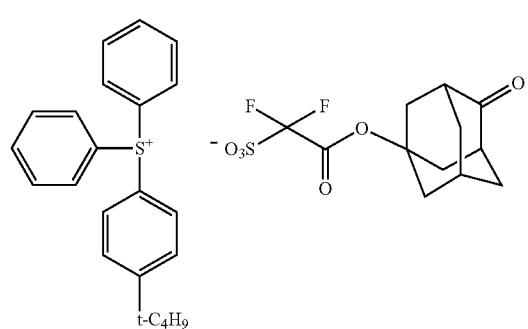
(B1-8)

(B1-9)
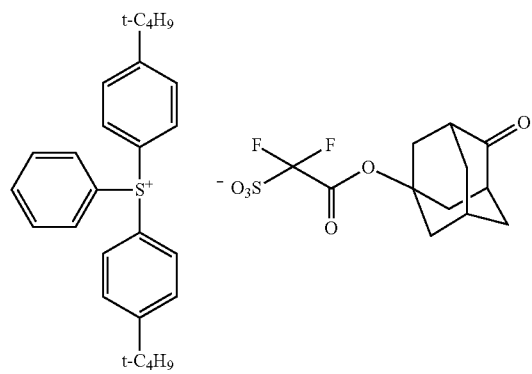
(B1-10)
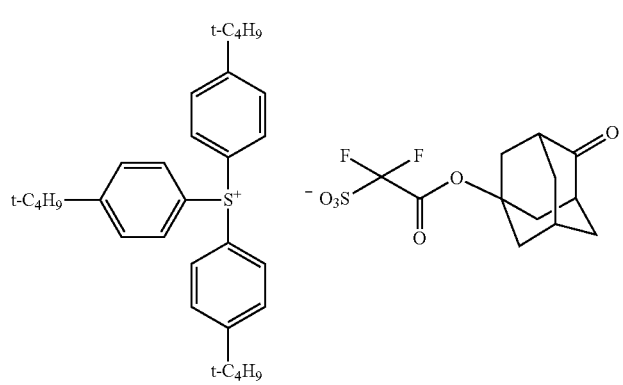
(B1-11)
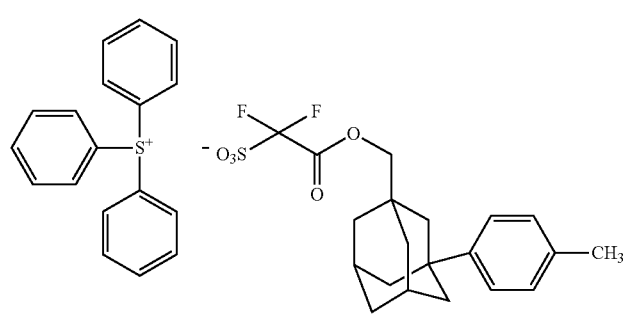
(B1-12)
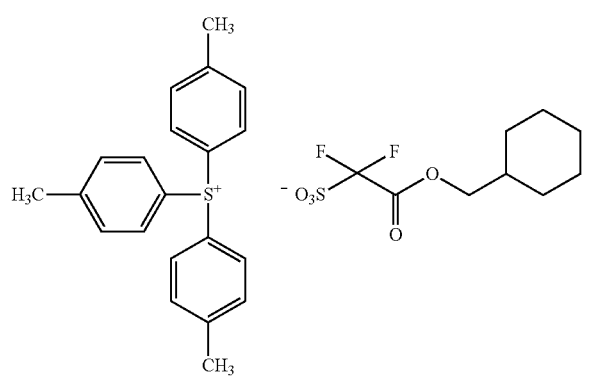

(B1-13)
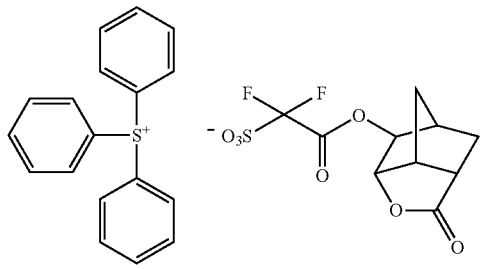
(B1-14)
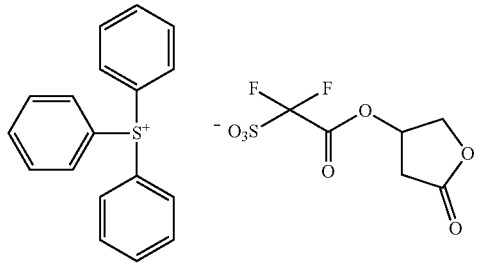
(B1-15)
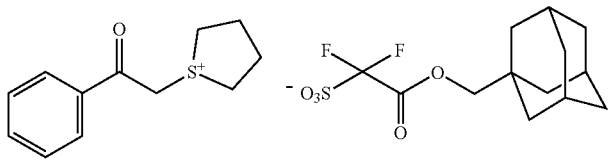
(B1-16)
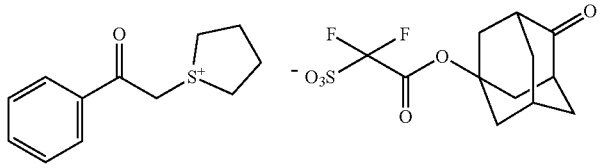
(B1-17)
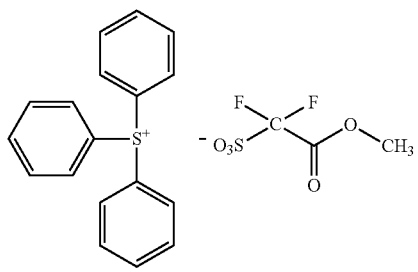
(B1-18)
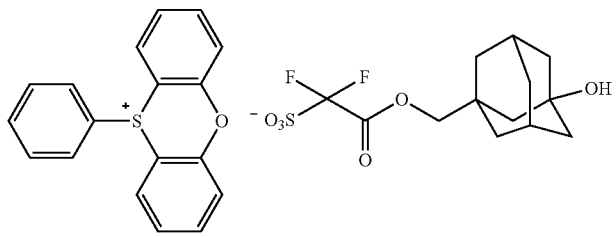
(B1-19)
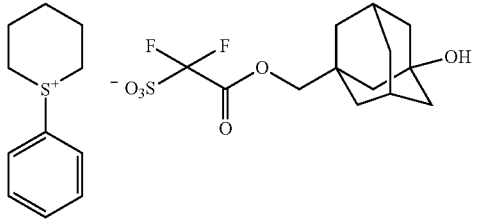

(B1-20)
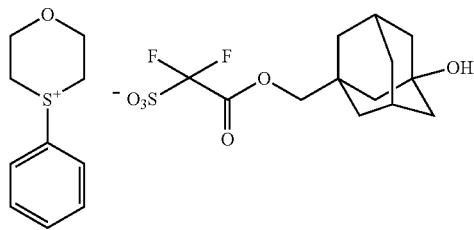
(B1-21)
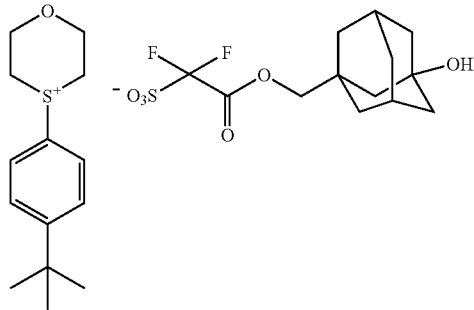
(B1-22)
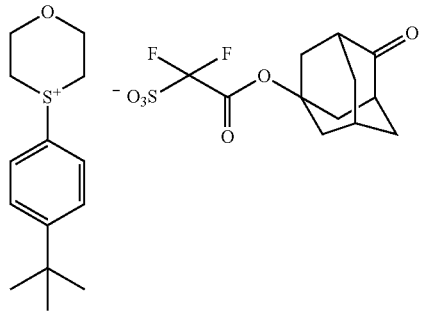
(B1-23)
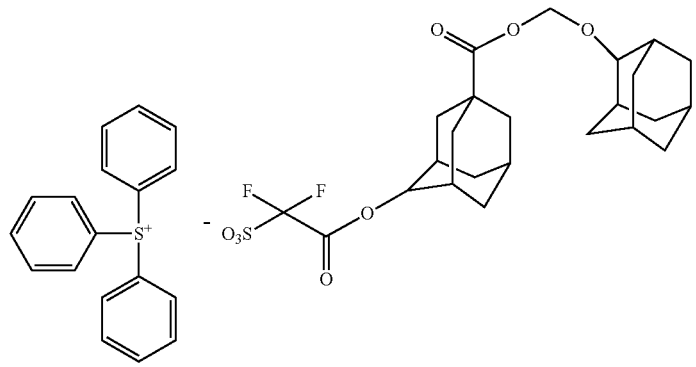
(B1-24)
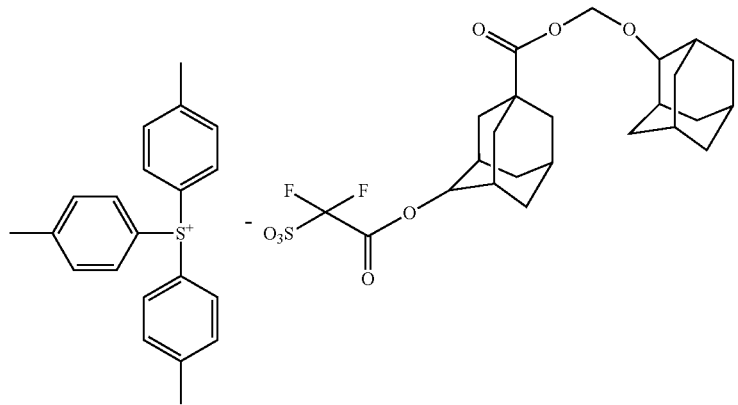

(B1-25)
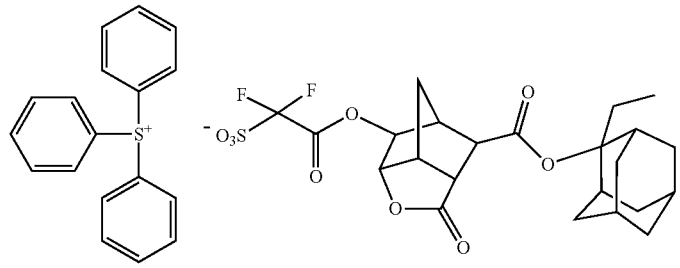
(B1-26)
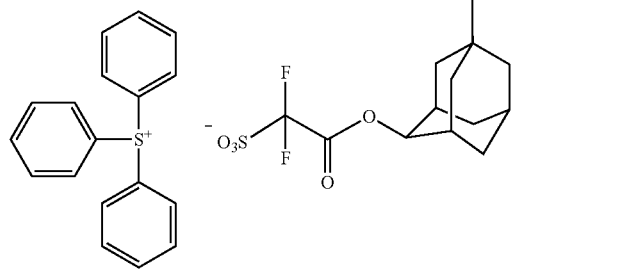
(B1-27)
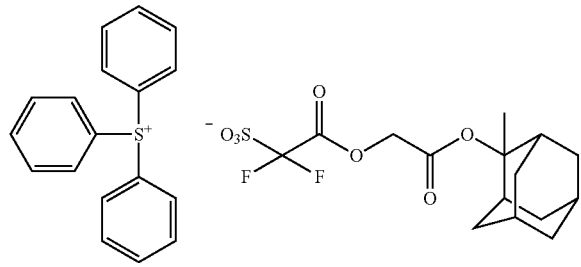
(B1-28)
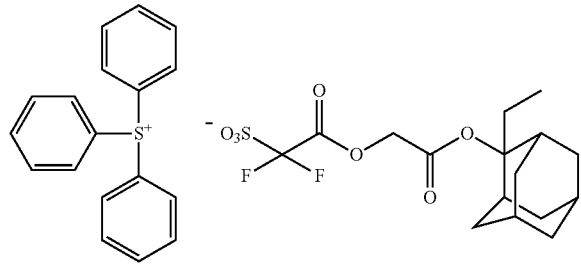
(B1-29)
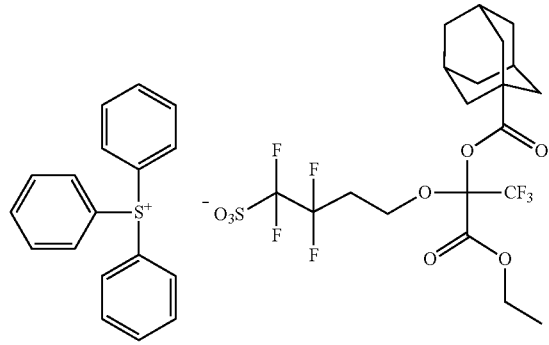

-continued
(B1-30)
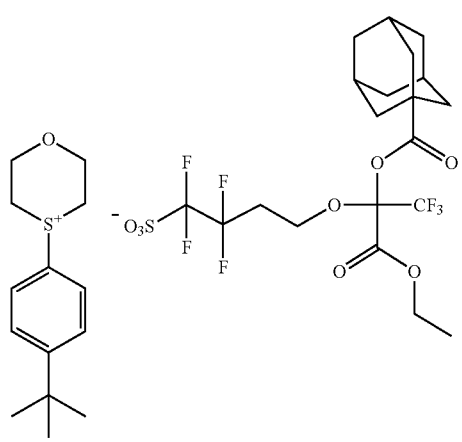
(B1-31)
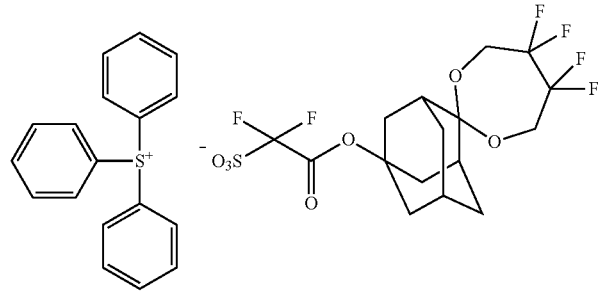
(B1-32)
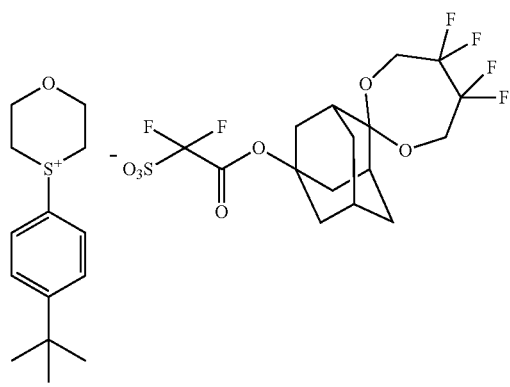
(B1-33)
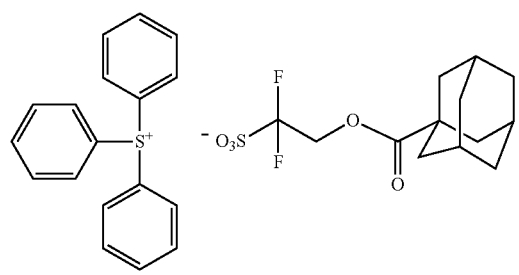

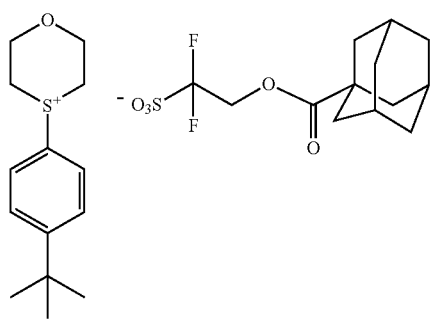
(B1-34)
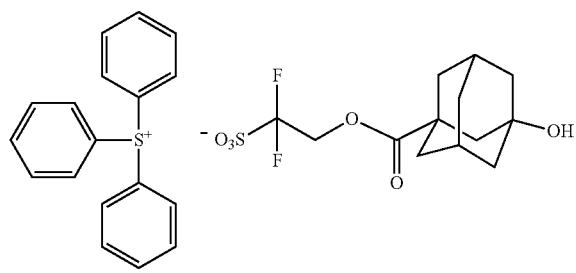
(B1-35)
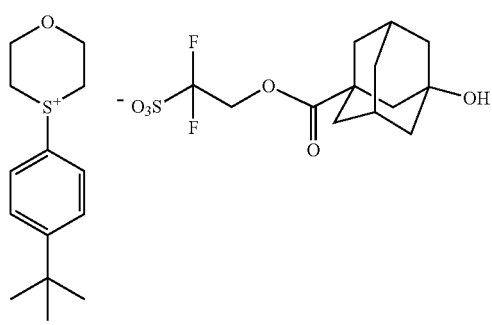
(B1-36)
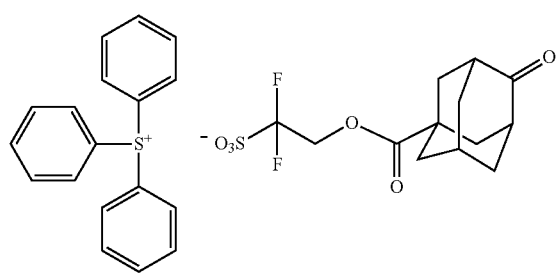
(B1-37)
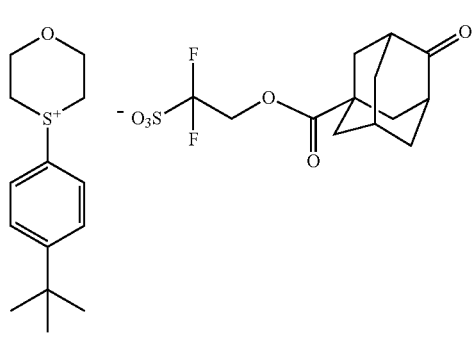
(B1-38)

-continued
(B1-39)
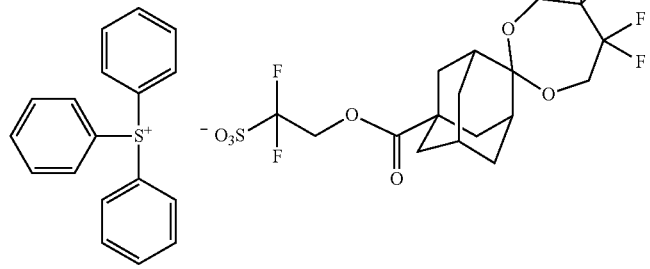
(B1-40)
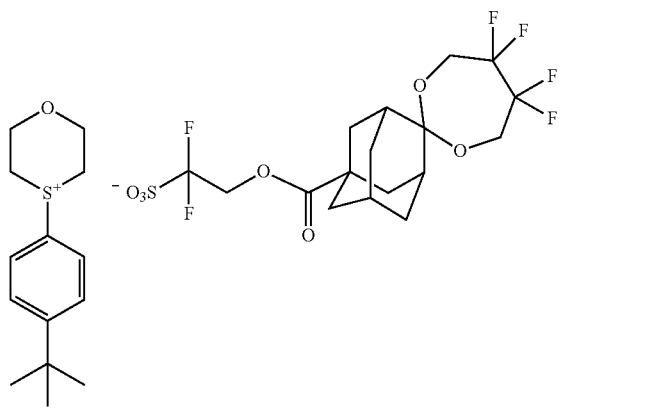
(B1-41)
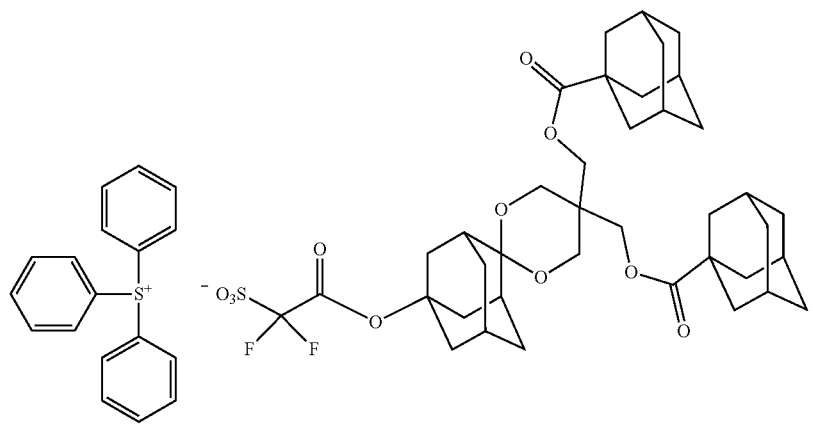
(B1-42)
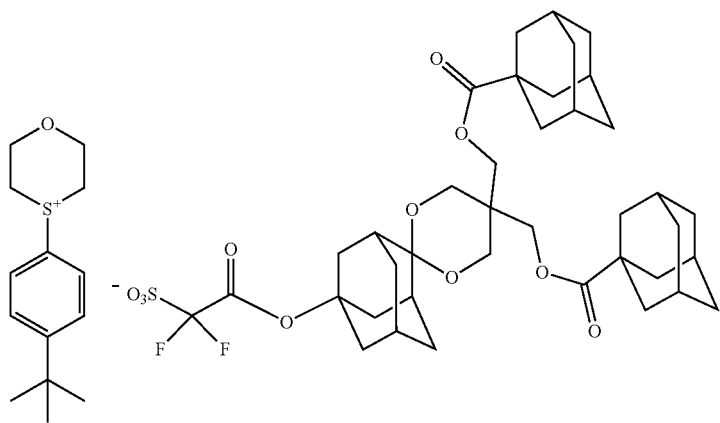

-continued
(B1-43)
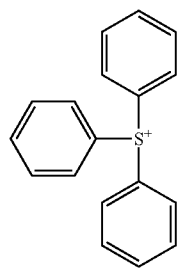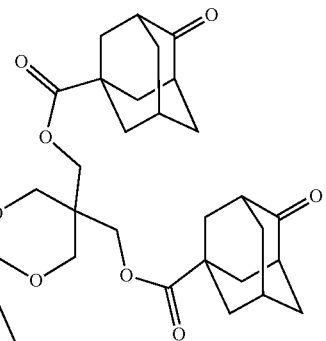
(B1-44)
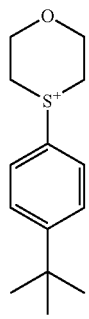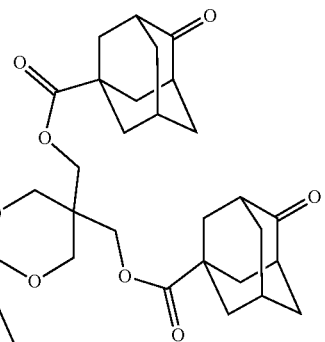
(B1-45)
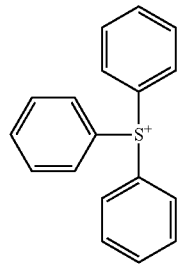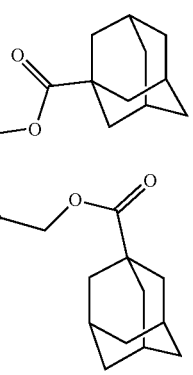

(B1-46)
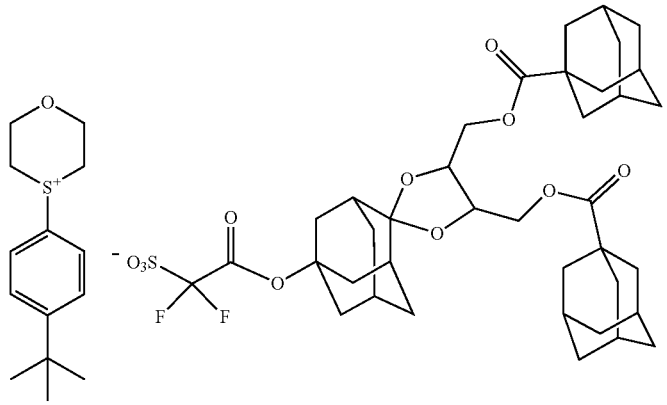
(B1-47)
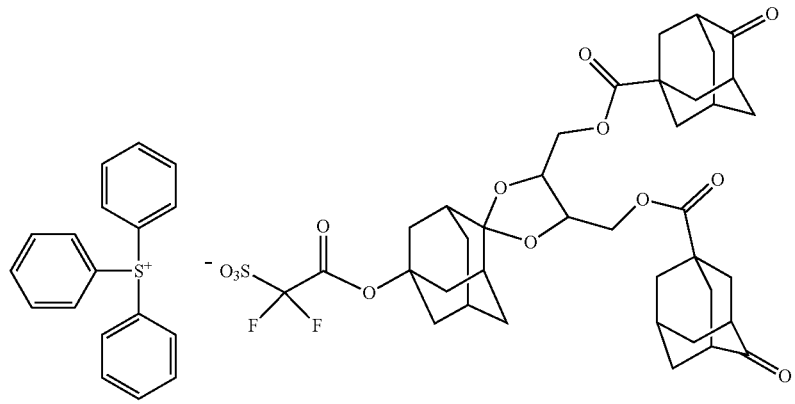
(B1-48)
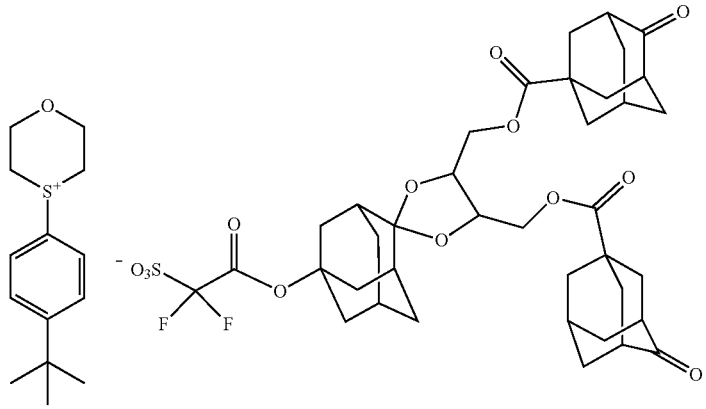
(B1-49)
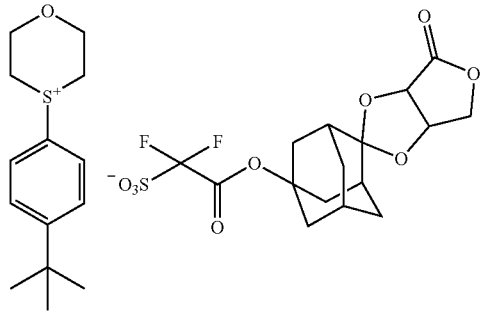

(B1-50)
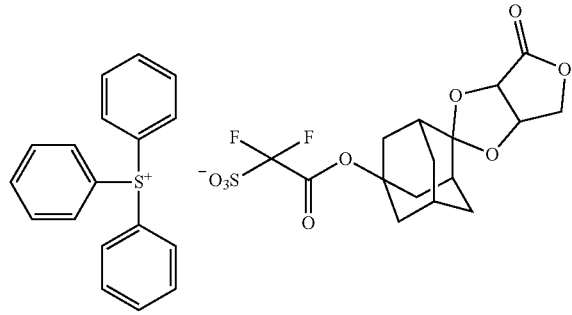
(B1-51)
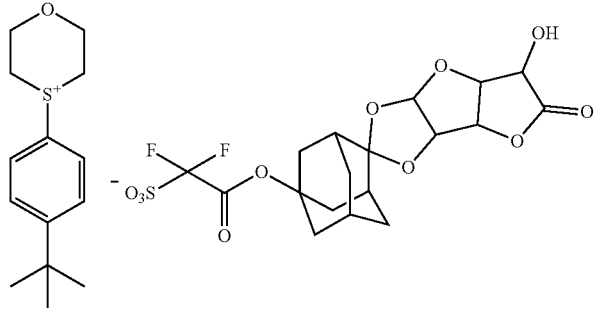
(B1-52)
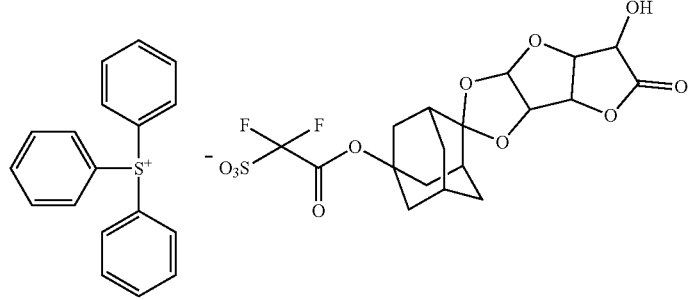
(B1-53)
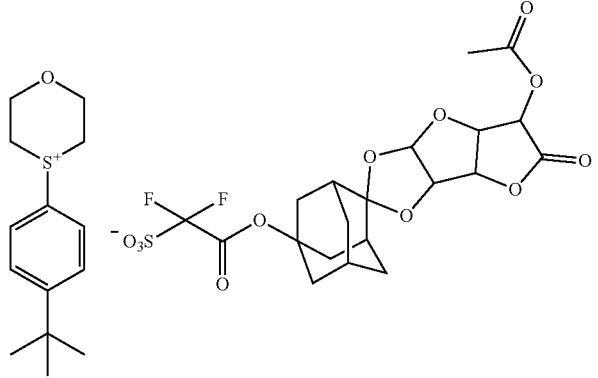

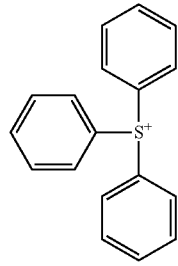
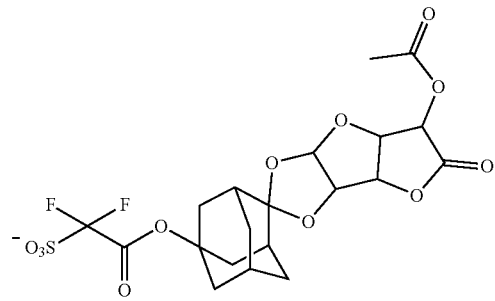

(B1-54)

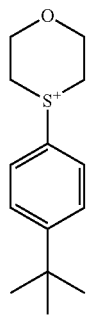
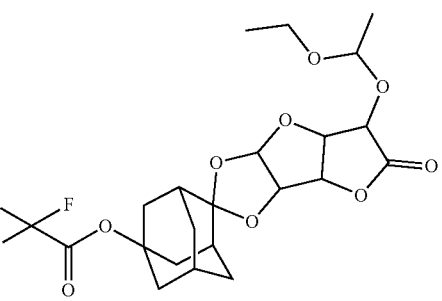

(B1-55)

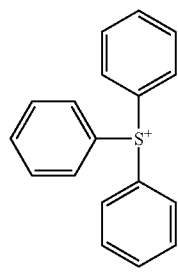
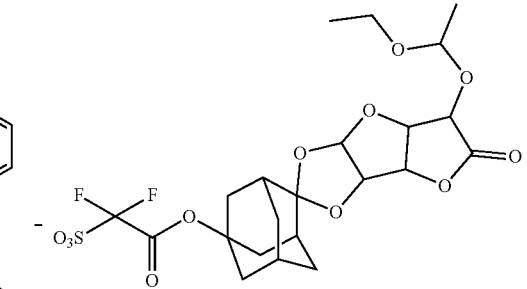

(B1-56)

In the resist composition of the present disclosure, the content of the acid generator is preferably 1 part by mass or more and 45 parts by mass or less, more preferably 1 part by mass or more and 40 parts by mass or less, and still more preferably 3 parts by mass or more and 35 parts by mass or less, based on 100 parts by mass of the resin (A). The resist composition of the present disclosure may include one acid generator (B) alone, or may include a plurality thereof.

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Quencher (C)>

Examples of the quencher (C) include a salt generating an acid having an acidity lower than that of an acid generated from an acid generator (B) and a basic nitrogen-containing organic compound. When the resist composition includes the quencher (C), the content of the quencher (C) is preferably about 0.01 to 15% by mass and more preferably about 0.01 to 10% by mass, still more preferably about 0.1 to 5% by mass based on the amount of the solid component of the resist composition.

<Salt Generating Acid Having Acidity Lower than that of Acid Generated from Acid Generator>

The acidity in a salt generating an acid having an acidity lower than that of an acid generated from the acid generator (B) is indicated by the acid dissociation constant (pKa). Regarding the salt generating an acid having an acidity lower than that of an acid generated from the acid generator (B), the acid dissociation constant of an acid generated from the salt usually meets the following inequality: −3<pKa, preferably −1<pKa<7, and more preferably 0<pKa<5.

Examples of the salt generating an acid having an acidity lower than that of an acid generated from the acid generator (B) include salts represented by the following formulas, a compound represented by formula (D) mentioned in JP 2015-147926 A (hereinafter sometimes referred to as "weak acid inner salt (D)", and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator (B) is a salt generating carboxylic acid having an acidity lower than that of an acid generated from the acid generator (B) (a salt having a carboxylic acid anion), and more preferably a weak acid inner salt (D).

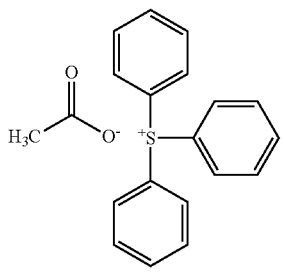

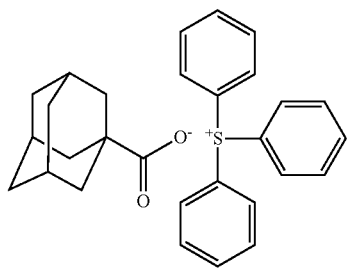

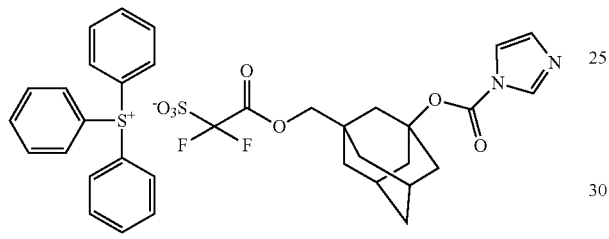

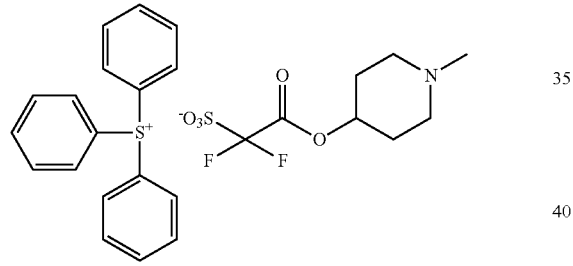

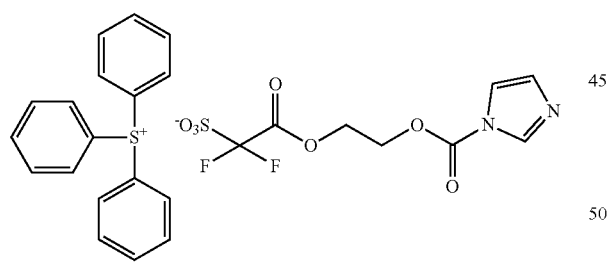

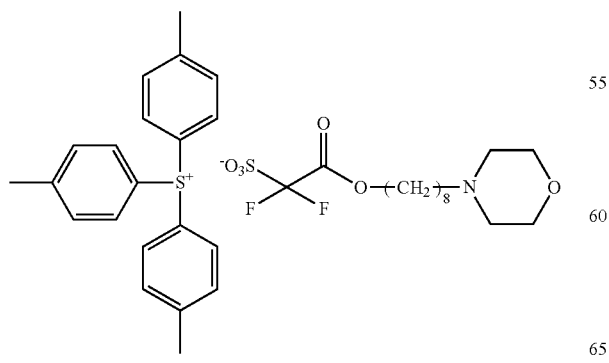

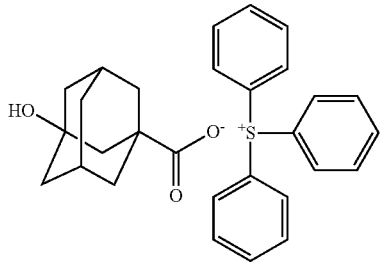

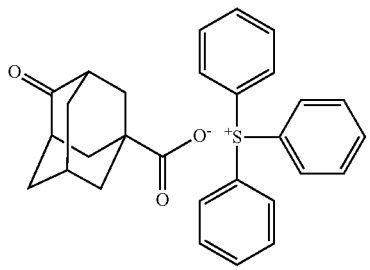

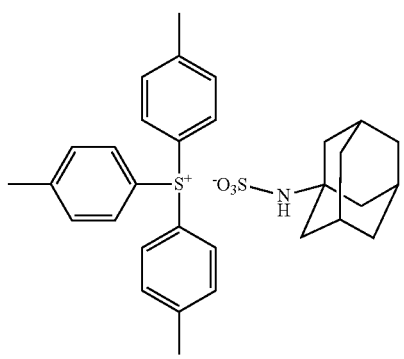

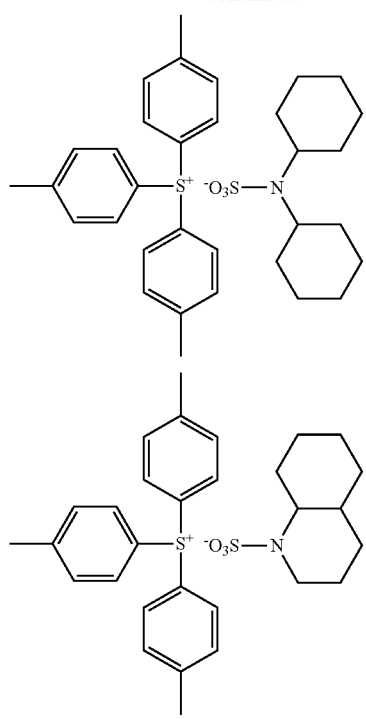
Examples of the weak acid inner salt (D) include the following salts.
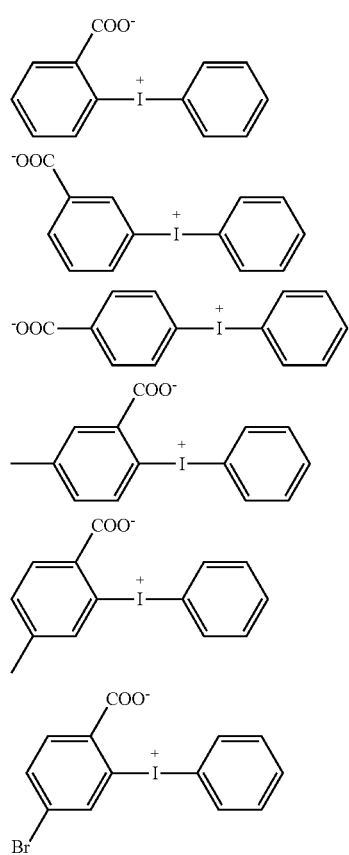
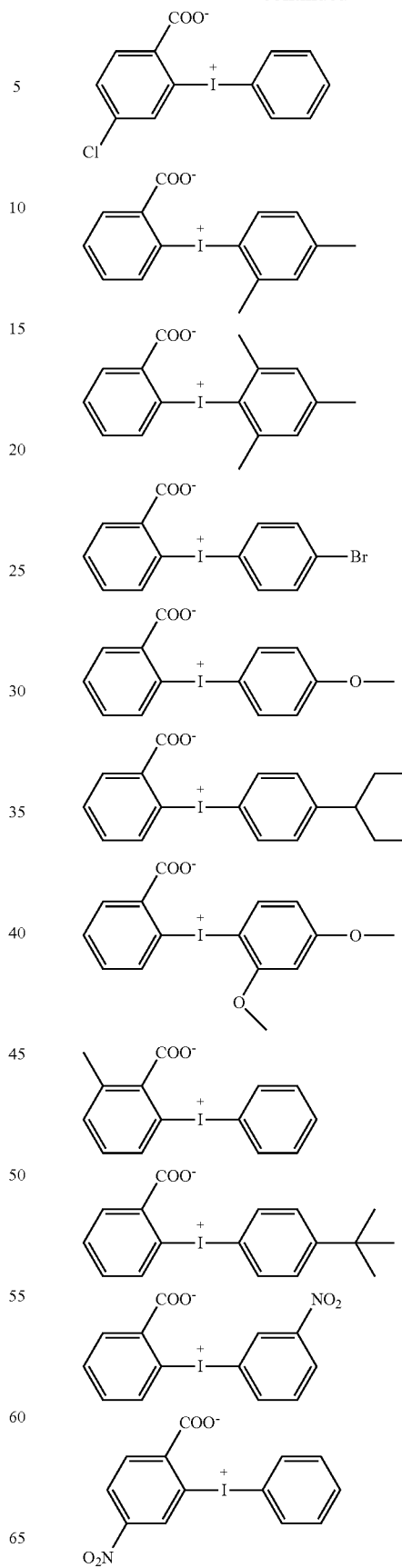

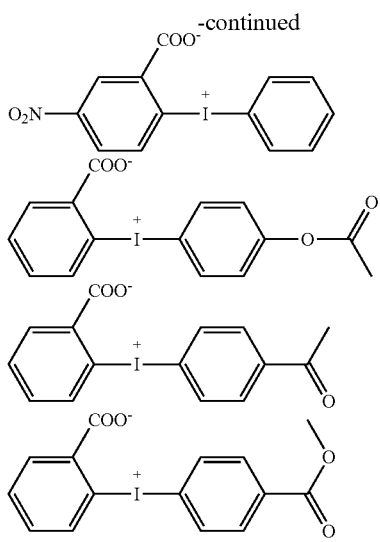

Examples of the basic nitrogen-containing organic compound include amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine, bipyridine and the like, and aromatic amines such as diisopropylaniline are preferable and 2,6-diisopropylaniline is more preferable.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

<Other Components>

The resist composition of the present disclosure may also include components other than the components mentioned above (hereinafter sometimes referred to as "other components (F)"). The other components (F) are not particularly limited and it is possible to use various additives known in the resist field, for example, sensitizers, dissolution inhibitors, surfactants, stabilizers and dyes.

<Preparation of Resist Composition>

The resist composition of the present disclosure can be prepared by mixing a resin of the present disclosure (A), an acid generator (B) and a salt generating an acid having an acidity lower than that of an acid generated from the acid generator, and, if necessary, a resin (A2), a resin (X), a quencher (C), a solvent (E) and other components (F). The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

<Method for Producing Resist Pattern>

The method for producing a resist pattern of the present disclosure comprises:
(1) a step of applying the resist composition of the present disclosure on a substrate,
(2) a step of drying the applied composition to form a composition layer,
(3) a step of exposing the composition layer,
(4) a step of heating the exposed composition layer, and
(5) a step of developing the heated composition layer.

The resist composition can be usually applied on a substrate using a conventionally used apparatus, such as a spin coater. Examples of the substrate include inorganic substrates such as a silicon wafer. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0 \times 10^5$ Pa.

The composition layer thus obtained is usually exposed using an aligner or a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and F2 excimer laser (wavelength of 157 nm), an exposure source capable of emitting harmonic laser beam in a far-ultraviolet or vacuum ultra violet region by wavelength-converting laser beam from a solid-state laser source (YAG or semiconductor laser), an exposure source capable of emitting electron beam or EUV and the like. In the present specification, such exposure to radiation is sometimes collectively referred to as exposure. The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present disclosure, an alkaline developing solution is used as the developing solution. The alkaline developing solution may be various aqueous alkaline solutions used in this field. Examples thereof include aqueous solutions of tetramethylammonium hydroxide and (2-hydroxyethyl) trimethylammonium hydroxide (commonly known as choline). The surfactant may be contained in the alkaline developing solution.

It is preferable that the developed resist pattern is washed with ultrapure water and then water remaining on the substrate and the pattern is removed.

When the negative resist pattern is produced from the resist composition of the present disclosure, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

<Applications>

The resist composition of the present disclosure is suitable as a resist composition for exposure of KrF excimer laser, a resist composition for exposure of ArF excimer laser, a resist composition for exposure of electron beam (EB) or a resist composition for exposure of EUV, and more suitable as a resist composition for exposure of electron beam (EB) or a resist composition for exposure of EUV, and the resist composition is useful for fine processing of semiconductors.

EXAMPLES

The present disclosure will be described more specifically by way of Examples. Percentages and parts expressing the contents or amounts used in the Examples are by mass unless otherwise specified.

The weight-average molecular weight is a value determined by gel permeation chromatography under the following conditions.

Equipment: HLC-8120 GPC type (manufactured by TOSOH CORPORATION)
Column: TSKgel Multipore $H_{XL}$-M×3+guardcolumn (manufactured by TOSOH CORPORATION)
Eluent: tetrahydrofuran
Flow rate: 1.0 mL/min
Detector: RI detector
Column temperature: 40° C.
Injection amount: 100 μl
Molecular weight standards: polystyrene standard (manufactured by TOSOH CORPORATION)

Structures of compounds were confirmed by measuring a molecular ion peak using mass spectrometry (Liquid Chromatography: Model 1100, manufactured by Agilent Technologies, Inc., Mass Spectrometry: Model LC/MSD, manufactured by Agilent Technologies, Inc.). The value of this molecular ion peak in the following Examples is indicated by "MASS".

Example 1: Synthesis of Compound Represented by Formula (I-5)

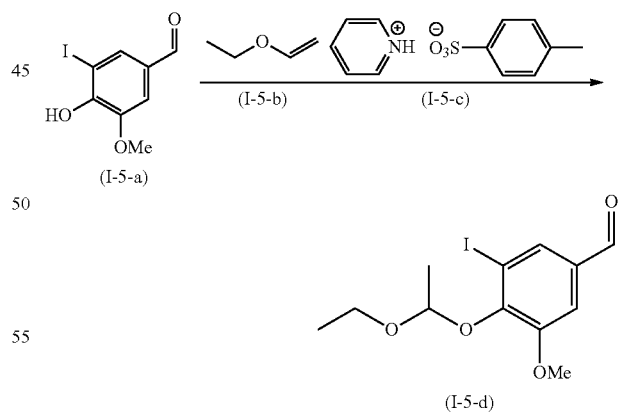

10 Parts of a compound represented by formula (I-5-a), 0.90 part of a compound represented by formula (I-5-c) and 100 parts of ethyl acetate were mixed, followed by stirring at 23° C. for 30 minutes and further cooling to 5° C. To the mixture thus obtained, 3.89 parts of a compound represented by formula (I-5-b) was added, followed by stirring at 5° C. for 30 minutes and further stirring at 23° C. for 8 hours. To the mixture thus obtained, 30 parts of an aqueous 4% sodium hydroxide solution was added, and after stirring at 23° C. for 30 minutes, the organic layer was isolated through separation. To the organic layer thus obtained, 50 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 9.78 parts of a compound represented by formula (I-5-d).

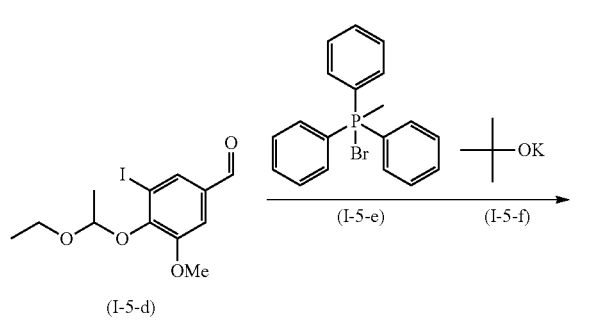

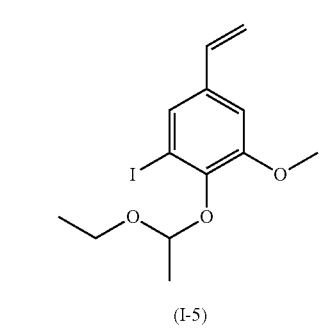

6.12 Parts of a compound represented by formula (I-5-e), 1.92 parts of a compound represented by formula (I-5-f) and 40 parts of tetrahydrofuran were mixed at 0° C., followed by stirring for 1 hour and further temperature rising to 5° C. To the mixture thus obtained, 5.00 parts of a compound represented by formula (I-5-d) was added over 1 hour, followed by temperature rising to 23° C. and further stirring at 23° C. for 12 hours. The mixture thus obtained was filtered and then 100 parts of methyl isobutyl ketone and 30 parts of ion-exchanged water were added to the filtrate thus recovered, and after stirring at 23° C. for 30 minutes, the organic layer was isolated through separation. To the organic layer thus obtained, 20 parts of ion-exchanged water was added, and after stirring at 23° C. for 30 minutes, the organic layer was isolated through separation. This water washing operation was repeated five times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 3.92 parts of a compound represented by formula (I-5).

MASS: 349.0 [M+H]$^+$

Example 2: Synthesis of Compound Represented by Formula (I-1)

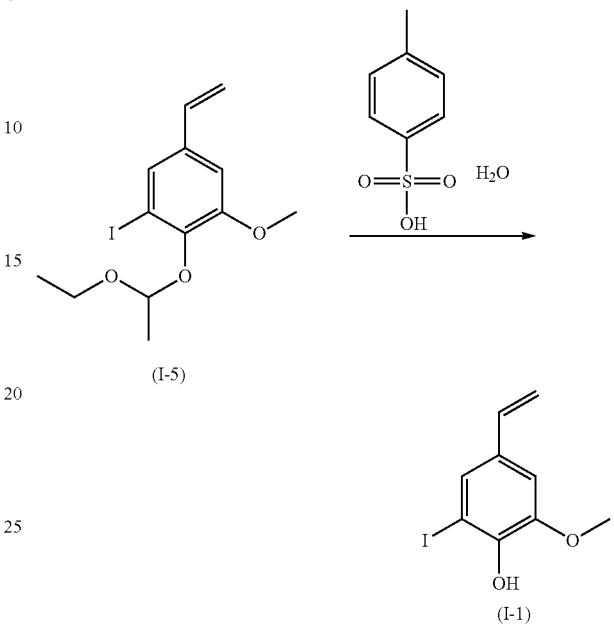

1.16 Parts of a compound represented by formula (I-5) and 3 parts of methyl isobutyl ketone were mixed, followed by stirring at 23° C. for 30 minutes. To the mixed solution thus obtained, 2.40 parts of an aqueous 2.5% p-toluenesulfonic acid solution was added dropwise, followed by stirring at 23° C. for 18 hours. To the reaction mixture thus obtained, 10 parts of methyl isobutyl ketone and 5 parts of ion-exchanged water were added, and after stirring at 23° C. for 30 minutes, the organic layer was isolated through separation. To the organic layer thus obtained, 5 parts of ion-exchanged water was added, and after stirring at 23° C. for 30 minutes, the organic layer was isolated through separation. This water washing operation was repeated five times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 0.67 part of a compound represented by formula (I-1).

MASS (Mass Spectrometry): 277.0 [M+H]$^+$

Example 3: Synthesis of Compound Represented by Formula (I-2)

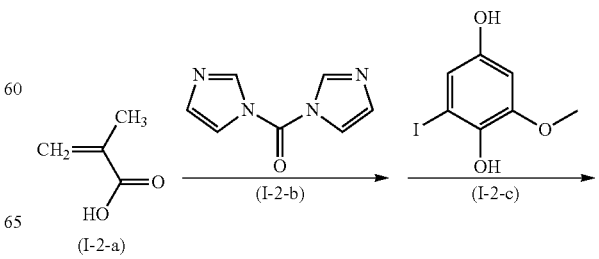

-continued

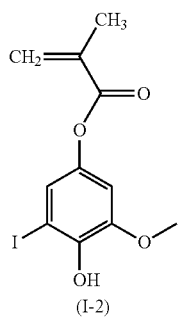

(I-2)

0.65 Part of a compound represented by formula (I-2-a) and 20 parts of acetonitrile were mixed, and after stirring at 23° C. for 30 minutes, 2.25 parts of a compound represented by formula (I-2-b) was added, followed by temperature rising to 50° C. and further stirring at 50° C. for 2 hours. To the mixture thus obtained, 2.00 parts of a compound represented by formula (I-2-c) was added, followed by stirring at 50° C. for 2 hours. The mixture thus obtained was cooled to 23° C. and then 50 parts of chloroform and 20 parts of ion-exchanged water were added, and after stirring at 23° C. for 30 minutes, the organic layer was isolated through separation. To the organic layer thus obtained, 20 parts of ion-exchanged water was added, and after stirring at 23° C. for 30 minutes, the organic layer was isolated through separation. This water washing operation was repeated five times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 1.48 parts of a compound represented by formula (I-2).

MASS: 335.0 [M+H]$^+$

Example 4: Synthesis of Compound Represented by Formula (I-25)

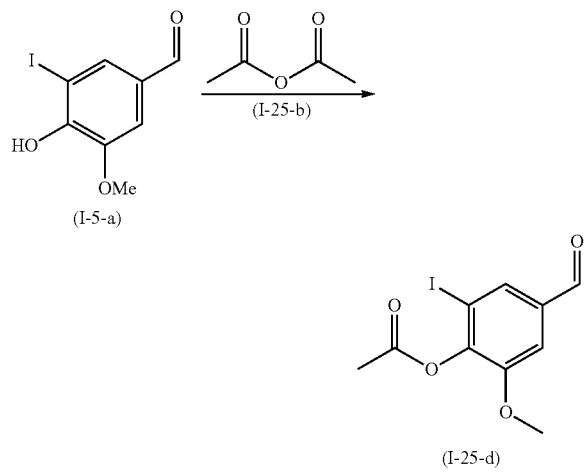

5 Parts of a compound represented by formula (I-5-a), 3.13 parts of pyridine, 0.44 part of dimethylaminopyridine and 40 parts of tetrahydrofuran were mixed, followed by stirring at 23° C. for 30 minutes and further cooling to 5° C. To the mixture thus obtained, 2.20 parts of a compound represented by formula (I-25-b) was added, followed by stirring at 5° C. for 30 minutes and further stirring at 23° C. for 2 hours. To the mixture thus obtained, 60 parts of chloroform and 15 parts of an aqueous 10% potassium carbonate solution were added, and after stirring at 23° C. for 30 minutes, the organic layer was isolated through separation. To the organic layer thus obtained, 15 parts of an aqueous 5% oxalic acid solution was added, and after stirring at 23° C. for 30 minutes, the organic layer was isolated through separation. This washing operation was repeated three times. To the organic layer thus obtained, 15 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 5.42 parts of a compound represented by formula (I-25-d).

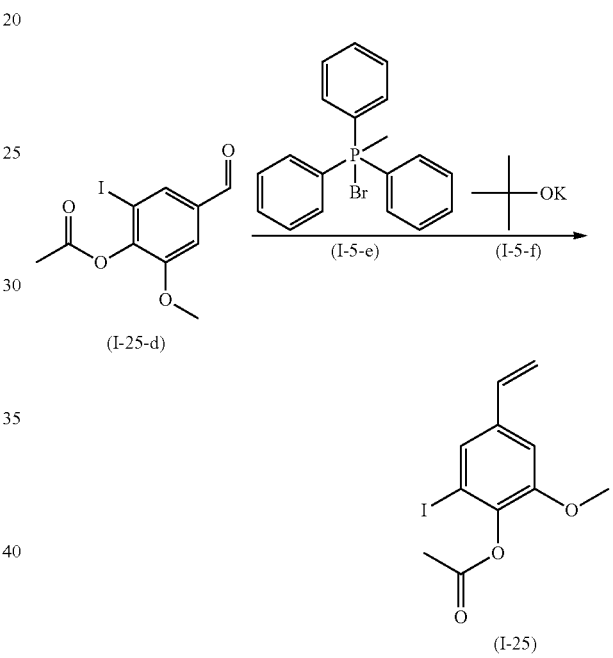

7.21 Parts of a compound represented by formula (I-5-e), 2.26 parts of a compound represented by formula (I-5-f) and 50 parts of tetrahydrofuran were mixed at 0° C., followed by stirring for 1 hour and further temperature rising to 5° C. To the mixture thus obtained, 5.38 parts of a compound represented by formula (I-25-d) was added over 1 hour, followed by temperature rising to 23° C. and further stirring at 23° C. for 12 hours. The mixture thus obtained was filtered and then 50 parts of hexane and 10 parts of ion-exchanged water were added to the filtrate thus recovered, and after stirring at 23° C. for 30 minutes, the organic layer was isolated through separation. To the organic layer thus obtained, 10 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 4.28 parts of a compound represented by formula (I-25).

MASS: 319.0 [M+H]$^+$

Example 5: Synthesis of Compound Represented by Formula (I-31)

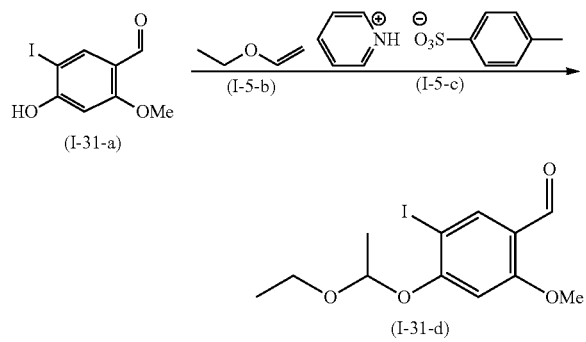

10 Parts of a compound represented by formula (I-31-a), 0.90 part of a compound represented by formula (I-5-c) and 100 parts of ethyl acetate were mixed, followed by stirring at 23° C. for 30 minutes and further cooling to 5° C. To the mixture thus obtained, 3.89 parts of a compound represented by formula (I-S-b) was added, followed by stirring at 5° C. for 30 minutes and further stirring at 23° C. for 8 hours. To the mixture thus obtained, 30 parts of an aqueous 4% sodium hydroxide solution was added, and after stirring at 23° C. for 30 minutes, the organic layer was isolated through separation. To the organic layer thus obtained, 50 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 9.89 parts of a compound represented by formula (I-31-d).

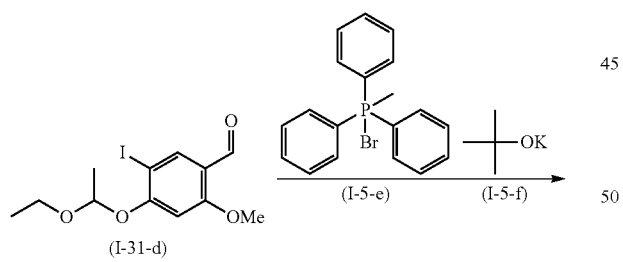

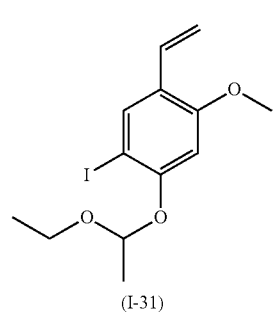

6.12 Parts of a compound represented by formula (I-31-e), 1.92 parts of a compound represented by formula (I-5-f) and 40 parts of tetrahydrofuran were mixed at 0° C., followed by stirring for 1 hour and further temperature rising to 5° C. To the mixture thus obtained, 5.00 parts of a compound represented by formula (I-5-d) was added over 1 hour, followed by temperature rising to 23° C. and further stirring at 23° C. for 12 hours. The mixture thus obtained was filtered and then 100 parts of methyl isobutyl ketone and 30 parts of ion-exchanged water were added to the filtrate thus recovered, and after stirring at 23° C. for 30 minutes, the organic layer was isolated through separation. To the organic layer thus obtained, 20 parts of ion-exchanged water was added, and after stirring at 23° C. for 30 minutes, the organic layer was isolated through separation. This water washing operation was repeated five times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 4.11 parts of a compound represented by formula (I-31).

MASS: 349.0 $[M+H]^+$

Example 6: Synthesis of Compound Represented by Formula (I-29)

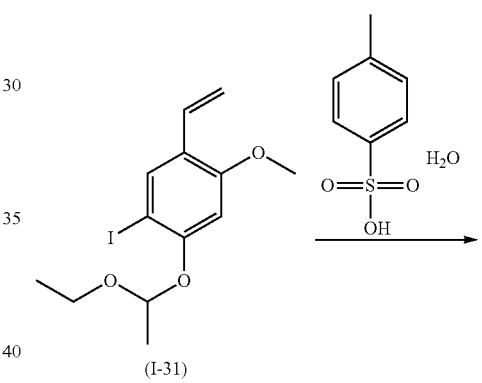

1.16 Parts of a compound represented by formula (I-31) and 3 parts of methyl isobutyl ketone were mixed, followed by stirring at 23° C. for 30 minutes. To the mixed solution thus obtained, 2.40 parts of an aqueous 2.5% p-toluenesulfonic acid solution was added dropwise, followed by stirring at 23° C. for 18 hours. To the reaction mixture thus obtained, 10 parts of methyl isobutyl ketone and 5 parts of ion-exchanged water were added, and after stirring at 23° C. for 30 minutes, the organic layer was isolated through separation. To the organic layer thus obtained, 5 parts of ion-exchanged water was added, and after stirring at 23° C. for 30 minutes, the organic layer was isolated through separation. This water washing operation was repeated five times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 0.74 part of a compound represented by formula (I-29).

MASS (Mass Spectrometry): 277.0 [M+H]⁺

Example 7: Synthesis of Compound Represented by Formula (I-47)

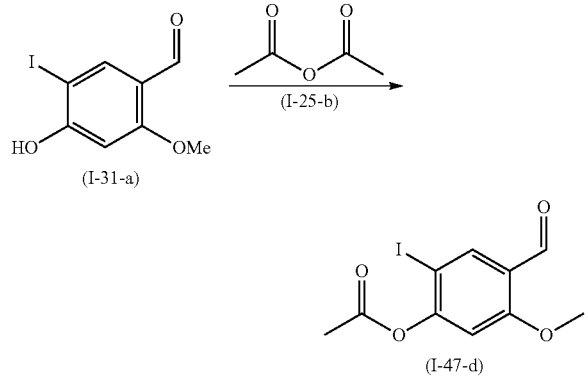

5 Parts of a compound represented by formula (I-31-a), 3.13 parts of pyridine, 0.44 part of dimethylaminopyridine and 40 parts of tetrahydrofuran were mixed, followed by stirring at 23° C. for 30 minutes and further cooling to 5° C. To the mixture thus obtained, 2.20 parts of a compound represented by formula (I-25-b) was added, followed by stirring at 5° C. for 30 minutes and further stirring at 23° C. for 2 hours. To the mixture thus obtained, 60 parts of chloroform and 15 parts of an aqueous 10% potassium carbonate solution were added, and after stirring at 23° C. for 30 minutes, the organic layer was isolated through separation. To the organic layer thus obtained, 15 parts of an aqueous 5% oxalic acid solution was added, and after stirring at 23° C. for 30 minutes, the organic layer was isolated through separation. This washing operation was repeated three times. To the organic layer thus obtained, 15 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 µm; manufactured by Kanto Chemical Co., Inc., developing solvent: n-heptane/ethyl acetate=1/1) to obtain 5.48 parts of a compound represented by formula (I-47-d).

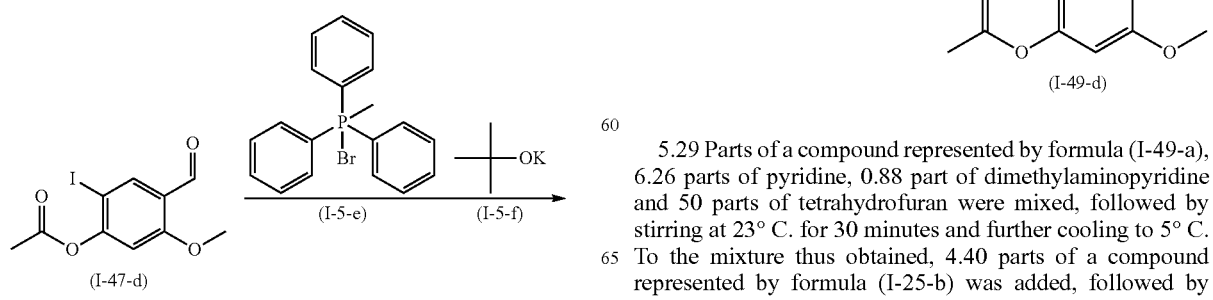

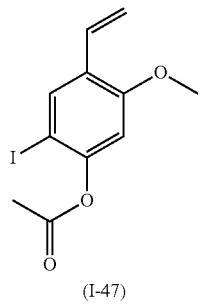

7.21 Parts of a compound represented by formula (I-5-e), 2.26 parts of a compound represented by formula (I-5-f) and 50 parts of tetrahydrofuran were mixed at 0° C., followed by stirring for 1 hour and further temperature rising to 5° C. To the mixture thus obtained, 5.38 parts of a compound represented by formula (I-47-d) was added over 1 hour, followed by temperature rising to 23° C. and further stirring at 23° C. for 12 hours. The mixture thus obtained was filtered and then 50 parts of hexane and 10 parts of ion-exchanged water were added to the filtrate thus recovered, and after stirring at 23° C. for 30 minutes, the organic layer was isolated through separation. To the organic layer thus obtained, 10 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 µm; manufactured by Kanto Chemical Co., Inc., developing solvent: n-heptane/ethyl acetate=1/1) to obtain 4.41 parts of a compound represented by formula (I-47).

MASS: 319.0 [M+H]⁺

Example 8: Synthesis of Compound Represented by Formula (I-49)

5.29 Parts of a compound represented by formula (I-49-a), 6.26 parts of pyridine, 0.88 part of dimethylaminopyridine and 50 parts of tetrahydrofuran were mixed, followed by stirring at 23° C. for 30 minutes and further cooling to 5° C. To the mixture thus obtained, 4.40 parts of a compound represented by formula (I-25-b) was added, followed by stirring at 5° C. for 30 minutes and further stirring at 23° C.

for 2 hours. To the mixture thus obtained, 60 parts of chloroform and 15 parts of an aqueous 10% potassium carbonate solution were added, and after stirring at 23° C. for 30 minutes, the organic layer was isolated through separation. To the organic layer thus obtained, 15 parts of an aqueous 5% oxalic acid solution was added, and after stirring at 23° C. for 30 minutes, the organic layer was isolated through separation. This washing operation was repeated three times. To the organic layer thus obtained, 15 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 6.42 parts of a compound represented by formula (I-49-d).

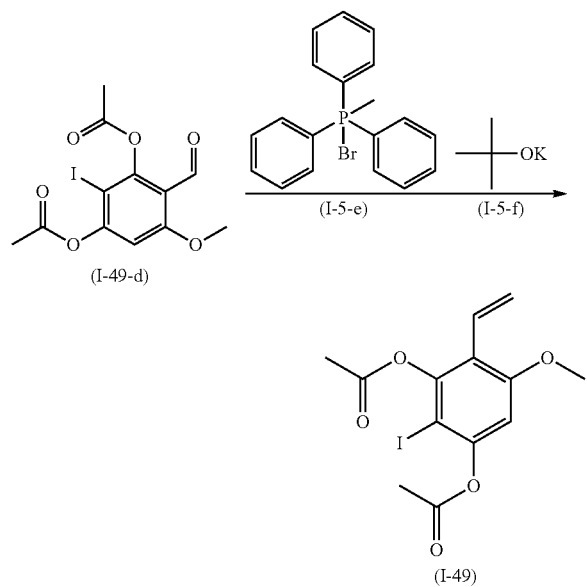

7.21 Parts of a compound represented by formula (I-5-e), 2.26 parts of a compound represented by formula (I-5-f) and 50 parts of tetrahydrofuran were mixed at 0° C., followed by stirring for 1 hour and further temperature rising to 5° C. To the mixture thus obtained, 6.36 parts of a compound represented by formula (I-49-d) was added over 1 hour, followed by temperature rising to 23° C. and further stirring at 23° C. for 12 hours. The mixture thus obtained was filtered and then 50 parts of hexane and 10 parts of ion-exchanged water were added to the filtrate thus recovered, and after stirring at 23° C. for 30 minutes, the organic layer was isolated through separation. To the organic layer thus obtained, 10 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 4.98 parts of a compound represented by formula (I-49).

MASS: 377.0 [M+H]$^+$

Example 9: Synthesis of Compound Represented by Formula (I-51)

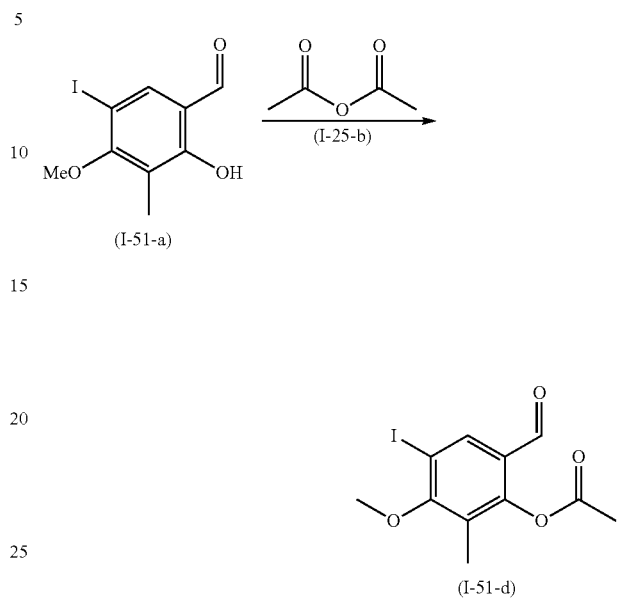

7.26 Parts of a compound represented by formula (I-51-a), 3.13 parts of pyridine, 0.44 part of dimethylaminopyridine and 40 parts of tetrahydrofuran were mixed, followed by stirring at 23° C. for 30 minutes and further cooling to 5° C. To the mixture thus obtained, 2.20 parts of a compound represented by formula (I-25-b) was added, followed by stirring at 5° C. for 30 minutes and further stirring at 23° C. for 2 hours. To the mixture thus obtained, 60 parts of chloroform and 15 parts of an aqueous 10% potassium carbonate solution were added, and after stirring at 23° C. for 30 minutes, the organic layer was isolated through separation. To the organic layer thus obtained, 15 parts of an aqueous 5% oxalic acid solution was added, and after stirring at 23° C. for 30 minutes, the organic layer was isolated through separation. This washing operation was repeated three times. To the organic layer thus obtained, 15 parts of ion-exchanged water was added, and after stirring at 23° C. for 30 minutes, the organic layer was isolated through separation. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 8.12 parts of a compound represented by formula (I-51-d).

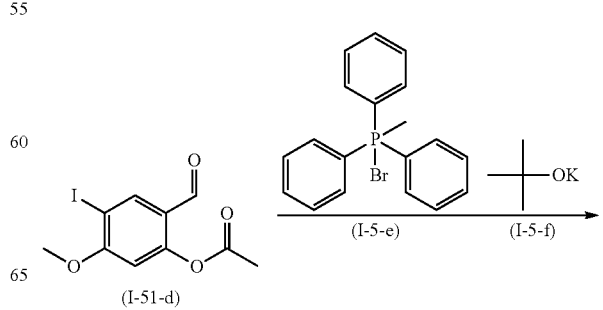

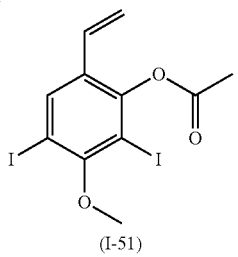

(I-51)

7.21 Parts of a compound represented by formula (I-5-e), 2.26 parts of a compound represented by formula (I-5-f) and 50 parts of tetrahydrofuran were mixed at 0° C., followed by stirring for 1 hour and further temperature rising to 5° C. To the mixture thus obtained, 7.50 parts of a compound represented by formula (I-51-d) was added over 1 hour, followed by temperature rising to 23° C. and further stirring at 23° C. for 12 hours. The mixture thus obtained was filtered and then 50 parts of hexane and 10 parts of ion-exchanged water were added to the filtrate thus recovered, and after stirring at 23° C. for 30 minutes, the organic layer was isolated through separation. To the organic layer thus obtained, 10 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 4.89 parts of a compound represented by formula (I-51).

MASS: 444.9 [M+H]$^+$

Example 10: Synthesis of Compound Represented by Formula (I-45)

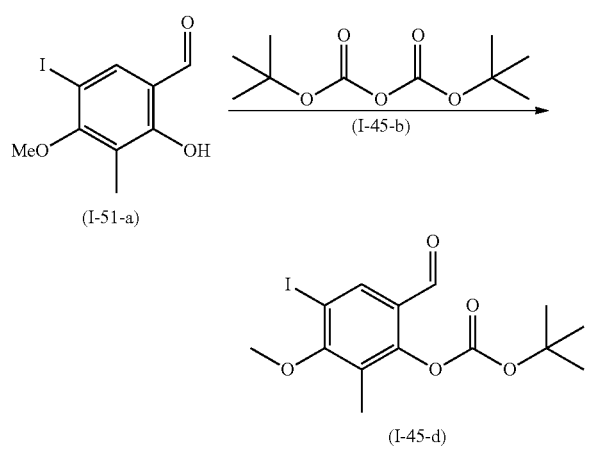

7.26 Parts of a compound represented by formula (I-51-a), 3.13 parts of pyridine, 0.44 part of dimethylaminopyridine and 40 parts of tetrahydrofuran were mixed, followed by stirring at 23° C. for 30 minutes and further cooling to 5° C. To the mixture thus obtained, 4.70 parts of a compound represented by formula (I-45-b) was added, followed by stirring at 5° C. for 30 minutes and further stirring at 23° C. for 2 hours. To the mixture thus obtained, 60 parts of chloroform and 15 parts of an aqueous 10% potassium carbonate solution were added, and after stirring at 23° C. for 30 minutes, the organic layer was isolated through separation. To the organic layer thus obtained, 15 parts of an aqueous 5% oxalic acid solution was added, and after stirring at 23° C. for 30 minutes, the organic layer was isolated through separation. This washing operation was repeated three times. To the organic layer thus obtained, 15 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 8.66 parts of a compound represented by formula (I-45-d).

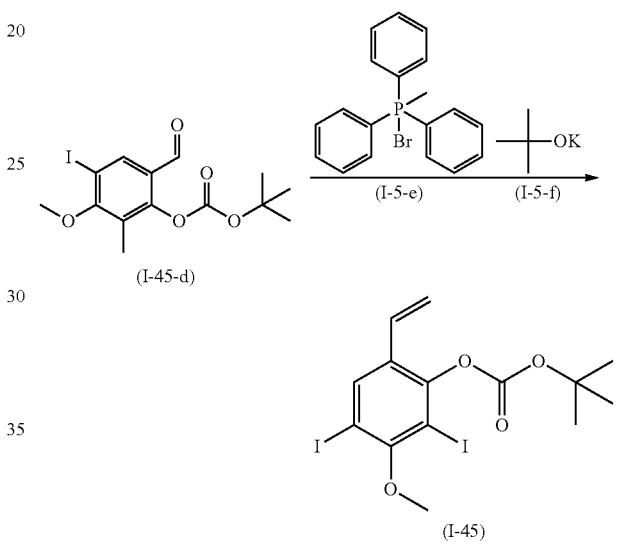

7.21 Parts of a compound represented by formula (I-5-e), 2.26 parts of a compound represented by formula (I-5-f) and 50 parts of tetrahydrofuran were mixed at 0° C., followed by stirring for 1 hour and further temperature rising to 5° C. To the mixture thus obtained, 8.48 parts of a compound represented by formula (I-45-d) was added over 1 hour, followed by temperature rising to 23° C. and further stirring at 23° C. for 12 hours. The mixture thus obtained was filtered and then 50 parts of hexane and 10 parts of ion-exchanged water were added to the filtrate thus recovered, and after stirring at 23° C. for 30 minutes, the organic layer was isolated through separation. To the organic layer thus obtained, 10 parts of ion-exchanged water was added, and after stirring at 23° C. for 30 minutes, the organic layer was isolated through separation. This water washing operation was repeated three times. The organic layer thus obtained was concentrated, and then the concentrated mixture was isolated from a column (silica gel 60 N (spherical, neutral) 100-210 μm; manufactured by Kanto Chemical Co., Inc., developing solvent: n-heptane/ethyl acetate=1/1) to obtain 5.23 parts of a compound represented by formula (I-45).

MASS: 502.9 [M+H]$^+$

Synthesis of Resin

Compounds (monomers) used in the synthesis of the resin are shown below.

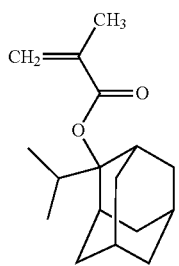
(a1-1-3)
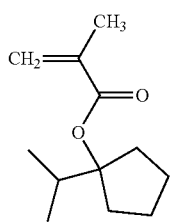
(a1-2-6)
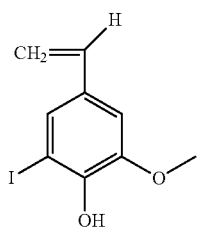
(I-1)
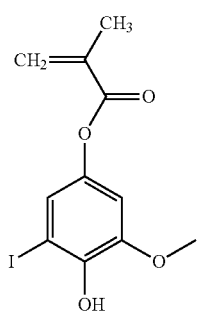
(I-2)
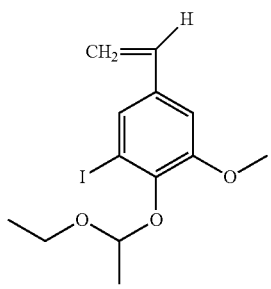
(I-5)
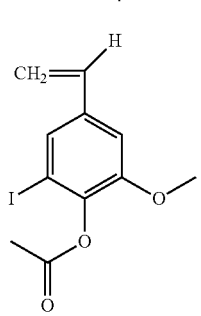
(I-25)
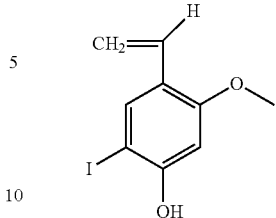
(I-29)
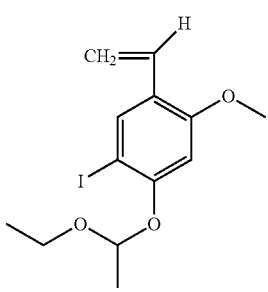
(I-31)
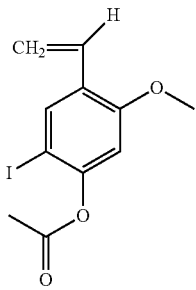
(I-47)
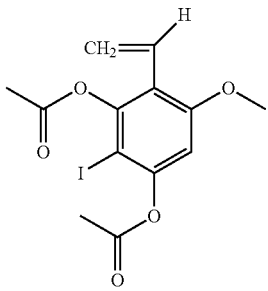
(I-49)
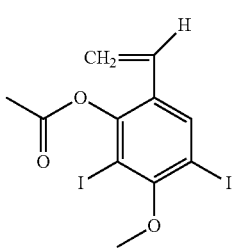
(I-51)
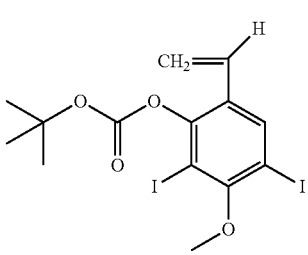
(I-45)

-continued (IX-1) 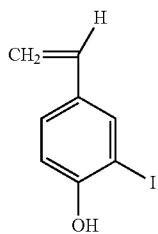

(IX-2) 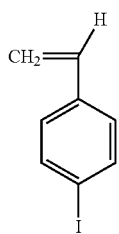

(IX-3) 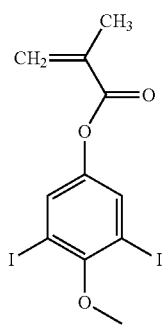

(IX-4) 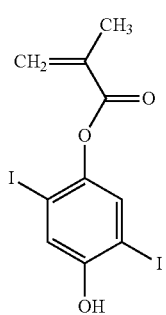

(IX-5) 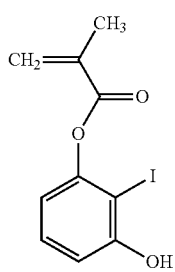

-continued (IX-6) 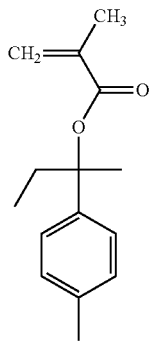

(a2-1-3) 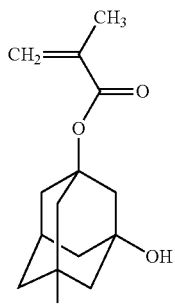

(a3-4-2) 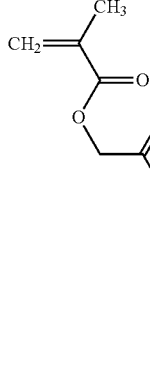

Hereinafter, these compounds are referred to as "monomer (a1-1-3)" according to the formula number.

Example 11: Synthesis of Resin A1

Using acetoxystyrene, a monomer (I-1), a monomer (a1-1-3) and a monomer (a1-2-6) as monomers, these monomers were mixed in a molar ratio of 28:10:32:30 [acetoxystyrene:monomer (I-1):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvaleronitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A1 having a weight-average molecular weight of about $5.2 \times 10^3$ in a yield of 68%. This resin A1 has the following structural units.

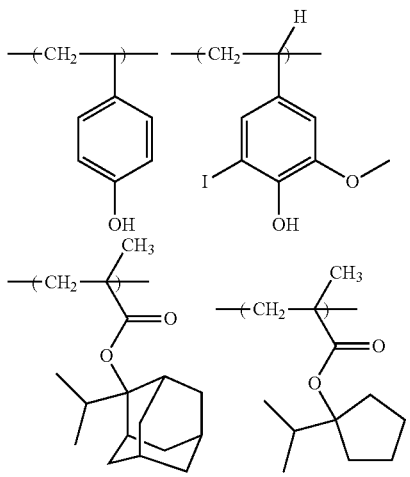

Example 12: Synthesis of Resin A2

Using acetoxystyrene, a monomer (I-2), a monomer (a1-1-3) and a monomer (a1-2-6) as monomers, these monomers were mixed in a molar ratio of 28:10:32:30 of [acetoxystyrene:monomer (I-2):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A2 having a weight-average molecular weight of about $5.5 \times 10^3$ in a yield of 65%. This resin A2 has the following structural units.

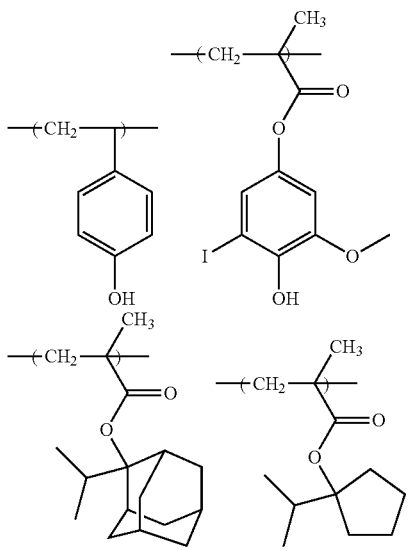

Example 13: Synthesis of Resin A3

Using acetoxystyrene, a monomer (I-5), a monomer (a1-1-3) and a monomer (a1-2-6) as monomers, these monomers were mixed in a molar ratio of 28:10:32:30 [acetoxystyrene:monomer (I-5):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A3 having a weight-average molecular weight of about $5.3 \times 10^3$ in a yield of 66%. This resin A3 has the following structural units.

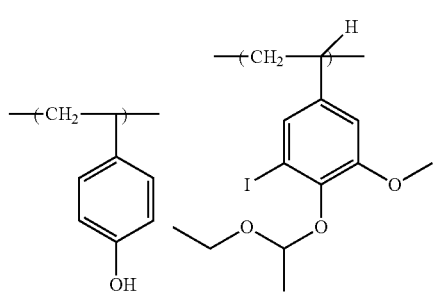

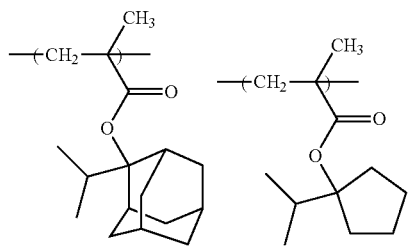

Example 14: Synthesis of Resin A4

Using a monomer (I-1) and a monomer (I-5) as monomers, these monomers were mixed in a molar ratio of 38:62 [monomer (I-1):monomer (I-5)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. Thereafter, the polymerization reaction was poured into a large amount of n-heptane to precipitate a resin, followed by filtration and recovery to obtain a resin A4 having a weight-average molecular weight of about $5.9 \times 10^3$ in a yield of 88%. This resin A4 has the following structural units.

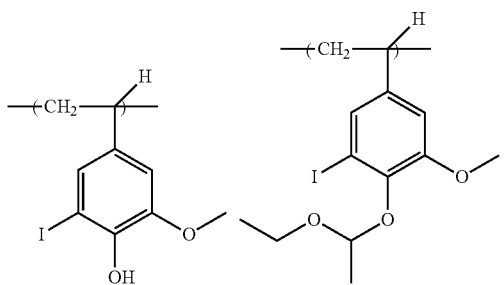

A4

Example 15: Synthesis of Resin A5

Using acetoxystyrene, a monomer (I-25), a monomer (a1-1-3) and a monomer (a1-2-6) as monomers, these monomers were mixed in a molar ratio of 28:10:32:30 [acetoxystyrene:monomer (I-25):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A5 having a weight-average molecular weight of about $5.1 \times 10^3$ in a yield of 79%. This resin A5 has the following structural units.

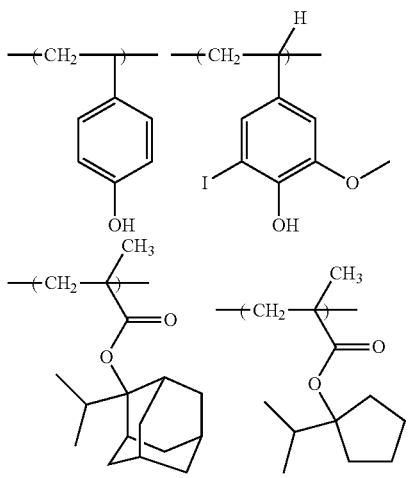

A5

Example 16: Synthesis of Resin A6

Using acetoxystyrene, a monomer (I-29), a monomer (a1-1-3) and a monomer (a1-2-6) as monomers, these monomers were mixed in a molar ratio of 28:10:32:30 [acetoxystyrene:monomer (I-29):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A6 having a weight-average molecular weight of about $5.4 \times 10^3$ in a yield of 67%. This resin A6 has the following structural units.

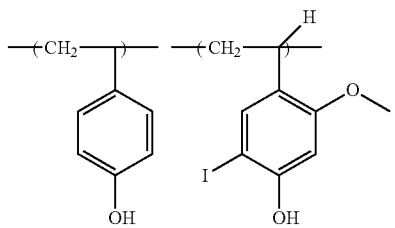

A6

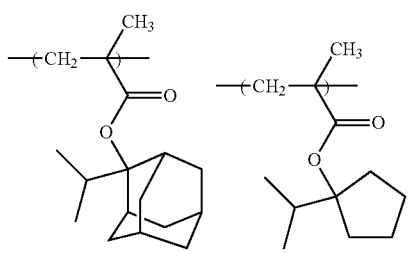

Example 17: Synthesis of Resin A7

Using acetoxystyrene, a monomer (I-31), a monomer (a1-1-3) and a monomer (a1-2-6) as monomers, these monomers were mixed in a molar ratio of 28:10:32:30 [acetoxystyrene:monomer (I-31):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A7 having a weight-average molecular weight of about $5.5 \times 10^3$ in a yield of 64%. This resin A7 has the following structural units.

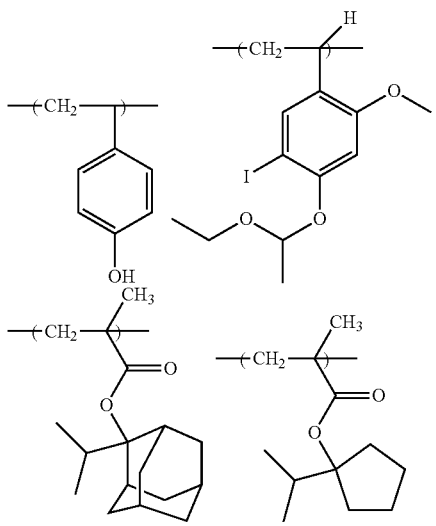

A7

Example 18: Synthesis of Resin A8

Using acetoxystyrene, a monomer (1-47), a monomer (a1-1-3) and a monomer (a1-2-6) as monomers, these monomers were mixed in a molar ratio of 28:10:32:30 [acetoxystyrene:monomer (I-47):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A8 having a weight-average molecular weight of about $5.2 \times 10^3$ in a yield of 80%. This resin A8 has the following structural units.

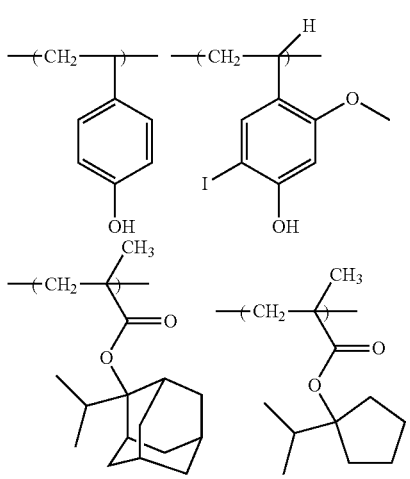

A8

Example 19: Synthesis of Resin A9

Using acetoxystyrene, a monomer (1-49), a monomer (a1-1-3) and a monomer (a1-2-6) as monomers, these monomers were mixed in a molar ratio of 28:10:32:30 [acetoxystyrene:monomer (I-49):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A9 having a weight-average molecular weight of about $5.5 \times 10^3$ in a yield of 69%. This resin A9 has the following structural units.

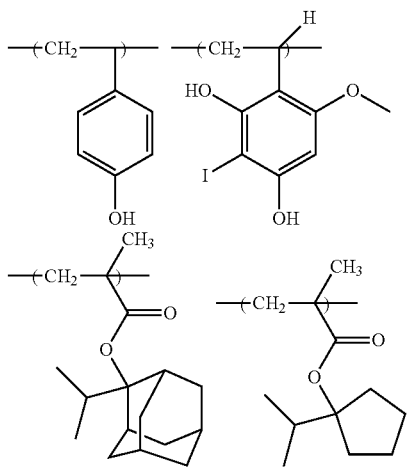

A9

Example 20: Synthesis of Resin A10

Using acetoxystyrene, a monomer (I-51), a monomer (a1-1-3) and a monomer (a1-2-6) as monomers, these monomers were mixed in a molar ratio of 28:10:32:30 [acetoxystyrene:monomer (I-51):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A10 having a weight-average molecular weight of about $5.1 \times 10^3$ in a yield of 65%. This resin A10 has the following structural units.

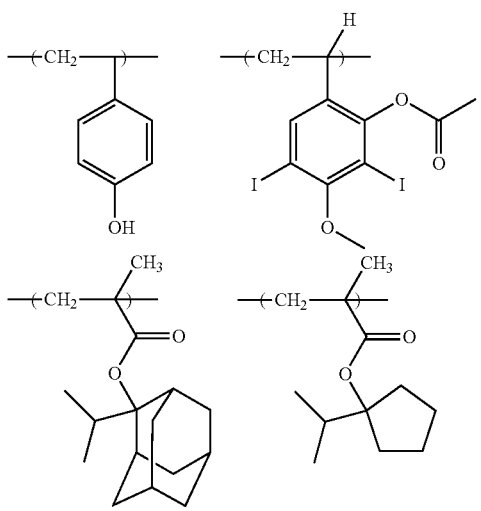

Example 21: Synthesis of Resin A11

Using acetoxystyrene, a monomer (1-45), a monomer (a1-1-3) and a monomer (a1-2-6) as monomers, these monomers were mixed in a molar ratio of 28:10:32:30 [acetoxystyrene:monomer (I-45):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A11 having a weight-average molecular weight of about $5.3 \times 10^3$ in a yield of 63%. This resin A11 has the following structural units.

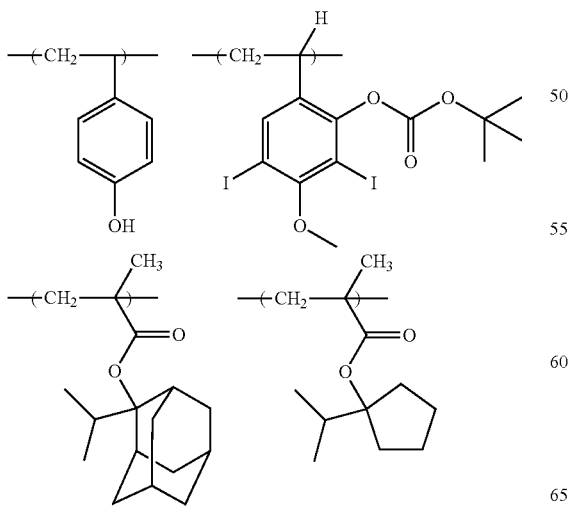

Example 22: Synthesis of Resin A12

Using acetoxystyrene, a monomer (I-1), a monomer (a1-1-3), a monomer (a1-2-6), a monomer (a2-1-3) and a monomer (a3-4-2) as monomers, these monomers were mixed in a molar ratio of 17:10:20:35:3:15 [acetoxystyrene:monomer (I-1):monomer (a1-1-3):monomer (a1-2-6):monomer (a2-1-3):monomer (a3-4-2)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin A12 having a weight-average molecular weight of about $5.3 \times 10^3$ in a yield of 65%. This resin A12 has the following structural units.

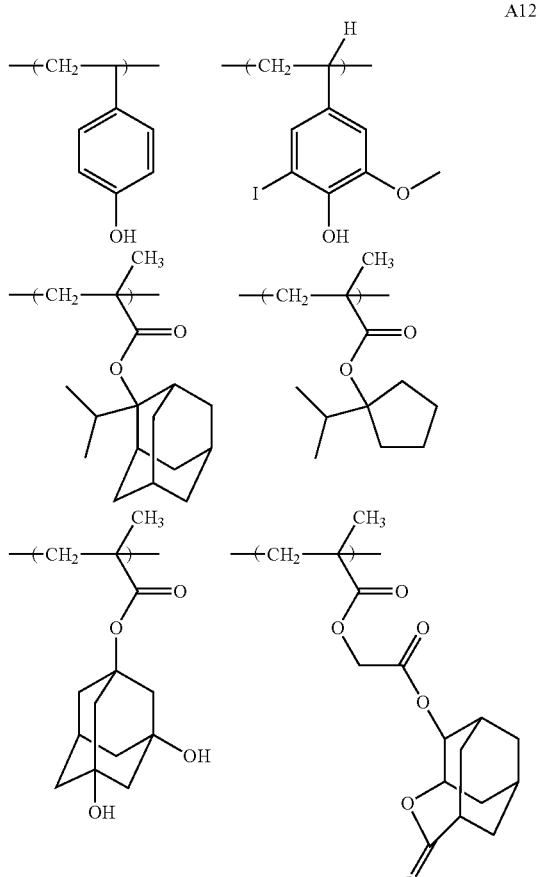

Synthesis Example 1 [Synthesis of Resin AX1]

Using acetoxystyrene, a monomer (IX-1), a monomer (a1-1-3) and a monomer (a1-2-6) as monomers, these monomers were mixed in a molar ratio of 28:10:32:30 [acetoxystyrene:monomer (IX-1):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin AX1 having a weight-average molecular weight of about $5.2 \times 10^3$ in a yield of 60%. This resin AX1 has the following structural units.

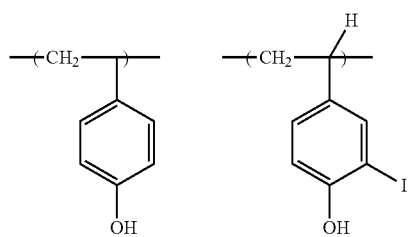

AX1

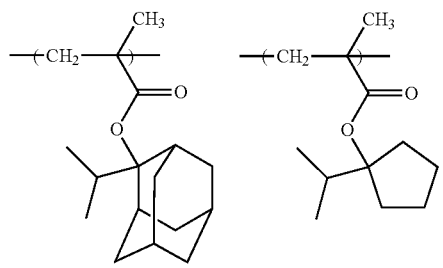

Synthesis Example 2 [Synthesis of Resin AX2]

Using acetoxystyrene, a monomer (IX-2), a monomer (a1-1-3) and a monomer (a1-2-6) as monomers, these monomers were mixed in a molar ratio of 28:10:32:30 [acetoxystyrene:monomer (IX-2):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus obtained was poured into a large amount of n-heptane to precipitate a resin, followed by filtration and recovery to obtain a resin AX2 having a weight-average molecular weight of about $5.5 \times 10^3$ in a yield of 64%. This resin AX2 has the following structural units.

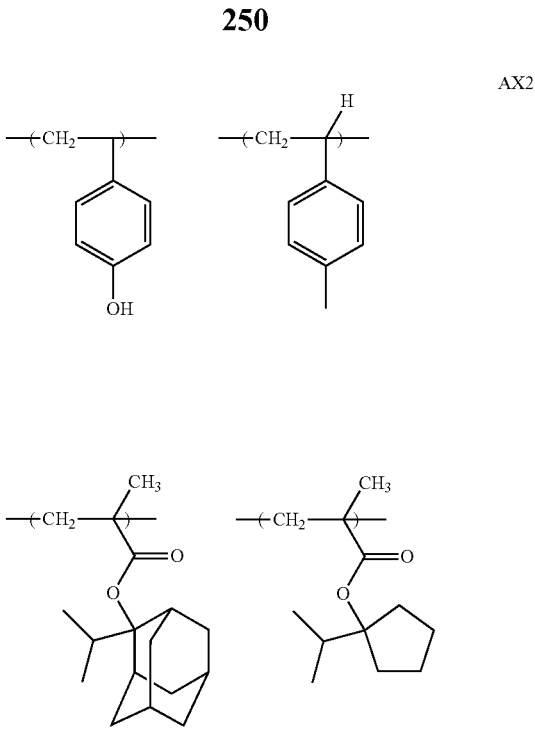

AX2

Synthesis Example 3 [Synthesis of Resin AX3]

Using acetoxystyrene, a monomer (IX-3), a monomer (a1-1-3) and a monomer (a1-2-6) as monomers, these monomers were mixed in a molar ratio of 28:10:32:30 [acetoxystyrene:monomer (IX-3):monomer (a1-1-3):monomer (a1-2-6)], and methyl isobutyl ketone was added in the amount of 1.5 mass times the total mass of all monomers. To the mixture thus obtained, azobisisobutyronitrile and azobis(2,4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin AX3 having a weight-average molecular weight of about $5.8 \times 10^3$ in a yield of 68%. This resin AX3 has the following structural units.

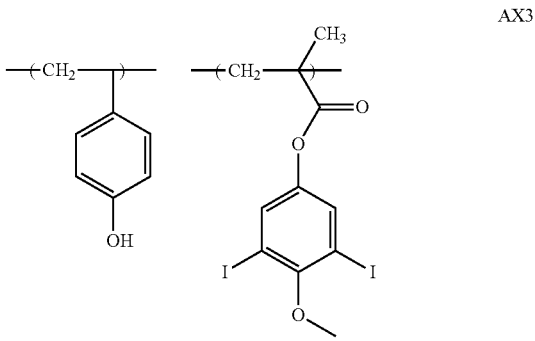

AX3

-continued

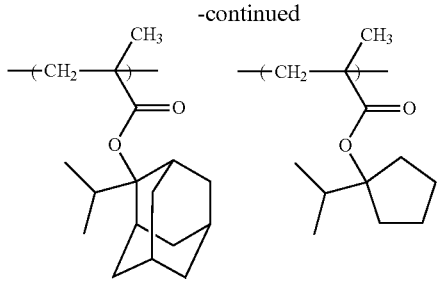

Synthesis Example 4 [Synthesis of Resin AX4]

Using acetoxystyrene, a monomer (IX-4), a monomer (a1-1-3) and a monomer (a1-2-6) as monomers, these monomers were mixed in a molar ratio of 28:10:32:30 [acetoxystyrene:monomer (IX-4):monomer (a1-1-3):monomer (a1-2-6)], and methyl isobutyl ketone was added in the amount of 1.5 mass times the total mass of all monomers. To the mixture thus obtained, azobisisobutyronitrile and azobis(2, 4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin AX4 having a weight-average molecular weight of about $5.6 \times 10^3$ in a yield of 65%. This resin AX4 has the following structural units.

AX4

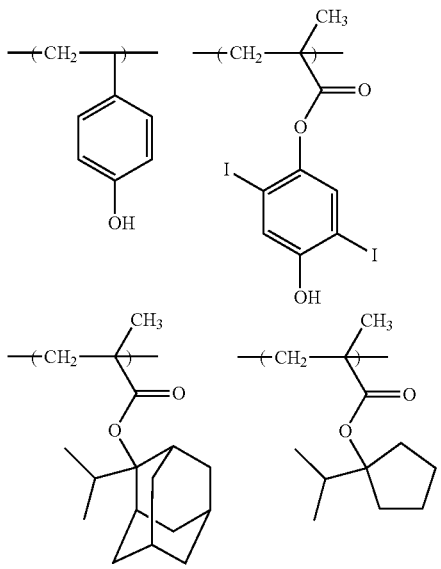

Synthesis Example 5 [Synthesis of Resin AX5]

Using acetoxystyrene, a monomer (IX-5), a monomer (a1-1-3) and a monomer (a1-2-6) as monomers, these monomers were mixed in a molar ratio of 28:10:32:30 [acetoxystyrene:monomer (IX-5):monomer (a1-1-3):monomer (a1-2-6)], and methyl isobutyl ketone was added in the amount of 1.5 mass times the total mass of all monomers. To the mixture thus obtained, azobisisobutyronitrile and azobis(2, 4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin AX5 having a weight-average molecular weight of about $5.4 \times 10^3$ in a yield of 70%. This resin AX5 has the following structural units.

AX5

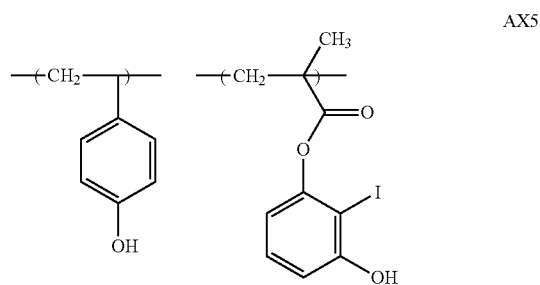

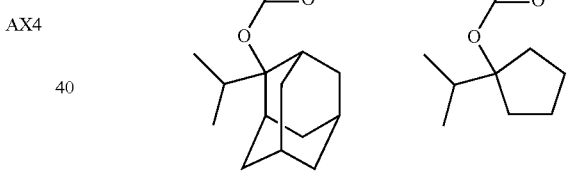

Synthesis Example 6 [Synthesis of Resin AX6]

Using acetoxystyrene, a monomer (IX-6), a monomer (a1-1-3) and a monomer (a1-2-6) as monomers, these monomers were mixed in a molar ratio of 28:10:32:30 [acetoxystyrene:monomer (IX-6):monomer (a1-1-3):monomer (a1-2-6)], and methyl isobutyl ketone was added in the amount of 1.5 mass times the total mass of all monomers. To the mixture thus obtained, azobisisobutyronitrile and azobis(2, 4-dimethylvarelonitrile) as initiators were added in the amounts of 1.2 mol % and 3.6 mol % based on the total molar number of all monomers, and then the mixture was heated at 73° C. for about 5 hours. To the polymerization reaction solution thus obtained, an aqueous 25% tetramethylammonium hydroxide solution was added, followed by stirring for 12 hours and further isolation through separation. The organic layer thus recovered was poured into a large amount of n-heptane to precipitate a resin, followed by filtration and recovery to obtain a resin AX6 having a weight-average molecular weight of about $5.8 \times 10^3$ in a yield of 59%. This resin AX6 has the following structural units.

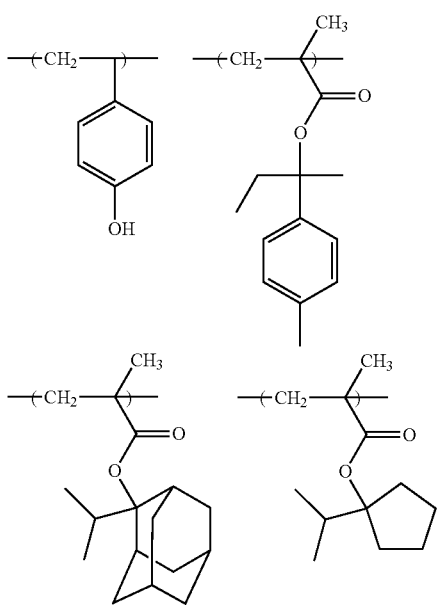

AX6

<Preparation of Resist Composition>

The mixture obtained by mixing the respective components shown in Table 1, followed by dissolving was filtered through a fluororesin filter having a pore diameter of 0.2 μm to prepare resist compositions.

TABLE 1

| Resist composition | Resin | Acid generator | Quencher | PB/PEB |
|---|---|---|---|---|
| Composition 1 | A1 = 10 parts | B1-43 = 3.4 parts | D1 = 0.7 part | 110° C./120° C. |
| Composition 2 | A2 = 10 parts | B1-43 = 3.4 parts | D1 = 0.7 part | 110° C./120° C. |
| Composition 3 | A3 = 10 parts | B1-43 = 3.4 parts | D1 = 0.7 part | 110° C./120° C. |
| Composition 4 | A4 = 10 parts | B1-43 = 3.4 parts | D1 = 0.7 part | 110° C./120° C. |
| Composition 5 | A5 = 10 parts | B1-43 = 3.4 parts | D1 = 0.7 part | 110° C./120° C. |
| Composition 6 | A6 = 10 parts | B1-43 = 3.4 parts | D1 = 0.7 part | 110° C./120° C. |
| Composition 7 | A7 = 10 parts | B1-43 = 3.4 parts | D1 = 0.7 part | 110° C./120° C. |
| Composition 8 | A8 = 10 parts | B1-43 = 3.4 parts | D1 = 0.7 part | 110° C./120° C. |
| Composition 9 | A9 = 10 parts | B1-43 = 3.4 parts | D1 = 0.7 part | 110° C./120° C. |
| Composition 10 | A10 = 10 parts | B1-43 = 3.4 parts | D1 = 0.7 part | 110° C./120° C. |
| Composition 11 | A11 = 10 parts | B1-43 = 3.4 parts | D1 = 0.7 part | 110° C./120° C. |
| Composition 12 | A12 = 10 parts | B1-43 = 3.4 parts | D1 = 0.7 part | 110° C./120° C. |
| Comparative Composition 1 | AX1 = 10 parts | B1-43 = 3.4 parts | D1 = 0.7 part | 110° C./120° C. |
| Comparative Composition 2 | AX2 = 10 parts | B1-43 = 3.4 parts | D1 = 0.7 part | 110° C./120° C. |
| Comparative Composition 3 | AX3 = 10 parts | B1-43 = 3.4 parts | D1 = 0.7 part | 110° C./120° C |
| Comparative Composition 4 | AX4 = 10 parts | B1-43 = 3.4 parts | D1 = 0.7 part | 110° C./120° C. |
| Comparative Composition 5 | AX5 = 10 parts | B1-43 = 3.4 parts | D1 = 0.7 part | 110° C./120° C. |
| Comparative Composition 6 | AX6 = 10 parts | B1-43 = 3.4 parts | D1 = 0.7 part | 110° C./120° C. |

<Resin>

A1 to A12, AX1 to AX6: Resin A1 to Resin A12, Resin AX1 to Resin AX6

<Acid Generator (B)>

B1-43: Salt represented by formula (B1-43); synthesized by the method mentioned in JP 2016-47815 A

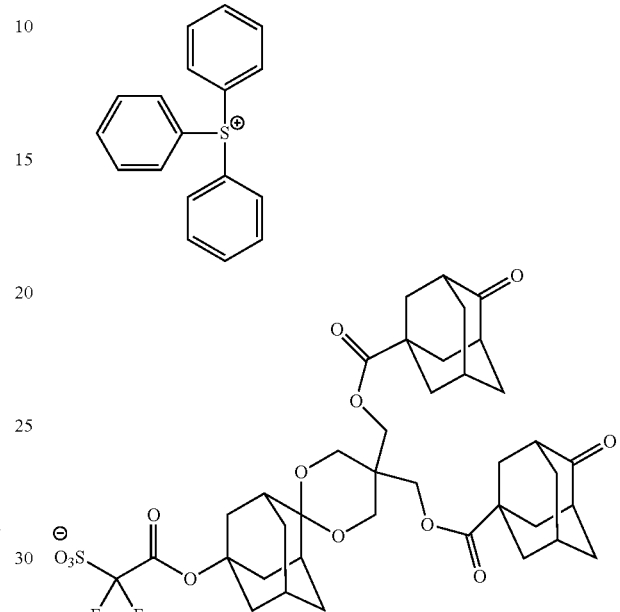

<Quencher (C)>

(Salt Generating an Acid Having an Acidity Lower than that of an Acid Generated from an Acid Generator)

D1: synthesized by the method mentioned in JP 2011-39502 A

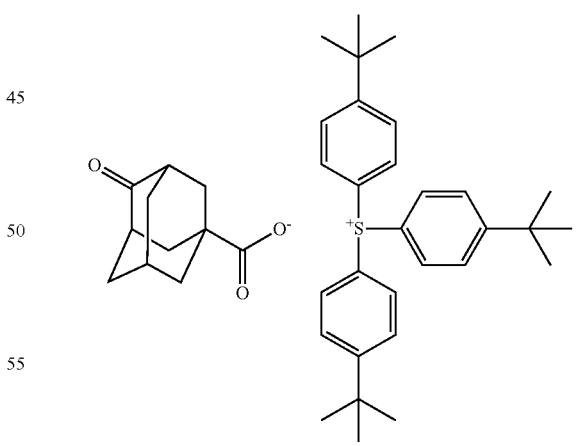

<Solvent>

| Propylene glycol monomethyl ether acetate | 400 parts |
|---|---|
| Propylene glycol monomethyl ether | 150 parts |
| γ-Butyrolactone | 5 parts |

(Evaluation of Exposure of Resist Composition with Electron Beam, Alkaline Solvent Development)

Each 6 inch-diameter silicon wafer was treated with hexamethyldisilazane and then baked on a direct hot plate at 90° C. for 60 seconds. A resist composition was spin-coated on the silicon wafer so that the thickness of the composition layer became 0.04 μm. The coated silicon wafer was prebaked on the direct hot plate at the temperature shown in the column "PB" of Table 1 for 60 seconds. Using an electron-beam direct-write system ("ELS-F125 125 keV", manufactured by ELIONIX INC.), contact hole patterns (hole pitch: 40 nm/hole diameter: 17 nm) were directly written on the composition layer formed on the wafer while changing the exposure dose stepwise.

After the exposure, post-exposure baking was performed on the hot plate at the temperature shown in the column "PEB" of Table 1 for 60 seconds, followed by paddle development with an aqueous 2.38% by mass tetramethylammonium hydroxide solution for 60 seconds to obtain a resist pattern.

In the resist pattern obtained after development, the exposure dose at which the hole diameter became 17 nm was regarded as effective sensitivity.

<Evaluation of CD Uniformity (CDU)>

In the effective sensitivity, the hole diameter of the pattern formed using a mask having a hole dimeter of 17 nm was determined by measuring 24 times per one hole and the average of the measured values was regarded as the average hole diameter. The standard deviation was determined under the conditions that the average diameter of 400 holes about the patterns formed using the mask having a hole dimeter of 17 nm in the same wafer was regarded to as population.

The results are shown in Table 2. The numerical value in the parenthesis represents the standard deviation (nm).

TABLE 2

|  | Resist composition | CDU |
| --- | --- | --- |
| Example 23 | Composition 1 | 2.92 |
| Example 24 | Composition 2 | 2.99 |
| Example 25 | Composition 3 | 3.03 |
| Example 26 | Composition 4 | 3.07 |
| Example 27 | Composition 5 | 2.92 |
| Example 28 | Composition 6 | 2.93 |
| Example 29 | Composition 7 | 3.01 |
| Example 30 | Composition 8 | 2.92 |
| Example 31 | Composition 9 | 2.88 |
| Example 32 | Composition 10 | 2.95 |
| Example 33 | Composition 11 | 3.04 |
| Example 34 | Composition 12 | 2.98 |
| Comparative Example 1 | Comparative Composition 1 | 3.16 |
| Comparative Example 2 | Comparative Composition 2 | 3.86 |
| Comparative Example 3 | Comparative Composition 3 | 3.69 |
| Comparative Example 4 | Comparative Composition 4 | 3.28 |
| Comparative Example 5 | Comparative Composition 5 | 3.31 |
| Comparative Example 6 | Comparative Composition 6 | 3.33 |

As compared with Comparative Compositions 1 to 6, Compositions 1 to 12 exhibited small standard deviation and satisfactory evaluation of CD uniformity (CDU).

(Evaluation of Exposure of Resist Composition with Electron Beam, Organic Solvent Development)

Each 6 inch-diameter silicon wafer was treated with hexamethyldisilazane on a direct hot plate at 90° C. for 60 seconds. A resist composition was spin-coated on the silicon wafer in such a manner that the thickness of the composition layer became 0.04 μm. Then, the coated silicon wafer was prebaked on the direct hot plate at the temperature shown in the column "PB" of Table 1 for 60 seconds to form a composition layer. Using an electron-beam direct-write system ("ELS-F125 125 keV", manufactured by ELIONIX INC.), contact hole patterns (hole pitch of 40 nm/hole diameter of 17 nm) were directly written on the composition layer formed on the wafer while changing the exposure dose stepwise.

After exposure, post-exposure baking was performed on the hot plate at the temperature shown in the column "PEB" of Table 1 for 60 seconds, followed by development with butyl acetate (manufactured by Tokyo Chemical Industry Co., Ltd.) as a developer at 23° C. for 20 seconds using the dynamic dispensing method to obtain resist patterns.

In the resist pattern obtained after development, the exposure dose at which the diameter of holes formed became 17 nm was defined as effective sensitivity.

<Evaluation of CD Uniformity (CDU)>

In the effective sensitivity, the hole diameter of the pattern formed using a mask having a hole dimeter of 17 nm was determined by measuring 24 times per one hole and the average of the measured values was regarded as the average hole diameter. The standard deviation was determined under the conditions that the average diameter of 400 holes about the patterns formed using the mask having a hole dimeter of 17 nm in the same wafer was regarded to as population.

The results are shown in Table 3. The numerical value in the parenthesis represents the standard deviation (nm).

TABLE 3

|  | Resist composition | CDU |
| --- | --- | --- |
| Example 35 | Composition 1 | 2.97 |
| Example 36 | Composition 12 | 2.80 |
| Comparative Example 7 | Comparative Composition 1 | 3.24 |
| Comparative Example 8 | Comparative Composition 2 | 3.88 |
| Comparative Example 9 | Comparative Composition 3 | 3.73 |
| Comparative Example 10 | Comparative Composition 4 | 3.30 |
| Comparative Example 11 | Comparative Composition 5 | 3.37 |
| Comparative Example 12 | Comparative Composition 6 | 3.40 |

As compared with Comparative Compositions 1 to 6, Compositions 1 and 12 exhibited small standard deviation and satisfactory evaluation of CD uniformity (CDU).

Priority is claimed on Japanese application No. 2020-095362, filed Jun. 1, 2020, the content of which are incorporated herein by reference.

The invention claimed is:

1. A resist composition comprising,
a resin including a first structural unit derived from a compound represented by formula (I) and a second structural unit represented by formula (a2-A), wherein a content of the first structural unit is 3 to 50 mol % based on all monomers in the resin, and
a content of the second structural unit is 15 to 50 mol % based on all the monomers in the resin

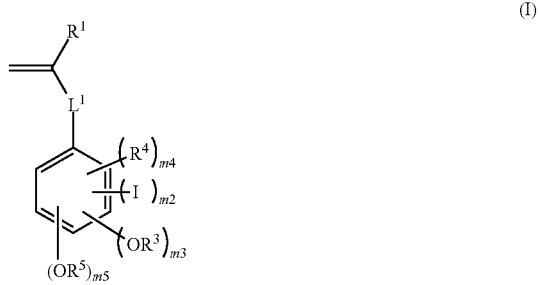

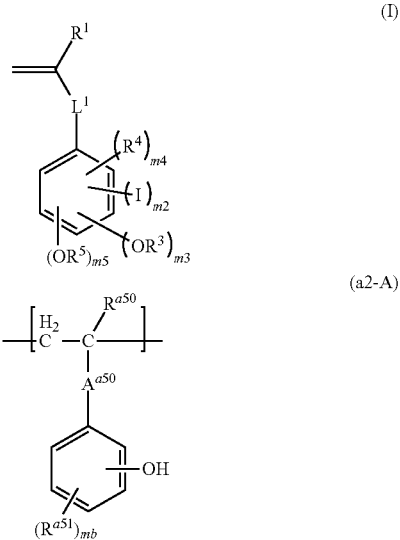

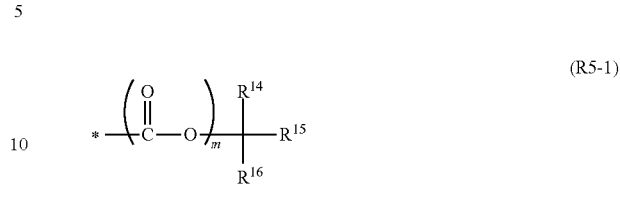

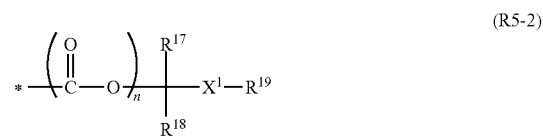

wherein, in formula (I),
- $R^1$ represents an alkyl group having 1 to 6 carbon atoms which may have a halogen atom, a hydrogen atom or a halogen atom,
- $L^1$ represents a single bond or —CO—O—* wherein * represents a bond to the benzene ring,
- $R^3$ represents an alkyl group having 1 to 6 carbon atoms, and —CH$_2$— included in the alkyl group may be replaced by —O— or —CO—,
- $R^4$ represents a fluorine atom, an alkyl fluoride group having 1 to 6 carbon atoms or an alkyl group having 1 to 12 carbon atoms, and —CH$_2$— included in the alkyl fluoride group and the alkyl group may be replaced by —O— or —CO—,
- $R^5$ represents a hydrogen atom, an alkylcarbonyl group having 2 to 6 carbon atoms or a first acid-labile group,
- m2 represents an integer of 1 to 3,
- m3 represents an integer of 1 to 3, and when m3 is 2 or more, a plurality of $R^3$ may be the same or different from each other,
- m4 represents an integer of 0 to 2, and when m4 is 2, two $R^4$ may be the same or different from each other, and
- m5 represents 1 or 2, and when m5 is 2, two $R^5$ may be the same or different from each other,
- in which 3≤m2+m3+m4+m5≤5; and wherein, in formula (a2-A),
- $R^{a50}$ represents a hydrogen atom, a halogen atom or an alkyl group having 1 to 6 carbon atoms which may have a halogen atom,
- $R^{a51}$ represents hydroxy group,
- $A^{a50}$ represents a single bond or *—$X^{a51}$-($A^{a52}$-$X^{a52}$)$_{nb}$—, and * represents a bond to carbon atoms to which —$R^{a50}$ is bonded,
- $A^{a52}$ represents an alkanediyl group having 1 to 6 carbon atoms,
- $X^{a51}$ and $X^{a52}$ each independently represent —O—, —CO—O— or —O—CO—,
- nb represents 0 or 1, and
- mb represents an integer of 0 to 4, and when mb is an integer of 2 or more, a plurality of $R^{a51}$ may be the same or different from each other.

2. The resist composition according to claim 1, wherein m2 is 1 or 2, m3 is 1, and m5 is 1 or 2.

3. The resist composition according to claim 1, wherein the first acid-labile group as for at least one R5 is a group represented by formula (R5-1) or a group represented by formula (R5-2):

wherein, in formula (R5-1), $R^{14}$, $R^{15}$ and $R^{16}$ each independently represent an alkyl group having 1 to 8 carbon atoms, an alkenyl group having 2 to 8 carbon atoms, an alicyclic hydrocarbon group having 3 to 20 carbon atoms, an aromatic hydrocarbon group having 6 to 18 carbon atoms, or a group obtained by combining these groups, or $R^{14}$ and $R^{15}$ are bonded to each other to form an alicyclic hydrocarbon group having 3 to 20 carbon atoms together with carbon atoms to which $R^{14}$ and $R^{15}$ are bonded, m represents 0 or 1, and

* represents a bonding site:

wherein, in formula (R5-2), $R^{17}$ and $R^{18}$ each independently represent a hydrogen atom or a hydrocarbon group having 1 to 12 carbon atoms, $R^{19}$ represents a hydrocarbon group having 1 to 20 carbon atoms, or $R^{18}$ and $R^{19}$ are bonded to each other to form a heterocyclic group having 3 to 20 carbon atoms together with carbon atoms and $X^1$ to which $R^{18}$ and $R^{19}$ are bonded, and —CH$_2$— included in the hydrocarbon group and the heterocyclic group may be replaced by —O— or —S—, $X^1$ represents an oxygen atom or a sulfur atom, n represents 0 or 1, and

* represents a bonding site.

4. The resist composition according to claim 1, wherein at least one $R^5$ is a hydrogen atom or an alkylcarbonyl group.

5. The resist composition according to claim 1, wherein a bonding site of at least one iodine atom is a m-position with respect to a bonding site of $L^1$ in the benzene ring.

6. The resist composition according to claim 1, wherein a bonding site of at least one $OR^5$ is an o-position or a p-position with respect to the bonding site of $L^1$ in the benzene ring.

7. The resist composition according to claim 1, wherein the resin further includes a third structural unit having a second acid-labile group other than the first structural unit derived from the compound represented by formula (I).

8. The resist composition according to claim 1, further comprising an acid generator.

9. The resist composition according to claim 8, wherein the acid generator comprises a salt represented by formula (B1):

(B1)

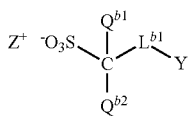

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$— included in the alicyclic hydrocarbon group may be replaced by —O—, —$SO_2$— or —CO—, and $Z^+$ represents an organic cation.

10. The resist composition according to claim 1, further comprising a salt generating an acid having an acidity lower than that of an acid generated from the acid generator.

11. A method for producing a resist pattern, which comprises:

(1) a step of applying the resist composition according to claim 1 on a substrate, (2) a step of drying the applied composition to form a composition layer, (3) a step of exposing the composition layer, (4) a step of heating the exposed composition layer, and (5) a step of developing the heated composition layer.

12. The resist composition according to claim 7, wherein the third structural unit includes a structural unit represented by formula (a1-1) or a structural unit represented by formula (a1-2):

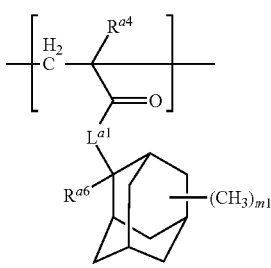

(a1-1)

-continued

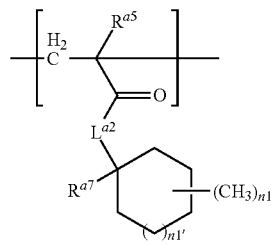

(a1-2)

wherein, in formula (a1-1) and formula (a1-2), $L^{a1}$ and $L^{a2}$ each independently represent —O— or *—O—$(CH_2)_{k1}$—CO—O—, k1 represents an integer of 1 to 7, and * represents a bond to —CO—, $R^{a4}$ and $R^{a5}$ each independently represent a hydrogen atom, a halogen atom, or an alkyl group having 1 to 6 carbon atoms which may have a halogen atom, $R^{a6}$ and $R^{a7}$ each independently represent an alkyl group having 1 to 8 carbon atoms, an alkenyl group having 2 to 8 carbon atoms, an alicyclic hydrocarbon group having 3 to 18 carbon atoms, an aromatic hydrocarbon group having 6 to 18 carbon atoms, or groups formed by combining these groups, m1 represents an integer of 0 to 14, n1 represents an integer of 0 to 10, and n1' represents an integer of 0 to 3.

13. The resist composition according to claim 1, wherein the resin further includes, a structural unit represented by formula (a3-4)':

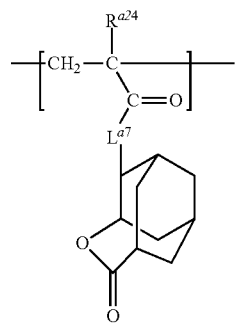

(a3-4)'

$L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^{a9}$-O— and * represents a bonding site to a carbonyl group, $L^{a8}$ and $L^{a9}$ each independently represent an alkanediyl group having 1 to 6 carbon atoms,

* represents a bonding site to a carbonyl group, $R^{a24}$ represents an alkyl group having 1 to 6 carbon atoms which may have a halogen atom, a hydrogen atom or a halogen atom.

* * * * *